US011793420B2

(12) United States Patent
Jones et al.

(10) Patent No.: US 11,793,420 B2
(45) Date of Patent: Oct. 24, 2023

(54) INGESTIBLE DEVICE FOR DELIVERY OF A DISPENSABLE SUBSTANCE

(71) Applicant: Biora Therapeutics, Inc., San Diego, CA (US)

(72) Inventors: Mitchell Lawrence Jones, La Jolla, CA (US); Christopher Loren Wahl, San Diego, CA (US); Gene Alan Wey, Victoria (CA); Aaron Olafur Laurence Philippsen, Victoria (CA); Mark Sasha Drlik, Victoria (CA); Ryan Elliott Jones, Providenciales (TC); Nathan John Muller, Victoria (CA); Andrew Carlos Garland, Victoria (CA); Iman Niknia, Victoria (CA)

(73) Assignee: Biora Therapeutics, Inc., San Diego, CA (US)

( * ) Notice: Subject to any disclaimer, the term of this patent is extended or adjusted under 35 U.S.C. 154(b) by 837 days.

(21) Appl. No.: 16/839,107

(22) Filed: Apr. 3, 2020

(65) Prior Publication Data

US 2020/0245897 A1    Aug. 6, 2020

Related U.S. Application Data

(63) Continuation of application No. 15/699,848, filed on Sep. 8, 2017, now abandoned.

(Continued)

(51) Int. Cl.
*A61B 5/07* (2006.01)
*A61B 1/04* (2006.01)
(Continued)

(52) U.S. Cl.
CPC .............. *A61B 5/073* (2013.01); *A61B 1/041* (2013.01); *A61M 31/002* (2013.01); *A61B 5/4839* (2013.01); *A61J 3/007* (2013.01)

(58) Field of Classification Search
CPC .......... A61M 31/002; A61M 2210/106; A61M 2210/1064; A61K 9/4808; A61P 1/04;
(Continued)

(56) References Cited

U.S. PATENT DOCUMENTS 3,057,344 A    10/1962  Alberto
3,118,439 A    1/1964   Barana
(Continued)

FOREIGN PATENT DOCUMENTS

CN    1856290       11/2006
CN    1856290 B     11/2006
(Continued)

OTHER PUBLICATIONS

Anselmo et al., "Non-invasive delivery strategies for biologics", Nature Reviews, Drug Discovery, vol. 18, 19-40, 2019.
(Continued)

*Primary Examiner* — Brandy S Lee
(74) *Attorney, Agent, or Firm* — Perkins Coie LLP

(57) ABSTRACT

Ingestible devices capable of delivering a dispensable substance, such as, for example, a therapeutic agent, as well as related components, systems and methods, are disclosed. A removably attachable storage reservoir configured to be used with an ingestible device and capable of storing dispensable substance, such as, for example, a therapeutic agent, as well as related components, systems and methods, are also disclosed.

10 Claims, 62 Drawing Sheets

Related U.S. Application Data

(60) Provisional application No. 62/545,129, filed on Aug. 14, 2017, provisional application No. 62/540,873, filed on Aug. 3, 2017, provisional application No. 62/480,187, filed on Mar. 31, 2017, provisional application No. 62/478,955, filed on Mar. 30, 2017, provisional application No. 62/478,753, filed on Mar. 30, 2017, provisional application No. 62/385,553, filed on Sep. 9, 2016.

(51) Int. Cl.
*A61M 31/00* (2006.01)
*A61B 5/00* (2006.01)
*A61J 3/00* (2006.01)

(58) Field of Classification Search
CPC .......... A61J 3/007; A61B 1/041; A61B 5/073; A61B 5/4839; A61B 1/00148
See application file for complete search history.

(56) References Cited

U.S. PATENT DOCUMENTS

| | | | |
|---|---|---|---|
| 3,315,660 A | 4/1967 | Abella |
| 3,485,235 A | 12/1969 | Felson |
| 4,036,214 A | 7/1977 | Bucalo |
| 4,172,446 A | 10/1979 | Bucalo |
| 4,223,680 A | 9/1980 | Jobsis |
| 4,239,040 A | 12/1980 | Hosoya |
| 4,292,961 A | 10/1981 | Kawashima |
| 4,425,117 A | 1/1984 | Hugeman |
| 4,481,952 A | 11/1984 | Pawelec |
| 4,507,115 A | 3/1985 | Kambara |
| 4,522,625 A | 6/1985 | Edgren |
| 4,573,447 A | 3/1986 | Thrash et al. |
| 4,844,076 A | 7/1989 | Lesho |
| 5,167,626 A | 12/1992 | Casper et al. |
| 5,170,801 A | 12/1992 | Casper |
| 5,217,449 A | 6/1993 | Yuda Shunichi et al. |
| 5,279,607 A | 1/1994 | Schentag |
| 5,316,015 A | 5/1994 | Sinaiko |
| 5,318,557 A | 6/1994 | Gross |
| 5,395,366 A | 3/1995 | Andrea |
| 5,604,531 A | 2/1997 | Iddan et al. |
| 5,738,110 A | 4/1998 | Beal et al. |
| 5,858,001 A | 1/1999 | Tsals et al. |
| 5,951,538 A | 9/1999 | Joshi |
| 5,971,942 A | 10/1999 | Gu et al. |
| 6,344,027 B1 | 2/2002 | Goll |
| 6,344,028 B1 | 2/2002 | Barry |
| 6,369,039 B1 | 4/2002 | Palasis et al. |
| 6,576,429 B1 | 6/2003 | Hallgren |
| 6,632,216 B2 | 10/2003 | Houzego |
| 6,884,239 B2 | 4/2005 | Houzego et al. |
| 6,950,690 B1 | 9/2005 | Meron et al. |
| 7,056,673 B2 | 6/2006 | Kamme et al. |
| 7,144,366 B2 | 12/2006 | Takizawa et al. |
| 7,160,258 B2 | 1/2007 | Imran et al. |
| 7,282,045 B2 | 10/2007 | Houzego et al. |
| 7,553,276 B2 | 6/2009 | Iddan |
| 7,611,480 B2 | 11/2009 | Levy |
| 7,662,093 B2 | 2/2010 | Gilad et al. |
| 7,717,862 B2 | 5/2010 | Stoltz |
| 7,763,014 B2 | 7/2010 | Houzeao et al. |
| 7,797,033 B2 | 9/2010 | D'Andrea et al. |
| 7,946,979 B2 | 5/2011 | Gilad et al. |
| 8,005,536 B2 | 8/2011 | Imran |
| 8,185,185 B2 | 5/2012 | Gilreath |
| 8,206,285 B2 | 6/2012 | Blijevsky |
| 8,216,130 B2 | 6/2012 | Glukhovsky et al. |
| 8,360,976 B2 | 1/2013 | Imran |
| 8,394,034 B2 | 3/2013 | Iddan |
| 8,540,623 B2 | 9/2013 | Blijevsky |
| 8,597,279 B2 | 12/2013 | Dijksman et al. |
| 8,626,268 B2 | 1/2014 | Adler |
| 8,696,602 B2 | 4/2014 | Semler et al. |
| 8,740,774 B2 | 6/2014 | Takizawa et al. |
| 8,809,271 B2 | 8/2014 | Imran |
| 8,911,368 B2 | 12/2014 | Rabinovitz et al. |
| 8,926,526 B2 | 1/2015 | Shuck |
| 9,014,799 B2 | 4/2015 | Uhland et al. |
| 9,026,192 B2 | 5/2015 | Blit et al. |
| 9,072,834 B2 | 7/2015 | Vogt |
| 9,131,842 B2 | 9/2015 | Old |
| 9,324,145 B1 | 4/2016 | Cherevatsky |
| 9,456,737 B2 | 10/2016 | Pascal |
| 9,511,121 B2 | 12/2016 | Imran |
| 10,172,598 B2 | 1/2019 | Amoako-Tuffour et al. |
| 10,588,608 B2 | 3/2020 | Jones et al. |
| 10,765,360 B2 | 9/2020 | Euliano et al. |
| 10,835,152 B2 | 11/2020 | Jones et al. |
| 11,007,356 B2 | 5/2021 | Shimizu et al. |
| 11,439,802 B2 | 9/2022 | Shimizu et al. |
| 2002/0099310 A1 | 7/2002 | Kimchy et al. |
| 2002/0198470 A1 | 12/2002 | Imran et al. |
| 2003/0139661 A1 | 7/2003 | Kimchy |
| 2003/0191430 A1 | 10/2003 | Andrea et al. |
| 2004/0162469 A1 | 8/2004 | Imran |
| 2004/0199054 A1 | 10/2004 | Wakefield et al. |
| 2004/0253304 A1* | 12/2004 | Gross ................ A61B 5/14539 424/451 |
| 2004/0254455 A1 | 12/2004 | Iddan |
| 2005/0010168 A1 | 1/2005 | Kendall |
| 2005/0049462 A1 | 3/2005 | Kanazawa |
| 2005/0065441 A1 | 3/2005 | Glukhovsky |
| 2005/0158246 A1 | 7/2005 | Takizawa |
| 2005/0266074 A1 | 12/2005 | Zilberstein et al. |
| 2006/0069317 A1 | 3/2006 | Horn et al. |
| 2006/0178557 A1 | 8/2006 | Mintchev |
| 2007/0027362 A1 | 2/2007 | Handa |
| 2007/0043320 A1 | 2/2007 | Kenany |
| 2007/0092401 A1 | 4/2007 | Liao et al. |
| 2007/0161928 A1 | 7/2007 | Sprenkels |
| 2007/0293736 A1 | 12/2007 | Casset |
| 2008/0027329 A1 | 1/2008 | Glukhovsky |
| 2008/0051633 A1 | 2/2008 | Blijevsky |
| 2008/0051635 A1 | 2/2008 | Tanaka |
| 2008/0194912 A1 | 8/2008 | Trovato |
| 2008/0208077 A1 | 8/2008 | Iddan et al. |
| 2008/0234548 A1 | 9/2008 | Amit |
| 2008/0294023 A1 | 11/2008 | Rabinovitz et al. |
| 2009/0131784 A1 | 5/2009 | Betesh |
| 2009/0275923 A1 | 11/2009 | Shimizu et al. |
| 2009/0306633 A1* | 12/2009 | Trovato ................ A61B 1/041 604/891.1 |
| 2010/0045786 A1 | 2/2010 | Kitamura |
| 2010/0063486 A1 | 3/2010 | Dijksman et al. |
| 2010/0111763 A1 | 5/2010 | Kahn et al. |
| 2010/0249645 A1 | 9/2010 | Semler et al. |
| 2010/0285475 A1 | 11/2010 | Palanisanny |
| 2010/0324381 A1 | 12/2010 | Glukhovskv et al. |
| 2011/0046458 A1 | 2/2011 | Pinedo |
| 2011/0092959 A1 | 4/2011 | Zou et al. |
| 2011/0106063 A1 | 5/2011 | Dijksman et al. |
| 2011/0125007 A1 | 5/2011 | Steinberg |
| 2011/0125031 A1 | 5/2011 | Blit et al. |
| 2011/0306055 A1 | 12/2011 | Haince |
| 2011/0313348 A1 | 12/2011 | Potter et al. |
| 2012/0041465 A1 | 2/2012 | Shalon |
| 2012/0136209 A1 | 5/2012 | Kostenich et al. |
| 2012/0253204 A1 | 10/2012 | Ben-Yehuda |
| 2012/0258473 A1 | 10/2012 | Moriya et al. |
| 2013/0013031 A1 | 1/2013 | Ben-Yehuda et al. |
| 2013/0018279 A1 | 1/2013 | Plante et al. |
| 2013/0022983 A1 | 1/2013 | Grifantini |
| 2013/0085414 A1 | 4/2013 | Yamatani |
| 2013/0158344 A1 | 6/2013 | Taniguchi |
| 2013/0171247 A1* | 7/2013 | Imran .................. A61M 25/10 604/174 |
| 2014/0113313 A1 | 4/2014 | Moreau |
| 2014/0128833 A1 | 5/2014 | Vogt |
| 2014/0206956 A1 | 7/2014 | Rabinovitz et al. |
| 2014/0296666 A1 | 10/2014 | Rabinovitz et al. |

(56) References Cited

U.S. PATENT DOCUMENTS

| | | |
|---|---|---|
| 2014/0343451 A1 | 11/2014 | Pannell |
| 2015/0011874 A1 | 1/2015 | Amoako-Tuffour et al. |
| 2015/0051589 A1 | 2/2015 | Sako et al. |
| 2015/0057548 A1 | 2/2015 | Kaufman |
| 2015/0065926 A1 | 3/2015 | Nakamura et al. |
| 2016/0033373 A1 | 2/2016 | Hill et al. |
| 2016/0038086 A1 | 2/2016 | Wrigglesworth |
| 2016/0066855 A1 | 3/2016 | Hyde |
| 2016/0114142 A1 | 4/2016 | Ziaie et al. |
| 2016/0213234 A1 | 7/2016 | Poon |
| 2016/0235663 A1 | 8/2016 | Zou et al. |
| 2016/0249793 A1 | 9/2016 | Wang |
| 2017/0006202 A1 | 1/2017 | Otani |
| 2017/0050006 A1 | 2/2017 | Imran et al. |
| 2017/0106099 A1 | 4/2017 | Bellinger et al. |
| 2017/0246438 A1 | 8/2017 | Aran et al. |
| 2017/0258583 A1 | 9/2017 | McCawley |
| 2017/0296092 A1 | 10/2017 | Jones et al. |
| 2018/0049725 A1 | 2/2018 | Jones et al. |
| 2018/0052084 A1 | 2/2018 | Jones et al. |
| 2018/0070857 A1 | 3/2018 | Jones et al. |
| 2018/0160950 A1 | 6/2018 | Rabinovitz et al. |
| 2018/0279908 A1 | 10/2018 | Jones et al. |
| 2018/0318496 A1 | 11/2018 | Zou et al. |
| 2020/0094031 A1 | 3/2020 | Jones et al. |
| 2020/0245897 A1 | 8/2020 | Jones et al. |
| 2020/0038268 A1 | 10/2020 | Imran |
| 2020/0316352 A1 | 10/2020 | Aran et al. |
| 2021/0015398 A1 | 1/2021 | Jones et al. |
| 2021/0093248 A1 | 4/2021 | Euliano et al. |
| 2021/0161805 A1 | 6/2021 | Zou et al. |
| 2022/0072286 A1 | 3/2022 | Bonner et al. |

FOREIGN PATENT DOCUMENTS

| | | |
|---|---|---|
| CN | 1951338 A | 4/2007 |
| CN | 101495164 | 7/2009 |
| CN | 103209632 | 7/2013 |
| CN | 103800100 A | 5/2014 |
| CN | 105916541 A | 8/2016 |
| CN | 103800100 B | 6/2017 |
| CN | 108784634 A | 11/2018 |
| DE | 19801573 A1 | 7/1999 |
| EP | 108607 | 2/1983 |
| EP | 1243524 | 9/2002 |
| EP | 1530950 | 5/2005 |
| EP | 1530950 A1 | 5/2005 |
| EP | 1932462 | 6/2008 |
| EP | 2057934 | 5/2009 |
| EP | 2515992 B1 | 10/2012 |
| EP | 3108810 | 12/2016 |
| JP | 2002-347737 A | 4/2002 |
| JP | 200573888 | 3/2005 |
| JP | 2005073888 A | 3/2005 |
| JP | 2007-312850 A | 6/2007 |
| JP | 2007312850 A | 12/2007 |
| JP | 2011093614 A | 5/2011 |
| JP | 2011-093614 A | 12/2011 |
| JP | 2013500815 | 1/2013 |
| JP | 2006-517827 A | 3/2015 |
| JP | 2015509744 | 4/2015 |
| KR | 100931946 | 12/2009 |
| RU | 2269343 | 2/2006 |
| WO | WO 2001045552 | 6/2001 |
| WO | 2004066903 A2 | 8/2004 |
| WO | WO 2004/066903 A2 | 8/2004 |
| WO | 2006077529 A2 | 7/2006 |
| WO | WO2008014439 A2 | 1/2008 |
| WO | WO2009104110 A1 | 8/2009 |
| WO | 2010045477 A2 | 4/2010 |
| WO | WO 2010091926 | 8/2010 |
| WO | WO 2010146588 | 12/2010 |
| WO | WO 2011016002 | 2/2011 |
| WO | WO2013003824 A1 | 1/2013 |
| WO | WO 2013088444 | 6/2013 |
| WO | WO 2013120184 | 8/2013 |
| WO | 2013145855 A1 | 10/2013 |
| WO | 2013153859 A1 | 10/2013 |
| WO | 2015059569 A | 4/2015 |
| WO | 2015059569 A1 | 4/2015 |
| WO | WO 2015/059569 A1 | 4/2015 |
| WO | WO 2015059569 | 4/2015 |
| WO | WO 2015099749 | 7/2015 |
| WO | WO 2015147305 | 10/2015 |
| WO | WO 2016049602 | 3/2016 |
| WO | WO 2016054015 | 4/2016 |
| WO | WO 2017004000 | 1/2017 |
| WO | 2018049133 A1 | 3/2018 |
| WO | WO 2018050647 | 3/2018 |
| WO | 2018183934 A1 | 10/2018 |
| WO | WO2018213588 A1 | 11/2018 |
| WO | WO2020041774 A1 | 2/2020 |
| WO | WO2020157324 A1 | 8/2020 |
| WO | WO2020160399 A1 | 8/2020 |

OTHER PUBLICATIONS

Aran et al., "An oral microjet vaccination system elicits antibody production in rabbits", Sci. Transl. Med. 9, eaaf6413,10 pages, 2017.
Barolet et al., "Current trends in needle-free jet injection: an update", Clinical, Cosmetic and Investigational Dermatology, 11, 231-238, 2018.
Battula et al., "A Miniature Shock Wave Driven Micro-Jet Injector for Needle-Free Vaccine/Drug Delivery", Biotechnology and Bioengineering, vol. 113, No. 11, 2507-2512, 2016.
Hunter et al., "Aerosol delivery of Virus-like Particles to the genital tract induces local and systemic antibody responses", Vaccine, 29(28): 4584-4592, 2011.
International Search Report and Written Opinion in International Application No. PCT/US2017/050642, dated Jan. 29, 2018, 28 pages.
Invitation to Pay Additional Fees and Where Applicable Protest Fee International Application No. PCT/US2017/050642, dated Dec. 8, 2017, 25 pages.
Iverson et al., "An innate antiviral pathway acting before interferons at epithelial surfaces", Nature Immunology, vol. 17, No. 2, 150-158, 2016.
Kale et al., "Needle free injection technology—An overview", Innovations in pharmacy, vol. 1, No. 1, Article 148, 10 pages, 2014.
Lambert et al., "Autonomous telemetric capsule to explore the small bowel," Med Biol Eng Comput 29(2): 191-196, 1991.
Lo et al., "The use of carbon dioxide in gastrointestinal endoscopy", Gastrointestinal Endoscopy, vol. 83, No. 5, 857-865, 2016.
Office Action in Israel Application No. 297016; dated Jan. 18, 20-23; 5 pages.
Office Action in Japanese Application No. 2022-098083; dated Feb. 7, 2023; 6 pages.
EP Extended European Search Report in European Appln. No. 20207295.5, dated Feb. 23, 2021, 7 pages.
U.S. Non-Final Office Action in U.S. Appl. No. 15/940,407, dated Apr. 7, 2021, 31 pages.
Office Action in JP application No. 2019-535193, dated Jan. 18, 2022.
Australian Office Action in Application No. 2015319850, dated Aug. 2, 2019, 4 pages.
Bao and Pahlavan, "Motion estimation of the endoscopy capsule using region-based kernel SVM classifier," 2013 IEEE International. Conf. Electro-Information Technol., EIT 2013, 5 pages.
Chen et al., "Developing assessment system for wireless capsule endoscopy videos based on event detection", Proceedings of Spie, 12 pages, 2009.
Chen et al., "Developing assessment system for wireless capsule endoscopy videos based on event detection", Proceedings of SPIE, vol. 7260, p. 72601G, 2009.
Chinese Office Action in Application No. 2015800635638, dated Sep. 29, 2019, 10 pages.

(56) References Cited

OTHER PUBLICATIONS

Dingle et al., "Stable and Noncompetitive RNA Internal Control for Routine Clinical Diagnostic Reverse Transcription-PCR", Journal of Clinical Microbiology, vol. 42(3): 1003-1011, Mar. 2004.
Eurasian Office Action in Application No. 201790706/31, dated May 29, 2019, 4 pages, (with English Translation).
European Exam Report in Application No. 157759119.9, dated Jan. 2, 2020, 4 pages.
European Exam Report in Application No. 157759119.9, dated Mar. 3, 2019, 4 pages.
European Exam Report in Application No. 157759119.9, dated May 28, 2018, 3 pages.
International Search Report and Written Opinion in International Application No. PCT/US2015/052500, dated Dec. 17, 2015, 15 pages.
International Search Report and Written Opinion in International Application No. PCT/US2018/025191, dated Oct. 19, 2018.
International Search Report Written Opinion. International Application No. PCT/US2017/047476, dated Jan. 22, 2018, 20 pages.
International Search Report Written Opinion. International Application No. PCT/US2017/047481, dated Jan. 17, 2018, 18 pages.
Invitation to Pay Additional Fees and Where Applicable Protest Fee International Application No. PCT/US2012/047476, dated Nov. 13, 2017, 13 pages.
Invitation to Pay Additional Fees for International Application No. PCT/US2017/047481, dated Nov. 24, 2017, 14 pages.
Invitation to Pay Fees om International Application No. PCT/US2018/025191, Jul. 12, 2018, 22 pages.
Jacques, "Optical properties of biological tissues: a review," Phys., Med. Biol., IPEM, 58, R37, 28 pages, 2013.
Japanese Office Action in Application No. 2017-516962, dated Jul. 22, 2019, 4 pages.
Kane et al., "Fecal Lactoferrin Is a Sensitive and Specific Marker in Identifying Intestinal Inflammation", The American Journal of Gastroenterology, 98(6): 1309-1314, 2003.
Kostic et al., "The Gut Microbiome and Disease", Gastroenterology, vol. 146(6): 1489-1499, 2014.
Lee et al., "Automatic Classification of Digestive Organs in Wireless Capsule Endoscopy Videos", Applied Computing, pp. 1041-1045, 2007.
Lehmann et al.," The role and utility of faecal markers in inflammatory bowel disease", Therapeutic Advances in Gastroenterology, vol. 8(1): 23-36, 2015.
Li et al., "Outlier detection and removal improves accuracy of machine learning approach to multispectral burn diagnostic imaging," J. Biomed. Opt., 2015, 20:121305.
Sanschagrin and Yergeau, Next-generation Sequencing of 16S Ribosomal RNA Gene Amplicons, Journal of Visualized Experiments, Issue 90: 51709, Aug. 2014.
Sartor and Mazmanian, "Intestinal Microbes in Inflammatory Bowel Diseases", The American Journal of Gastroenterology Supplements, vol. 1, 12-21, 2012.
U.S. Final Office Action in U.S. Appl. No. 15/680,400, dated Jan. 15, 2020, 14 pages.
U.S. Non-Final Office Action in U.S. Appl. No. 15/514,413, dated Mar. 20, 2020, 12 pages.
U.S. Non-Final Office Action in U.S. Appl. No. 15/680,400, dated Mar. 5, 2020, 18 pages.
U.S. Non-Final Office Action in U.S. Appl. No. 15/680,400, dated Oct. 1, 2019, 11 pages.
U.S. Non-Final Office Action in U.S. Appl. No. 15/940,407, dated Jun. 15, 2020, 17 pages.
Wright et al., "Recent Advances in Characterizing the Gastrointestinal Microbiome in Crohn's Disease: A Systematic Review", Inflammatory Bowel Disease Journal, vol. 21(6): 1219-1228, 2015.
Examination Report No. 1 for Australian Application No. 2017322324; dated Nov. 11, 2021; 4 pages.
Examination Report No. 2 for Australian Application No. 2017322324; dated Aug. 24, 2022; 3 pages.
Examination Report No. 3 for Australian Application No. 2017322324; dated Oct. 19, 2022; 4 pages.
Extended European Search Report for European Application No. 22176814.6; dated Oct. 26, 2022; 7 pages.
IP Australia, Examination Report No. 1 in Application No. 2017322324, dated Nov. 11, 2021,4pgs.
CN Office Action in Chinese Appln. No. 201780065257.7, dated Apr. 2, 2021, 24 pages (with English translation).
Examination Report for Canadian Application No. 3,036,364; dated Feb. 14, 2023; 6 pages.
Notice of Preliminary Rejection issued on KR patent application No. 10-2022-7022586; dated Jan. 16, 2023; 5 pages.
KIPO Notice of Preliminary Rejection of Korean Application No. KR-10-2023-7009208; dated May 30, 2023; 9 pages.
Office Action in Japanese Application No. 2022-098083; dated May 24, 2023; 4 pages.

\* cited by examiner

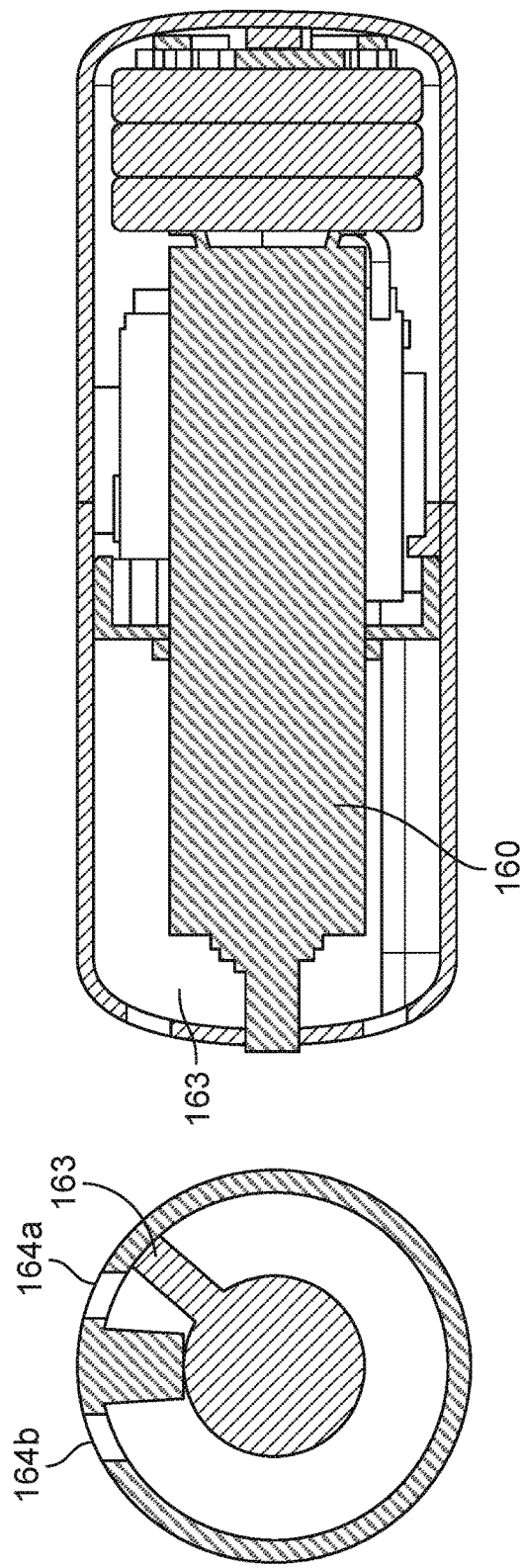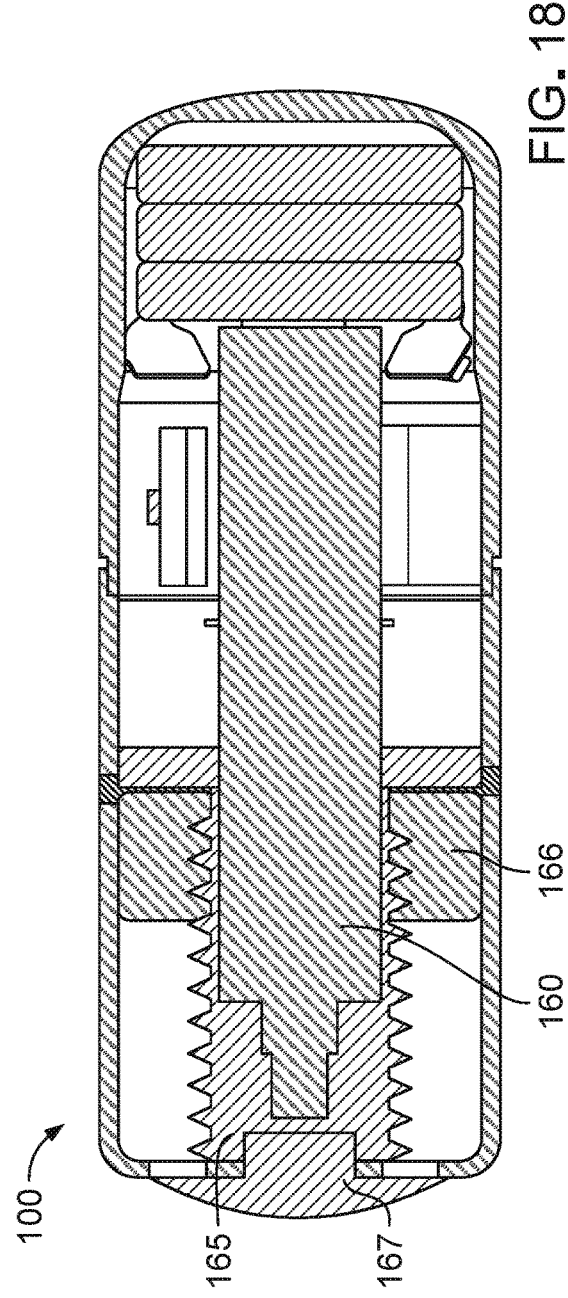

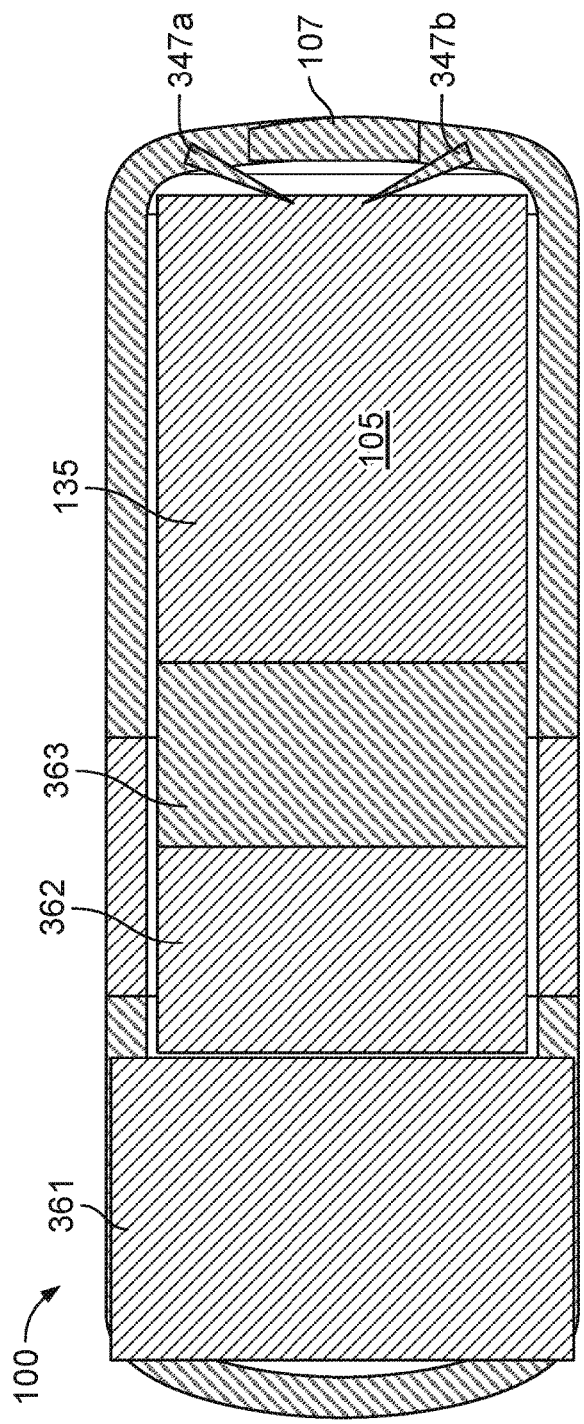
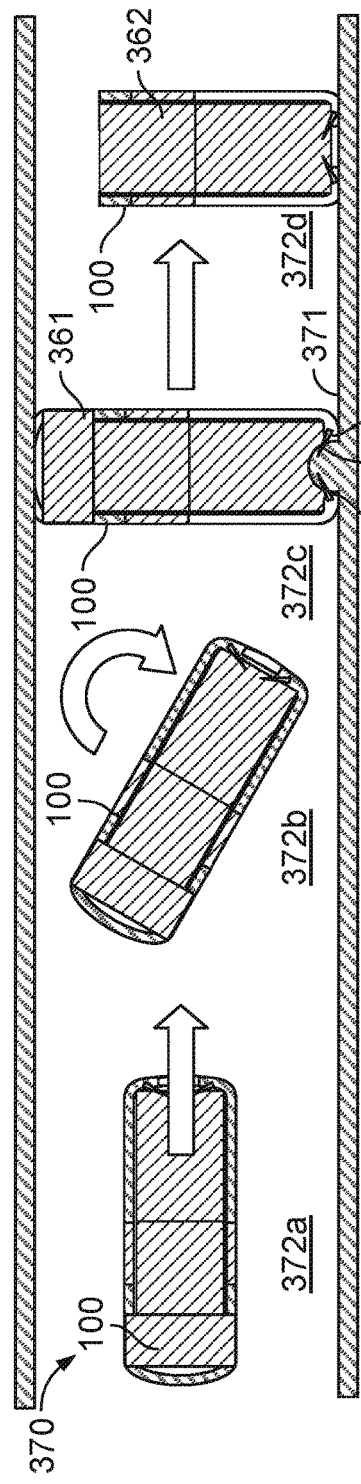
FIG. 39
FIG. 40

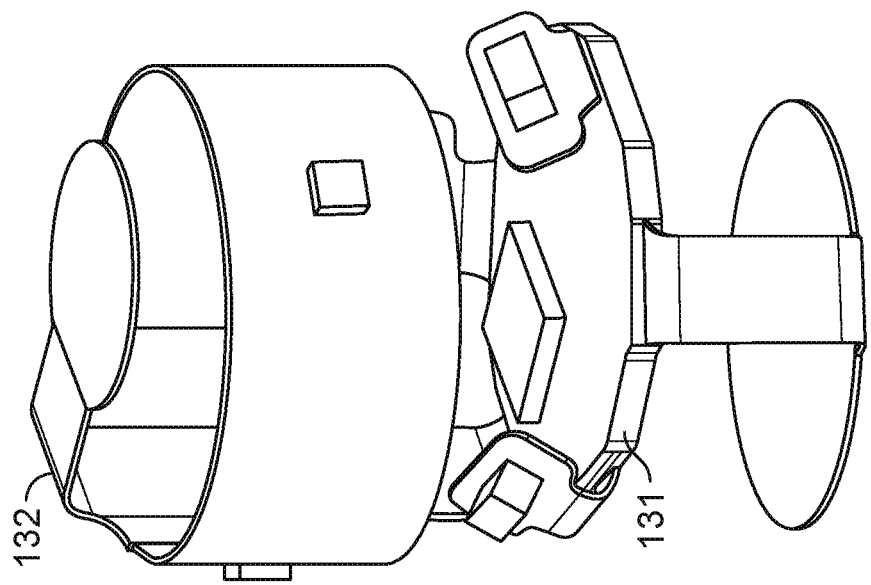
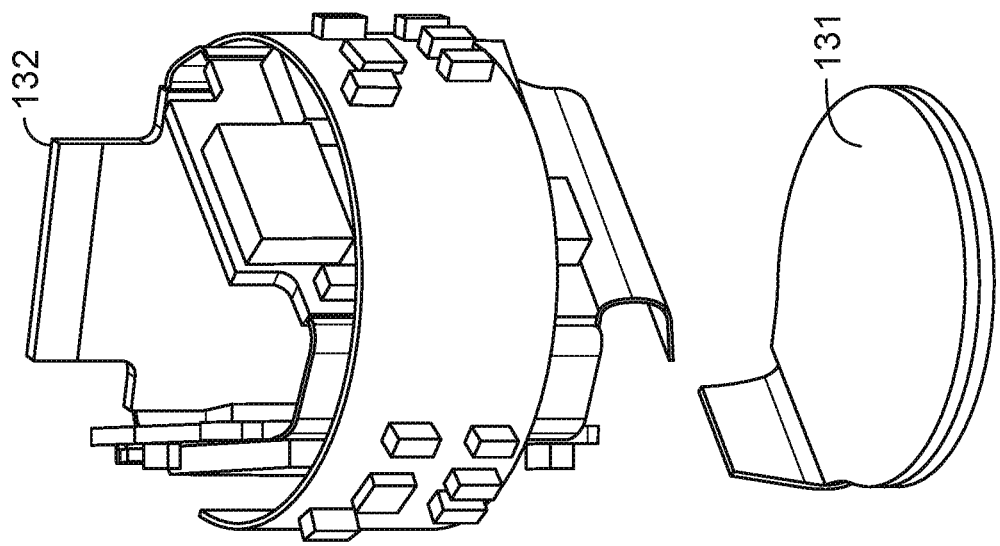
FIG. 44

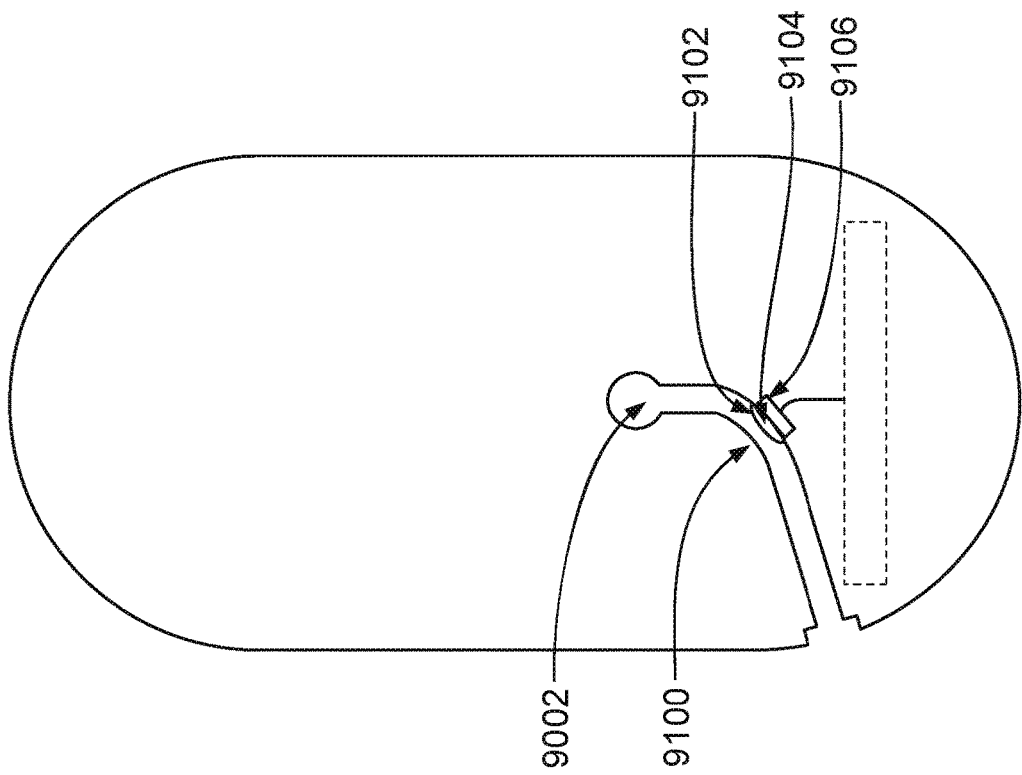
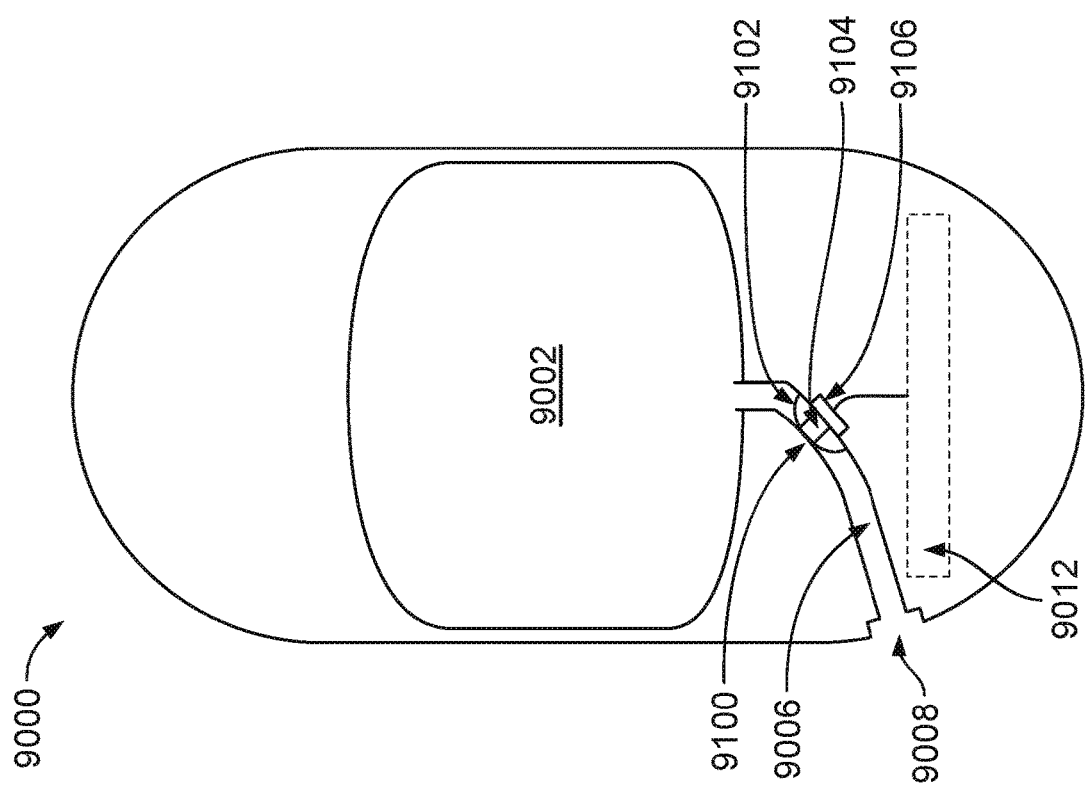

INGESTIBLE DEVICE FOR DELIVERY OF A DISPENSABLE SUBSTANCE

CROSS-REFERENCE TO RELATED APPLICATIONS

The present application is a continuation of U.S. patent application Ser. No. 15/699,848, filed Sep. 8, 2017, entitled "Electromechanical Ingestible Device for Delivery of a Dispensable Substance" which claims priority under 35 U.S.C. § 119 to: U.S. Provisional Patent Application No. 62/385,553, filed on Sep. 9, 2016, entitled "Electromechanical Ingestible Device for Delivery of a Dispensable Substance;" U.S. Provisional Patent Application No. 62/478, 955, filed on Mar. 30, 2017, and entitled "Electromechanical Ingestible Device for Delivery of a Dispensable Substance;" U.S. Provisional Patent Application No. 62/478,753, filed on Mar. 30, 2017, and entitled "Treatment of a Disease of the Gastrointestinal Trace with an IL-6R Inhibitor;" U.S. Provisional Patent Application No. 62/480,187 filed on Mar. 31, 2017, entitled "Localization Systems and Method for an Ingestible Device;" U.S. Provisional Patent Application No. 62/540,873 filed on Aug. 3, 2017, entitled "Localization Systems and Method for an Ingestible Device;" and U.S. Provisional Patent Application No. 62/545,129 filed on Aug. 14, 2017, entitled "Treatment of a Disease of the Gastrointestinal Tract with a CD40/CD40L Inhibitor."

INCORPORATION BY REFERENCE

This application incorporates by reference the following patent applications: U.S. Ser. Nos. 14/460,893; 15/514,413; 15/680,400; 15/680,430; 15/694,458; 62/376,688; 62/385, 553; 62/478,753; 62/478,955; 62/434,188; 62/434,320; 62/431,297; 62/434,797; 62/480,187; 62/502,383; 62/540, 873; and 62/545,129.

FIELD

The disclosure generally to ingestible devices capable of delivering a dispensable substance, such as, for example, a therapeutic agent, as well as related components, systems and methods. The disclosure also generally relates to an attachable storage reservoir configured to be used with an ingestible device and capable of storing dispensable substance, such as, for example, a therapeutic agent, as well as related components, systems and methods.

BACKGROUND

The gastrointestinal (GI) tract generally provides a therapeutic medium for an individual's body. At times, therapeutic agents may need to be dispensed to specified locations within the small intestine, which is more effective than oral administration of the therapeutic agents to cure some medical conditions. For example, therapeutic agents applied directly within the small intestine would not be contaminated in the stomach, and thus allow a higher dose to be delivered at a specific location within the small intestine. However, dispensing therapeutic agents directly within the small intestine inside a human body can be difficult, because a device or mechanism is needed to carry the therapeutic agents to a desired location within the small intestine and then automatically deliver the therapeutic agent at the desired location. Such a device or mechanism also needs to be operated in a safe manner as the device or mechanism needs to enter the human body.

SUMMARY

The disclosure provides ingestible devices that can deliver a dispensable substance, such as, for example, a therapeutic agent within the GI tract of a subject. The delivery can be highly controlled. The delivery can be performed at a desired location with the GI tract of the subject with relatively high accuracy. Optionally, the ingestible device can include a mechanism that can be used to control/manipulate the position of the ingestible device within the GI tract of the subject. The amount of dispensable substance delivered, as well as its release profile, can be controlled to a relatively high accuracy.

The disclosure also provides attachable storage reservoirs that can be, for example, configured for use with an ingestible device. The storage reservoirs can be developed so that, for example, a dispensable substance (e.g., a therapeutic agent) can be disposed in the storage reservoir before, during or after the storage reservoir is packaged, shipped and/or housed. With such an approach, it is possible to provide a storage reservoir containing a desired dispensable substance a relatively short time period before the dispensable substance is to be delivered. For example, the dispensable substance can be disposed with the storage reservoir at a given point in time, and soon thereafter the storage reservoir containing the dispensable substance can be attached to/within the ingestible device shortly before ingestion of the ingestible device.

In one aspect, the disclosure provides an ingestible device includes a storage reservoir configured to store a dispensable substance, and a force generator component configured so that, when the force generator generates a force, the dispensable substance exits the ingestible device via an opening in the ingestible device.

The ingestible device can include a housing.

The force generator can be at least partially disposed within the housing.

The force generator can be completely disposed within the housing.

The storage reservoir can be at least partially disposed within the housing.

The storage reservoir can be completely disposed within the housing.

The housing can include a first end, a second end a wall extending between the first and second ends. The storage reservoir can be adjacent the first end.

The storage reservoir can be attachable to the ingestible device.

The storage can be an integral component of the ingestible device.

The ingestible device can further include an injection device configured so that, when the force generator generates the force, the force moves the injection device to force the dispensable substance out of the ingestible device via the opening.

The injection device can include a syringe.

The ingestible device can further include a component configured to position the injection device at an epithelial layer and spread the epithelial layer prior to a delivery of the dispensable substance.

The injection device can be configured so that the force it generates is sufficient to penetrate a mucosa membrane.

The injection device can include: a piston; a needle guide disposed within the storage reservoir and having an end attached to the piston; a spring connected to the needle guide; and an injection needle through a portion of the needle guide and the spring.

The spring can be configured to be compressed, and the injection needle can be configured to extend out of the ingestible device as the piston moves.

The injection device can include: a truss mechanism supporting an injection needle; and a balloon configured to expand to force the truss mechanism with the injection needle to extend out of the storage reservoir.

The injection device can include a membrane configured so that, when the force generator generates the force, the force moves the membrane to force the dispensable substance out of the ingestible device via the opening.

The membrane can include a piston configured so that, when the force generator generates the force, the force moves the membrane to force the dispensable substance out of the ingestible device via the opening.

The ingestible device can further include an optical sensing unit configured to detect a reflectance from an environment external to the ingestible device.

The ingestible device can include a housing, and the optical sensing unit configured to detect a reflectance from an environment external to the housing.

The ingestible device can be configured to determine a location of the ingestible device based on the reflectance detected by the optical sensing unit.

The force generator can generate the force based on the reflectance detected by the optical sensing unit.

The ingestible device can further include an electronic component within the housing, wherein the electronic component is configured to activate the force generator.

The force generator can be adjacent the electronic component.

The ingestible device can further include a safety device configured to relieve an internal pressure within the housing.

The storage reservoir can store the dispensable substance.

The ingestible device can further include an occluder. The occlude can have a first state in which it is configured to prevent the dispensable substance from exiting the ingestible device via the opening in the ingestible device. The occluder can have a second state in which it is configured to allow the dispensable substance to exit the ingestible device via the opening in the ingestible device.

The occluder can include magnets.

The occluder can include a sliding pin.

The occluder can include a burst disc.

The occluder can include an enteric coating.

The occluder can include an enteric coating and a sliding pin.

The occluder can include an enteric coating and magnets.

The occluder can include a dissolvable pin.

The occluder can include a dissolvable pin and an enteric coating.

The occluder can include wax.

The wax can be in the form of a plug.

The occluder can include can further include wire leads configured to melt the wax.

The wire leads can be configured to be activated by a power source in response to a command from at least one computer processor.

The occluder can be disposed within a housing of the ingestible device.

The ingestible device can further include a bellow between the force generator and the storage reservoir.

The force generator can be configured to apply the force to the bellow to cause the dispensable substance to exit the opening in the ingestible device.

The ingestible device can further include a member in the opening of the ingestible device.

The member can be in the shape of a plug.

The member can include a bioabsorable material.

The force generator can include a gas generating cell configured to generate a gas to provide the force.

The force generator can include a pressurized gas chamber.

The force generator can include a vacuumed chamber.

The force generator can include a spring.

The force generator can include a compressed spring and a tensioned spring.

The force generator can include a gear motor.

The ingestible device can include an inlet configured to draw fluid into the storage reservoir.

The ingestible device can further include an auger device disposed around a portion of the gearmotor that is within the storage reservoir. The auger device can be configured to be driven by the gearmotor to rotate to mix the dispensable substance and fluid drawn into the storage reservoir.

The ingestible device can further include a wiper device longitudinally connected to a portion of the gearmotor that is within the storage reservoir. The wiper device can be configured to be driven by the gearmotor to rotate to mix the dispensable substance and fluid drawn into the storage reservoir.

The ingestible device can further include: a helix component disposed around a portion of the gearmotor that is within the storage reservoir; and a piston disposed at one end of the helix component. The helix component can be configured to be driven by the gearmotor to rotate such that the piston is configured to move longitudinally along pitches of the helix component and towards the exit valve.

The ingestible device can include a housing configured to maintain its mechanical integrity during use of the ingestible device.

The ingestible device can include a housing configured to maintain its mechanical integrity when a pressure within the housing increases during use of the ingestible device.

The ingestible device can further include a mechanism configured to reduce a gas pressure within ingestible device.

The mechanism can include a gas absorbing material.

The mechanism can include an oxygen absorbing material.

The mechanism can include a relief valve configured to open when a pressure within at least a region of the ingestible device reaches a threshold level.

The storage reservoir can include a plurality of chambers.

Each of the plurality of the chambers can be configured to store a different dispensable substance.

The ingestible device can be configured to release the different dispensable substances from the ingestible device at the same time.

The ingestible device can be configured to release the different dispensable substances from the ingestible device in a sequential manner.

The ingestible device can include an electronic component configured to control generation of the force by the force generator to provide a metered dose of the dispensable substance to exit the opening in the ingestible device.

The dispensable substance can include a therapeutic agent.

The therapeutic agent can be in at least one form selected from the group consisting of a powder, a granule, a liquid, and a semi-liquid gel.

The ingestible device can further include a mechanism to attach the ingestible device to a wall of the GI tract of a subject.

The mechanism can include a hook which is extendable.

The hook can be retractable.

The hook can include a needle configured to pierce the wall of the GI tract.

The hook can be hollow and configured to provide the dispensable substance to the wall of the GI tract.

The hook can include a bioresorable material.

The ingestible device can further include an enteric coating supported by at least a portion of a housing of the ingestible device.

The ingestible device can further include an actuator.

The actuator can include a pump.

The actuator can include an osmotic pump.

The ingestible device can further include at least two different enteric coatings.

In one aspect the disclosure provides an ingestible device that includes: a housing; an enteric coating supported by at least a portion the housing; and a storage reservoir in the housing. The storage reservoir can be configured to store a dispensable substance.

The housing can have an opening. In a first state of the ingestible device, the enteric coating can cover the opening so that the enteric coating completely prevents the dispensable substance from exiting the ingestible device via the opening. In a second state of the ingestible device, the enteric coating can be at least partially dissolved so that enteric coating at least partially allows the dispensable substance to exit the ingestible device via the opening.

The housing can include first and second portions. In a first state of the ingestible device, the enteric coating can hold the first and second portions together. In a second state of the ingestible device, the enteric coating can be at least partially dissolved so that enteric coating at least partially releases the first and second portions from each other.

In one aspect, the disclosure provides an ingestible device that include: a housing; an actuator located within the housing; and a storage reservoir located within the housing. The storage reservoir can be configured to store a dispensable substance.

The actuator can include a pump.

The pump can include an osmotic pump and/or a peristalsis-driven pump.

The ingestible device can further include: a semipermeable membrane; and a pressure chamber disposed adjacent the semipermeable membrane.

The ingestible device can include: a first reagent chamber configured to store a first reagent; a second reagent chamber configured to store a second reagent; and a diaphragm sealing both the first reagent chamber from the second reagent chamber.

The diaphragm can be configured to break by a first pressure generated by the pump so that: the first reagent enters the pressure chamber via the semipermeable membrane; the second reagent enters the pressure chamber via the semipermeable membrane; and the first reagent interacts with the second reagent to generate a second pressure.

The ingestible device can further include a piston adjacent to the pressure chamber, wherein the piston is configured to move under the influence of the second pressure.

The storage reservoir can include a bellow configured to be compressed under the influence of the second pressure.

The actuator can include: a detachable section; an osmotic pump disposed adjacent to the detachable section; and a dissolvable material attaching the detachable section to the osmotic pump. The detachable section can be configured to detach from the osmotic pump when the dissolvable material dissolves.

The ingestible device can further include a suction device configured to suck a portion of an intestinal wall into the housing through the dispensing outlet when a portion of the ingestible device contacts a wall of the GI tract of a subject.

The suction device can include a barb disc disposed inwardly within the storage device.

The ingestible device can further include first and second enteric coatings.

The actuator can include: a first semipermeable membrane adjacent the first enteric coating; a first chamber adjacent the first semipermeable membrane and storing soluble particles; and a mesh at an outlet of the first chamber and configured to prevent the soluble particles from exiting the first chamber.

The actuator can be configured to generate a suction force into the ingestible device when the first enteric coating dissolves.

The actuator can further include: a second semipermeable membrane adjacent the second enteric coating; a second chamber adjacent the second semipermeable membrane and storing soluble particles; and a piston between the second chamber and the storage reservoir. The actuator can be configured so that, when the second enteric coating dissolves, the piston move.

In one aspect, the disclosure provides an ingestible device that includes: a housing; a first actuation component in the housing; a second actuation component, both located within the housing; a first enteric coating attached to the first actuation component; a second enteric coating attached to the second actuation component; and a storage reservoir located within the housing. The storage reservoir can be configured to store a dispensable substance, and the housing can have an opening in fluid communication with the storage reservoir. The first enteric coating can be configured to dissolve when exposed to luminal fluid within a first period of time, and the second enteric coating can be configured to dissolve when exposed to luminal fluid within a second period of time that is longer than the first period of time.

The actuator can include: a first semipermeable membrane adjacent the first enteric coating; a first chamber adjacent the first semipermeable membrane and storing soluble particles; and a mesh at an outlet of the first chamber and configured to prevent the soluble particles from exiting the first chamber.

The ingestible device can further include a suction device proximate to the opening. The actuator can be configured to generate a suction force into the ingestible device when the first enteric coating dissolves.

The actuator can further include: a second semipermeable membrane adjacent the second enteric coating; a second chamber adjacent the second semipermeable membrane and storing soluble particles; and a piston between the second chamber and the storage reservoir. The actuator can be configured so that, when the second enteric coating dissolves, the piston moves toward the opening.

The ingestible device can further include an injection device having a first end proximate to the dispensing outlet and a second end connected to the storage reservoir. The injection device can be configured to deliver the dispensable substance when the piston is propelled towards the dispensing outlet.

The ingestible device can include a plurality of exit valves.

The exit valve can have a tapered sidewall.

The exit valve can have a straight sidewall.

The ingestible device can include a plurality of dispensing outlets configured to deliver the dispensable substance out of the housing from the storage reservoir.

The dispensing outlet can have a tapered sidewall.

The dispensing outlet can have a straight sidewall.

A method can include moving, by the second pressure, the traveling member to deliver the pre-loaded dispensable substance out of the ingestible device via a plurality of dispensing outlets.

The ingestible device can include a plurality of openings configured so that, when the force generator generates a force, the dispensable substance exits the ingestible device via the plurality of openings.

The housing can have a plurality of openings configured to allow the dispensable substance to exit the ingestible device via the plurality of openings.

The ingestible device can further include: one or more processing devices; and one more machine readable hardware storage devices storing instructions that are executable by the one or more processing devices to determine a location of the ingestible device in a portion of a GI tract of a subject to an accuracy of at least 85%.

The ingestible device can further include one or more processing devices; and one more machine readable hardware storage devices storing instructions that are executable by the one or more processing devices to determine that the ingestible device is in the cecum of a subject to an accuracy of at least 70%.

The ingestible device can further include one or more processing devices; and one more machine readable hardware storage devices storing instructions that are executable by the one or more processing devices to transmit data to a device capable of implementing the data to determine a location of the medical device in a portion of a GI tract of a subject to an accuracy of at least 85%.

The ingestible device can further include: one or more processing devices; and one more machine readable hardware storage devices storing instructions that are executable by the one or more processing devices to transmit data to an external device capable of implementing the data to determine that the ingestible device is in the cecum of subject to an accuracy of at least 70%.

The ingestible device can further include first and second light sources, wherein the first light source is configured to emit light at a first wavelength, and the second light source is configured to emit light at a second wavelength different from the first wavelength.

The ingestible device can further include first and second detectors, wherein the first detector is configured to detect light at the first wavelength, and the second detector is configured to detect light at the second wavelength.

The reservoir can include a dispensable substance.

The reservoir can be configured to partially fit within the housing of the ingestible device.

The reservoir can be configured to entirely fit within the housing of the ingestible device.

The reservoir can include a housing, and the housing comprises a plastic.

The plastic can include at least one material selected from the group consisting of PVC, silicone and polycarbonate.

The reservoir can include a housing, and the housing comprises a metal-based material.

The metal-based material can include an alloy.

The metal-based material can include stainless steel.

The reservoir can be configured to attach to the housing of the ingestible device.

The reservoir can be configured to friction fit with the ingestible device.

The reservoir can be configured to be held to the ingestible device via a biasing mechanism.

The biasing mechanism can include at least one member selected from the group consisting of a spring, a latch, a hook, a magnet, and electromagnetic radiation.

The reservoir can be configured to fit into a groove or a track in the housing of the ingestible device.

The reservoir can be configured to snap fit to the ingestible device.

The reservoir can be configured to be pierced.

The reservoir can be configured to carry electronic components.

The ingestible device can satisfy FDA requirements.

The reservoir can be configured to be used with an ingestible device disclosed herein.

In one aspect, the disclosure provides a kit that includes: an ingestible device; and a reservoir configured for use in an ingestible device. The reservoir can be configured to hold a dispensable substance.

The kit can further include the dispensable substance in the reservoir.

The reservoir can be a reservoir as disclosed herein.

In one aspect, the disclosure provides a method that includes delivering a therapeutic agent to a subject using an ingestible device as disclosed herein.

The therapeutic agent can be delivered to a location in the GI tract of a subject.

In one aspect, the disclosure provides a method that includes attaching a reservoir as disclosed herein to an ingestible device.

The method can further include disposing a therapeutic agent in the reservoir before attaching the reservoir to the ingestible device.

The method can further include, after attaching the reservoir to the ingestible device, using the ingestible device to deliver the therapeutic agent to a subject.

The therapeutic agent can be delivered to a location in the GI tract of a subject.

The method can further include determining a location of the ingestible medical device in a portion of a GI tract of a subject to an accuracy of at least 85%.

Determining the location of the ingestible device within the GI tract of a subject can include determining reflected light signals within the GI tract, wherein the reflected signals comprise light of at least two different wavelengths.

The reflected signals can include light of at least three different wavelengths.

The electromechanical ingestible device for delivery of a dispensable substance provides an ingestible device that has a housing, an electric component, a gas-generating cell, a storage reservoir, an exit valve, and a safety device, according to some embodiments described herein. The housing is defined by a first end, a second end substantially opposite from the first end, and a wall extending longitudinally from the first end to the second end. The electronic component is located within the housing. The gas-generating cell is located within the housing and adjacent to the electronic component, and the electronic component is configured to activate the gas-generating cell to generate gas. The storage reservoir located within the housing, and the storage reservoir stores a dispensable substance and a first end of the storage reservoir is connected to the first end of the housing.

The exit valve is located at the first end of the housing, and the exit valve is configured to allow the dispensable substance to be released out of the first end of the housing from the storage reservoir. The safety device is placed within or attached to the housing, and the safety device is configured to relieve an internal pressure within the housing when the internal pressure exceeds a threshold level.

In some embodiments, the housing has a polycarbonate wall of a thickness substantially sufficient to withstand an internal explosion without a fracture.

In some embodiments, the safe device includes oxygen absorbing material that absorbs oxygen within the housing to avoid an internal explosion.

In some embodiments, the safety device includes an inert non-conductive dielectric that isolates the gas-generating cell from other components within the housing.

In some embodiments, the safety device includes a relief valve placed at the first end of the housing, and the relief valve is configured to open when the internal pressure inside the housing reaches the threshold level.

In some embodiments, the safety device includes a rupture disc placed at the first end of the housing, and the rupture disc is configured to breach when the internal pressure inside the housing reaches the threshold level.

In some embodiments, the housing is configured to breach in a controlled manner when the internal pressure inside the housing reaches the threshold level.

In some embodiments, the gas-generating cell is a hydrogen-generating cell that is mounted above and sealed from the electronic component.

In some embodiments, the ingestible device has a piston adjacent to the gas-generating cell, wherein the piston is propelled to move towards the first end of the housing via a pressure from the gas-generating cell.

In some embodiments, the piston is integrated with the gas-generating cell in a form of a silicone seal wrapping around the gas-generating cell, and the gas-generating cell is movable with the piston.

In some embodiments, the storage reservoir is in a form of a bellow that is configured to be compressed via a pressure from the gas-generating cell.

In some embodiments, the storage reservoir includes a plurality of chambers, and each of the plurality of the chambers stores a different dispensable substance.

In some embodiments, the different dispensable substances are released at a same time via the exit valve.

In some embodiments, the different dispensable substance from each of the plurality of the chambers is delivered via the exit valve in a sequential manner.

In some embodiments, the different dispensable substances from each of the plurality of the chambers is controlled by a different membrane, and the electronic component controls the gas-generating cell to release gas to propel a membrane to deliver a respective dispensable substance.

In some embodiments, the ingestible device includes a flexible diaphragm adjacent to the gas-generating cell, wherein the flexible diaphragm is configured to deform towards the first end of the housing via a pressure from the gas-generating cell.

In some embodiments, the ingestible device includes a capillary plate placed between the gas-generating cell and the first end of the housing, and a wax seal between the gas-generating cell and the storage reservoir, wherein the wax seal is configured to melt and the dispensable substance is pushed through the capillary plate by a pressure from the gas-generating cell.

In some embodiments, the capillary plate is made up of concentric rings of micro channels.

In some embodiments, the gas-generating cell is wrapped within a bent foil that is configured to deform via the pressure from the gas-generating cell.

In some embodiments, the wall is configured to split into two clamshell halves along a longitudinal axis, and the ingestible device further includes a diaphragm placed along the longitudinal axis in one clamshell half and wrapping around the electronic component. The diaphragm is configured to deflect into the other clamshell half via a pressure from the gas-generating cell.

In some embodiments, the exit valve has an umbrella shape and the first end of the housing has a plurality of ports under the exit valve to direct the dispensable substance out of the housing radially.

In some embodiments, the exit valve has a ring around the first end of the housing and has a plurality of evenly distributed ports on the ring to direct the dispensable substance out of the housing.

In some embodiments, the exit valve includes a dome slit extending out of the first end of the housing, and the dispensable substance is delivered through the dome slit.

In some embodiments, the exit valve includes a hole at the first end of the first end of the housing, and the hole is sealed by a wax or silicone material configured to break by the internal pressure from within the housing.

In some embodiments, the exit valve is placed at a center of gravity at the first end of the housing to reduce unbalanced force and rotation of capsule when the dispensable substance is delivered through the exit valve.

In some embodiments, the ingestible device further includes an optical sensing unit located proximal to the first end or the second end of the housing. The optical sensing unit is configured to transmit an illumination towards an environment external to the housing and to detect a reflectance from the environment resulting from the illumination. The electronic component is further configured to: identify a location of the ingestible device based on the reflectance; and activate the gas-generating cell to generate gas when the identified location matches with a predefined location.

In some embodiments, the electronic component is further configured to control the gas-generating cell to cause an internal pressure for a metered dose of the dispensable substance to be delivered out of the housing based on a characteristic of the reflectance.

In some embodiments, the electronic component includes a variable resistor to control an amount of gas generated by the gas-generating cell to meter the dose of the dispensable substance.

In some embodiments, the metered dose of the dispensable substance is a one-time dose or a systematic delivery of multiple doses.

In some embodiments, the storage reservoir stores 10 μL to 1500 μL of the dispensable substance.

In some embodiments, the housing includes a loading port to load the dispensable substance into the storage reservoir.

In some embodiments, the dispensable substance includes a therapeutic agent in a form of powder, granule, liquid, or semi-liquid gel.

Some embodiments described herein provide an ingestible device that includes a housing, an electronic component, a gas-generating cell, a storage reservoir, an injection device and a safety device. The housing is defined by a first end, a second end substantially opposite from the first end, and a wall extending longitudinally from the first end to the second end. The electronic component is located within the housing. The gas-generating cell located within the housing and adjacent to the electronic component, and the electronic component is configured to activate the gas-generating cell to generate gas. The storage reservoir is located within the housing, and the storage reservoir stores a dispensable substance and a first end of the storage reservoir is connected to the first end of the housing. The injection device is located at the first end of the housing, and the jet injection device is configured to inject the dispensable substance out of the housing from the storage reservoir. The safety device placed within or attached to the housing, and the safety device is configured to relieve an internal pressure within the housing.

In some embodiments, the dispensable substance is released through the injection device with a force substantially strong to penetrate a mucosa membrane.

In some embodiments, the ingestible device further includes a component attached to an exterior of the housing, wherein the component is configured to position the injection device at an epithelial layer and spread the epithelial layer prior to a delivery of the dispensable substance.

In some embodiments, the injection device is a syringe connected to or located within the housing and having an injecting part extending out of the housing.

In some embodiments, the injection device includes an injecting outlet that is configured to penetrate an epithelial layer to inject the dispensable substance.

Some embodiments described herein provide an ingestible device that includes a housing, an optical sensing unit, an electronic component, a gas-generating cell, a storage reservoir, a membrane, and a dispensing outlet. The housing is defined by a first end, a second end substantially opposite from the first end, and a wall extending longitudinally from the first end to the second end. The optical sensing unit is located on a side of the housing, and the optical sensing unit is configured to detect a reflectance from an environment external to the housing. The electronic component is located within the housing. The gas-generating cell is located within the housing and adjacent to the electronic component. The electronic component is configured to activate the gas-generating cell to generate gas in response to identifying a location of the ingestible device based on the reflectance. The storage reservoir is located within the housing, and the storage reservoir stores a dispensable substance and a first end of the storage reservoir is connected to the first end of the housing. The membrane is in contact with the gas-generating cell and configured to move or deform into the storage reservoir by a pressure generated by the gas-generating cell. The dispensing outlet is placed at the first end of the housing, and the dispensing outlet is configured to deliver the dispensable substance out of the housing from the storage reservoir.

In some embodiments, the dispensing outlet includes an exit valve located at the second end of the storage reservoir, and the exist valve is configured to allow the dispensable substance to be released out of the first end of the housing from the storage reservoir.

In some embodiments, the dispensing outlet has an umbrella shape and the second end of the housing has a plurality of ports under the exit valve to direct the dispensable substance out of the housing radially.

In some embodiments, the dispensing outlet has a ring around the second end of the housing and has a plurality of evenly distributed ports on the ring to direct the dispensable substance out of the housing.

In some embodiments, the dispensing outlet includes a dome slit extending out of the second end of the housing, and the dispensable substance is delivered through the dome slit.

In some embodiments, the dispensing outlet includes a hole at the second end of the second end of the housing, and the hole is sealed by a wax or silicone material configured to break by a burst of internal pressure from within the housing.

In some embodiments, the dispensing outlet is placed at a center of gravity at the second end of the housing to reduce unbalanced force and rotation of capsule when the dispensable substance is delivered through the dispensing outlet.

In some embodiments, the dispensing outlet includes an injection nozzle located at the first end of the storage reservoir and an injection outlet configured to inject the dispensable substance out of the housing from the storage reservoir In some embodiments, the dispensable substance is released through the dispensing outlet with a force substantially strong to penetrate a mucosa membrane.

In some embodiments, the ingestible device further includes a component attached to an exterior of the housing, and the component is configured to position the dispensing outlet at an epithelial layer and spread the epithelial layer prior to a delivery of the dispensable substance.

In some embodiments, the dispensing outlet is connected to a syringe connected to or located within the housing and having an injecting part extending out of the housing, and a gas actuator is located within the housing. The gas actuator electronically controls the syringe to inject the dispensable substance to a location that the injecting part is in contact with.

In some embodiments, the injecting part is configured to penetrate an epithelial layer to inject the dispensable substance.

In some embodiments, the electronic component is configured to automatically activate the gas-generating cell in response to an identification of the location of the ingestible device without any triggering mechanism external to the ingestible device, or any pre-programmed activation condition.

In some embodiments, the location of the ingestible device is identified based on the reflectance indicative of optical characteristics of the location without assessing a pH level of the external environment.

In some embodiments, the location includes any of a first section immediately after a pyloric sphincter, or a second section immediately prior to an ileocecal valve.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 17 provides example structural diagrams illustrating aspects of an ingestible device using a wiper to dispense the dispensable substance out of the storage reservoir, according to some embodiments described herein.

FIG. 18 provides example structural diagrams illustrating aspects of an ingestible device using a piston to drive the wiper described in FIG. 17, according to some embodiments described herein.

FIG. 39 provides an example structural diagram illustrating an ingestible device employing an osmotic mechanism and a suction device as illustrated in FIG. 38, according to some embodiments described herein.

FIG. 40 provide example structural diagrams illustrating aspects of tumbling suction by an ingestible device as described in FIG. 39, according to some embodiments described herein.

FIG. 44 provides an example structural diagram illustrating aspects of an electronic component including a printed circuit board (PCB) within the housing of the ingestible device, according to some embodiments described herein.

FIG. 92A illustrates a wax valve system in a closed position.

FIG. 92B illustrates a wax valve system in an open position.

DETAILED DESCRIPTION

Figure 1:
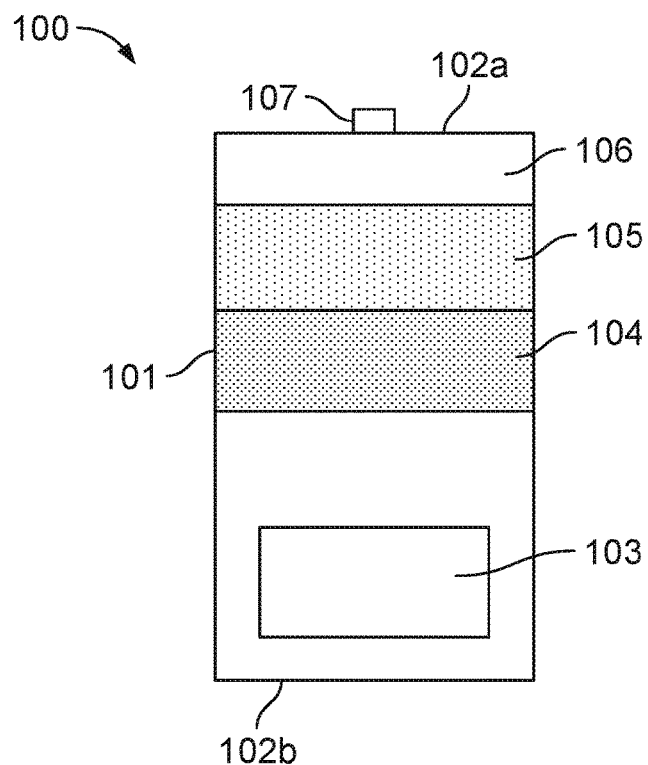
FIG. 1 provides an example mock-up diagram illustrating aspects of a structure of an ingestible device 100 for delivering a dispensable substance, according to some embodiments described herein.

Following below are more detailed descriptions of various concepts related to, and exemplary embodiments of, ingestible devices capable of delivering a dispensable substance, such as, for example, a therapeutic agent, as well as related components, systems and methods. Also following below are more detailed descriptions of various concepts related to, and exemplary embodiments of, attachable storage reservoir configured to be used with an ingestible device and capable of storing dispensable substance, such as, for example, a therapeutic agent, as well as related components, systems and methods.

Various systems, devices, and methods are described herein to provide an example of at least one embodiment for the subject matter described herein. No embodiment limits any subject matter described herein and any claimed subject matter may cover systems, devices, and methods that differ from those described herein. It is possible that the claimed subject matter are not limited to systems, devices, and methods having all of the features of any one systems, devices, and methods described herein or to features common to multiple or all of the systems, devices, and methods described herein. It may be possible that a system, device, or method described herein is not an embodiment of any claimed subject matter. Any subject matter disclosed in systems, devices, and methods described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that, for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. In addition, the description is not to be considered as limiting the scope of the embodiments described herein.

It should be noted that terms of degree such as "substantially", "about" and "approximately" when used herein mean a reasonable amount of deviation of the modified term such that the result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

As used herein, the term "coupled" indicates that two elements can be directly coupled to one another or coupled to one another through one or more intermediate elements.

As used herein, the term "body" refers to the body of a patient, a subject or an individual who receives the ingestible device. The patient or subject is generally a human or other animal.

As used herein, the term "gastrointestinal tract" or "GI tract" refers to all portions of an organ system responsible for consuming and digesting foodstuffs, absorbing nutrients, and expelling waste. This includes orifices and organs such as the mouth, throat, esophagus, stomach, small intestine, large intestine, rectum, anus, and the like, as well as the various passageways and sphincters connecting the aforementioned parts.

As used herein, the term "reflectance" refers to a value derived from light emitted by the device, reflected back to the device, and received by a detector in or on the device. For example, in some embodiments this refers to light emitted by the device, wherein a portion of the light is reflected by a surface external to the device, and the light is received by a detector located in or on the device.

As used herein, the term "illumination" refers to any electromagnetic emission. In some embodiments, an illumination may be within the range of Infrared Light (IR), the visible spectrum and ultraviolet light (UV), and an illumination may have a majority of its power centered at a particular wavelength in the range of 100 nm to 1000 nm. In some embodiments, it may be advantageous to use an illumination with a majority of its power limited to one of the infrared (750 nm-1000 nm), red (620 nm-750 nm), green (495 nm-570 nm), blue (450 nm-495 nm), or ultraviolet (100 nm-400 nm) spectrums. In some embodiments, a plurality of illuminations with different wavelengths may be used.

The various embodiments described herein generally relate to an ingestible device that is configured to arrive at a specific location within the gastrointestinal (GI) tract via oral consumption and, in some embodiments, for releasing substances including medicaments and therapeutics at the specific location. In another embodiment, the ingestible device may be used for releasing substances including medicaments and therapeutics in other parts of the body, such as but not limited to the female reproductive tract, and/or the like. In some embodiments, the release of the dispensable substances may take a form similar to a bolus or a bust of dispensing. In some embodiments, the release of the substances may take a form similar to systemic therapeutic agent delivery. The ingestible device may include a release structure that helps the substance to be delivered on the inner surface, e.g., the mucosa layer, of the GI tract, or through a penetration of the mucosa layer.

FIG. 1 provides an example mock-up diagram illustrating aspects of a structure of an ingestible device 100 for delivering a dispensable substance, according to some embodiments described herein. In some embodiments, the ingestible device 100 may generally be in the shape of a capsule, a pill or any swallowable form that may be orally consumed by an individual. In this way, the ingestible device 100 may be ingested by a patient and may be prescribed by healthcare practitioners and patients.

The ingestible device 100 includes a housing 101 that may take a shape similar to a capsule, a pill, and/or the like, which may include two ends 102a-b. The housing 101 may be designed to withstand the chemical and mechanical environment of the GI tract (e.g., effects of muscle contractile forces and concentrated hydrochloric acid in the stomach). A broad range of materials that may be used for the housing 101. Examples of these materials include, but are not limited to, thermoplastics, fluoropolymers, elastomers, stainless steel and glass complying with ISO 10993 and USP Class VI specifications for biocompatibility; and any other suitable materials and combinations thereof. In certain embodiments, these materials may further include liquid silicone rubber material with a hardness level of 10 to 90 as determined using a durometer (e.g., MED-4942™ manufactured by NuSil™), a soft biocompatible polymer material such as, but not limited to, polyvinyl chloride (PVC), polyethersulfone (PES), polyethylene (PE), polyurethane (PU) or polytetrafluoroethylene (PTFE), and a rigid polymer material coated with a biocompatible material that is soft or pliable (e.g., a poly(methyl methacrylate) (PMMA) material coated with silicone polymer). Use of different materials for different components may enable functionalization of certain surfaces for interaction with proteins, antibodies, and other biomarkers. For example, Teflon® may be used as a material in the ingestible device 10 for movable components in order to reduce friction between these components. Other example materials may include other materials commonly used in micro-fabrication, such as polydimethylsiloxane (PDMS), borosilicate glass, and/or silicon. Although specific materials may be referred to herein as being used to construct the device for illustrative purposes, the materials recited are not intended to be limiting, and one skilled in the art may easily adapt the device to use any number of different materials without affecting the overall operation or functionality of the device.

In some embodiments, the housing 101 of the ingestible device 100 may be manufactured from a type of plastic, such as a photosensitive acrylic polymer material or an inert polycarbonate material. The housing 101 may also be formed using material that can be sterilized by chemicals. In some implementation, the wall of the housing 101 may have a thickness of 0.5 mm-1 mm, which is sufficient to sustain an internal explosion (e.g., caused by hydrogen ignition or over pressure inside the housing).

The housing 101 may or may not have a pH-sensitive enteric coating to detect or otherwise be sensitive to a pH level of the environment external to the ingestible device. In some specific parts of the GI tract, such as but not limited to sections immediately after passing through the pyloric sphincter, or sections immediately prior to the ileocecal valve, it may be difficult to target a specific location solely based on the pH level. Instead of relying on the pH level, the ingestible device 100 includes an optical sensing unit that transmits an illumination to the environment and collects a reflectance, based on which, the region-specific location of the ingestible device may be identified based on optical characteristics of the reflectance. For example, the ingestible device may deliver a therapeutic agent to a specific location within the GI tract that harbors an injury such as a lesion. The specific location may be pre-determined through a previously conducted endoscopy. Further discussion on determining a location of the ingestible device may be found in connection with FIG. 44.

The housing 101 may be formed by coupling two enclosure portions together. For example, the two enclosure portions can be mated and fused together with an adhesive material, such as a cyanoacrylate variant. The housing 101, in effect, protects the interior of the ingestible device 100 from its external environment and protects the external environment (e.g., the gastrointestinal tract) from components inside the ingestible device 100.

The ingestible device 100 may include an electronic component within the housing 100. The electronic component may be placed proximally to an end 102b of the housing, and includes a printed circuit board (PCB), a battery, an optical sensing unit, and/or the like. Further example structures of the electronic component may be illustrated in FIG. 44.

The ingestible device 100 further includes a gas-generating cell 103 that is configured to generate gas and thus cause an internal pressure within the housing 101. In one implementation, the gas-generating cell 103 may be a hydrogen-generating cell, such as but not limited to a Varta® Hydrogen Gas-generating Cell. In another implementation, one or more other gas-generating cells that generate an inert gas that is harmless to the human body may be used.

In some implementations, the gas-generating cell may include or be connected to a separate channel or valve of the ingestible device such that gas may be release through the channel or valve to create a motion to alter the position of the ingestible device within the GI tract. Such gas release can also be used to position the ingestible device relative to the intestinal lining. In another implementation, gas may be released through the separate channel or valve to alter the surface orientation of the intestinal tissue prior to delivery of the dispensable substance.

A traveling plunger 104 may be placed on top of the gas-generating cell 103 within the housing 101. The traveling plunger 104 is a membrane that separates the gas-generating cell 103 and a storage reservoir that stores the dispensable substance 105. In some implementations, the traveling plunger 104 may be a movable piston, as is further illustrated in FIGS. 3-4. In some implementations, the traveling plunger 104 may instead be a flexible membrane such as but not limited to a diaphragm, as further illustrated in FIG. 10. In some implementations, the traveling plunger 104, which may have the form of a flexible diaphragm, may be placed along an axial direction of the housing 101, instead of being placed on top of the gas-generating cell 103, as is further illustrated in FIG. 44. The traveling plunger or the membrane 104 may move (when the membrane 104 is a piston) or deform (when the membrane 104 is a diaphragm) towards a direction of the end 102a of the housing, when the gas-generating cell 103 generates gas to create an internal pressure that pushes the membrane 104. In this way, the membrane or traveling plunger 104 may push the dispensable substance 105 out of the housing via a dispensing outlet 107.

The housing 101 may include a storage reservoir storing one or more dispensable substances 105 adjacent to the traveling plunger 104. The dispensable substance 105 may be a therapeutic or medical agent that may take a form of a powder, a compressed powder, a fluid, a semi-liquid gel, or any other dispensable or deliverable form. The delivery of the dispensable substance 105 may take a form such as but not limited to bolus, semi-bolus, continuous, systemic, burst therapeutic agent delivery, and/or the like.

In some implementations, the storage reservoir may include multiple chambers, and each chamber stores a different dispensable substance. For example, the different dispensable substances can be released at the same time via the dispensing outlet 107. Alternatively, the multiple chambers may take a form of different layers within the storage reservoir such that the different dispensable substance from each chamber is delivered sequentially in an order. In one example, each of the multiple chambers is controlled by a separate traveling plunger, which may be propelled by gas generation. The electronic component may control the gas-generating cell 103 to generate gas to propel a specific traveling plunger, e.g., via a separate gas generation chamber, etc., to deliver the respective substance. In some embodiments, the content of the multiple chambers may be mixed or combined prior to release, for example, to activate the therapeutic agent.

The ingestible device 100 may include a dispensing outlet 107 at one end 102a of the housing 101 to direct the dispensable substance 105 out of the housing. The dispensing outlet 107 may include an exit valve (as further illustrated in FIGS. 5-6), a slit or a hole (as further illustrated in FIGS. 7-8), a jet injection nozzle with a syringe, and/or the like. When the traveling plunger 104 moves towards the end 102a of the housing 101, an internal pressure within the storage reservoir may increase and push the dispensing outlet to be open to let the dispensable substance 105 be released out of the housing 101.

The use of a hydrogen-generating cell within an ingestible device 100 may incur a variety of safety risks, which can be mitigated by proper device design. For example, hydrogen ignition/heating within or external to the ingestible device 100, over pressure within the housing 101, hydrogen toxicity may damage the use of the ingestible device. A safety device such as a pressure relief device 106 may be placed within or attached to the housing 101 to mitigate the safety risk.

In some embodiments, hydrogen ignition inside the ingestible device may occur if air (containing oxygen) is present inside the ingestible device 100. For example, hydrogen requires very little energy to initiate combustion, e.g., with a minimum energy for ignition in air of just 0.017 mJ. When silver oxide batteries (e.g., see 131 in FIG. 3) are used in the ingestible device 100, the likelihood of a spark (though remote) cannot be eliminated and may result from inductive charges and introduced air gap, or other scenarios.

For example, the pressure $P_1$ within the ingestible device 100 may be estimated based on a worst-scenario analysis of Hydrogen-Air mixture as approximately $P_1$=1479 kPa or 215 psi. As the hydrogen concentration within the ingestible device 100 may likely increase with respect to time, a sufficient concentration of hydrogen may be assumed to lie between the Lower Explosive Limit (LEL) and Upper Explosive Limit (UEL) of 4% and 75% respectively. Thus the final pressure may be higher, given the initial pressure within the ingestible device may exceed 101.3 kPa due to the addition of hydrogen. Assuming the housing 101 fractures at this maximum pressure, the amount of energy E released may be given by:

$$E = \left(\frac{P_1 - P_0}{Y_1 - 1}\right) \times V_1$$

$$E = \left(\frac{1479000Pa - 101300Pa}{1.4 - 1}\right) \times 0.000001 m^3 = 3.4 \text{ Joules}$$

where $V_1$ denotes an approximate volume of the ingestible device. As a reference, this energy translates to a 1 g mass (approximately ¼ of an assembled capsule) travelling at 82 m/s (~180 mph), or about the same amount of energy contained in a propelled BB gun pellet, which may cause harm to the patient.

To mitigate the hydrogen ignition, in one implementation, the housing 101 may be made of polycarbonate with a wall thickness of 1.6 mm, which may sustain a pressure of 410 psi and thus withstand the effects of an internal explosion without fracture.

In an implementation, the interior wall of the housing 101 may be made of (or include a layer made of) oxygen absorbing material to reduce the concentration of oxygen (e.g., below 2%) to avoid an internal explosion.

In an implementation, an inert non-conductive liquid dielectric (such as silicone oil, food grade castor oil, wax, and/or the like) may be applied to contain electrical connections within the ingestible device 100 to isolate any possible ignition from hydrogen within the ingestible device 100. For example, the isolation may also reduce the risk of hydrogen ignition external to the ingestible device, e.g., when the generated hydrogen from the gas-generating cell 103 mixed with an appropriate amount of air (oxygen) contained in bubbles travels along the GI tract, any ignition may result in an injury to the small intestine.

In one scenario, over pressurization may happen within the ingestible device 100, e.g., when the dispensing outlet 107 becomes blocked or otherwise sealed from the release of hydrogen. In this case, the housing 101 may have a fracture when the hydrogen gas reaches a threshold level of pressure. For example, when the ingestible device has a volume of 500 μL (the volume hydrogen may communicate with), and the hydrogen released can be 40 mL, the internal pressure generated by the hydrogen can be as high as:

$$P_1 = P_0 \times \frac{V_0}{V_1}$$

$$P_1 = 14.7 psi \times \frac{40}{0.5} = 1176 psi = 0.100 MPa$$

The energy released via a fracture or explosion of the over pressurization may be calculated as:

$$E = \left(\frac{8.108 MPa - .1013 MPa}{1.869 - 1}\right) * 5 * 10^{-7} = 4.6 \text{ Joules}$$

The amount of energy may inflict harm to the patient.

In one implementation, the housing 101 may be designed to breach or fracture in a controlled manner and thus can relieve the internal pressure. For example, when the internal pressure within a chamber filled with the gas from the gas-generating cell 103 exceeds a threshold level, the wall around the chamber may be designed to fracture or break to relieve the pressure.

In an implementation, a pressure relief device 106 may be placed within the housing 101, e.g., at the end 102a of the housing 101. For example, the pressure relief device 106 may be a pressure relief rupture disc that is configured to release content within housing 101. Thus if the dispensing outlet 107 is clogged or blocked and the pressure within the storage reservoir exceeds a threshold level, the pressure relief device 106 may be torn to release the dispensable substance out. The advantage of the pressure relief device 106 is that it may also, in part, serve to prevent upstream contamination of the dispensable substance, because the internal pressure is relieved by directing the dispensable substance out of the housing such that the gas would not leak into the storage reservoir.

In some implementations, the housing 101 may include small holes (e.g., with a diameter smaller than 2 mm), e.g., on the side of the housing 101, or at the end 102a to facilitate loading the dispensable substance into the storage reservoir. The holes, when more than two, may be positioned axially or radially on the housing 101. The holes may subsequently be sealed with a UV curable cyanoacrylate.

In some implementations, a feedback control circuit (e.g., a feedback resistor, etc.) may be added to send feedback from the gas-generating cell 103 to the electronic component such that when the internal pressure reaches a threshold level, the electronic component may control the gas-generating cell 103 to turn off gas generation, or to activate other safety mechanism (e.g., feedback-controlled release valve, etc.). For example, an internal pressure sensor may be used to measure the internal pressure within the ingestible device and generate feedback to the feedback control circuit.

Figure 2:
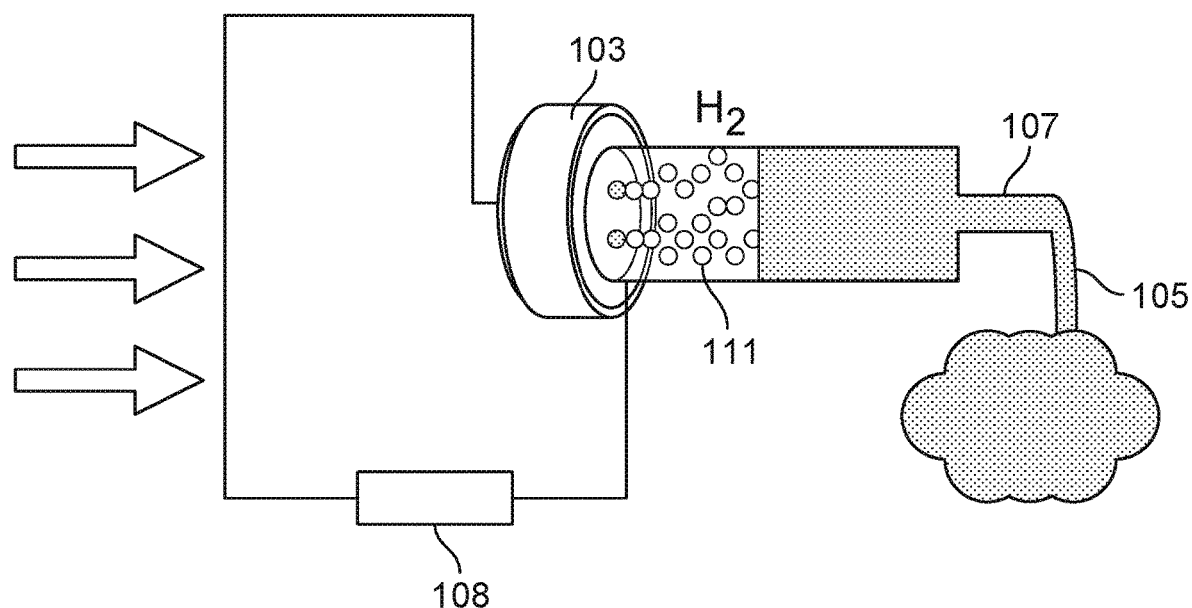
FIG. 2 provides an example diagram illustrating aspects of a mechanism for a gas-generating cell configured to generate a gas to dispense a substance, according to some embodiments described herein.

FIG. 2 provides an example diagram illustrating aspects of a mechanism for a gas-generating cell 103 configured to generate a gas to dispense a substance, according to some embodiments described herein. As shown in FIG. 2, the gas-generating cell 103 generates a gas 111, which can propel the dispensable substance 105 out of the dispensing outlet 107. A variable resistor 108 may be connected to a circuit with the gas-generating cell 103 such that the variable resistor 108 may be used to control an intensity and/or an amount of gas 111 (e.g., hydrogen) generated by the cell 103. Specifically, the gas-generating cell 103 may be a battery form factor cell that is capable of generating hydrogen when a resistor is applied. In this way, as the gas-generating cell 103 only needs the use of a resistor only without any active power requirements, the gas-generating cell 103 may be integrated into an ingestible device such as a capsule with limited energy/power available. For example, the gas-generating cell 103 may be compatible with a capsule at a size of 26 mm×13 mm or smaller.

In some implementations, based on the elution rate of gas from the cell, and an internal volume of the ingestible device, it may take time to generate sufficient gas 111 to deliver the substance 105, and the time required may be 30 seconds or longer. For example, the time to generate a volume of hydrogen equivalent to 500 µL of fluid would be approximately 5 minutes. A longer period of time may be needed based upon non-ideal conditions within the ingestible device, such as friction, etc. Thus, given that the production of gas (e.g., hydrogen) may take time, gas generation may need to start prior to the ingestible device arriving at the site of delivery to build pressure up within the device. The ingestible device may then need to know when it is approaching the site of delivery. For example, the device may start producing gas on an "entry transition," which is determined by temperature, so as to produce enough gas to be close to the pressure high enough to deliver the dispensable substance. The ingestible device may then only start producing gas again when it arrives at the site of delivery, which will cause the internal pressure within the ingestible device to reach a level required by the dispensing outlet to release the dispensable substance. In addition, for region-specific delivery, the ingestible device may estimate the time it takes to build up enough pressure to deliver the dispensable substance before the ingestible device arrives at a specific location, to activate gas generation.

For example, for systemic delivery, when an internal volume of the ingestible device is around 500 µL, a gas generation time of 2 hours, an initial pressure of approximately 300 pound per square inch absolute (psia) may be generated, with higher and lower pressures possible. The generated pressure may drop when air enters the storage reservoir, which was previously occupied by the dispensable substance during the dispensing process. For systemic dispensable substance delivery, a force with a generated pressure of approximately 100 to 360 pound per square inch (psi) may be required to penetrate the mucosa or epithelial layer. The pressure may also vary depending on the nozzle design at the dispensing outlet, fluid viscosity, and surrounding tissue proximity and properties.

The gas 111 that may be generated for a continuous delivery of dispensable substance (e.g., 1 cc H2 in 4 hours, 16 breaths per minute at 0.5 L tidal volume) may equate to 1 cc hydrogen in approximately 2000 L of exhaled air, or approximately 0.5 ppm H2, which is below physiologic values of exhaled hydrogen. Reducing this time to 10 minutes equates to approximately 13 ppm hydrogen. Thus, due to the length of intestine that may be covered during this time period, the ingestible device may possess a higher localized value than physiologic.

Figure 3:
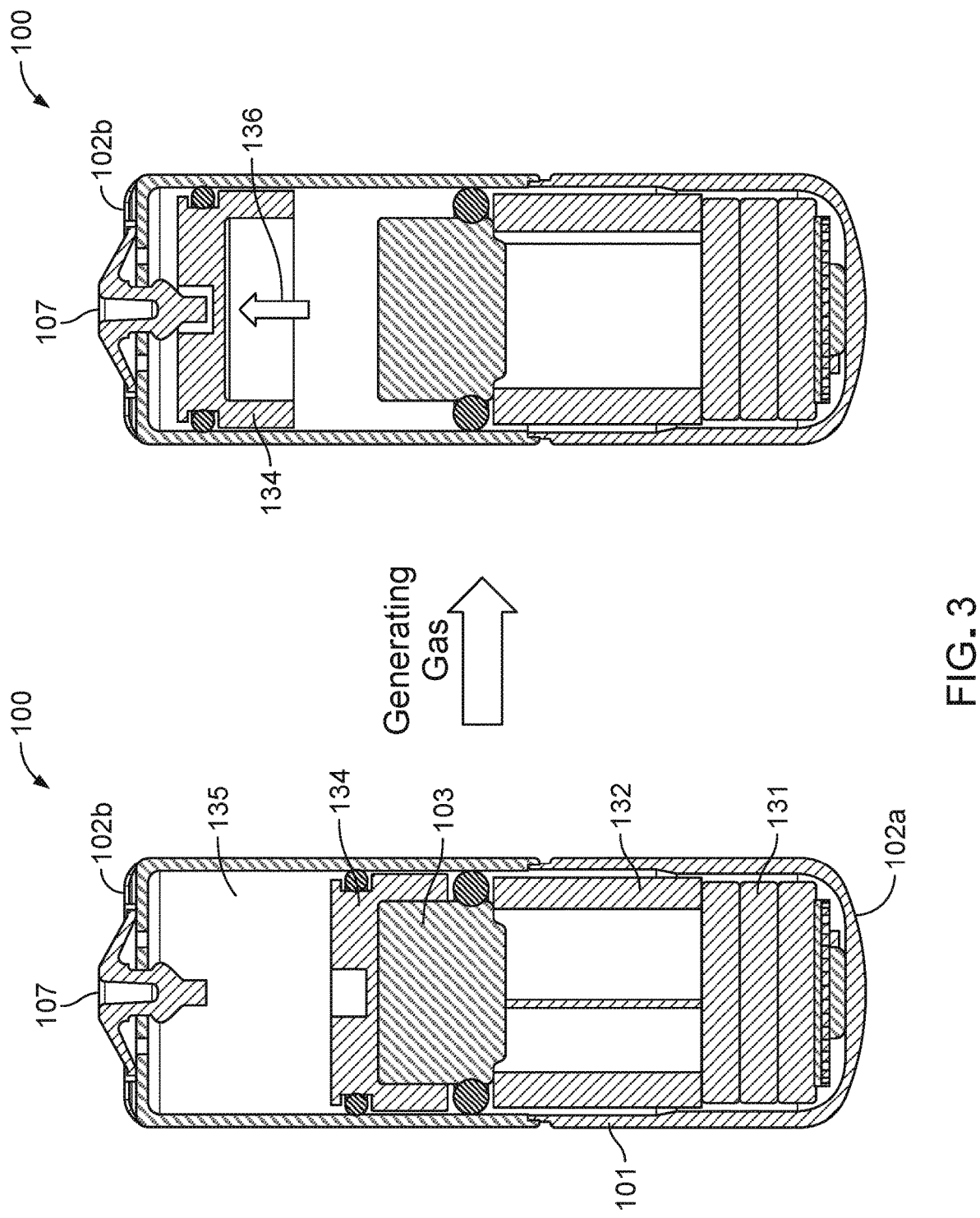
FIG. 3 provide example structural diagrams illustrating aspects of an ingestible device 100 having a piston to push for dispensable substance delivery, according to some embodiments described herein.

FIG. 3 provides example structural diagrams illustrating aspects of an ingestible device 100 having a piston to push for dispensable substance delivery, according to some embodiments described herein. The ingestible device 100 may have one or more batteries 131 placed at one end 102a of the housing 101 to provide power for the ingestible device 100. The PCB 132 may be placed adjacent to the battery 131, and the gas-generating cell 103 may be mounted above the PCB 132. The gas-generating cell 103 may be sealed from the bottom chamber (e.g., space including 131 and 132) of the ingestible device 100. A movable piston 134 may be placed adjacent to the gas-generating cell 103. In this way, gas generation from the gas-generating cell 103 may propel the piston 134 to move towards the other end 102b of the housing 101 such that the dispensable substance in the storage reservoir 135 can be pushed out of the housing through the dispensing outlet 107, e.g., the movement is shown at 136, with the piston 134 at a position after dispensing the substance. The storage reservoir 135 may have a volume of approximately 600 µL or even more dispensable substance, which may be dispensed at one shot, or gradually over a period of time.

The battery cells 131 may have a height of 1.65 mm each, and one to three batteries may be used. The height of the piston may be reduced with custom molded part for around 1.5 mm to save space. If the gas-generating cell 103 is integrated with the piston 134 (e.g., as further illustrated in FIG. 10), the overall height of the PCB, batteries and gas-generating cell in total can be reduced to around 5 mm, thus providing more space for dispensable substance storage. For example, for an ingestible device of 7.8 mm in length (e.g., from end 102a to the other end 102b), a storage reservoir 134 of approximately 600 µL may be used for dispensable substance delivery. For another example, for an ingestible device of 17.5 mm in length, a storage reservoir 134 of approximately 1300 µL may be used for dispensable substance delivery.

Figure 4:
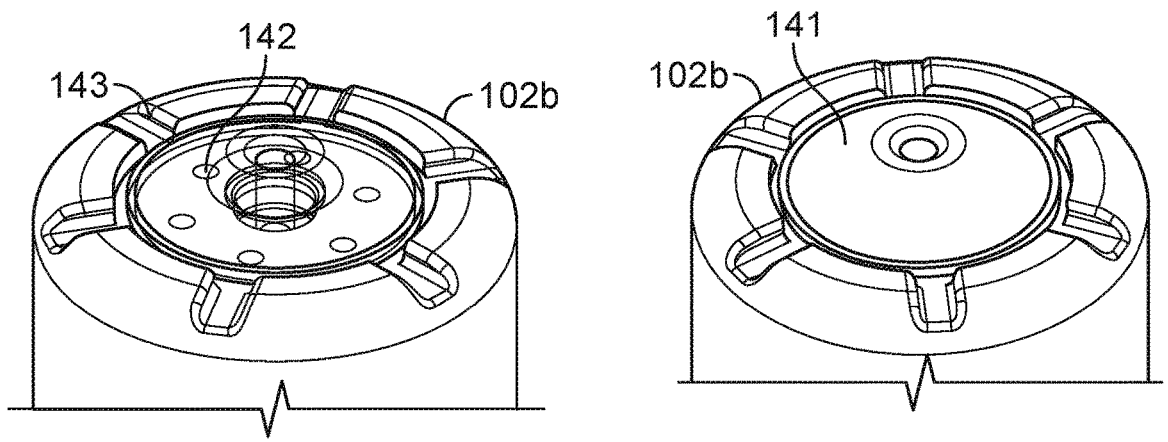
FIG. 4 provides an example structural diagram illustrating aspects of an umbrella-shaped exit valve structure as a dispensing outlet of the ingestible device, according to some embodiments described herein.

FIG. 4 provides an example structural diagram illustrating aspects of an umbrella-shaped exit valve structure as a dispensing outlet of the ingestible device, according to some embodiments described herein. The exit valve may be placed at one end 102b of the housing of an ingestible device (e.g., 100 in FIG. 3). The exit valve may include an umbrella-shaped lid 141 placed on top of one end 102b of the housing, under which the end 102b of the housing may include radially and evenly distributed holes 142 around the center of the round-shaped end 102b. When the dispensable substance is pushed out from inside the housing through the holes 142, the umbrella-shaped valve 141 may be lifted due to the pressure to let the dispensable substance out of the holes 142 be radially directed through the radially distributed notches 143 on the edge of the round-shaped end 102b of the housing. The umbrella-shaped valve 141, which covers the delivery holes 142, may also serve to keep the dispensing outlet holes 142 free of contaminants outside the ingestible device 100. The notches 143 and the holes 142 may be radially and evenly distributed around a central axis of gravity based on the geometry of the ingestible device (e.g., a cylinder shape, etc.) to reduce or avoid rotation or tilting of the ingestible device under a movement force of the dispensable substance.

Figure 5:
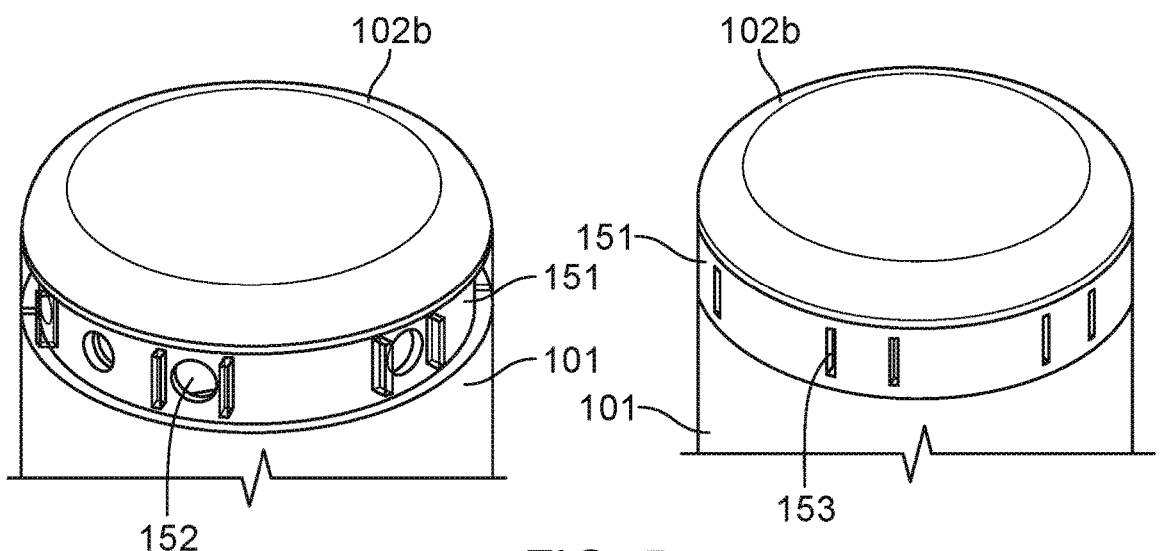
FIG. 5 provides an example structural diagram illustrating aspects of a ring-shaped exit valve structure as a dispensing outlet of the ingestible device, according to some embodiments described herein.

FIG. 5 provides an example structural diagram illustrating aspects of a ring-shaped exit valve structure as a dispensing outlet of the ingestible device, according to some embodiments described herein. The housing 101 of the ingestible device may include a ring-shaped valve 151 at a place around the housing 101 and proximal to the end 102b of the housing 101. The ring-shaped valve 151 may have evenly and radially distributed ports 157 around the ring to direct the dispensable substance out of the housing 101. The ring-shaped valve 151 may also designed to prevent blockage from contaminants outside the ingestible device 100. The ring-shaped valve 151 may optionally have a number of evenly distributed slits 153 for even distribution of the dispensable substance to maintain balance of the ingestible device.

Figure 6:
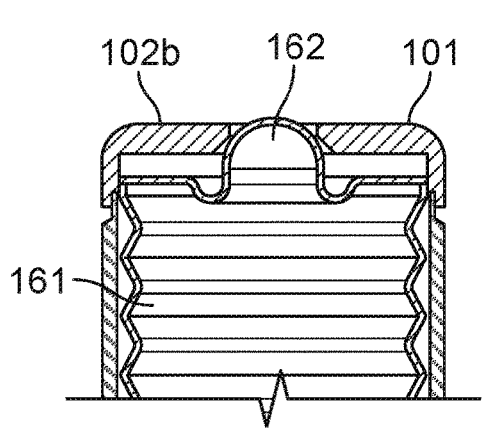
FIG. 6 provides an example structural diagram illustrating aspects of a dome slit as a dispensing outlet of the ingestible device, according to some embodiments described herein.

FIG. 6 provides an example structural diagram illustrating aspects of a dome slit as a dispensing outlet of the ingestible device, according to some embodiments described herein. The storage reservoir of the ingestible device may include a bellow 161 (further illustrated in FIG. 8), and one end of the bellow 161 may include a dome slit 162 extending out of the end 102b of the housing 101. Thus, when the bellow is being compressed, the dispensable substance may be propelled out of the bellow through the dome slit 162.

In one implementation, unlike the radial distribution through the valve in FIGS. 4-5, the bellow 161 with the dome slit 162 may be able to eject the dispensable substance at a high velocity and thus a jet delivery may be implemented. The internal pressure generated to compress the bellow 161 may be sufficient to generate a delivery at a velocity to penetrate a mucosa layer within the small intestine.

Figure 7:
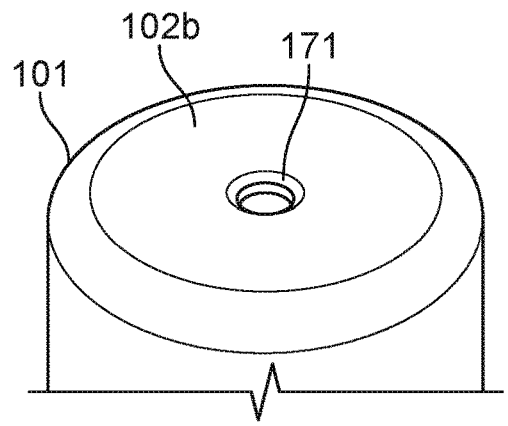
FIG. 7 provides an example structural diagram illustrating aspects of a hole placed at one end of the housing as a dispensing outlet of the ingestible device, according to some embodiments described herein.

FIG. 7 provides an example structural diagram illustrating aspects of a hole placed at one end of the housing as a dispensing outlet of the ingestible device, according to some embodiments described herein. A delivery hole 171 may be placed at the end 102b of the housing 101 for burst delivery. The hole 171 may be sealed with thin wax or silicone, which may be broken by a force from inside of the housing 101 such that the dispensable substance can be released.

In one implementation, an injection nozzle (not shown in FIGS. 6-7) or a syringe may be placed at one end 102b of the housing 101 for a jet delivery. For example, the nozzle or syringe may have an injecting needle extending out of the dome slit 162 or the delivery hole 171. The injection nozzle may use osmotic pressure from luminal fluid inside the small intestine to drive the dispensing mechanism. The injecting needle may be used to penetrate into a mucosa layer within the small intestine. The various delivery mechanisms described in FIGS. 4-7 may be configured to deliver the dispensable substance out of the ingestible device either radially or longitudinally.

Figure 8:
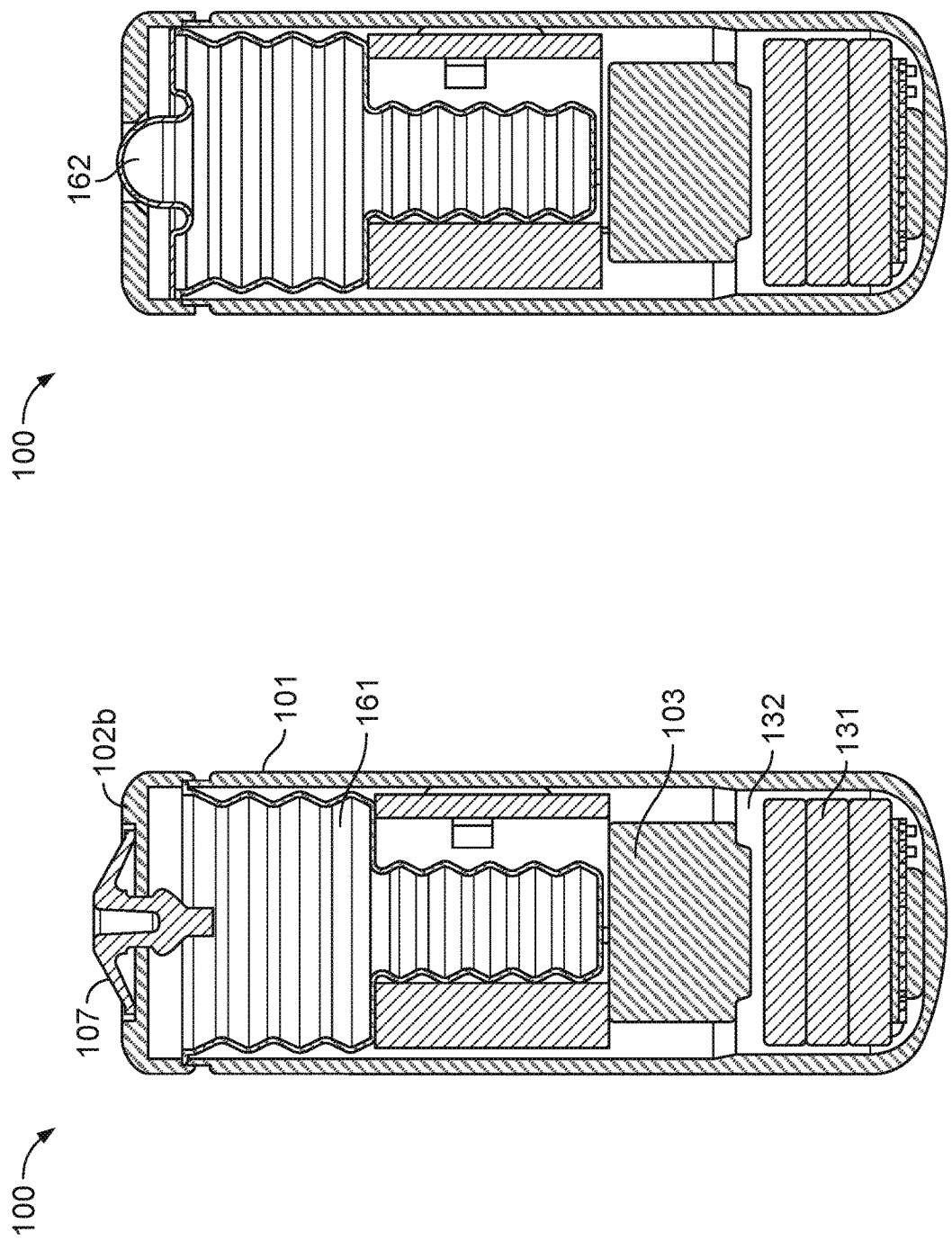
FIG. 8 provides an example structural diagram illustrating aspects of an ingestible device 100 having a bellow structure for a storage reservoir of dispensable substances, according to some embodiments described herein.

FIG. 8 provides an example structural diagram illustrating aspects of an ingestible device 100 having a bellow structure for a storage reservoir of dispensable substances, according to some embodiments described herein. A gas-generating cell 103 (similar to that described in FIGS. 1-3) may be mounted to the PCB 132 and batteries 131. A collapsible silicone bellow 161 is placed on top of the gas-generating cell 103, with one end of the bellow 161 in contact with the gas-generating cell 103 and the other end in contact with one end 102b of the housing 101. Dispensable substance may be loaded into the bellow 161, which may be compressed by gas generation from the gas-generating cell 103 to dispense the dispensable substance out of the housing 101. The shape of the bellow 161 may aid in controlled delivery. The dispensing outlet 107 may use any of the exit valves described in FIGS. 4-5, or the dome slit 162 as described in FIG. 6.

Figure 9:
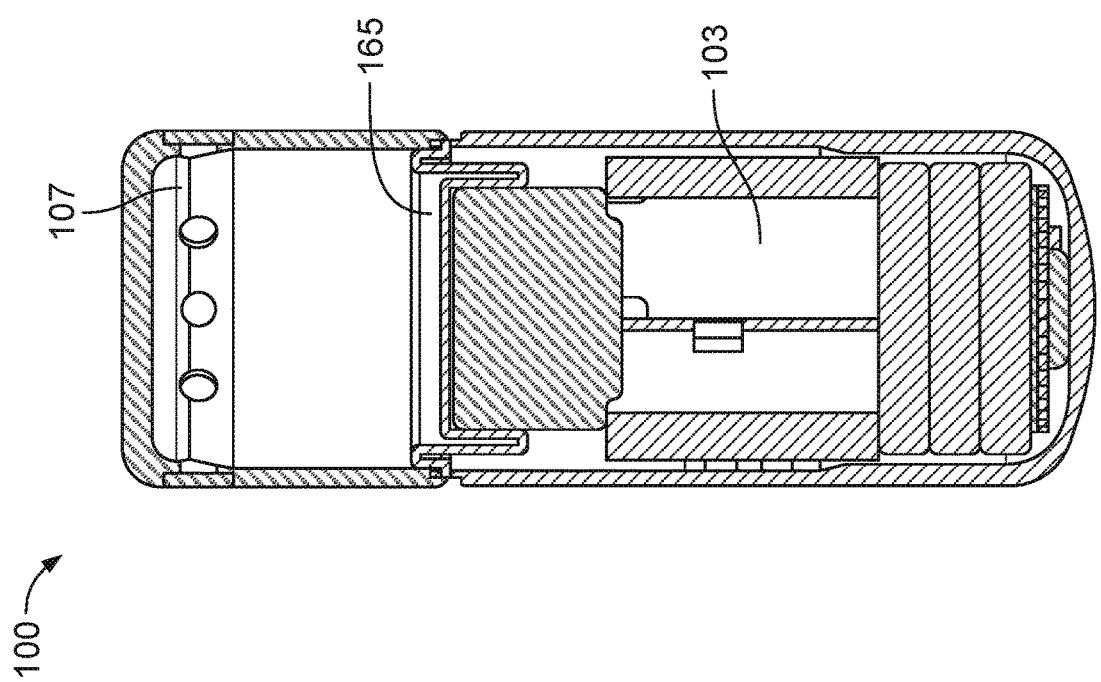
FIG. 9 provides an example structural diagram illustrating aspects of an ingestible device having a flexible diaphragm to deform for dispensable substance delivery, according to some embodiments described herein.

FIG. 9 provides an example structural diagram illustrating aspects of an ingestible device having a flexible diaphragm to deform for dispensable substance delivery, according to some embodiments described herein. The ingestible device 100 may have a flexible diaphragm 165 that may deform towards the dispensing outlet 107 when the gas-generating cell 103 generates gas. The dispensable substance may then be propelled by the deformed diaphragm out of the housing through the dispensing outlet 107. The dispensing outlet 107 shown at FIG. 9 is in the form of a ring valve as discussed in FIG. 5, however, any outlet design described in FIGS. 4-7 can be applied.

For the respective example ingestible device with the deformable diaphragm, with a total length of 7.8 mm, the ingestible device may store and deliver approximately 600 µL of dispensable substance. For another example, for an ingestible device of 17.5 mm in length, the ingestible device may store and deliver approximately 1250 µL of dispensable substance.

Figure 10:
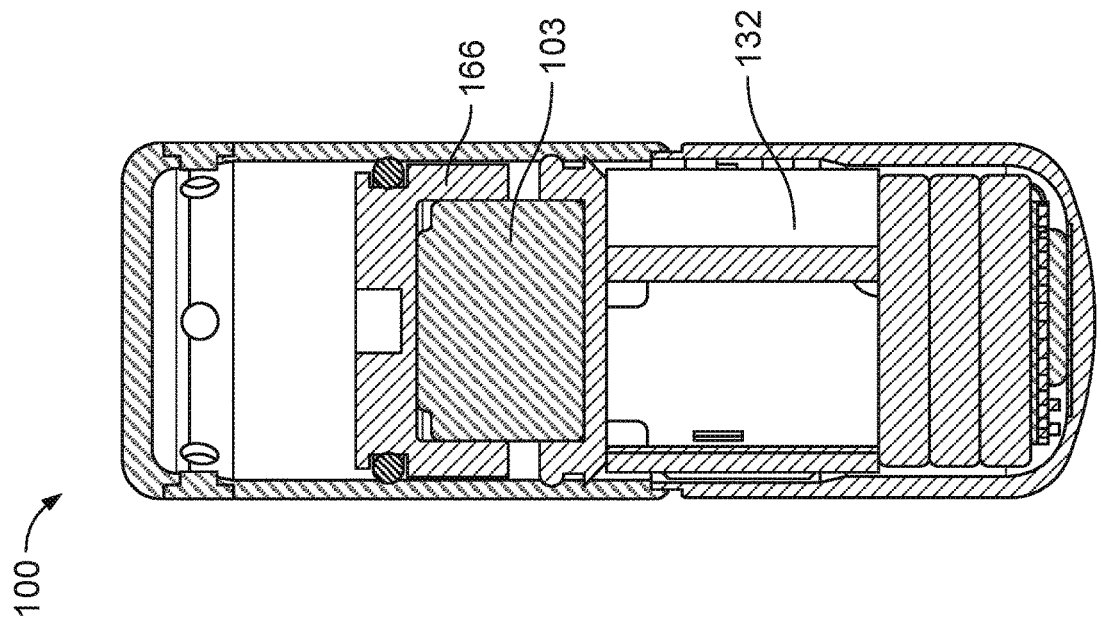
FIG. 10 provides an example structural diagram illustrating aspects of an ingestible device having an integrated piston and gas-generating cell such that the gas-generating cell is movable with the piston to push for dispensable substance delivery, according to some embodiments described herein.

FIG. 10 provides an example structural diagram illustrating aspects of an ingestible device having an integrated piston and gas generating cell such that the gas-generating cell is movable with the piston to push for dispensable substance delivery, according to some embodiments described herein. The ingestible device 100 may include a piston 166 that is made up of, or is integrated with, the gas generation cell 103. The gas-generating cell 103 may be sealed with custom silicone. In this way, the gas-generating cell 103 may move with the piston 166 when generating gas. Contacts may be embedded in a seal 166 wrapping around the gas-generating cell 103 with leads connected to PCB 132. The moving gas-generating cell structure may allow approximately 400 µL capacity for dispensable substance storage and delivery.

Figure 11:
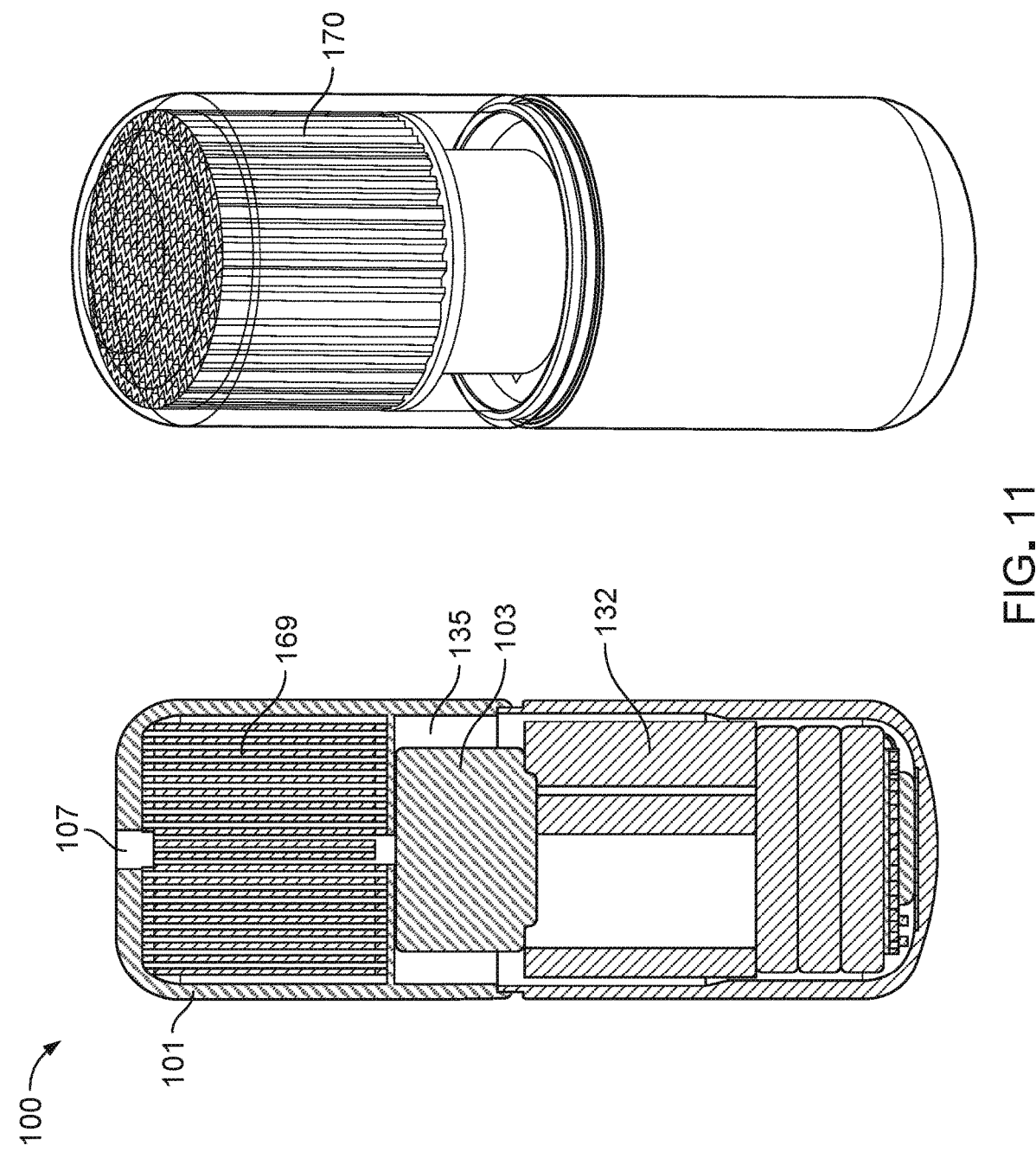
FIG. 11 provides an example structural diagram illustrating aspects of an ingestible device having a capillary to direct dispensable substances out of the storage reservoir, according to some embodiments described herein.

FIG. 11 provides an example structural diagram illustrating aspects of an ingestible device having a capillary to direct dispensable substances out of the storage reservoir, according to some embodiments described herein. A capillary structure 169 may be placed between the gas-generating cell 103 and an end of the housing 101. The dispensable substance may be stored in the empty chamber 135 around the gas-generating cell 103 and within the capillary structure 169. A wax seal may be applied between the gas-generating cell 103 and the capillary structure 169. At an appropriate time when it is identified that the ingestible device is at a specific location within the intestine, the wax seal may melt, e.g., via a generated heat by the PCB 132 or the gas-generating cell 103, and then the gas generation pressure may push the dispensable substance in the chamber 135 through the capillary plates 169 for dispensing through a dispensing outlet 107 out of the housing 101. Optionally, an exterior wax seal may be positioned between the capillary structure 169 and the dispensing outlet 107 to avoid leakage or early delivery.

In one example, the capillary structure 169 may include concentric rings of capillary plates. In another example, the capillary structure 170 between the storage reservoir 135 and an end of the housing 101 may be made of a bent foil. The ingestible device 100 with the capillary structure may have approximately 450 µL capacity of dispensable substance. In some implementations, additional volume may be obtained by reducing the size of PCB 132, removing one or two batteries, integrating the gas-generating cell 103 into the PCB 132, and/or the like. The dispensable substance volume may increase to 900 µL.

Figure 12:
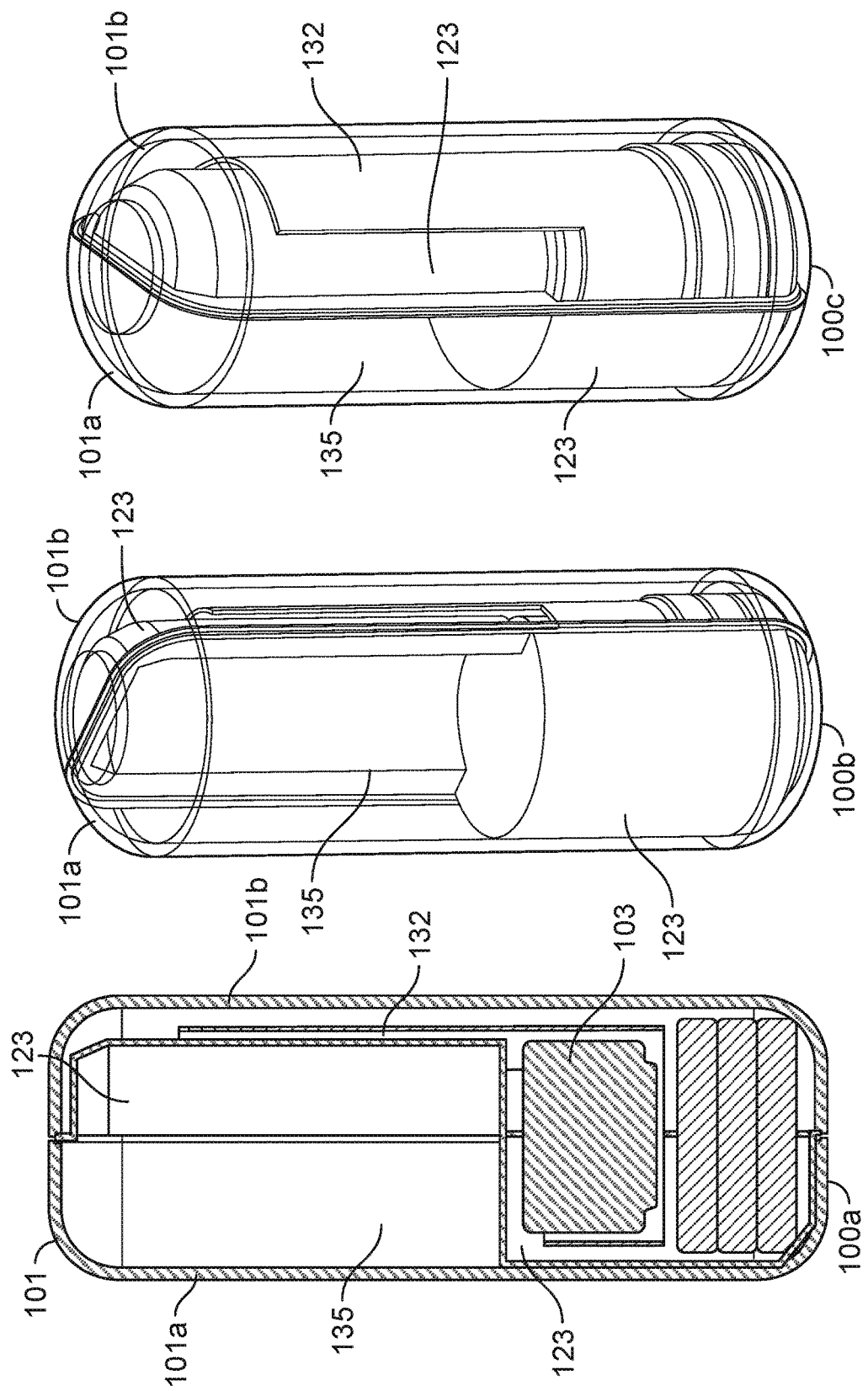
FIG. 12 provides an example structural diagram illustrating aspects of an ingestible device having a clamshell-shaped housing and a sideways split diaphragm to deform for dispensable substance delivery, according to some embodiments described herein.

FIG. 12 provides an example structural diagram illustrating aspects of an ingestible device having a clamshell-shaped housing and a sideways split diaphragm to deform for dispensable substance delivery, according to some embodiments described herein. The housing 101 of ingestible device may include two clamshell halves 101a-b along the long axis of the housing. The clamshell structure may be used to open and load dispensable substance into the ingestible device, or to insert a separate storage reservoir into the ingestible device. In the ingestible device 100a, a diaphragm 123 may be placed along one clamshell half 101b and extend to wrap around the gas-generating cell 103. In this manner, the diaphragm 123 may act as a dam between the storage reservoir 135 storing the dispensable substance and electronics 132 to protect the electronics 132. When the gas-generating cell 103 generates a gas, an internal pressure may deflect the diaphragm 123 into other half of clamshell 101a, and thus propel the dispensable substance within the storage reservoir 135 to be released out of the housing 101. The ingestible devices 100b-c provide different views of the sideway split diaphragm 123 from two different angles.

Figure 13:
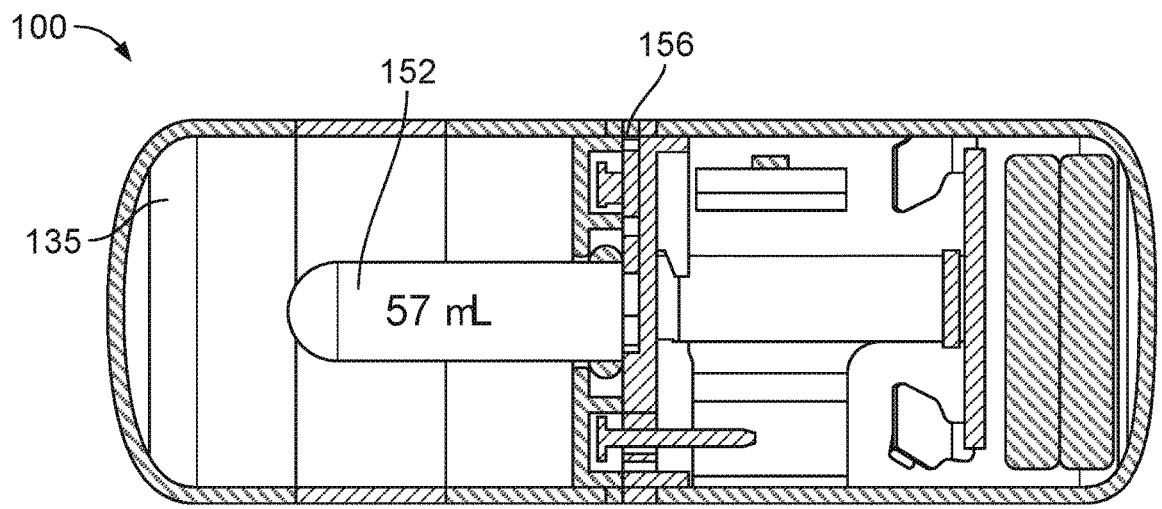
FIG. 13 provides an example structural diagram illustrating aspects of an ingestible device having an elastomer bladder, according to some embodiments described herein.

FIG. 13 provides an example structural diagram illustrating aspects of an ingestible device having an elastomer bladder to provide the pressure to deliver the dispensable substance, according to some embodiments described herein. An elastomeric component 152 (e.g., a bladder, a balloon, etc.) can be placed in the storage reservoir 135 storing the dispensable substance such that when the elastomeric component 152 expands to fill the volume of the storage reservoir 135, the dispensable substance can be pushed out of the ingestible device via an outlet, e.g., one or more holes 156 on the wall of the ingestible device.

The elastomeric component 152 may be made of flexible material that takes up a small volume in its free state but able to expand to fill the volume of the storage reservoir 135. A residual volume may exist, as the elastomeric component 152 at its free state still takes up space within the storage reservoir and thus reduces the volume of dispensable substance that can be filled into the storage reservoir 135. For example, as shown in FIG. 13, the elastomeric component 152, e.g., a balloon, even at a free state, may be slightly inflated, and thus takes up a volume of 57 µL.

One or more holes 156 on the outer shell of the ingestible device 100 can allow luminal fluid to be drawn into the void behind the elastomeric component 152. The ports of the holes 156 on the outer wall may be shaped to prevent irritation during the use the ingestible device 100, e.g., with no edges to catch any tissue within the GI tract during travel, and also to reduce fouling from the back filling of luminal fluid.

A wax plug can be used to seal the one or more holes 156, which can be pushed out by pressure when the dispensable substance is released. Additional coating, removable casing or decal can be added, e.g., on top of the one or more holes 156, to ensure the dispensable substance is not dispensed during handling.

Figure 14:
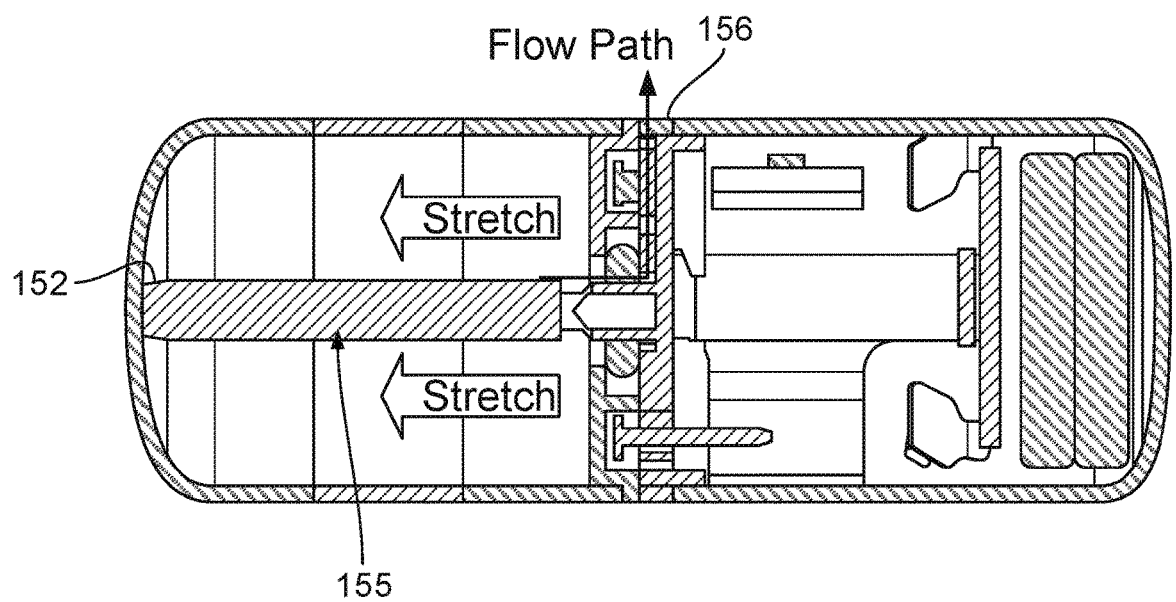
FIG. 14 provides example structural diagrams illustrating aspects of an ingestible device using an elastomer bladder to provide the pressure to deliver the dispensable substance, according to some embodiments described herein.

FIG. 14 provides example structural diagrams illustrating aspects of pre-loading an ingestible device having an elastomer bladder to reduce the residual volume, according to some embodiments described herein. To reduce the residual volume and to load the ingestible device with the maximum possible dispensable substance, the elastomeric component 152 can be stretched and filled by a rod 155 prior to filling the storage reservoir 154 with the dispensable substance. In this way, the free state of the elastomeric component 152 is preloaded under tension, which can reduce the residual volume. One or more holes 156 on the outer shell of the ingestible device 100 can allow luminal fluid to be drawn into the void behind the elastomeric component 152. The ports of the holes 156 on the outer wall may be shaped to prevent irritation during the use the ingestible device 100, e.g., with no edges to catch any tissue within the GI tract during travel, and also to reduce fouling from the back filling of luminal fluid.

In this way, when the residual volume is reduced, the payload capacity of the ingestible device can be increased, e.g., a dose of up to 800 µL can be carried by the ingestible device. Because of the increased payload capacity, the overall size of the ingestible device can thus be reduced, which may be easier for a patient to administer and may also increase packing density to improve distribution logistics.

Figure 15:
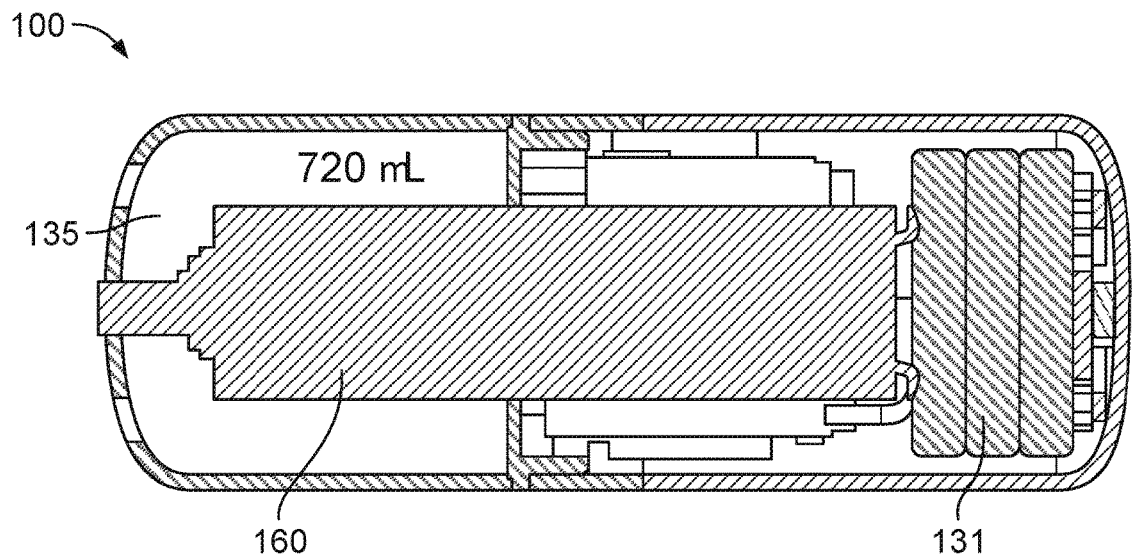
FIG. 15 provides example structural diagrams illustrating aspects of an ingestible device having a gear motor to dispense the dispensable substance out of the storage reservoir, according to some embodiments described herein.

FIG. 15 provides example structural diagrams illustrating aspects of an ingestible device having a gear motor to dispense the dispensable substance out of the storage reservoir, according to some embodiments described herein. A gear motor mechanism 160 may be placed within the ingestible device, with one end connected to the battery cells 131, and the other end placed at the opposite end of the ingestible device 100. The gear motor 160 can be driven to a specific motion, e.g., rotating, etc., such that the dispensable substance in the storage reservoir can be dispensed out of the ingestible device 100 by the motion. The dispensable substance can be dispensed as a bolus or a gradual dose over a given time period with a variable dose rate, e.g., by adjusting the velocity, pattern, and power of the gear motor motion. The storage reservoir 135 may carry a volume of up to 720 µL, as the gear motor mechanism may need an enhanced battery system that can limit the overall payload volume.

Figure 16:
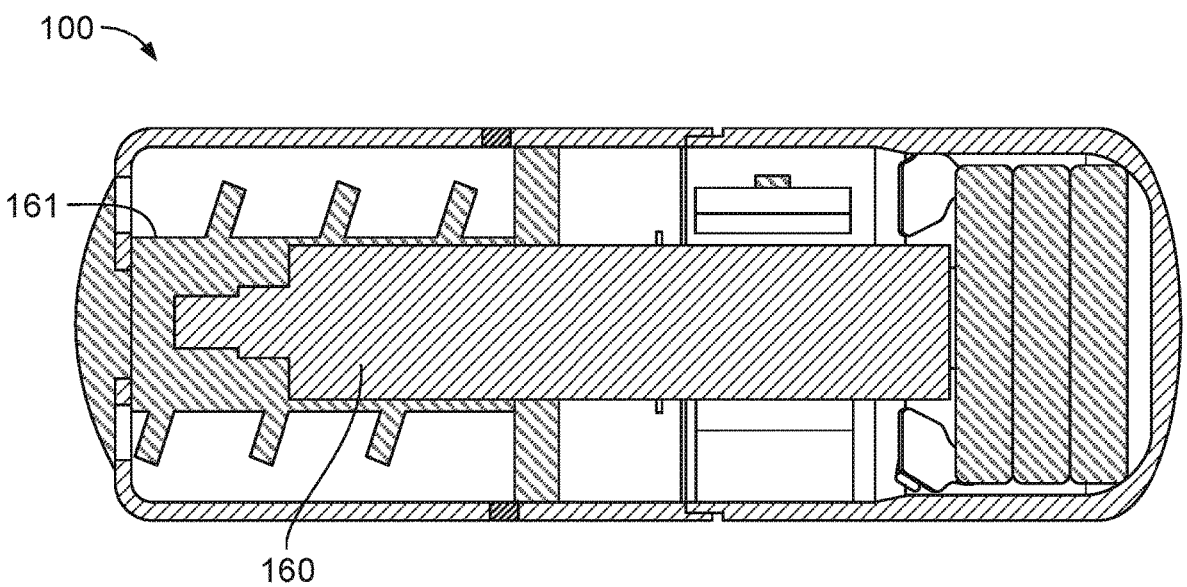
FIG. 16 provides example structural diagrams illustrating aspects of an ingestible device using an auger to dispense the dispensable substance out of the storage reservoir, according to some embodiments described herein.

FIG. 16 provides example structural diagrams illustrating aspects of an ingestible device using an auger to dispense the dispensable substance out of the storage reservoir, according to some embodiments described herein. The gear motor 160 can be equipped with an auger device around the outer wall of the gear motor 160 such that the auger device can be driven to stir or wipe the dispensable substance to be dispensed out of the storage reservoir.

The diameter of the auger device 161 is smaller than the diameter of the storage reservoir such that the auger device 161 does not touch the inner wall of the ingestible device 100, to avoid any scratch or damage to the wall of the ingestible device 100. The sealing of the ingestible device 100 can be static between the housing of the gear motor 160 and the body of the ingestible device 100. This can reduce the amount of torque required to drive the auger 161, and may allow the user of a smaller gear motor 160, which can increase the available payload volume within the ingestible device 100.

The auger mechanism can allow the dispensable substance to be flushed out of the ingestible device 100 and to be progressively diluted as the luminal fluid is drawn into the storage reservoir. The dispensable substance is then delivered out of the storage reservoir at a declining concentration. As a result, a low residual volume of dispensable substance may remain within the storage reservoir, depending on the number of times the auger mechanism is instantiated to dispense the dispensable substance.

FIG. 17 provides example structural diagrams illustrating aspects of an ingestible device using a wiper to dispense the dispensable substance out of the storage reservoir, according to some embodiments described herein. A wiper device 163 can be connected to the gear motor 160 such that the gear motor 160 rotationally drives the wiper device 163 to dispense the dispensable substance. Two ports 164a-b on the outer casing of the ingestible device 100 on either side of the wiper would act as inlets or outlets. The inlet (e.g., 164a or 164b) is configured to allow luminal fluid to fill the void created by the moving wiper 163 and regulate the resulting negative pressure. The wiper 163 is configured in a size that the edge of the wiper 163 substantially touches the inner wall of the storage reservoir to maintain a seal and properly deliver the dispensable substance. As a result, the batter may need to provide a higher power to maintain the rotation of the gear motor 160 against friction. A wax seal may be used to retain the dispensable substance while not in use. The wiper mechanism in FIG. 17 is effective at delivering the entire payload (low/zero residual volume) to maximize the delivery of the dispensable substance and to minimize waste of the substance.

FIG. 18 provides example structural diagrams illustrating aspects of an ingestible device using a piston to drive the wiper described in FIG. 17, according to some embodiments described herein. A fine pitch helix 165 is disposed over the gear motor 160, and a piston 166 disposed around a portion of the gear motor 160 and at one end of the helix 165. Thus, when the gear motor 160 rotates, the fine pitched helix 165 is driven to rotate to cause the piston to move towards the opposite end of the helix 165. As a result, the movement of the piston pushes the dispensable substance out of the storage reservoir.

A passive umbrella valve 167, e.g., see also 141 in FIG. 4, can be used at the outlet of the ingestible device 100. The pitch of the helix 165 can be specified to improve control of metering the dispensing dose over time. A low residual volume can be achieved, as the piston 166 can empty the payload volume of the storage reservoir.

Figure 19:
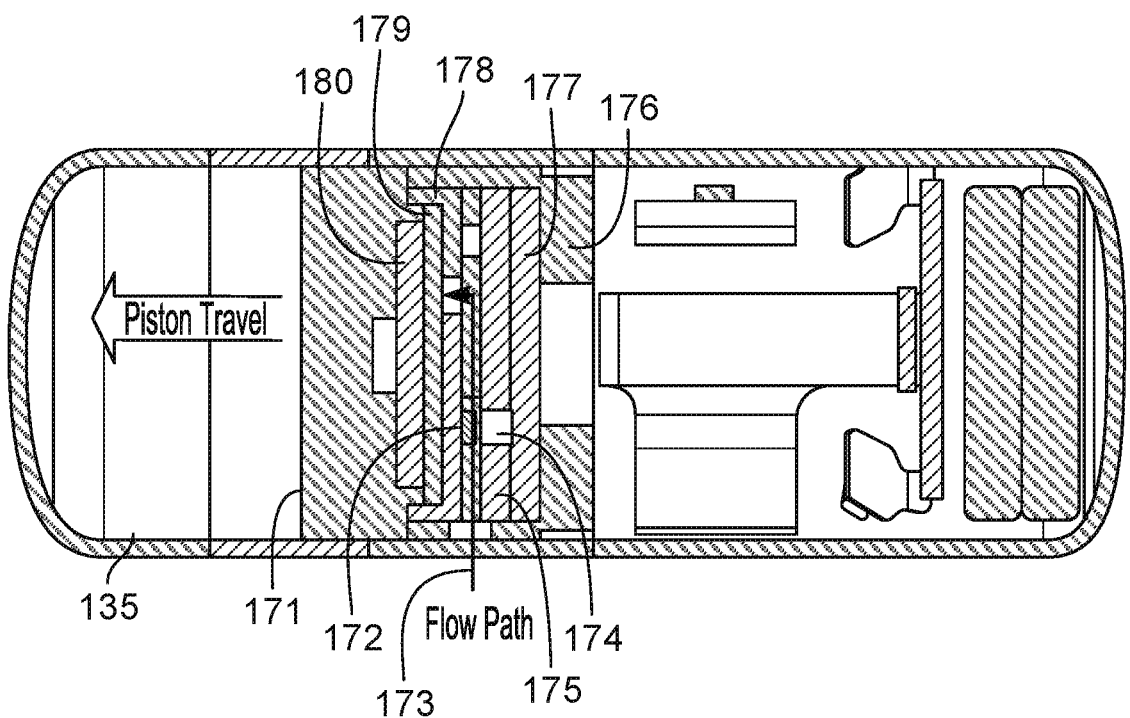
FIG. 19 provides an example structural diagram illustrating aspects of an ingestible device using osmotic pressure to dispense a dispensable substance, according to some embodiments described herein.

FIG. 19 provides an example structural diagram illustrating aspects of an ingestible device using osmotic pressure to dispense a dispensable substance, according to some embodiments described herein. In some implementations, osmosis may be used to increase internal pressure of the ingestible device in order to dispense the substance. Osmosis or luminal fluid can enter the ingestible device through a flow path 173 via an inlet on the outer wall of the ingestible device. A wax plug 172 may be used to keep the luminal fluid separated from the semipermeable membrane 179 until the ingestible device is in the desired location, e.g., the wax plug can be flushed away to allow luminal fluid in to the chamber adjacent to the membrane 179. Thus, the fluid can permeate through the semipermeable membrane 179, which is placed at one end of the storage reservoir 15, to enter the storage reservoir 135.

A volume of dry salt 180 (solute) can be positioned on one side (e.g., the side of the storage reservoir) of a semipermeable membrane 179 that allow water from the GI fluid (solvent) to be drawn through to combine into a solution. The solution is not able to move through the reverse direction of the semipermeable membrane 179. Thus, as more and more GI fluid is drawn into the storage reservoir 135 to form the solution, pressure can be built on the one side of the membrane 179, which can be harnessed to evacuate the dispensable substance.

When mucus and mineral "residue" (e.g., from the GI fluid) may impede water from passing smoothly through the membrane 179, a variety of different options can be adopted. For example, a piston 171 can be used to drive the dispensable substance out of the ingestible device. Or for another example, as part of the dispensable substance is pushed out of the ingestible device due to osmotic pressure, luminal fluid can slowly fills in the cavity within the storage reservoir 135 (as further discussed in connection with FIG. 20) to diffuse the remaining dispensable substance. The mixture of the diffused dispensable substance can thus be forced out of a one-way valve.

The osmotic dispensing mechanism can be built upon a housing 176 placed inside the ingestible device. The PCB 177 can be mounted on top of the housing 176. An insulator 175 can be placed between the PCB 177 and the flow path channel 173 to insulate the PCB 177 from any direct contact with GI fluid. The resistor 174 may be configured to provide a low-cost heating element. When the PCB 177 generates a current to pass through the resistor 174, the resistor 174 may generate heat such that the wax plug 172 that is placed adjacent to or proximate to the resistor may transition from solid to liquid upon heating. Any external gastric pressure or internally generated pressure may then cause the melted wax plug 172 to be pushed out of the original position, thus allowing gastric fluid to enter the device to drive the osmotic mechanism.

The ingestible device using osmotic pressure can provide more safety advantage over a gas-generating cell, as the gas, usually hydrogen, can be a combustible gas and may cause safety hazard when administered into a human body.

Figure 20:
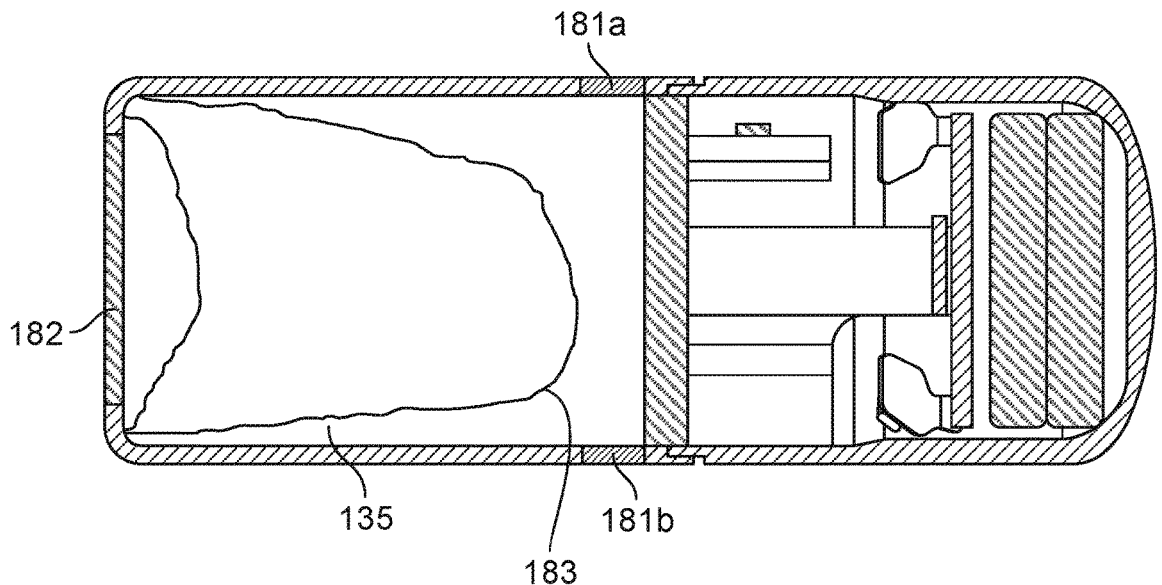
FIG. 20 provides an example structural diagram illustrating aspects of an ingestible device using diffusion of the dispensable substance by luminal fluid, according to some embodiments described herein.

FIG. 20 provides an example structural diagram illustrating aspects of an ingestible device using diffusion of the dispensable substance by luminal fluid, according to some embodiments described herein. Various ports 181a-b and 182 may be added to the outer wall of the ingestible device. These ports may be temporarily sealed, e.g., using a wax seal or enteric coating. Once activated, the ports may be opened and the dispensable substance may slowly mix into the GI tract with the luminal fluid. An elastomeric membrane 183b filled with the dispensable substance may be placed within storage reservoir 135 to utilize peristaltic pressure within the GI tract to encourage mixing of the luminal fluid with the dispensable substance. For example, the port 182 may be sealed with an enteric coating or a wax plug. When the enteric coating melts or the wax plug is removed from the original position by peristaltic pressure, the luminal fluid can enter the storage reservoir 135 to mix with the dispensable substance. When the ports 181a-b are open, luminal fluid may also enter the storage reservoir via the ports 181a-b to generate a pressure to force the elastomeric membrane 183b to collapse to a position 183a, and thus dispensing the dispensable substance mixed with the luminal fluid out of the storage reservoir 135 via the port 182.

As the dispensable substance is gradually dispensed out of the storage reservoir 135, the cavity in the storage reservoir can be flushed multiple times, e.g., by drawing in luminal fluid into the storage reservoir 135. As a result, a higher concentration of the dispensable substance is delivered to the GI tract at the beginning, and the concentration may decline over time.

Figure 21:
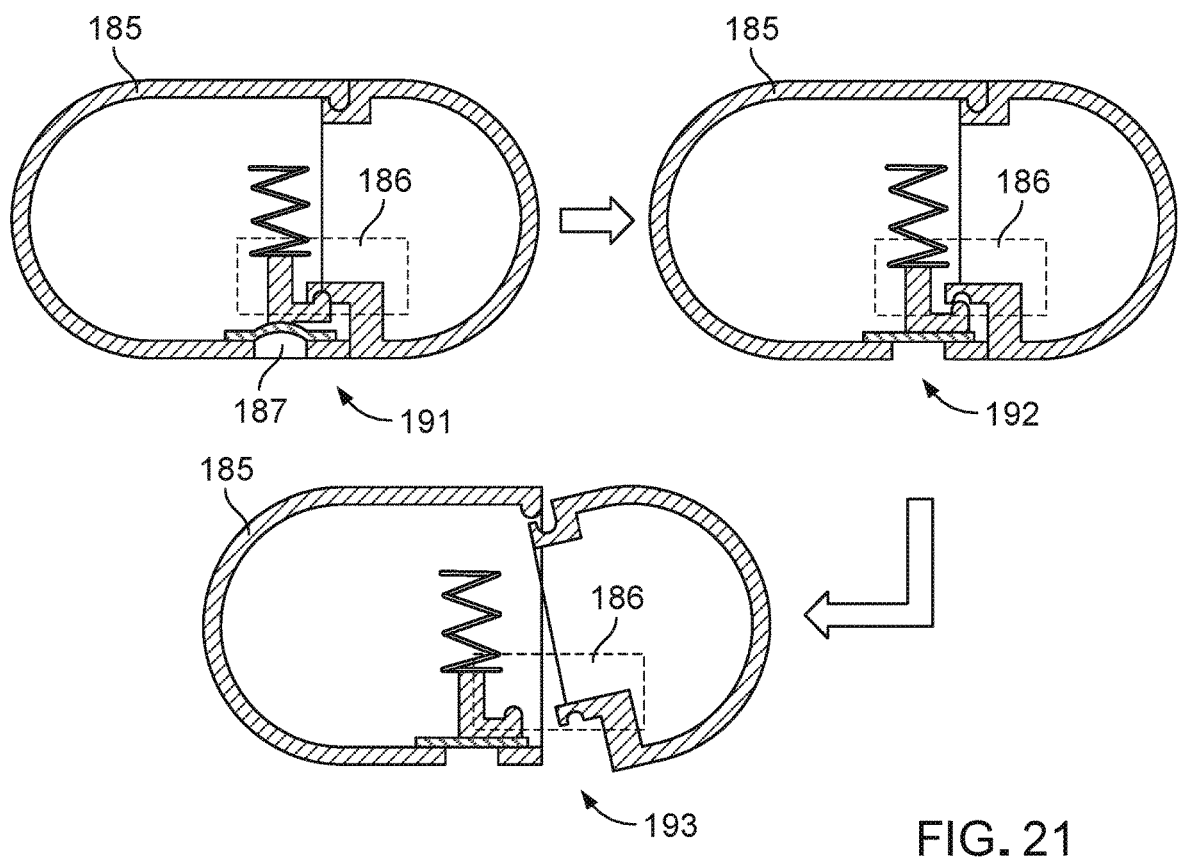
FIG. 21 provides an example structural diagram illustrating aspects of an ingestible device having a splittable housing, according to some embodiments described herein.

FIG. 21 provides an example structural diagram illustrating aspects of an ingestible device having a splittable housing, according to some embodiments described herein. Instead of using ports on the outer wall of the ingestible device to allow luminal fluid to draw into the storage reservoir and mix with the dispensable substance, as shown in FIG. 20, a splittable housing 183 can be adopted with a combination of a mechanical latch 186 and an enteric coating 187. At 191, the latch 186 is held closed with an enteric coating 187. At 192, the enteric coating may dissolve when the ingestible device enters into the GI tract, and the latch 186 releases. At 193, when the latch releases, the housing 185 may split into two halves, and thus release the dispensable substance. In this way, the entire payload can be dispensed.

The release of the latch can be activated at a predetermined location, e.g., by using a melting wax plug to release the latching mechanism and/or by using the localization system to determine the location for activation. Further discussion of localization of the ingestible device may be found in PCT International Application No. PCT/US2015/052500, filed on Sep. 25, 2015, which is herein expressly incorporated by reference. The splittable housing can also be actuated by osmotic pressure.

Figure 22:
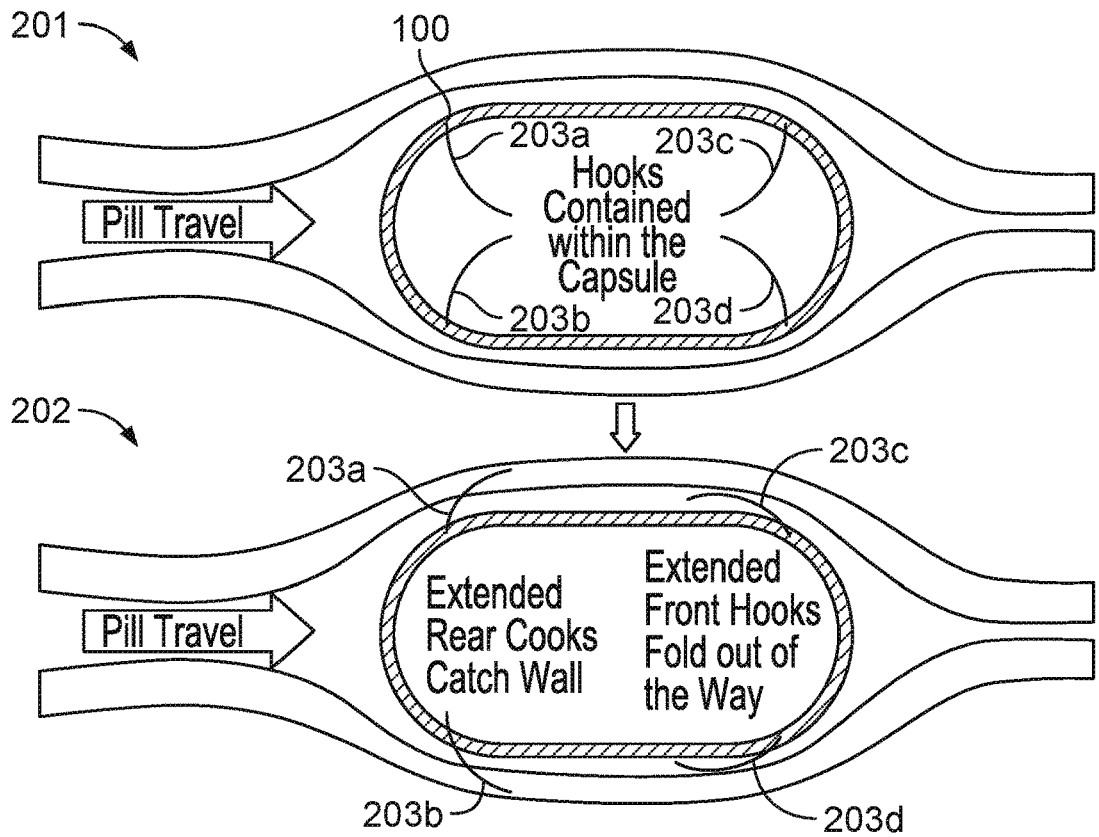
FIGS. 22-24 provide example structural diagrams illustrating aspects of anchoring mechanisms of an ingestible device to anchor the ingestible device to the intestine for dispensable substance delivery, according to some embodiments described herein.
Figure 23:
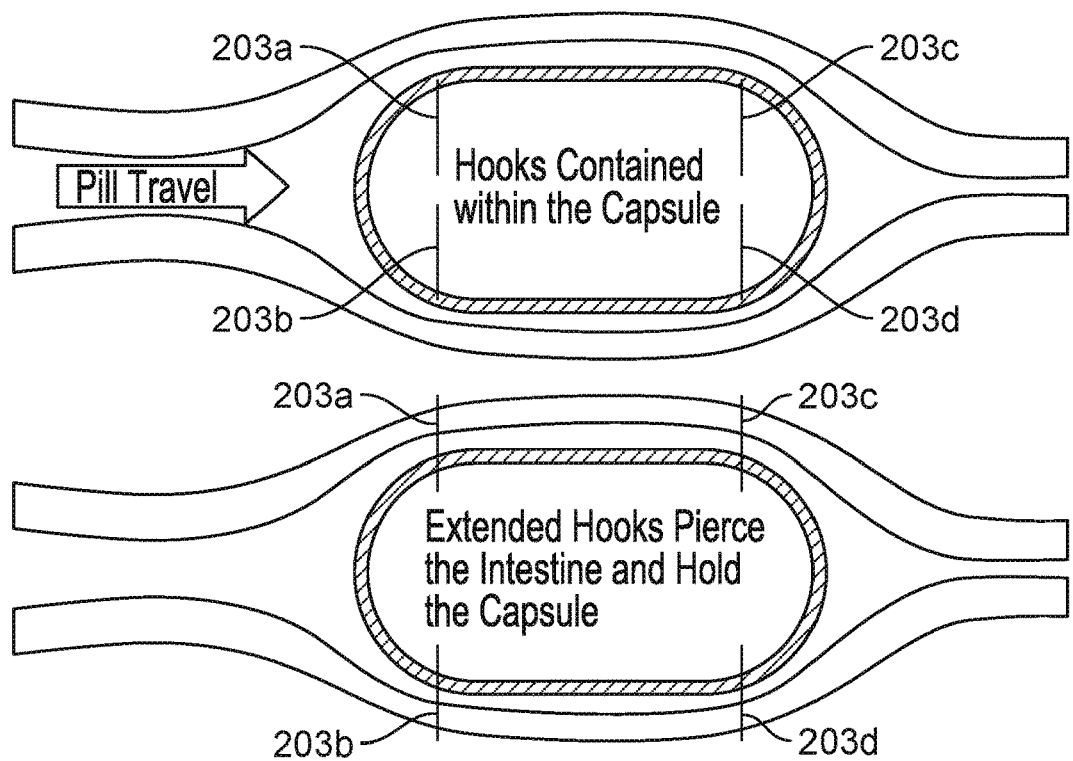
Figure 24:
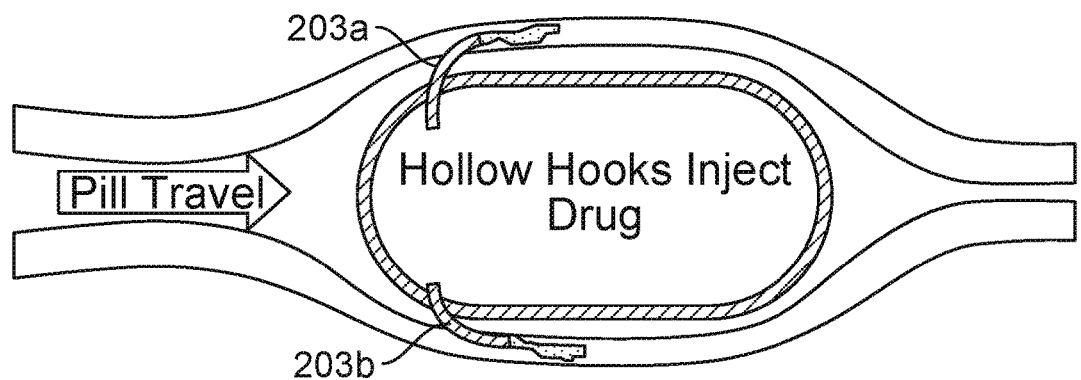

FIGS. 22-24 provide example structural diagrams illustrating aspects of anchoring mechanisms of an ingestible device to anchor the ingestible device to the intestine for dispensable substance delivery, according to some embodiments described herein. As shown in FIG. 22, the ingestible device 100 can be anchored within the intestine by extending hooks 203a-d from the ingestible device 100 after it has entered the region of interest. At 201, as the ingestible device 100 travels along the GI tract, the hooks 203a-d are contained within the ingestible device. At 202, when the ingestible device 100 determines it has arrived at a location within the GI tract, the hooks 203a-d can be actuated to extend outside of the ingestible device 100 to catch in the intestinal wall and hold the ingestible device 100 in the respective location. The hooks 203a-d can be oriented to catch the intestinal wall regardless of the instant orientation of the ingestible device 100. The hooks 203a-d can also retract, dissolve, or detach from the intestinal wall after the dispensable substance has been delivered at the anchored location.

As shown in FIG. 23, the hooks 203a-d could also extend radially from the ingestible device, and pierce into the intestinal wall to hold the ingestible device 100 in place. As shown in FIG. 24, if the extending hooks (e.g., 203a-b) are hollow, the hooks can be used to both anchor the ingestible device and inject the dispensable substance into the intestinal wall.

Figure 25:
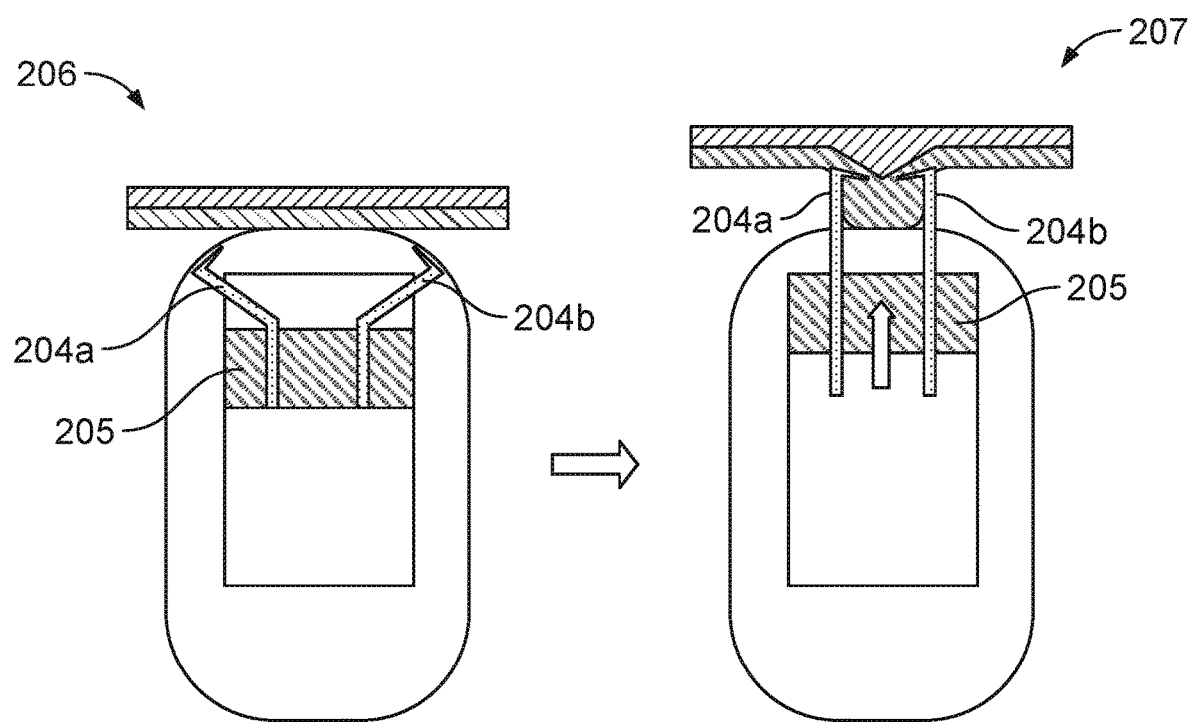
FIGS. 25-26 provide example structural diagrams illustrating aspects of an intestinal gripper of the ingestible device to grip a portion of the intestinal wall for delivering the dispensable substance, according to some embodiments described herein.
Figure 26:
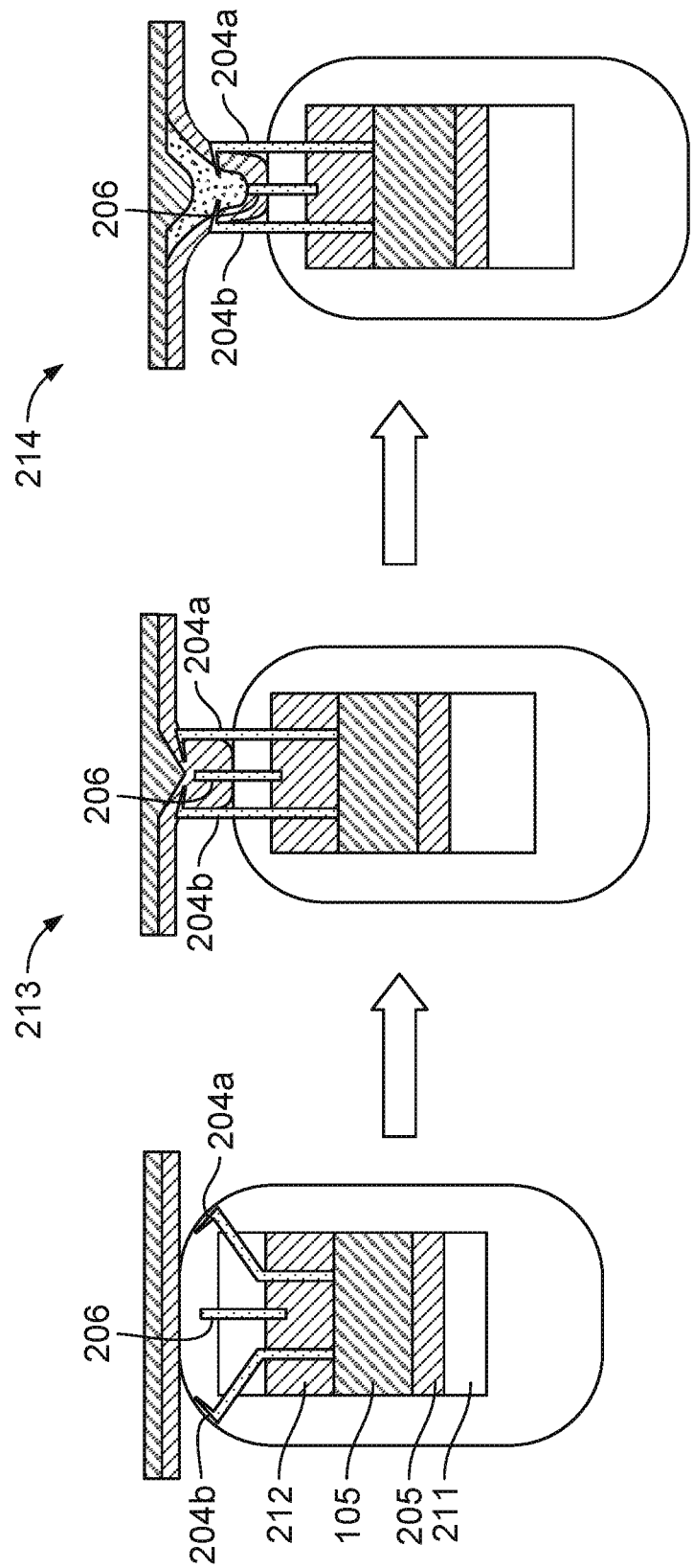

FIGS. 25-26 provide example structural diagrams illustrating aspects of an intestinal gripper of the ingestible device to grip a portion of the intestinal wall for delivering the dispensable substance, according to some embodiments described herein. As shown in FIG. 25, a piston 205 is connected to two anchoring arms 204a-b within the ingestible device, e.g., at 206. When internally generated pressure (e.g., by a gas-generating cell or osmotic pressure as discussed throughout this disclosure) moves the piston 205 forward, the two anchoring arms 204a-b can be consequently pushed to extend out of the ingestible device and close to grip a portion of the intestinal wall, e.g., at 207. The anchoring arms 204a-b (two arms are shown in FIG. 25 for illustrative purpose), which can be two or more arms, can be arranged in a circular pattern to form a suction-like form at state 207. Alternatively, the anchoring arms 204a-b can be arranged in a rectangular pattern for a simple construction (e.g., fewer anchoring arms may be used). The anchoring arms 204a-b can be made of a rigid material but with a pivot allowing the arms to close at state 207, or the anchoring arms 204a-b can be made of flexible metal elements that can be bent as the piston 205 moves towards the outlet of the ingestible device.

As shown in FIG. 26, an injecting needle 206 can be used with the anchoring arms 204a-b to inject dispensable substance into the intestinal wall after a portion of the intestinal wall is gripped. For example, as pressure from a actuation mechanism (e.g., gas or osmotic pressure, etc.) 211 can propel the piston 205 to move towards an outlet of the ingestible device, the storage reservoir 135 storing the dispensable substance 105, e.g., therapeutic agent, and a plunger 212 housing the anchoring arms 204a-b and an extendable needle 206 can all be moved towards the outlet of the ingestible device. At state 213, the plunger 212 can move to a position that the anchoring arms 204a-b and the needle 206 are extended out of the ingestible device, and consequently, the anchoring arms 204a-b grip a portion of the intestinal wall and the needle 206 is inserted into the gripped portion. At state 214, a fluid path can be opened at one end of the plunger 212 such that the dispensable substance 105 is injected via the needle 206 into the intestinal wall.

Figure 27:
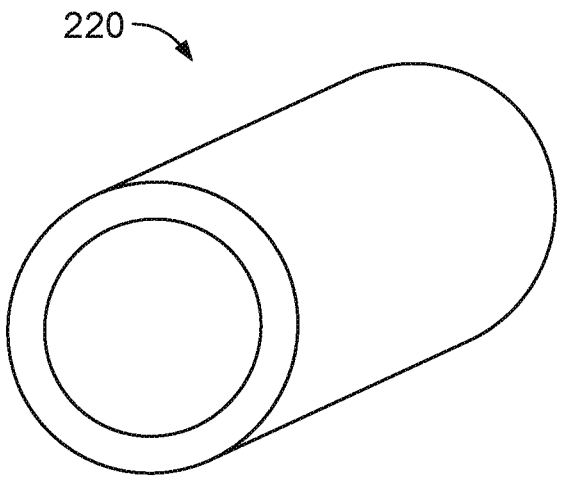
FIGS. 27-30 provide example structural diagrams illustrating aspects of an expanding stent of the ingestible device to lodge the ingestible device at a particular location in the GI tract for dispensing, according to some embodiments described herein.
Figure 28:
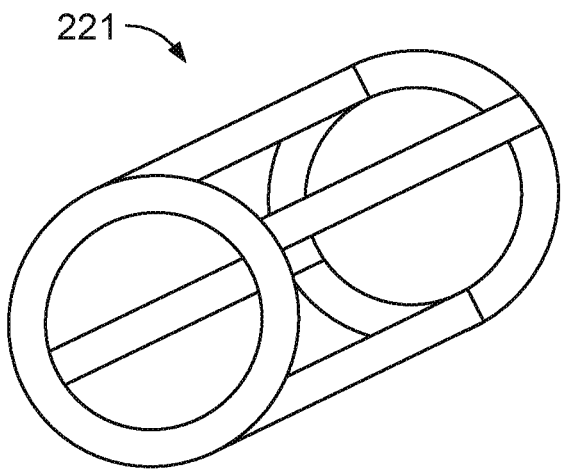

FIGS. 27-30 provide example structural diagrams illustrating aspects of an expanding stent to lodge the ingestible device at a particular location in the GI tract for dispensing, according to some embodiments described herein. Examples of cylindrical stents are shown in FIGS. 27-28, e.g., a solid cylinder 220 or a hollow frame stent 21, etc. The outer surface of the stent 220-221 may be coated in patches that may diffuse the dispensable substance into the small intestine while the stent itself protects the dispensable substance from enzymes in the luminal fluid.

In some implementations, the stent may be formed by a shape memory alloy that returns to an expanded state upon transition to body temperature. The stent may be formed by a pre-tensioned structure that expand upon dissolving of an enteric coating. The stent material may also dissolve or is comprised of material that releases therapeutic agent. Expanding stent geometries, e.g., unravelling coils, or other geometries that allow expansion of the device along the short or long axis of the cylinder 220 may be utilized. The patch may consist of an embedded therapeutic agent in a dissolvable matrix. The dissolvable matrix allows for the re-collapsing of the therapeutic agent, or the stent material itself dissolves over time.

Figure 29:
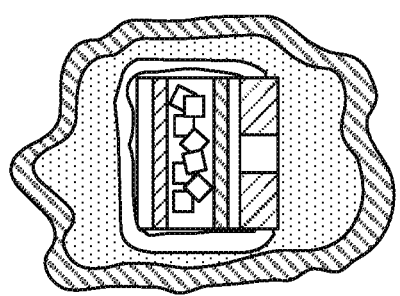
Figure 30:
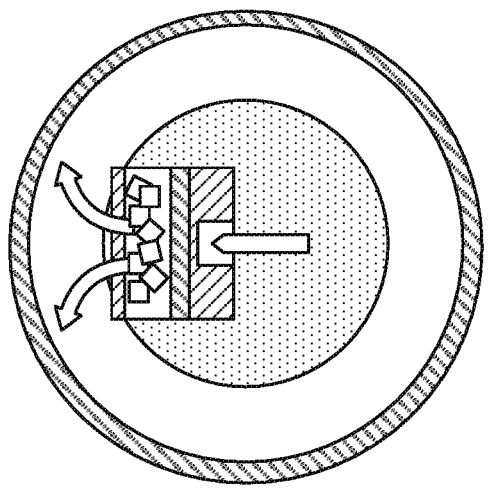

As shown in FIG. 29, the stent is placed pressing or adhering a patch or other dispensable substance-dispensing object to the surface of the mucosal layer. The intent is to allow dispensable substance to diffuse through the front of the patch towards the epithelial cells while protecting the body of dispensable substance from degrading agents in the luminal fluid. The outer surface of the stent may also contain dissolving micro-needles to encourage delivery of the dispensable substance. The stent may be deployed by splitting open the ingestible device to allow a mechanically driven stent to expand by spring force. The stent may also inflate like a balloon when deployed. An example of an inflatable stent inflated using osmotic pressure is shown in FIG. 30.

If the stent is in the form of a hollow cylinder, intestinal fluid can still pass through the center of the stent and thus does not cause a blockage while the dispensable substance is being dispensed. The surface of the stent may include needles, hooks, or mucosal adhesives to provide grip to the intestinal wall to lodge the ingestible device to a certain location within the GI tract.

Figure 31:
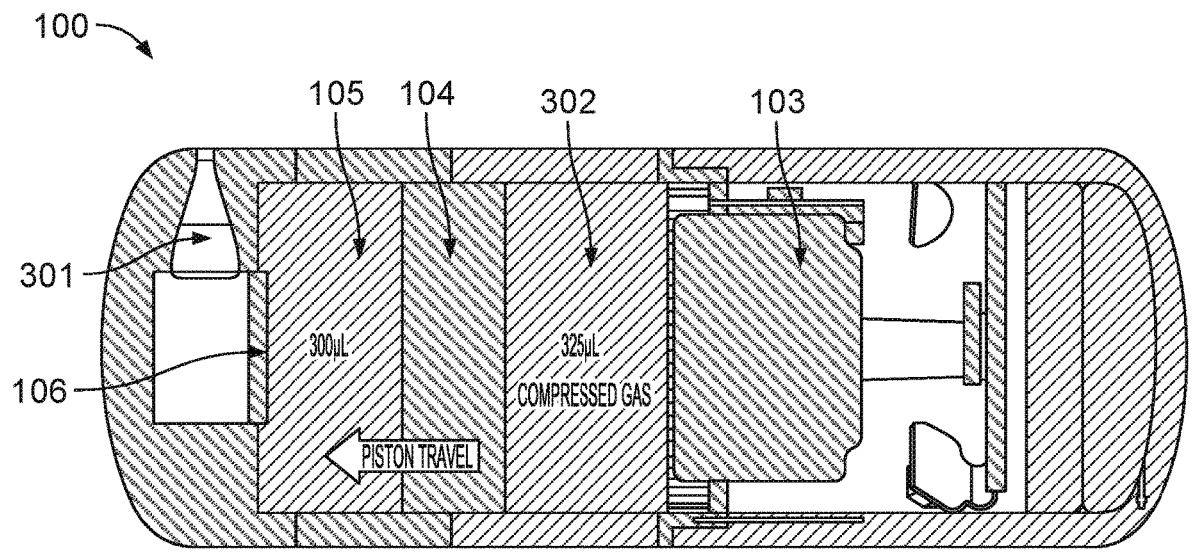
FIG. 31 provides an example structural diagram illustrating aspects of an ingestible device having a jet delivery mechanism, according to some embodiments described herein.

FIG. 31 provides an example structural diagram illustrating aspects of an ingestible device having a jet delivery mechanism, according to some embodiments described herein. The ingestible device 100 may be a variant of the ingestible device 100 described in FIG. 1, with the outlet 107 being an injection nozzle 301. In some implementations, when the gas-generating cell 103 generates gas 302 to propel the piston 104 to move towards the nozzle 301 such that the dispensable substance 105 can be pushed under the pressure to break the burst disc 106 to be injected via the nozzle 301. To generate sufficient pressure within the ingestible device for injection, an amount of 325 μL gas may be required to expel the dispensable substance 105. Thus the payload of the dispensable substance 105 may be limited, e.g., 300 μL maximum.

The ingestible device may be pushed away from the intestinal wall before injection so that the dispensable substance 105 can penetrate the tissues.

Figure 32:
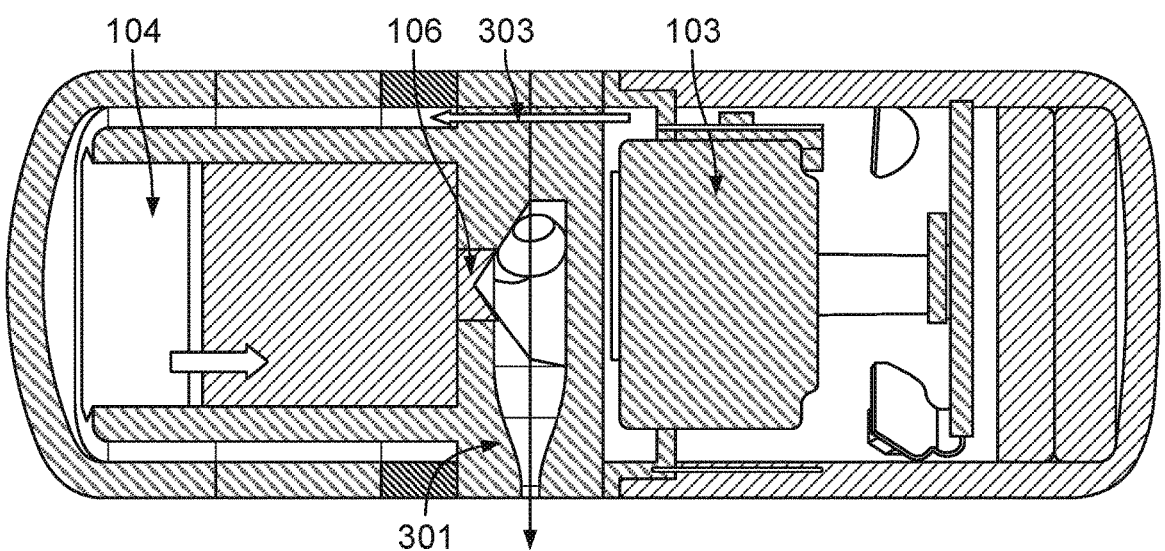
FIG. 32 provides alternative example structural diagram for an ingestible device having a jet delivery mechanism with enhanced usable volume of dispensable substance, according to some embodiments described herein.

FIG. 32 provides alternative example structural diagram for an ingestible device having a jet delivery mechanism with enhanced usable volume of dispensable substance, according to some embodiments described herein. The nozzle 301 may be placed at the center of the ingestible device. Gas channels 303 may be placed longitudinally along the wall of the ingestible device to transport gas from the gas-generating cell 103 to propel the piston 104, which is placed at an end of the ingestible device. The direction of piston 104 movement may be reversed, e.g., from one end of the ingestible device towards the center of the ingestible device. In this way, approximately 690 μL of total gas space can be used within the ingestible device, and as a result, greater force can be generated to inject the dispensable substance to break the burst disc 106. The mechanism described in FIG. 32, with a larger pressure chamber for gas, may be used for multiple jets, as shown in FIG. 32.

Figure 33:
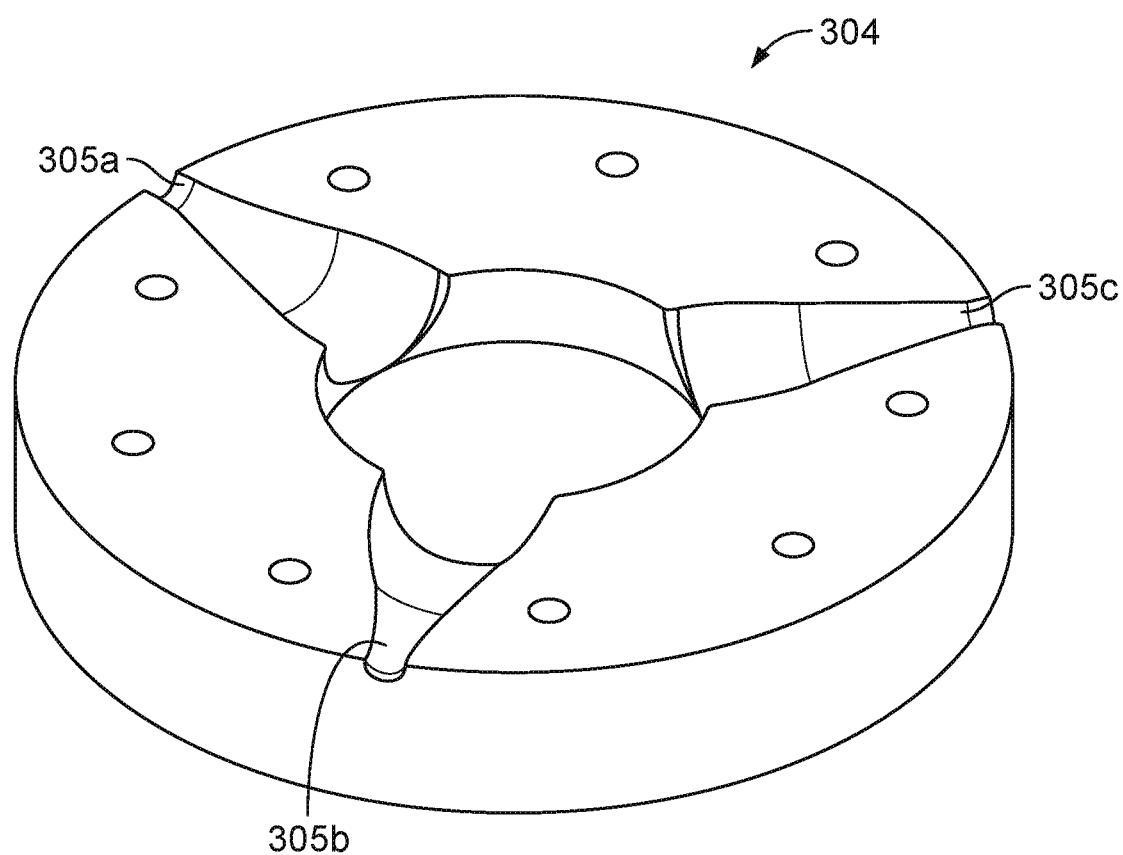
FIG. 33 provides an example structural diagram for a jet delivery mechanism with multiple nozzles, according to some embodiments described herein.

FIG. 33 provides an example structural diagram for a jet delivery mechanism with multiple nozzles, according to some embodiments described herein. A three-position nozzle 304 is configured with three evenly spaced jets 305*a-c*, which can balance the reaction forces of the jet delivery and deliver the dispensable substance at three sites 305*a-c*. In some implementations, a different number of nozzles, e.g., two, four, five, six, etc., may be used in a similar way as illustrated by the three-position nozzle 304. In some implementations, a two-position nozzle is configured with the nozzles 180 degrees apart.

In some implementations, a multi-nozzle outlet similar to 304, can be used to deliver the dispensable substance with controlled pressured based on factors such as but not limited to the location of the GI tract that the ingestible device, the thickness of the mucosal wall, the nature of the dispensable substance (how deep the dispensable substance is to be delivered into the wall of the GI tract), and/or the like. For example, when the dispensable substance is to be delivered locally, e.g., past the mucus and into the first layer of cells, the ingestible device may adjust the amount of pressure to be generated for the local delivery. As another example, when the dispensable substance is to be delivered systemically, e.g., to be delivered in to the submucosa, the ingestible device may configure a relatively higher pressure amount for the high velocity jet to initiate a jet delivery.

In some implementations, the ingestible device may delivery the dispensable substance in a series of release events by controlling the timing and amount of pressure generated. For example, a pre-defined delivery pattern may be stored at the PCT 132 (as further illustrated in FIG. 44) to deliver the dispensable substance in a series of delivery events, e.g., intermittently (e.g., every few seconds, etc.), constantly or continuously (e.g., delivering the full payload within a few seconds, etc.). The amount of pressure to be generated by the ingestible device is thus pre-programmed into the PCT 132 based on the delivery pattern.

In some implementations, a microcontroller in the PCB 132 (as further illustrated in FIG. 44) may control the amount of pressure generated for delivery based on a matrix of delivery variables. The delivery variables may include, but not limited to the number of radial nozzles (e.g., 1, 2, 3, 4, 5, etc.), the design of the nozzle (e.g., shape and geometry parameters of the nozzle, etc.), the number of release events (e.g., 1, 2, 3, 4, 5, continuous, etc.), time duration between the release events (e.g., 5 seconds, 10 seconds, 30 seconds, 2 minutes, etc.), the range of pressure that the ingestible device is configured to generate (e.g., 50 psi, 150 psi, 300 psi, etc.), the amount of dispensable substance (e.g., payload 10 μl to 1500 μl, etc.), the distance of the ingestible device from tissue or the inner wall of the GI tract (referred to as "offset distance"), and/or the like.

Figure 34:
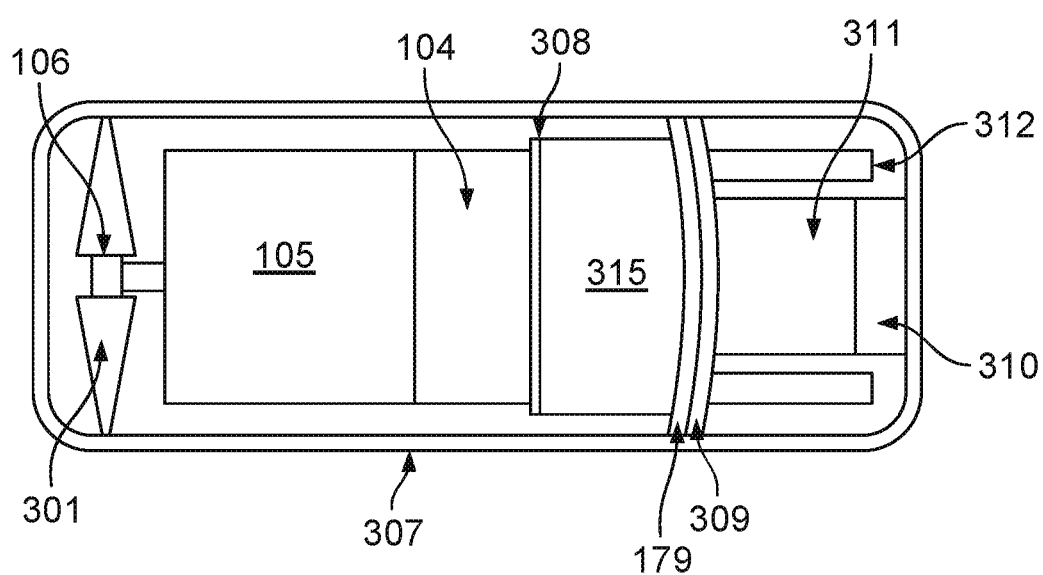
FIG. 34 provides an alternative example structural diagram for a jet delivery mechanism with chemical actuation, according to some embodiments described herein.

FIG. 34 provides an alternative example structural diagram for a jet delivery mechanism with chemical actuation, according to some embodiments described herein. The ingestible device may use chemical reaction of mixing one or more reagents 311-312 to generate a sufficient volume of gas into the pressure chamber 315 to propel the piston 104 for dispensable substance delivery. The chemical reaction may be initiated using a combination of an enteric coating 307 on the outer wall of the ingestible device, which may dissolve to expose the pump 310 in the GI tract. Once exposed to the GI fluid, the pump 310 may be driven by osmosis (osmotic-driven pump) or by peristalsis (peristalsis-driven pump, such as a physiologic peristalsis-driven pump)

and may apply enough pressure to break the diaphragm seal/spring 309. When the diaphragm seal 309 is broken, a first reagent 311 that is pre-stored in a separate chamber from a second reagent 312 can get in contact with the second reagent 312 to initiate the chemical reaction. The reaction can create gas that may pass through the semipermeable membrane 179 into the pressure chamber 315. An integrated shear ring 308 is disposed on one end of the piston 104 to stabilize the piston 104, and may release the stored energy from the pressure chamber 315 to deliver the payload substance 105 through the jet nozzles 301 (two nozzles are shown for illustrative purpose).

The release of gases during chemical reactions can increase the pressure within the ingestible device, providing the desired drive mechanism. The chemical reaction between acids and bases is considered as a fast reaction which can produce large amounts of gas as a product. The accumulation of product gas within the small capsule may provide the required pressure for a drug delivery jet. The amount of gas and pressure can be controlled by careful selection of the reaction and the stoichiometry of the process. An ideal chemical reaction has to be fast and should not release toxic or unsafe products for in-vivo use.

The reaction between acetic acid and sodium bicarbonate may be implemented. The products include carbonic acid and sodium acetate. Preliminary analysis of acid and base dissociation constants (pKa, pKb) of the chemical reaction indicates that the equilibrium tends to favor the right side of reaction, producing large quotients of the products relative to the reactants.

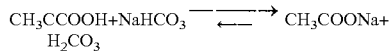

Completion of the reaction involves dissociation of the reactants in water and release of their ions.

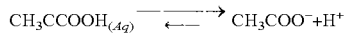

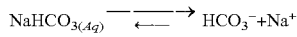

In a low pressure aquatic environment, carbonic acid decomposes into water and carbon dioxide in gaseous form. With the release of carbon dioxide in a small container, the pressure within the container will rise providing the pressure drive needed for pushing a jet of drug toward the target tissue. Initial analysis of the equilibrium constant (KC and KP) and Henry's law for gases, suggest that, with sufficient carbonic acid production, carbon dioxide is released into the closed chamber adequate to meet the pressure requirements.

In an aquatic environment carbonic acid will also dissociate and release protons. The rate of dissociation of carbonic acid, is a function of alkalinity of the solution and the partial pressure of the released gas.

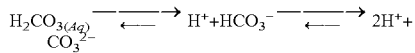

The above described reactions are reversible reactions suggesting that with an increase in the ratio of the products to the reactants, the rate of reaction will decrease. In addition to the stoichiometric ratios, the partial pressures of the products can also affect the rate and direction of reaction. The release of multiple ions, limitations on ionization and solubility of the reactants and products, and impacts of the changes in pressure make the chemical drive system a complicated environment to model. As a result, careful selection and analysis of the stoichiometric ratios, molarities of acid and size of the chamber is needed before an efficient and safe chemical drive system is implemented.

As an example, the ingestible device may have a 400 μl of payload 105, 50% of which by volume is acetic acid in water combining with dry carbonate. The ingestible device may need a 1651 μl pressure chamber 315 and a 30 μl of reagents 312. Moving the 30 μl reagent with an osmotic pump at 100 pound-force per square inch (PSI) may require less than 1 μl of salt for the osmotic pump 310 having a 4 mm-diameter osmotic membrane.

Figure 35:
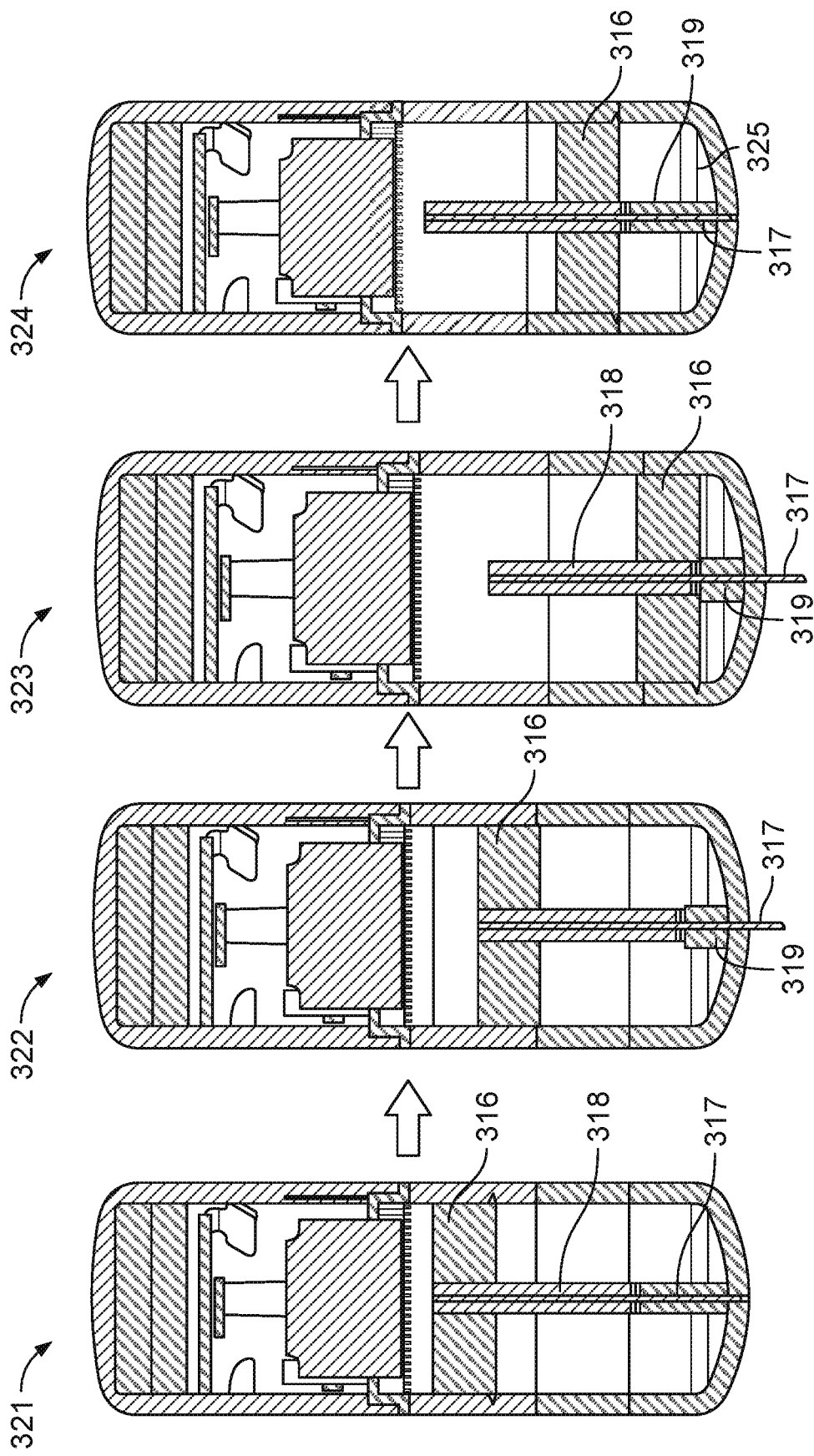
FIG. 35 provides example structural diagrams illustrating direct injection of dispensable substance with a needle by an ingestible device, according to some embodiments described herein.

FIG. 35 provides example structural diagrams illustrating direct injection of dispensable substance with a needle by an ingestible device, according to some embodiments described herein. The ingestible device may include a single needle 317 that is housed within a needle guide 318, or an array of needles (now show in FIG. 35), which may be extended out of and retracted back inside the ingestible device. One end of the needle guide 318 is placed within a piston 316.

At state 321, the needle 317 is inside the ingestible device and the piston 316 is in a home position at one end of the storage reservoir. At state 322, when the ingestible device is actuated, e.g., by a gas-generating cell generating gas, the piston 316 moves towards an outlet of the ingestible device. The friction between the piston 316 and the needle guide 318 is higher than the impedance force at the inner wall of the ingestible device, so that the needle 317 advances out of the ingestible device. A spring 319 can be compressed at the axial end of the ingestible device to allow the needle 317 to extend out of the ingestible device. At state 323, once the spring 319 is fully collapsed, the pressure from the gas-generating cell may keep building up to a level sufficient to overcome the static friction between the piston 318 and the needle guide 318 so that the piston 316 keeps moving towards the outlet of the ingestible device and thus expose dispensable substance to the end of the needle 317 that is still inside the ingestible device. In this way, the substance can be dispensed through the needle 317 (with a hollow center) when the piston keeps moving. At state 324, after the dispensing, the gas-generating cell is turned off. Spikes may be placed at the inner wall at one end 325 of the ingestible device to puncture holes in the piston 316 when the piston 316 reaches the end 325. After the holes are punched, the pressure on the two sides of the piston 316 may be balanced and the spring 316 may drive the piston 316 and needle 317 back into a retracting position, e.g., the needle 317 within the ingestible device.

Figure 36:
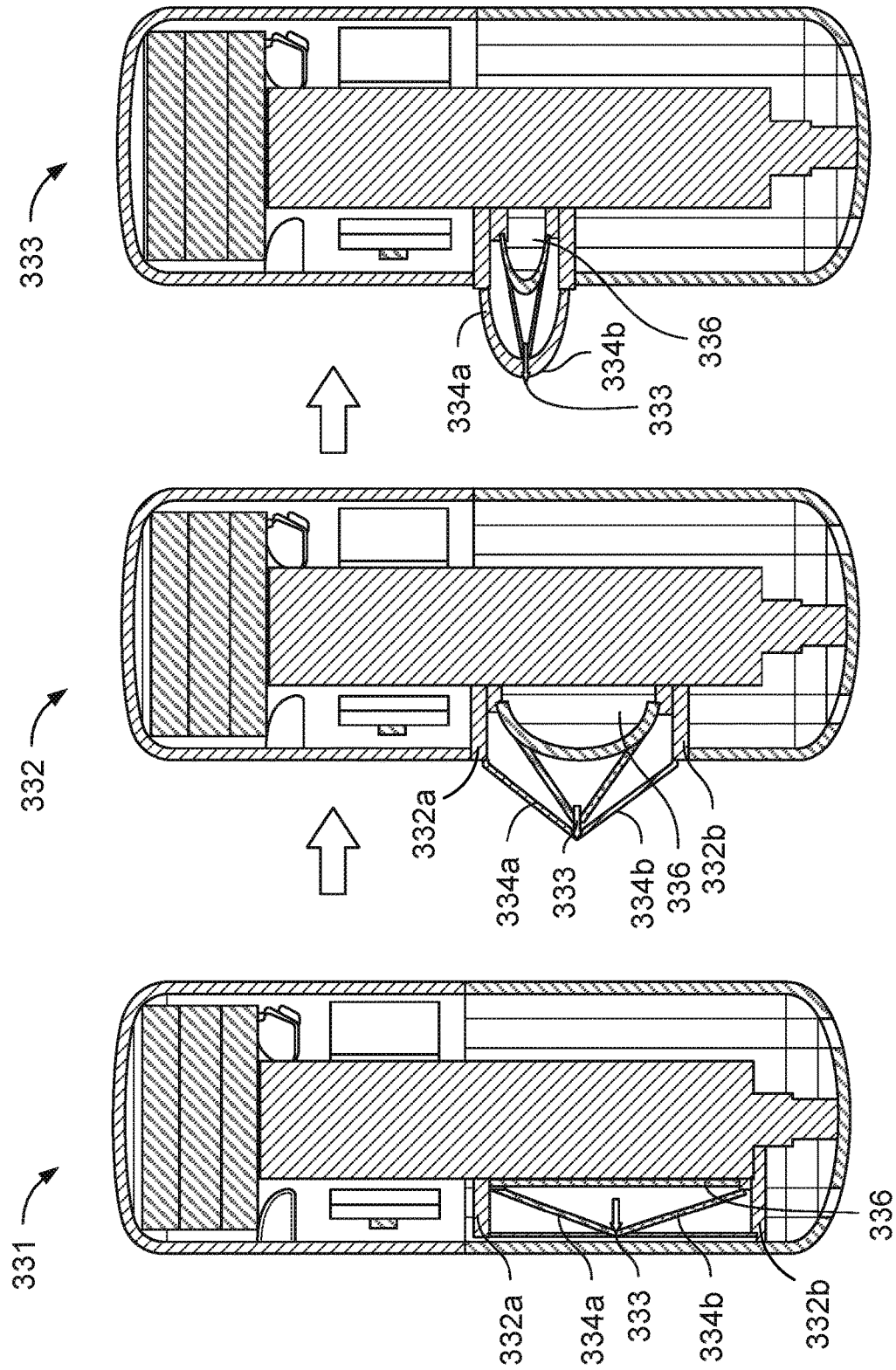
FIG. 36 provides alternative example structural diagrams illustrating a non-axial configuration of the injection needle for delivery, according to some embodiments described herein.

FIG. 36 provides alternative example structural diagrams illustrating a non-axial configuration of the injection needle for delivery, according to some embodiments described herein. A radial version of the direct injection as described in FIG. 35 is illustrated in FIG. 36, by using a balloon 336 (similar to a catheter balloon) filled with the dispensable substance and placed inside the ingestible device. A flexible truss or linkage mechanism 334a-334b and 332a-b can be used to support a needle 333 to be moved out of the ingestible device. At state 331, when the balloon 336 is deflated, the needle and the linkage mechanism 332a-b and 334a-b are within the ingestible device. At state 332, when the balloon 336 is activated, e.g., by gas generated by a gas-generating cell, the two nodes of the linkage mechanism 332a-b may be propelled to move towards each other because of the deformation of the balloon 336. As a result, the truss 334a-b with the needle 333 may be forced out of the ingestible device. At state 333, when the balloon keeps deforming 336 and thus further pushes the truss 334a-b, the needle 333 may be pushed out to inject the dispensable substance from the ingestible device to the GI tract.

Figure 37:
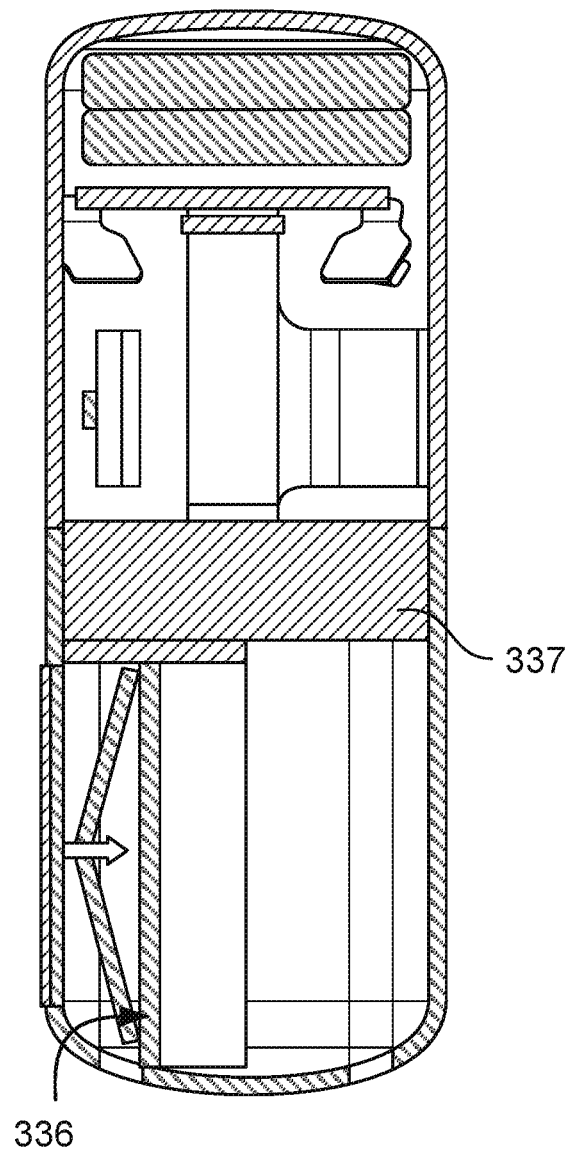
FIG. 37 provides an example structural diagram illustrating a non-axial configuration of the injection needle driven by an osmotic cell, according to some embodiments described herein.

A gear motor or optionally a piston driven by either osmosis or a gas cell can be used to inflate the balloon 336. FIG. 37 provides an example structural diagram illustrating a non-axial configuration of the injection needle driven by an osmotic cell, according to some embodiments described herein. An osmotic cell 337 can be used to generate pressure to inflate the balloon 336. Once the balloon 336 is inflated, the needle may deliver the substance out of the ingestible device in a similar manner as discussed in FIG. 36.

Figure 38:
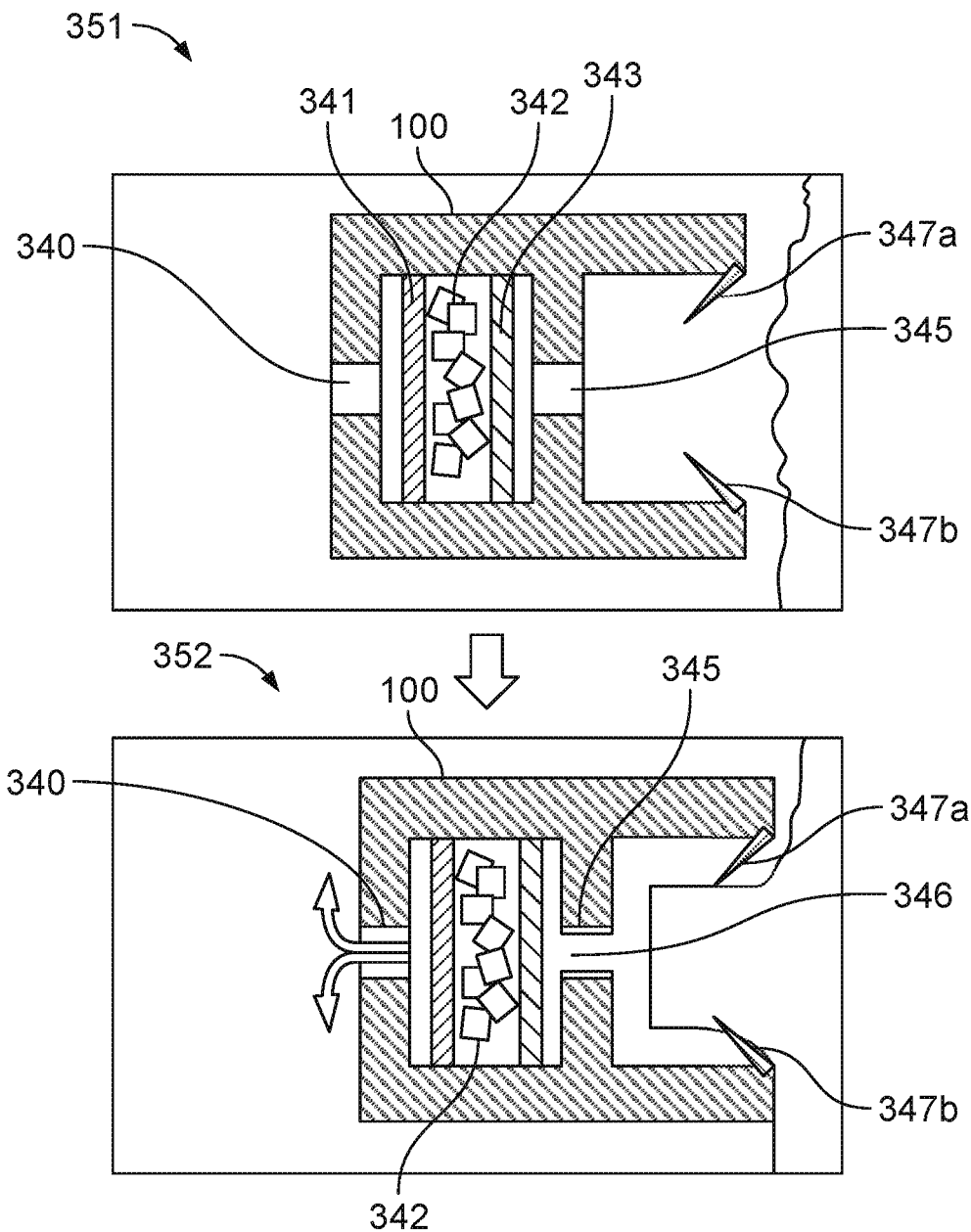
FIG. 38 provides example structural diagrams illustrating using osmotic pressure to adhere a suction device of the ingestible device to the intestinal wall, according to some embodiments described herein.

FIG. 38 provides example structural diagrams illustrating using osmotic pressure to adhere a suction device of the ingestible device to the intestinal wall, according to some embodiments described herein. The ingestible device 100 may have an osmotic mechanism that has a chamber 342 storing salt crystals. The chamber 342 includes a mesh 341 placed in proximate to a burst valve 340 at one end of the chamber 342, and a reverse osmosis (RO) membrane 343 placed in proximate to a valve 345 on the other end of the chamber 342. A suction device, e.g., two or more suction fingers 347*a-b* (two fingers are shown in FIG. 38 for illustrative purpose), is placed outside of the chamber 342, with an open outlet exposed to luminal fluid in the GI tract.

At state 351, the osmotic mechanism is inactivated, e.g., the valve 345 is closed so that no luminal fluid is drawn into the osmotic chamber 342. At state 352, when the osmotic mechanism is activated by opening the valve 345, luminal fluid enters the ingestible device 100 through an outlet of the suction device 347*a-b* and enters the osmotic chamber 342 through the valve 345. The salt in the chamber 342 is then dissolved into the fluid. The RO membrane 343 prevent any fluid to flow in the reverse direction, e.g., from inside the chamber 342 to the valve 345. The fluid continues to flow, e.g., through the flow path 346, until all the salt contained in the chamber 342 is dissolved or until intestinal tissue is drawn into the suction device 347*a-b*. As luminal fluid keeps flowing into the chamber 342, the solution of the luminal fluid with dissolved salt in the chamber 342 may reduce osmotic pressure such that the suction force at 347*a-b* may also be reduced. In this way, suction of the intestinal tissue may stall before the tissue is in contact with the valve 345 to avoid damage to the intestinal tissue. If the valve 340 is a burst valve, when more and more luminal fluid enters into the chamber 342, the luminal fluid may eventually break the burst valve 340 and osmotic flow may reverse, actively pushing the intestinal tissue out of the suction device 347*a-b*. The mesh 341 placed in proximate to the burst valve 340 may prevent the salt crystals from exiting the chamber 342.

FIG. 39 provides an example structural diagram illustrating an ingestible device employing an osmotic mechanism and a suction device as illustrated in FIG. 38, according to some embodiments described herein. The ingestible device 100, as shown in FIG. 39, an outlet 107 is placed at one end of the ingestible device 100. A suction device, e.g., two or more suction fingers 347*a-b* (similar to those depicted in FIG. 38), is disposed in proximate to the outlet 107. The outlet 107 is in connection with a storage reservoir 135 storing the dispensable substance (e.g., therapeutic agent) 105. The storage reservoir 135 is in contact with a piston 363 (similar to 104 in FIG. 1), which can be propelled by pressure generated from the osmotic pump 362 to move towards the outlet 107. The osmotic pump 362 is similar to the osmotic mechanism described in FIG. 38. A breakaway section 361 is placed in proximate to the other end (opposite to the end where the outlet 107 is disposed) of the ingestible device 100, as further described in FIG. 40.

FIG. 40 provide example structural diagrams illustrating aspects of tumbling suction by an ingestible device as described in FIG. 39, according to some embodiments described herein. As shown in FIG. 39, the ingestible device 100 does not require any electronics or other actuation elements. As shown in FIG. 40, the ingestible device 100 may constantly, intermittently, or periodically tumble when travelling through the intestine 370. When the ingestible device tumbles to a position that the outlet 107 is in direct contact with the intestinal wall 371, a suction process similar to that described in FIG. 38 may occur. Additional structural elements such as fins, flutes or the like may be added to the outer wall of the ingestible device 100 to promote the tumbling motion.

As shown in FIG. 40, when the ingestible device 100 tumbles from position 372*a* or 372*b* to position 372*c*, the axial end, e.g., the outlet 107, contacts the intestinal wall 371 with some pressure. The amount of pressure may push a small amount of tissue of the intestinal wall 371 to enter the outlet 107, such that the inward-pointing suction fingers 347*a-b* may latch onto the intestinal wall 371. At position 372*d*, the breakaway section 361, which is pre-fixed at one end of the ingestible device using an enteric coating or glucose based retaining feature, may be removed from the ingestible device 100 to expose the osmotic pump 362, as the enteric coating or glucose can dissolve in the GI tract.

Figure 41:
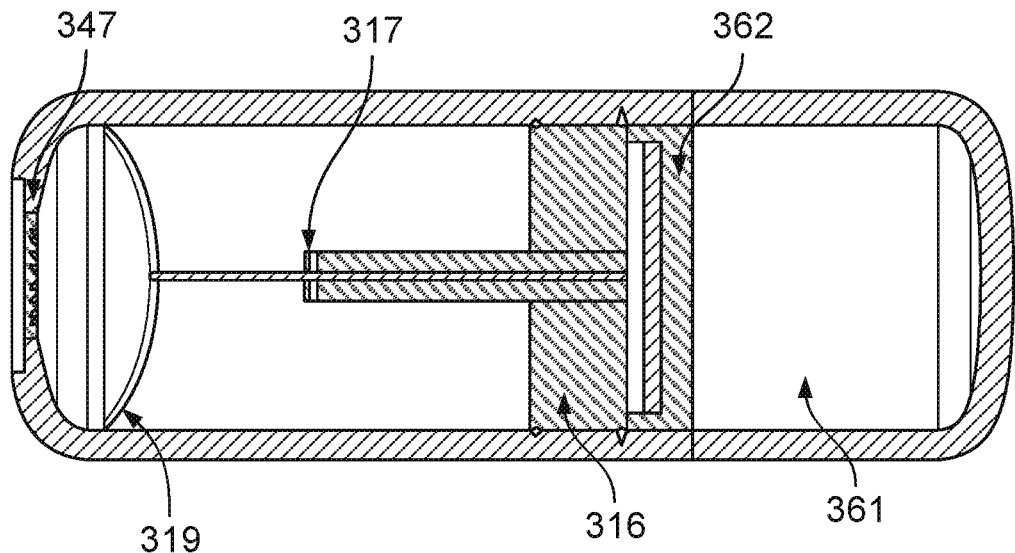
FIG. 41 provides an example structural diagram illustrating an ingestible device employing a combination of a tumbling suction and needle injection, according to some embodiments described herein.

FIG. 41 provides an example structural diagram illustrating an ingestible device employing a combination of a tumbling suction and needle injection, according to some embodiments described herein. As shown in FIG. 41, the ingestible device includes an inward barb disc 347 hosting a number of suction fingers/barbs (e.g., similar to 347*a-b* as shown in FIG. 39). A diaphragm spring 319 is connected to one end of a storage reservoir of the ingestible device, and one end of a needle 317 is connected to the spring 319. The other end of the needle 317 is housed within a piston 316 at the other end of the storage reservoir. The piston is located proximate to an osmotic cell 363, which is similar to the osmotic pump 362 in FIG. 39. The dissolving material 361 is similar to the breakaway device 361 in FIG. 39.

Therefore, as the ingestible device enters and travels along the intestine, which the dissolving material 361 may dissolve and thus expose the osmotic cell 362 to the luminal fluid. The osmotic cell 362 may then generate osmotic pressure to propel the piston 316 to move towards the inward barb disc 347. In the meantime, the ingestible device may suck a portion of the intestinal tissue by the inward barb disc 347, e.g., in a similar manner as described in FIG. 40. The needle 317 may then, when the piston 316 keeps moving due to the osmotic pressure, extend into the intestinal tissue grabbed by the inward barb disc 327, and inject the dispensable substance into the intestinal tissue. The needle movement and injection process may be similar to that described in FIG. 35.

Figure 42:
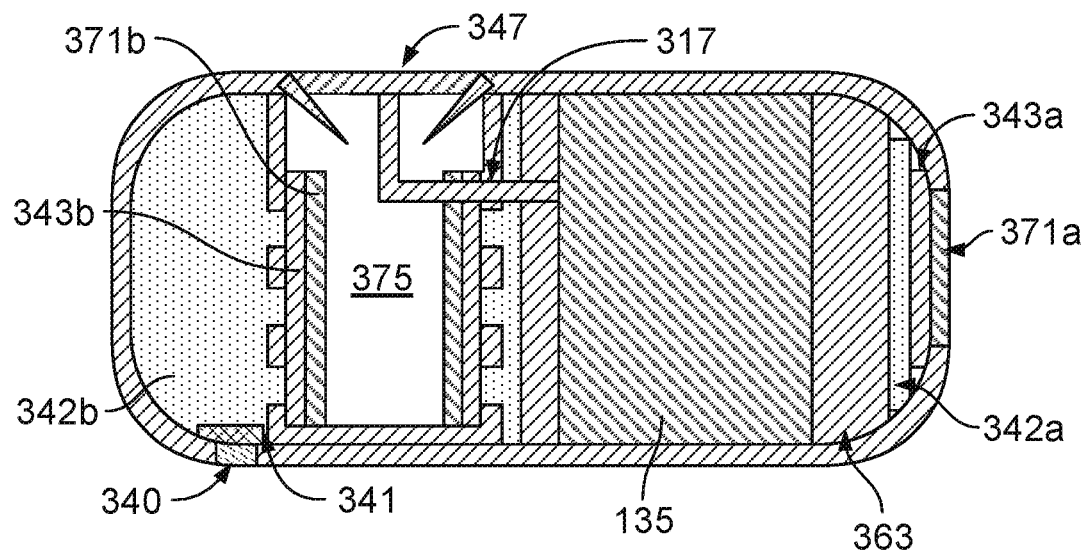
FIGS. 42-43 provide example structural diagrams illustrating an ingestible device employing a combination of a tumbling suction and needle injection, according to some embodiments described herein.
Figure 43:
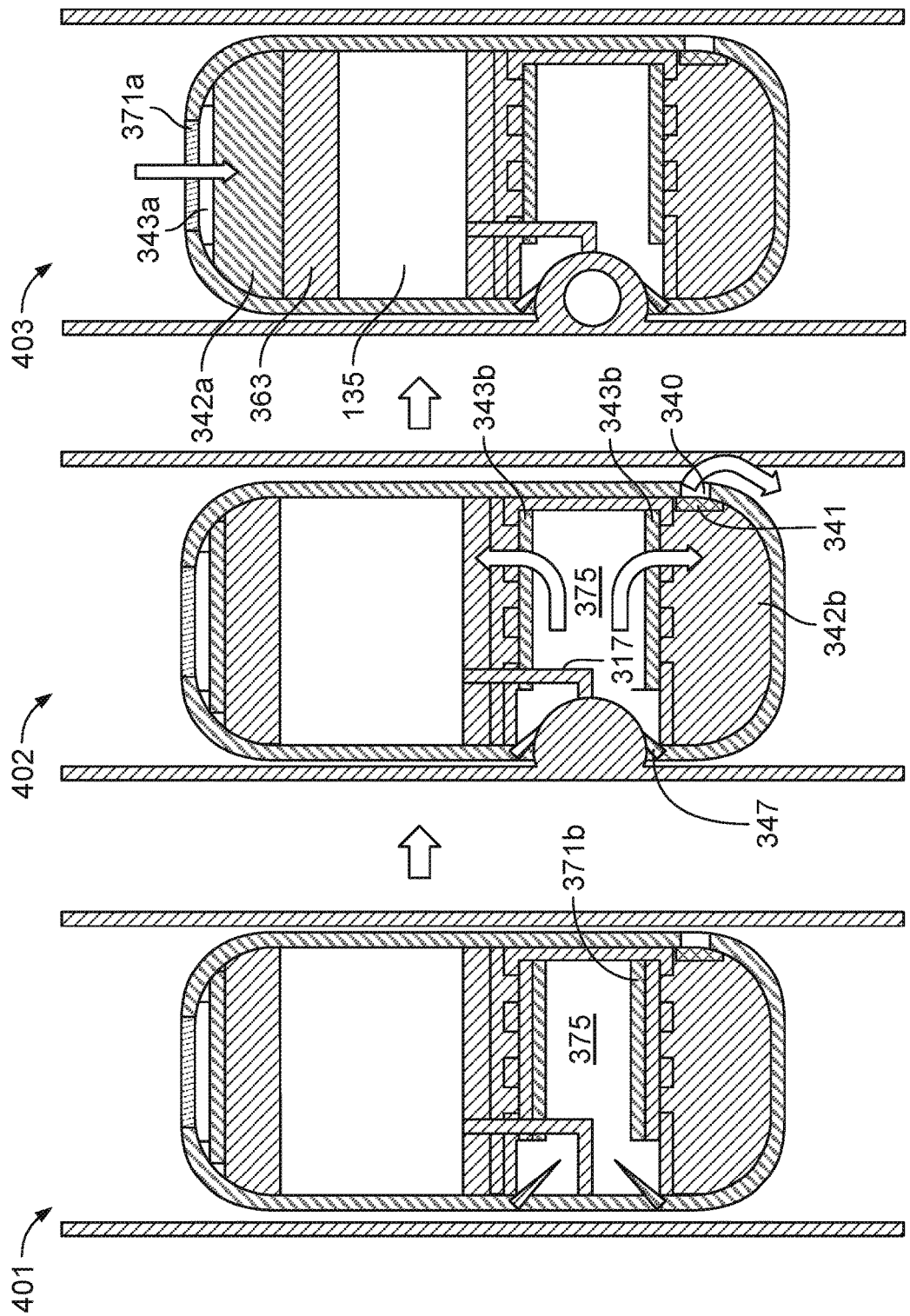

FIGS. 42-43 provide example structural diagrams illustrating an ingestible device employing a combination of a tumbling suction and needle injection, according to some embodiments described herein. The osmotic mechanism described in FIG. 38 may be combined with an osmotically driven piston 363, a statically positioned needle 317 that has a hollow center and is exposed to the dispensable substance stored in the storage reservoir 135, and two enteric coatings 371*a-b* to inject a dispensable substance into the intestinal wall.

The ingestible device has an empty chamber 375 connected to a suction device 347 for the luminal fluid to draw into. The inner wall of the empty chamber 375 may be covered by short-delay enteric coating 371*b*. As shown in FIG. 43, at state 401, the ingestible device, similar to that described in FIG. 42, may enter into the intestine. At state 402, the short-delay enteric coating 371b may break down and thus allow luminal fluid to contact the semipermeable membrane 343b. Water is then drawn into the salt chamber 342b from the luminal fluid in the chamber 375, and then released out of the slat chamber 342b by breaking the burst valve 340. A mesh screen 341 prevents whole salt crystals from being released outside the ingestible device. In this way, as water keeps being drawn from the luminal fluid in chamber 375, the osmotic actuation draws more luminal fluid into the chamber 375, and tissue of the intestinal wall may be sucked into the chamber 375 by the suction device 347. The suction device 347, when drawing the intestinal tissue, can also anchor the ingestible device to the intestinal wall. The needle 317 may pierce into the grabbed tissue of intestinal wall.

At state 403 in FIG. 43, after tissue of the intestinal wall has been grabbed by the suction device 347, the long-delay enteric coating 371a, which is placed at an end of the ingestible device, may break down and allow luminal fluid to contact the semipermeable membrane 343a placed in proximate to the end of the ingestible device. Water is then drawn into the salt chamber 342a, and actuates a piston 363 by creating osmotic pressure. The piston 363 then pushes the dispensable substance out of the storage reservoir 135 via the needle 317 into the intestinal tissue grabbed by the suction device 347.

After the dispensable substance payload is fully released from the storage reservoir 135, osmotic pressure will build behind the piston 363 within the storage reservoir. This pressure can be used to retract the needle 317 or expand the suction device 347 opening to release the tissue of the intestinal wall. Alternatively, after a period, after the dispensable substance has been delivered and the piston 363 is pushed to the end of the storage reservoir 135, the ingestible device may naturally detach from the intestinal wall and can then be safely passed. The needle 317 and barbs of suction device 347 are located within the ingestible device and cannot contact the intestinal wall without vacuum.

The example ingestible device shown in FIG. 42 may deliver 400 μl of payload dispensable substance, with a reduced total size as compared to that having a gas-generating cell and a gas chamber.

The hooks, stents, needles, barbs, suction devices or the like, shown throughout FIGS. 1-43, may be made of bioresorbable or biodegradable materials, such as, but not limited to polyglycolide, poly-L-lactic acid (PLLA), poly-L-D-lactic acid (PLDA), Poly ε-caprolactone-Poly Lactic Acid (PCL-PLA) blends and alloys, polyorthoester (POE), poly (DL-lactide) (PDLLA), poly(lactide-co-glycolide)(PLGA), polydioxanone (PDS), polycaprolactone (PCL), Poly (alkyl cyanoacrylates) (PCA), Polyanhydrides, Poly(ortho esters), or any bioresorbable polymer with suitable material properties such as the degradation rates and rigidity to hook, grab, pierce into, or grip the intestinal wall and may dissolve or be absorbed in the human body after an amount of time.

FIG. 44 provides an example structural diagram illustrating aspects of an electronic component including a PCB within the housing of the ingestible device, according to some embodiments described herein. The PCB 132 may take a form that fit into the ingestible device and wrap around the gas-generating cell. In one example, when the PCB 132 has a separate battery cell 131, the overall height of the PCB 132 may be substantially 19 mm. In another example, the PCB 132 may achieve a reduced height of 14 mm with an integrated gas-generating cell 131, which may further reduce the height of the PCB 132 to be under 10 mm. In this way, the PCB design may save space for the storage reservoir.

In some embodiments, the PCB 132 may include (but is not limited to) any combination of a microcontroller, an optical sensing unit, a power supply (such as a battery 131), a communication unit, communication peripherals to connect the different components, and/or the like.

In some embodiments, the microcontroller includes programming, control and memory circuits for holding and executing firmware or software, and coordinating all functions of the ingestible device (e.g., see 100 in FIG. 1) and the other peripherals embedded on the PCB 132. For example, the microcontroller may be implemented using a 32-bit microcontroller, such as the STM32 family of microcontrollers from STMicroelectronics™, although any suitable microcontroller may be used.

In some embodiments, the communication unit can receive operating instructions from an external device, such as a base station (e.g., an infrared transmitter and/or receiver on a dock). The base station may be used for initially programming the ingestible device (e.g., 100 in FIG. 1) with operating instructions and/or communicating with the ingestible device 10 during operation in real-time or after the ingestible device is retrieved from the body. In some embodiments, the communication unit does not receive any operating instructions from an external device, and instead the ingestible device operates autonomously in vivo.

In another embodiment, endoscopic tattooing may be used to mark or identify a location of disease (e.g., luminal digestive tract lesions) or an upstream of a disease. The identification of the specific location of disease may in turn trigger an operation of the ingestible device. For example, the optical sensing unit may detect the presence of an endoscopic tattoo (e.g., a green dye) administered during an earlier procedure, which may trigger the release of a therapeutic at or near the disease site by activating gas generation of the gas-generating cell.

In other embodiments, a triggering mechanism or marker such as a stainless steel clip or a magnet may be used to mark or identify sites of disease. For example, the mechanism may trigger an operation of the ingestible device, e.g., the magnet may open a valve on the ingestible device such that the dispensable substance may be delivered. The local triggering mechanism (e.g., endoscopic tattooing) may not necessarily be for region-specific delivery of dispensable substances, such as, for example, therapeutic agents.

In some embodiments, the communication sub-unit can include an optical encoder, such as an infrared emitter and receiver. The IR emitter and receiver can be configured to operate using modulated infrared light, i.e. light within a wavelength range of step 850 nm to 930 nm. Furthermore, the IR receiver may be included in the ingestible device for receiving programming instructions from the IR transmitter at the base station and the IR transmitter may be included in the ingestible device for transmitting data to the IR receiver at the base station. Bidirectional IR communication between the ingestible device and the base station can therefore be provided. It will be understood that other types of optical encoders or communication sub-units can be used in some embodiments; for example, some communication sub-units may utilize Bluetooth, radio frequency (RF) communications, near field communications, and the like, rather than (or in addition to) optical signals.

The optical sensing unit can be placed on the PCB at a position that is on the side of the housing of the ingestible device. The optical sensing unit may include various sensors to obtain in vivo information while the ingestible device is in transit inside the body. Various sensors, such as radial sensors around the housing of the ingestible device and axial sensors along the axis of the ingestible device, can be provided at different locations of the ingestible device to help identify where the ingestible device may be within the body. In some embodiments, the data provided by the sensors can be used for triggering an operation of the ingestible device, e.g., to trigger the gas-generating cell (e.g., 103 in FIG. 3) to start generating gas. Each sensor can include an illuminator that can generate an illumination to an external environment of the ingestible device, and a detector that can detect a reflectance from the environment in response to the generated illumination. The reflectance may be transmitted to the microcontroller via the communication peripherals on the PCB 132, to identify a specific location of the ingestible device.

For example, the optical sensing unit may include sensors with an infrared Light-Emitting Diode (IR-LED) as an illuminator, and a detector sensitive to illumination in the infrared spectrum. The sensors may, in some embodiments, include a yellow-green LED emitting light having a wavelength of approximately 571 nm as an illuminator. In some embodiments, the sensors may comprise a green LED emitting light having a wavelength of approximately 517 nm and a red LED emitting light having a wavelength of approximately 632 nm. In some embodiments, the sensors may include an RGB LED package capable of emitting illumination at a plurality of different wavelengths.

In some embodiments, the sensors may include collimated light sources. The collimated light sources can orient reflective light in order to maximize reflectance from certain external environments, such as anatomies that are circular in shape. For example, the illumination may be provided by collimated light sources, which may be provided using LED binning or supplemental lenses, or by a combination of collimated and non-collimated light sources.

The detected reflectance in response to the illumination may be used to determine by the microcontroller a location of the ingestible device in the GI tract. In this way, the ingestible device may keep track of a current region of the gastrointestinal tract surrounding the device, and monitor the environment around the device to determine changes from one region to another. In some embodiments, the ingestible device may autonomously identify a location of the device within the gastrointestinal tract of a body by monitoring the changes from one region to another. In some embodiments, the ingestible device may function as a state machine, wherein the state tracks the current portion of the gastrointestinal tract where the ingestible device is located. The ingestible device may distinguish between various locations including a starting point outside the body, a stomach, a duodenum, a jejunum, a caecum, a large intestine, and an exit point outside the body. In some embodiments the ingestible device may distinguish only between a stomach, a small intestine, (e.g., a small intestine which may include the duodenum and the jejunum), and a large intestine (e.g., a large intestine which may include the caecum, and the large intestine). In some embodiments, the ingestible device may distinguish between a subset of the above mentioned locations, and/or a combination of the above locations and other locations, such as a mouth, an ileum, or a rectum.

In some embodiments, the ingestible device may transmit illumination at a first wavelength towards an environment external to a housing of the ingestible device, detect the resulting reflectance, and store a reflectance value in a data set based on the first reflectance. For example, the ingestible device may transmit illumination at a red wavelength, detect a red reflectance, and store a reflectance value in a red data set that indicates how much light was measured in the red reflectance. The ingestible device may repeat this process for a number of other types of illumination at other wavelengths, such as blue, green, or infrared wavelengths. The ingestible device may keep track of reflectance data gathered from reflectance sensors (i.e., radial detectors) in each of the red, green, blue and IR spectra.

This data may then be used by an onboard microprocessor to perform a localization algorithm that identifies a pyloric transition from stomach to the duodenum portion of the small intestine; a treitz transition from the duodenum to the jejunum; an ileocaecal transition from the ileum (i.e., the area located at the end of the jejunum) to the caecum; and a caecal transition from the caecum to the rest of the large intestine. This can be accomplished by using a plurality of different wavelengths of light, measuring the different amounts of light reflected by the environment around the device, and determining the location of the device in view of the different optical absorption properties of the different regions of the gastrointestinal tract. The ingestible device may gather this data at periodic intervals, and in some embodiments, these may be spaced one second to 10 minutes apart. For example, the ingestible device may intermittently, constantly or periodically detect a location of the ingestible device until it is determined that the ingestible device is within the small intestine, and then the ingestible device may activate the gas-generating cell to generate gas and thus propel a dispensable substance out of the housing. It is to be noted that in at least some implementations, the electronic component is configured to automatically activate the gas-generating cell in response to an identification of the location of the ingestible device, e.g., based on analyzing the obtained reflectance as discussed above. No external triggering outside the ingestible device is needed. Alternatively, the electronic component is not pre-programmed with any activation condition, such as but not limited to activation after a pre-determined period, and/or the like. In at least another implementation, the ingestible device does not rely on a pH-sensitive enteric coating to determine the location, e.g., especially in specific parts of the GI tract where it is difficult to target based solely on pH-sensitive enteric coating, such as but not limited to sections immediately after passing through the pyloric sphincter, or sections immediately prior to the ileocecal valve. Further discussion of localization of the ingestible device may be found in PCT International Application No. PCT/US2015/052500, filed on Sep. 25, 2015, which is herein expressly incorporated by reference.

The memory unit can be provided with a memory storage component, such as a flash storage, EEPROM, and the like. The memory unit can be used to store the instructions received from the base station and to store various other operational data, such as transit data and sensor data collected by the optical sensing unit. For example, the memory unit can store pre-defined reflectance parameters that indicates a specific location and instructions to identify an instant location of the ingestible device based on a measured reflectance. For another example, the memory unit can store pre-defined parameters and instructions for an amount of the dispensable substance to be delivered, and when there are multiple chambers for different dispensable substances, instructions to determine and to dispense a dispensable substance based on the obtained reflectance. In some embodiments, the microcontroller can operate to execute the instructions stored at the memory unit, which may involve operating other components of the ingestible device, such as the optical sensing unit, the communication unit and the power supply.

In some embodiments, the power supply can include one or more batteries 131 formed from different chemical compositions, such as lithium polymer, lithium carbon, silver oxide, alkaline, and the like. This can be helpful in accommodating the different power requirements of the various components in the ingestible device. In some embodiments, the power supply may include a silver oxide battery cell for supplying power to the various components in the ingestible device. The battery cells 131 that supply power to the power supply may operate at 1.55V. For example, a silver oxide coin cell type battery, such as those manufactured by Renata™, may be used since the silver oxide coin cell battery has discharge characteristics that suit the operation of the ingestible device. In some embodiments, other types of battery cells may be used.

In some embodiments, it is possible to include one or more battery cells 131. For example, multiple coin cells may be used to provide higher voltage for the operation of the ingestible device. It may also be possible for the power supply 131 to include one or more different types of battery cells.

Also, the power supply may be split into one or more cell groups to prevent a temporary interruption or change at the power supply from affecting the overall operation of the ingestible device. For example, an example power supply can include three cells and each cell is operable to provide 1.55 volts. In one example embodiment, the three cells can be provided as one cell group operable to provide 4.65 volts as the full voltage. A voltage regulator may control the voltage that is provided by the cell group. The voltage regulator may operate to provide a regulated voltage, such as 3.3 volts, to the microcontroller, while operating to provide the full voltage to the optical sensing unit. In another example embodiment, the three cells can be provided as two different cell groups, with a first cell group including two cells and a second cell group including one cell. The first cell group, therefore, can provide 3.1 volts while the second cell group can provide 1.55 volts. The first cell group may be operable to provide 3.1 volts to the microcontroller to prevent voltage variations. The first cell group and the second cell group can then be combined to provide 4.65 volts to the optical sensing unit.

In some embodiments, the power supply 131 may be removed from the ingestible device to be recharged by recharging circuitry that is external to the ingestible device. In some embodiments, the power supply 131 may be recharged while in the ingestible device when recharging circuitry is included on the PCB 132; for example, by providing circuitry that allows the ingestible device to be inductively coupled to a base station and charged wirelessly.

In some embodiments, an ingestible device has a drive mechanism that provides positive pressure to provide sufficient energy to deliver a bolus of dispensable substance (e.g., therapeutic agent) to a desired location, such as the side wall of the small intestine, by way of a high velocity jet through a nozzle. Exemplary alternative applications for the drive mechanisms include providing energy to release mechanisms, and providing suction to attach devices to the intestinal wall.

Figure 45:
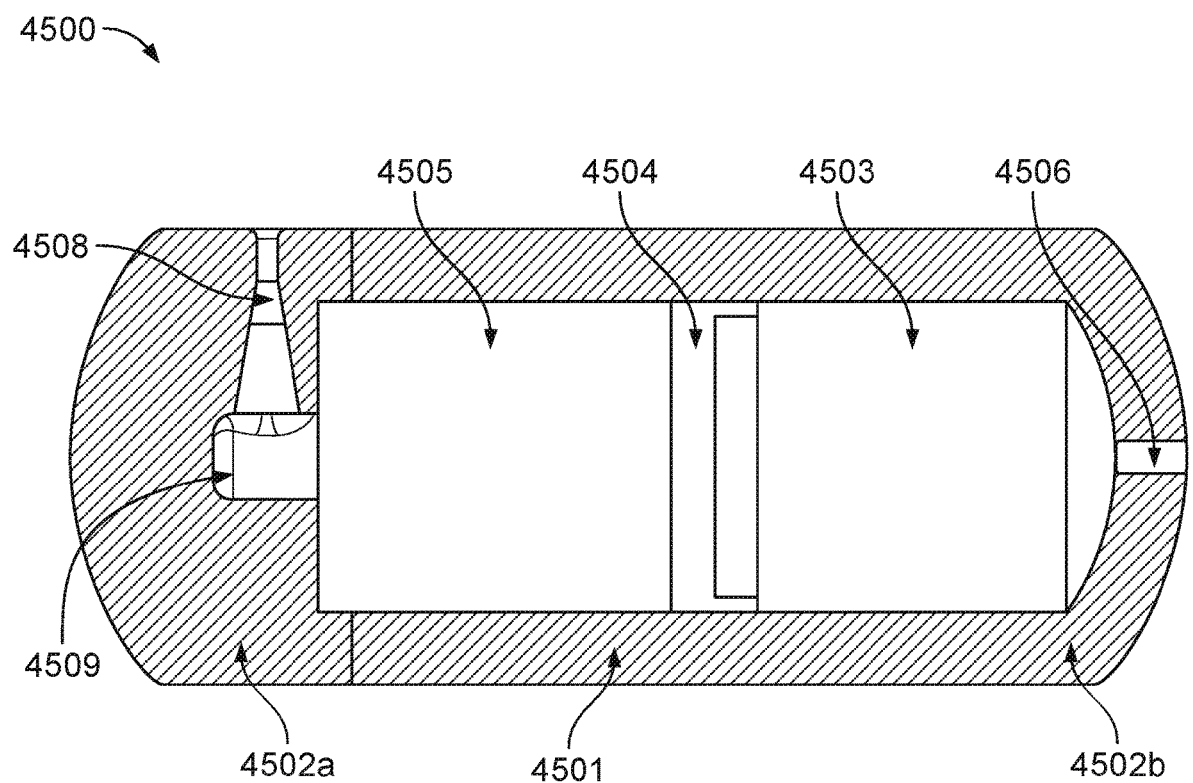
FIG. 45 illustrates an ingestible device including a pre-pressurized actuator chamber and a sliding piston, according to some embodiments described herein.

FIG. 45 illustrates an ingestible device 4500 including a pre-pressurized actuator chamber 4503 and a sliding piston 4504, according to some embodiments described herein.

Ingestible device 4500 includes a device housing 4501. The device housing 4501 is composed of a cap portion 4502a and a base portion 4502b in the illustrated embodiments. Ingestible device 4500 also includes a pre-pressurized actuator chamber 4503 that is pressurized to a target pressure, for example during manufacture or via air fill port 4506 prior to ingestion. The capsule incorporates an active release mechanism that activates as the capsule reaches the target location. As the release mechanism activates, sliding piston 4504 will rapidly move to the left, pushing a high pressure jet of dispensable substance (e.g., therapeutic agent) through the nozzle.

Depending on the material used to form the walls of the device housing 4501, the material could diffuse the compressed gas in the pre-pressurized actuator chamber 4503 over time, decreasing the internal pressure. To ensure that pressure is maintained in the ingestible device 4500 over a period between fabrication and patient use, packaging could be pressurized to equal the internal pressure of the pill in certain embodiments; therefore, preventing the permeation of compressed gas from the ingestible device 4500. Assuming the gas expansion within the capsule occurs very fast and an adiabatic polytropic process takes place, gas laws are used to correlate the initial and final pressure of the gas with its volume change ratio.

For a polytropic process $$pv^k = CTE$$

$$\frac{p_1}{p_2} = \frac{v_2^k}{v_1^k}$$

where p is the pressure, v is gas volume and k is the specific heat ratio of the gas (1.4 for air).

The delivery pressure profile for a range of initial pressure and volume change ratios are presented in Table 1. It can be observed that with increasing the volume ratio of the compressed gas in the pre-pressurized actuator chamber 4503, the variations in the delivery pressure becomes smaller. However, increasing the volume ratio will be at the cost of reduced dispensable substance (e.g., therapeutic agent) volume. A compromise between the two parameters can be made to arrive at a desirable pressure profile with adequate dispensable substance (e.g., therapeutic agent) volume. Table 1 below provides sample results of implementation of pressurized gas for dispensable substance (e.g., therapeutic agent) delivery embodiments disclosed herein.

TABLE 1

| Gas initial pressure (psi) | Gas volume change ratio* | Estimated volume of the therapeutic agent | Delivery pressure start-end (psi) |
| --- | --- | --- | --- |
| 250 | 2/3 | 333 | 250-141 |
|  | 1/2 | 500 | 250-94 |
|  | 1/3 | 666 | 250-53 |
|  | 1/4 | 750 | 250-35 |
| 200 | 2/3 | 333 | 200-113 |
|  | 1/2 | 500 | 200-75 |
|  | 1/3 | 666 | 200-42 |
|  | 1/4 | 750 | 200-28 |
| 150 | 2/3 | 333 | 150-85 |
|  | 1/2 | 500 | 150-56 |
|  | 1/3 | 666 | 150-32 |
|  | 1/4 | 750 | 150-21 |

TABLE 1-continued

| Gas initial pressure (psi) | Gas volume change ratio* | Estimated volume of the therapeutic agent | Delivery pressure start-end (psi) |
|---|---|---|---|
| 100 | 2/3 | 333 | 100-56 |
|  | 1/2 | 500 | 100-37 |
|  | 1/3 | 666 | 100-21 |
|  | 1/4 | 750 | 100-14 |

*Represents the ratio of the initial to final volume of the gas before and after drug delivery.
** Assumes the total available volume within the capsule for both gas and the drug is 1000 ul.

In certain embodiments, the ingestible device 4500 is filled with a liquid dispensable substance (e.g., liquid therapeutic agent) in reservoir 4505. The liquid dispensable substance is ejected from reservoir 4505 via piston 4504 sliding in reservoir 4505 in response to actuation by pressurized gas in the pre-pressurized actuator chamber 4503 equilibrating. The pressurized gas in the pre-pressurized gas chamber 4503 is initially maintained in a pressurized state via an occlusion component, such as plug 4508, preventing the ejection of the dispensable substance from reservoir 4505. For example, the device 4500 is placed in an external pressure chamber and chamber 4503 within the ingestible device 4500 is elevated to a target pressure. Air fill port 4506 is sealed (with adhesive or similar) in pressure chamber 4503 and plug 4508 is installed in conduit 4509. When plug 4508 is removed, for example by being dissolved based on a reaction occurring at or near the target site the pressure in chamber 4503 is lowered as the chamber 4503 volume increases as the piston 4504 moves further into reservoir 4505 as the dispensable substance is evacuated from reservoir 4505 via exit conduit 4509.

In certain embodiments, the pressure in chamber 4503 is generated within the chamber itself via the release of gases during chemical reactions within the chamber. The chemical reaction between acids and bases is considered as a fast reaction, which can produce large amounts of gas as a product. The accumulation of product gas within the small capsule may provide the required pressure for a dispensable substance (e.g., therapeutic agent) delivery jet. The amount of gas and pressure can be controlled by careful selection of the reaction and the stoichiometry of the process. An ideal chemical reaction has to be fast and should not release toxic or unsafe products for in-vivo use. In particular embodiments, acetic acid and sodium bicarbonate are employed for the chemical reaction. All the reactants and products are considered to be ingestible in small quantities. The products include carbonic acid and sodium acetate. In a low-pressure aquatic environment, Carbonic acid will decompose into water and carbon dioxide in gaseous form. With the release of carbon dioxide in a small container, the pressure within the chamber 4503 will rise providing the force needed for pushing piston 4504 through reservoir 4505 towards the exit conduit 4509 to eject the dispensable substance therefrom.

In some embodiments, a burst disc may enable the release of drug by purposefully fracturing at a targeted pressure. This approach is commonly utilized in industrial applications as a safety mechanism in pressurized systems.

Figure 46A:
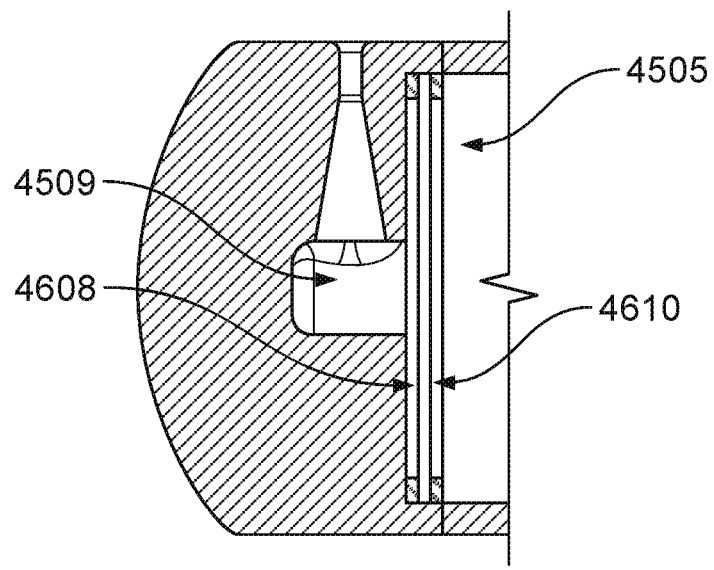
FIG. 46A illustrates a portion of an ingestible device including burst disc in line with a nozzle portion, according to some embodiments described herein.
Figure 46B:
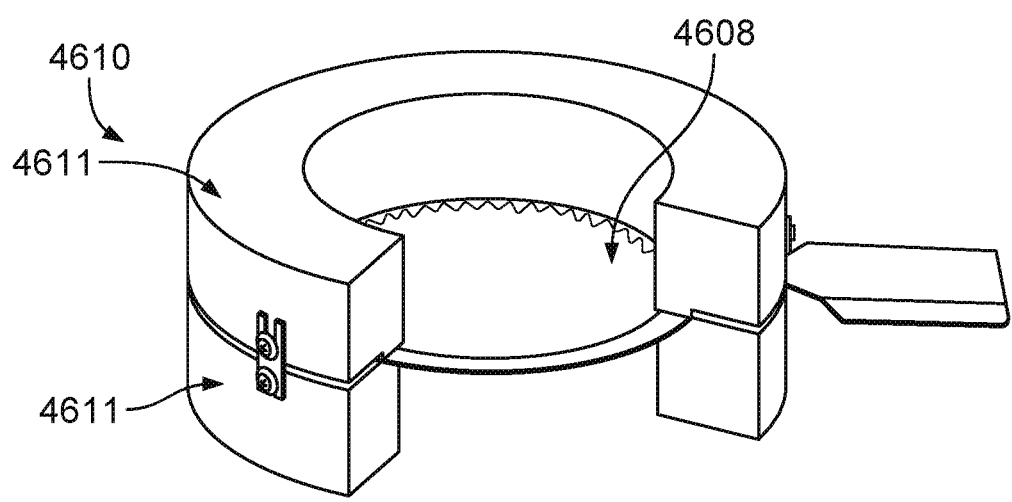
FIG. 46B illustrates a partial sectional view of a burst disc holder, according to some embodiments described herein.

FIG. 46A illustrates a burst disc 4608 with an in line nozzle 4509. FIG. 46B illustrates a partial sectional view of a burst disc holder 4610, according to some embodiments described herein. A burst disc 4608 may enable the release of a dispensable substance, such as, for example, a therapeutic agent (for example from reservoir 4505) by purposefully fracturing at a targeted pressure allowing the dispensable substance to exit a nozzle 4509 to a target location within the GI tract. A burst disc 4608 can be used as the sole occlusion component in certain embodiments and can be used to provide isolation between upstream contamination and the dispensable substance payload in embodiments including another occlusion component. The burst disc 4608 can be held in place via clamped outer rings 4611 of disc holder 4610 as demonstrated in FIG. 46B.

In certain embodiments, a custom built burst disc may be used. Advantages to this approach can include one or more of the following: reduced cost; increased control over the design and sizing; customization of design for operational and burst pressure properties; increased options for material type; and quality and tolerance control. Assuming for the sake of discussion that the burst disc is designed in the form of a portion of a thin walled spherical pressure vessel (concave inside-convex outside), as shown in FIG. 46B, an analytical approach can be taken as follows. In this approach the shear and tensile stresses on the thin walled pressure vessel are estimated. Mohr circle theorem is used to estimate the principal stresses including tensile and shear stresses. For a thin walled spherical sphere the principal stresses on the outer wall are given by:

$$\sigma_1 = \sigma_2 = \frac{pr}{2t}$$
$$\tau_{max} = \frac{pr}{4t}$$

where p is the pressure on the inner surface, r is the radius of the sphere that the burst disc is cut from and t is the thickness of the vessel.

The maximum shear stress on the inner wall of the vessel is given by:

$$\tau_{max} = \frac{1}{2}(\sigma_1 + p) = \frac{pr}{2t}\left(1 + \frac{t}{r}\right)$$

As described by the equations, the maximum stresses on the burst disc are a function of pressure, diameter, and thickness of the wall. The impacts of stress concentrations on the perimeter of the disc is not considered in this approach. In order for a burst disc to operate properly through the envisioned operating pressures, the principal stresses (normal and shear stresses) on the inner and outer surface of the vessel are desirably smaller than the maximum allowable stress. The maximum allowable stresses are often the ultimate tensile and shear stresses of the material.

Another factor that can affect the performance of a burst disc is the elongation of material just before rupture. Plastic deformation and elongation of a material before rupture, results in changes in the equivalent diameter of the sphere under stress. This can result in a delay in rupture. It can be desirable to select material with minimal plastic elongation before the rupture. The design limitations, material availability from the supplier, and the product thickness and tolerances make the process of burst disc design a complicated process. A dynamic model was developed. The model receives the design properties as the inputs, subsequently calculating the minimum thickness of the material required. Beyond this, it also investigates the impacts of thickness tolerance and estimates a pressure range for the rupture of the material. This model compares the maximum principal stress of the system with the maximum tensile and shear stress of each material. Table 2 lists results for 11 different shim materials from a supplier. The definition for operating pressure in Table 2 is a nominal pressure for design and does not impact conveyed results, whereas minimum and maximum pressures are anticipated pressures for rupture. This analysis does not consider variations to the tensile strength of the base material, which could add further spread for minimum and maximum pressures.

exterior surface of the enteric coating to provide isolation of the dispensable substance (e.g., therapeutic agent) from the enteric coating (which may dissolve the coating), or to add structural support. In some embodiments, an advantage of incorporating the enteric coating on a tapering geometry of conduit 4509 is that any pressure provided on the interior surface further compresses the coating.

TABLE 2

|  | Al1100-H14 | Stainless Steel-AISI302 | Steel-AISI1010 | Steel-AISI1095 |
|---|---|---|---|---|
| Material No. | 1 | 2 | 3 | 4 |
| Foil thickness (inch) | 0.01100 | 0.00200 | 0.00250 | 0.00100 |
| Foil tolerance (inch) | 0.00005 | 0.00005 | 0.00010 | 0.00010 |
| Operating pressure (psi) | 200 | 200 | 200 | 200 |
| Rupture pressure-Min (psi) | 300 | 410 | 210 | 210 |
| Rupture pressure-Max (psi) | 300 | 410 | 220 | 270 |
| Elongation at rupture (% per 2 inch) | 9 | 12 | 20 | 9 |

|  | Al1145-foil | Al1235-foil | Brass110-soft-annealed | Ni200-annealed |
|---|---|---|---|---|
| Material No. | 5 | 6 | 7 | 8 |
| Foil thickness (inch) | 0.00700 | 0.01600 | 0.00700 | 0.00100 |
| Foil tolerance (inch) | 0.00005 | 0.00005 | 0.00010 | 0.00005 |
| Operating pressure (psi) | 200 | 200 | 200 | 200 |
| Rupture pressure-Min (psi) | 300 | 300 | 300 | 230 |
| Rupture pressure-Max (psi) | 300 | 300 | 300 | 240 |
| Elongation at rupture (% per 2 inch) | 3 | 2 | 20 | 17 |

|  | Titanium | Brass260-hard | Bronze 510 |
|---|---|---|---|
| Material No. | 9 | 10 | 11 |
| Foil thickness (inch) | 0.00500 | 0.00250 | 0.00550 |
| Foil tolerance (inch) | 0.00050 | 0.00010 | 0.00055 |
| Operating pressure (psi) | 200 | 200 | 200 |
| Rupture pressure-Min (psi) | 230 | 300 | 750 |
| Rupture pressure-Max (psi) | 290 | 300 | 900 |
| Elongation at rupture (% per 2 inch) | 54 | 14 | 7 |

From the analysis, a number of off the shelf available materials could be considered suitable for use. Selection may depend upon relevant pressures, material properties, and material compatibility to dispensable substance (e.g., therapeutic agent). In some embodiments, it may be desirable to use materials with similar properties as Material #3 and #4 with which chemical resistance and biocompatibility can be simulated and used. In certain embodiments, it may be desirable to use stainless steel 316L.

Figure 47:
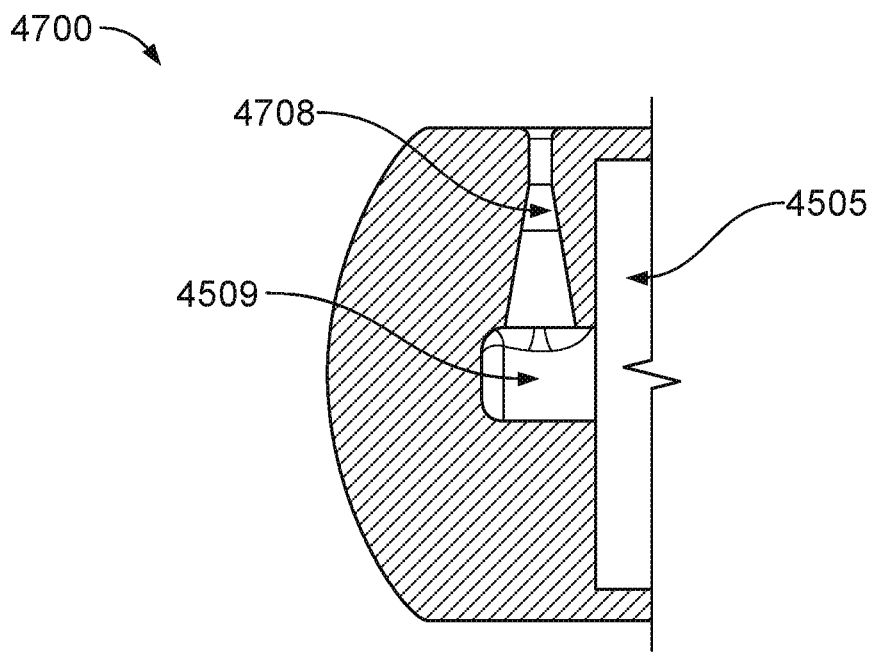
FIG. 47 illustrates a portion of an ingestible device including enteric coating occlusion component, according to some embodiments described herein.
Figure 48:
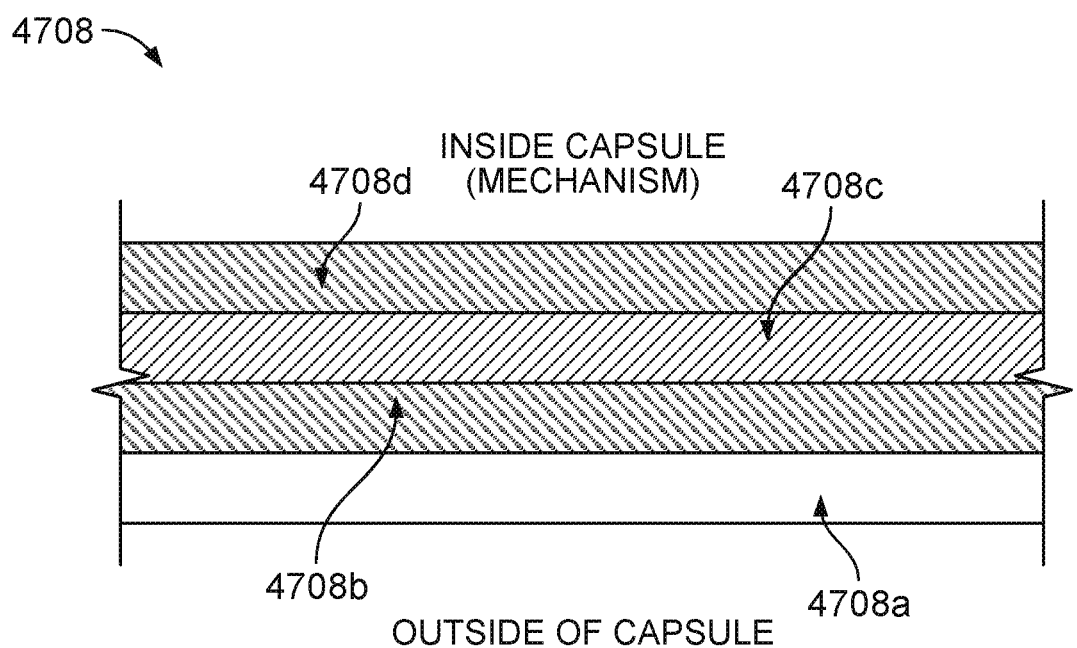
FIG. 48 shows stacked layers of an enteric coating for an ingestible device, according to some embodiments described herein.

In some embodiments, one or more enteric coatings may be used as a trigger mechanism. FIG. 47 illustrates a portion of an ingestible device 4700 including an enteric coating occlusion component 4708, according to some embodiments described herein. As a cost-effective method to detect general entry into the small intestine, enteric coatings are used in particular embodiments as the occlusion component or as at least a portion of the occlusion component that is reconfigured based on changes in the regional pH levels. Accordingly, the pH level provides an effective location detection signal for reconfiguring the occlusion component and activating or releasing the dispensable substance actuator. In certain embodiments, pressure acts on the underside of the enteric coating 4708, and as the coating 4708 is weakened due to exposure to the small intestinal luminal fluid, it fails, allowing the release of a dispensable substance from the reservoir 4505. Complimentary coatings for sealing or strength (e.g. wax) may be incorporated on the interior or FIG. 48 shows stacked layers of an enteric coating 4708 for an ingestible device, according to some embodiments described herein. As an alternative to direct actuation with enteric coatings, concepts are disclosed that utilize a coating to expose a secondary feature that cause jet release. Some of these mechanisms rely on the exposure of an osmogen layer 4708d to drive fluid. FIG. 48, shows an implementation of an enteric coating 4708a exposing a membrane 4708c and osmogen 4708d via mesh layer 4708b, which would drive the flow of water into the capsule.

Figure 49:
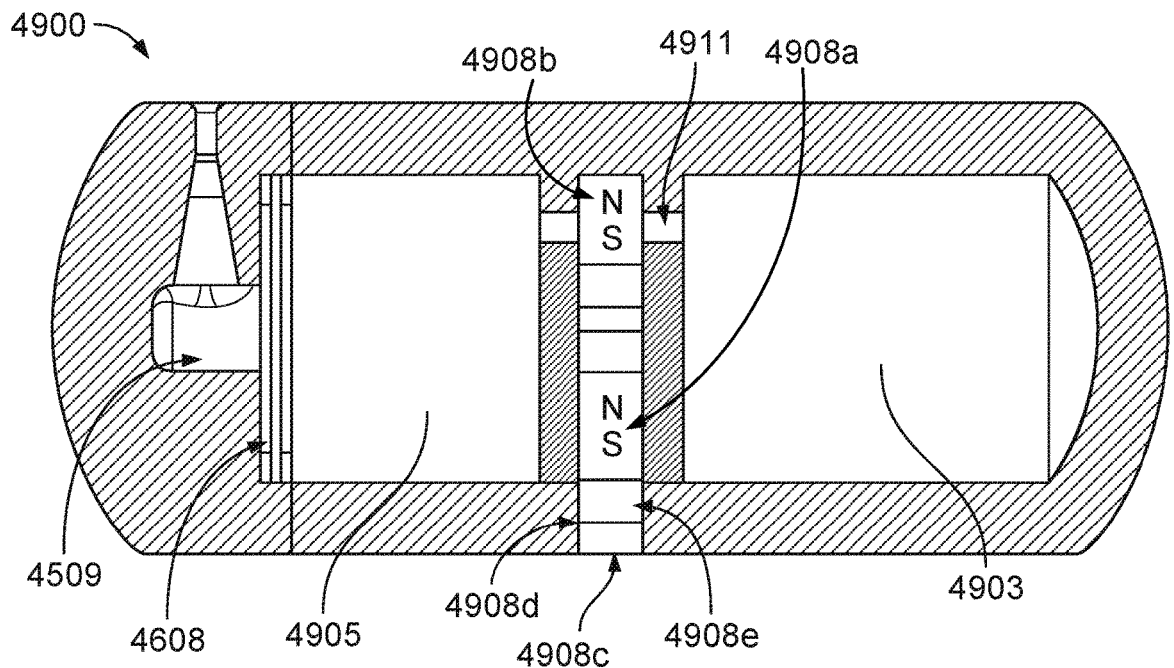
FIG. 49 illustrates an ingestible device including a magnetic occlusion component, a burst disc, and a pre-pressurized actuator chamber, according to some embodiments described herein.
Figure 50:
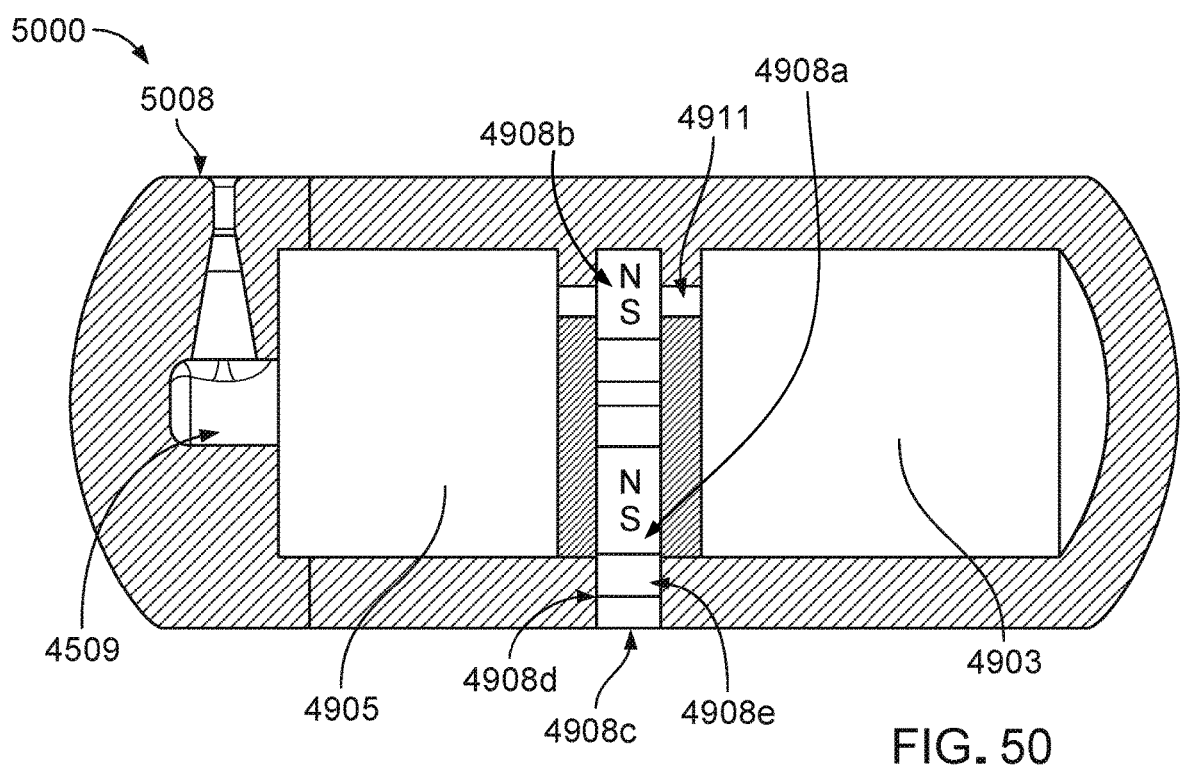
FIG. 50 illustrates an ingestible device including a magnetic occlusion component and pre-pressurized actuator chamber, according to some embodiments described herein.

FIG. 49 illustrates an ingestible device 4900 including a magnetic occlusion component 4908b, a burst disc 4608, and a pre-pressurized actuator chamber 4903, according to some embodiments described herein. FIG. 50 illustrates an ingestible device 5000 including a magnetic occlusion component, a pre-pressurized actuator chamber 4903 and a bioabsorbable plug 5008, according to some embodiments described herein. A magnetic stack (as shown FIG. 49 and FIG. 50), which upon peristaltic or osmotic pressure application releases pneumatic pressure, allowing for the delivery of a jet of dispensable substance through a conduit 4509. As shown by FIG. 49 and FIG. 50, osmotic pressure may be used to reconfigure the occlusion component that includes magnets 4908a and 4908b in FIGS. 49 and 50. The enteric coating 4908c dissolves when exposed to luminal fluid, exposing the membrane 4908d and osmogen 4908e. The membrane 4908d and osmogen 4908e facilitate the movement of liquid to create osmotic pressure on the magnet

4908*a*. As the osmotic pressure builds up, magnet 4908*a* will be pushed up in proximity to magnet 4908*b*. Magnet 4908*b* will be pulled down providing a flow through path for a gas from pressurized chamber 4905 to interact with the reservoir 4905 via connecting conduit 4911. The advantage of this system is that the mechanism may be completely sealed from the exterior of the capsule, allowing for pressure to only project into the chamber 4905. Note that an enteric coating/membrane stack 4908*c*, 4908*d* could be replaced by a method of leveraging peristalsis for pushing magnet 4908*a*. FIG. 49 is implemented with a burst disc 4608 as the sealing/release mechanism once the chamber 4905 is exposed to the pressurized chamber 4903. FIG. 50 is implemented with a bioabsorbable plug 5008 (e.g. enteric coating) that is dissolved and expelled once the reservoir 4905 is exposed to the pressurized actuator chamber 4903.

Figure 51:
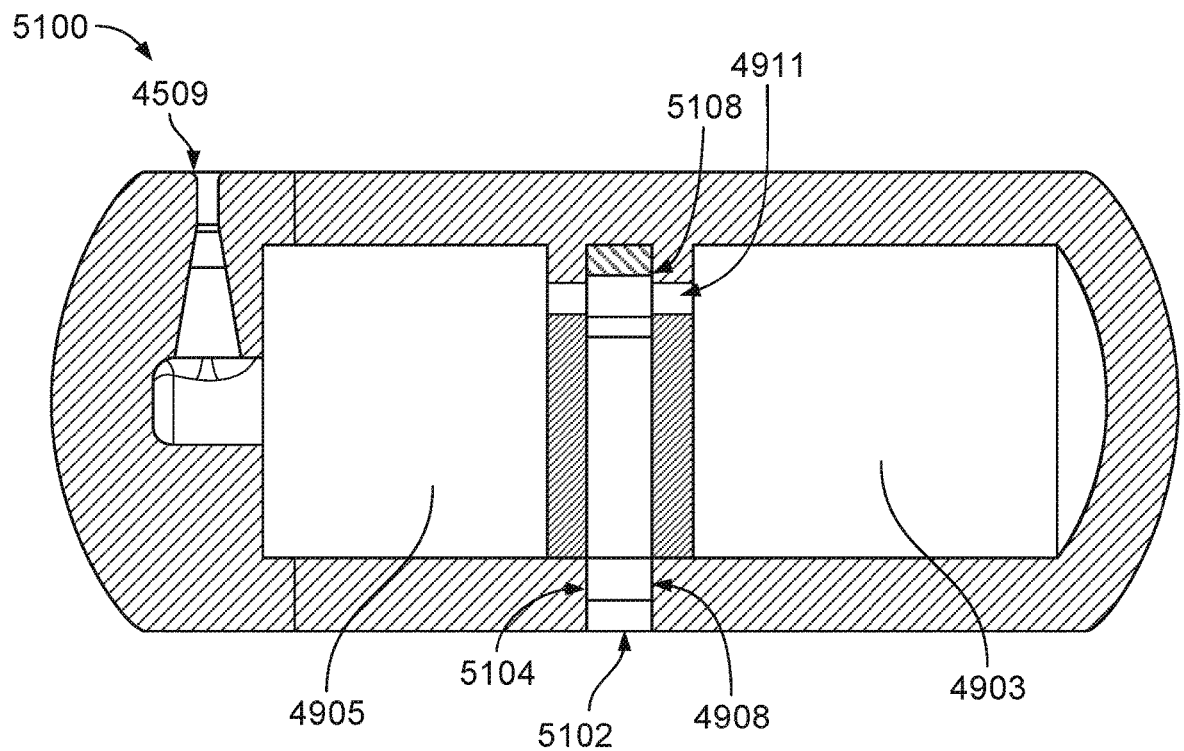
FIG. 51 illustrates an ingestible device including enteric sliding occlusion component and pre-pressurized actuator chamber and a sliding piston, according to some embodiments described herein.

FIG. 51 illustrates an ingestible device 5100 including enteric sliding occlusion component 5102, a pre-pressurized actuator chamber 4903 and a sliding component 5108, according to some embodiments described herein. An osmotic drive 4908, including an enteric coating 5102 and semipermeable membrane 5104, is configured to move a sliding component 5108. The sliding component 5108, once pushed by the osmotic drive 4908, will allow a flow-through port 4911 to connect the pressurized actuator chamber 4903 to the reservoir 4905, providing dispensable substance delivery through the nozzle 5108.

Figure 52:
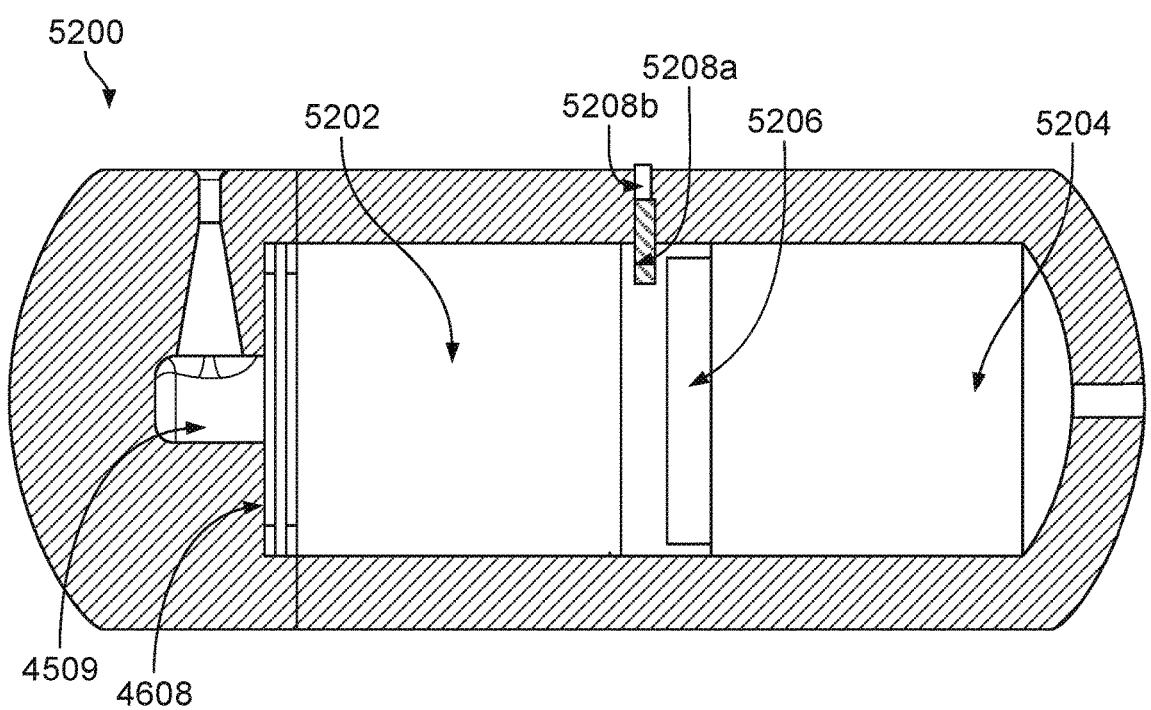
FIG. 52 illustrates an ingestible device including dissolvable pin occlusion component and a pre-pressurized chamber and a sliding piston, according to some embodiments described herein.

FIG. 52 illustrates an ingestible device 5200 including dissolvable pin occlusion component, a drug chamber 5202, a pre-pressurized chamber 5204 and a sliding piston 5206, according to some embodiments described herein. In another embodiment, an enteric coating 5208*b* is dissolved, exposing a structural pin 5208*a* (such as a glucose spike or hydrogel) that dissolves in the presence of intestinal luminal fluid. With this design, as long as the pin 5208*a* is in place, the force exerted on the piston 5206 and the drug chamber 5202 is not large enough for the burst disk 4608 to rupture. The enteric coating 5208*b* and pin 5208*a* will dissolve as the capsule 5200 is ingested and as a result, the pressure force on the piston 5206 will increase. The full force of the pre-pressurized chamber 5204 translated onto the drug chamber 5202 via the piston 5206 is large enough to rupture the burst disk 4608. The rupture of the burst disk 4608 results in a pressurized jet of liquid being delivered from the drug chamber 5202 through the nozzle 4509.

Figure 53:
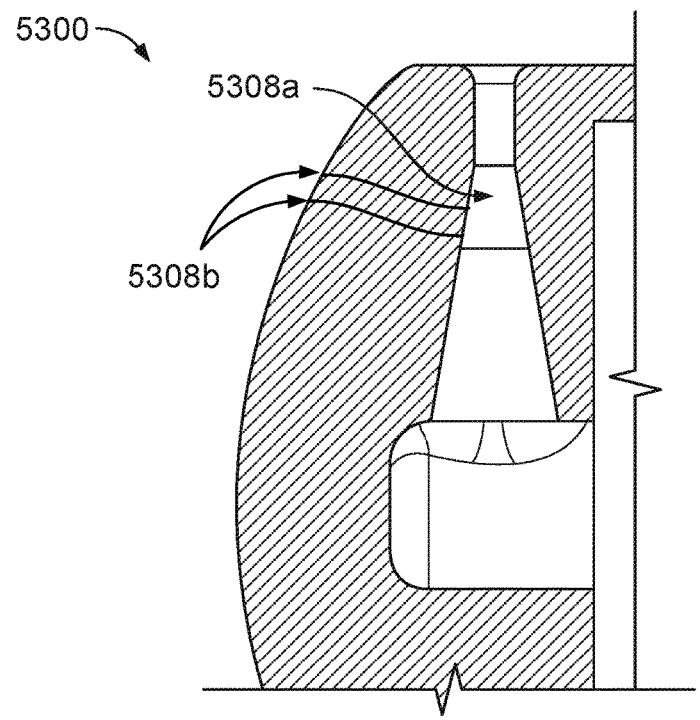
FIG. 53 illustrates an ingestible device including wax plug with wire lead activators, according to some embodiments described herein.

FIG. 53 illustrates an ingestible device 5300 including wax plug 5308*a* with wire lead activators 5308*b*, according to some embodiments described herein. In this method, the dispensing site is identified based on collected reflected light. The reflectance of light in green and red spectrums (with iterations to this methodology and algorithm actively being pursued) are measured and an algorithm is used to correlate the measured reflectance with the location in the Gastrointestinal (GI) tract. This method provides a non-pH based system to determine the anatomical locations of the capsule during fasted transit. As the capsule 5300 reaches the target location, a signal is generated which will be used to activate an alternative release mechanism.

With the inclusion of a printed circuit board assembly (herein referred to as PCBA) with light-based localization technologies, a melting wax-based approach is presented. This functions by receiving an electronic signal from an algorithmically defined detection point and providing energy to a resistive heating element. This heating element causes a phase transition from solid to liquid, releasing the pressure and driving the jet of dispensable substance into the intestinal wall. One of the limiting factors to this approach is the additional cost associated with the PCBA.

Various embodiments disclosed herein use a nozzle, such as nozzle 4509, to create a high-pressure jet of fluid able to penetrate the intestinal wall. The nozzle can be directly connected to the dispensable substance reservoir (except, for example, when burst disc is used) and as a result the dispensable substance may dispense inadvertently if the opening of the nozzle is not sealed off. One approach to mitigate this includes using a bioabsorbable material to close off the opening of the nozzle. A bioabsorbable plug refers to a plug made out of material that can be absorbed by the body if injected into the intestinal wall or luminal region. If the plug is in direct contact with the dispensable substance, a small sealant layer can be used to separate the plug from the dispensable substance to avoid unwanted dissolution. Particular embodiments use a passive bioabsorbable plug that only operates as a sealing mechanism to close of the nozzle. A passive bioabsorbable plug may be used to seal off the dispensable substance chamber and avoid any unwanted spill of the dispensable substance. In this case, the internal pressure of the dispensable substance chamber is low and another mechanism is used to activate the release of the dispensable substance. As the capsule reaches the target location, the pressure within the dispensable substance chamber rises up to a predefined value. This can be done through use of any of the above-discussed release mechanisms. With the activation of the release mechanism, high-pressure fluid will overcome the adhesion of the bioabsorbable plug to the nozzle wall and will push the plug out with a jet of fluid. In this case, the plug does not play a significant role in activation and release of the dispensable substance. After being shut out of the nozzle, the plug might fall within the GI tract or be injected into the intestinal wall. In both cases after a certain period, it will be absorbed into the body.

Certain embodiments implement an active plug that acts both as the sealing mechanism and reconfigurable occlusion component for releasing the actuator mechanism. An active bioabsorbable plug acts as both the release mechanism and the sealing mechanism on the dispensable substance chamber. In this case, the plug is used to close off the opening of the nozzle. The dispensable substance chamber is already pressurized and, as a result, the plug is under pressure. The external body of the plug might be in contact with the GI fluid or be covered with an enteric coating. As the capsule transits through the GI tract, the plug will start dissolving (in case of enteric covered plug, the cover will dissolve before the plug starts dissolving). With time, the structural integrity of the plug will weaken as parts of the plug dissolves. After a predefined amount of time, the structure of the plug will weaken and will not be able to hold of the high-pressure liquid any longer. At this point, the plug will shear off from the opening of the nozzle and will be pushed out with the flow of high-pressure dispensable substance. In this case, the plug acts both as the sealing and release mechanism and as a result the term "active" is used.

Figure 54:
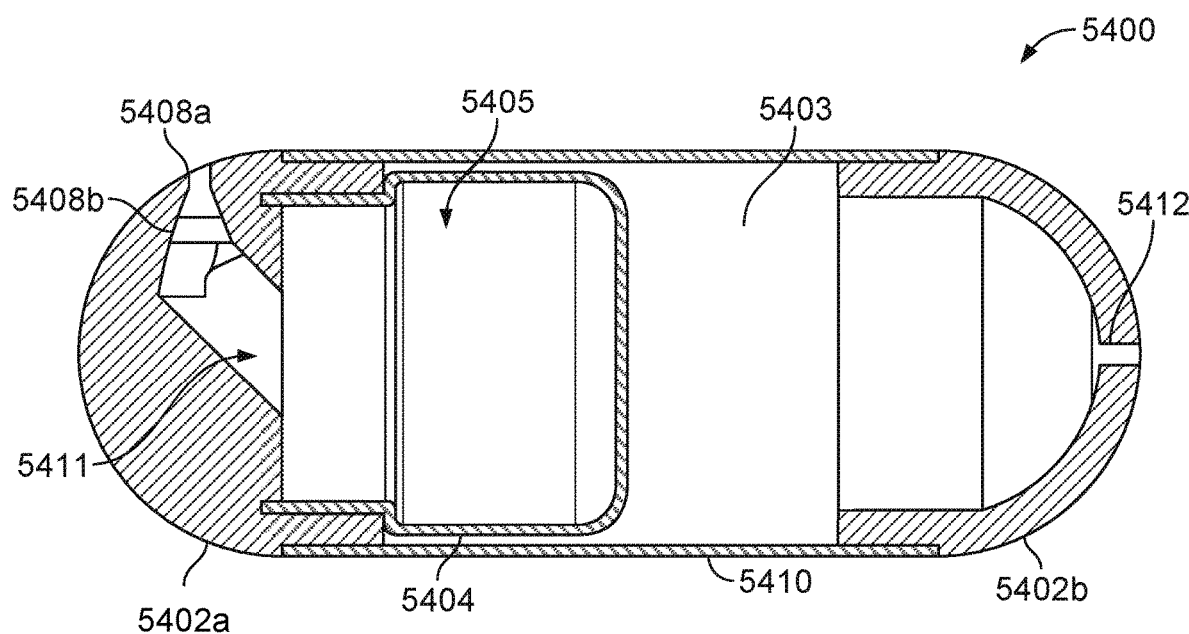
FIG. 54 illustrates an ingestible device including a pre-pressurized chamber and a bellows, according to some embodiments described herein.

FIG. 54 illustrates an ingestible device 5400 including a pre-pressurized chamber 5403 and a bellows 5404, according to some embodiments described herein. Ingestible device 5400 includes two chambers: pressure actuator chamber 5403 and reservoir 5405 (FIG. 11). These two chambers are separated by the bellows 5404. The pressure chamber 5403 is filled with high-pressure gas and provides the drive mechanism needed to push the dispensable substance out of the nozzle 5411. An adhesive layer 5412 is located on the housing opposite the nozzle 5411. The occlusion component or release mechanism for this concept consists of a bioabsorbable plug 5408*a* (enteric coatings, glucose based with other matrices and combinations possible, see section 5.5) separated from the liquid dispensable substance by a protectant layer 5408*b*. The plug 5408*a* is configured to withstand the pressure force exerted by the gas in pressurized actuator chamber 5403. The force needed to keep the plug 5408*a* in place is a function of cross section area where the plug 5408*a* is installed. Because in this embodiment, plug is 5408*a* placed at the small cross section area of the nozzle outlet 5411, the force exerted on the plug 5408*a* is relatively small. As the capsule 5400 is digested and moves through GI tract, the bioabsorbable plug 5408*a* will start dissolving (see section 5.5). After certain amount of time (which can be controlled by the properties of the bioabsorbable plug), the plug 5408*a* will weaken or fully dissolve in GI fluid. After the plug 5408*a* dissolves, the protectant layer 5408*b* will be ejected and the dispensable substance (e.g., in the form of a jet) will hit desired tissue, such as the internal wall of the target location (e.g., the internal wall of the small intestine).

In some embodiments, an alternative to a pre-pressurized gas chamber is to use a spring mechanism to provide the required pressure for the jet delivery mechanism. In certain embodiments, it may be desirable to satisfy one or more of the following:

Outer diameter of the spring smaller than inner diameter of the capsule.

Compressed length of the spring minimized to leave more space for drug.

Free length of the spring maximized and larger than free length of inner cavity of the capsule to ensure an acceptable driving pressure is provided throughout the entire time step of jet delivery.

Spring rate should be large enough to provide acceptable pressure from the beginning until the end of drug delivery.

Initial pressure provided by the spring should be in the range of 100 to 250 PSI and the final pressure should not fall below 50 psi.

Figure 55:
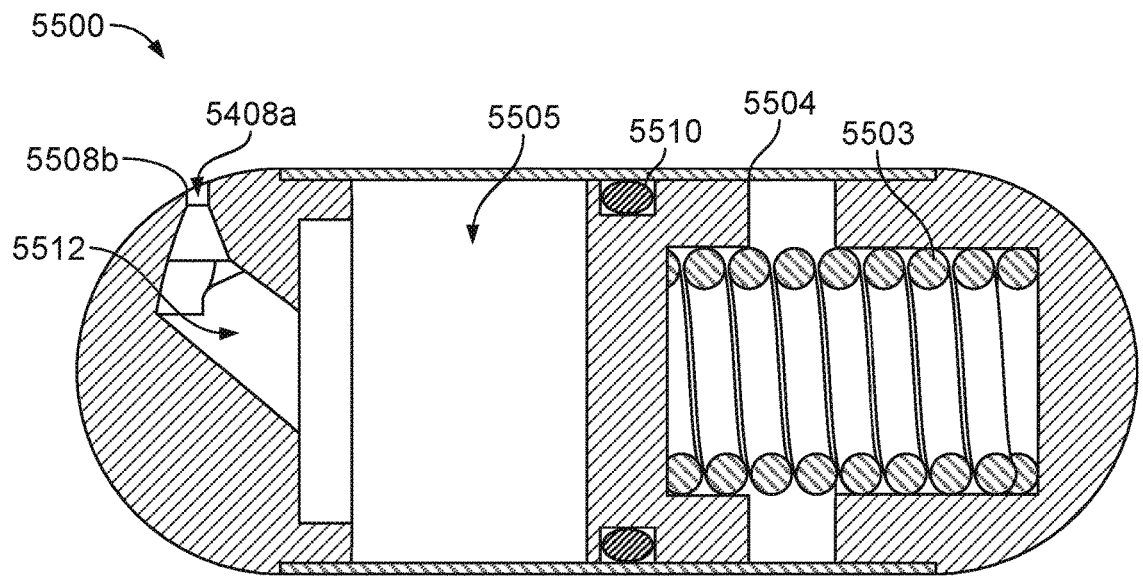
FIG. 55 illustrates an ingestible device including a spring actuator and a sliding piston, according to some embodiments described herein.

Based on the above factors, different springs from various suppliers may be considered. Sample results of spring analysis/selection are presented in Table 3. Optionally, a custom spring may be implemented. The use of conical springs could also be implemented, potentially with a reduction in the solid length of the spring. In some embodiments, a piston may be implemented with a spring such that piston could drive the fluid from the chamber. In certain embodiments, the piston could have one or more sealed interfaces.

ponent or release mechanism consists of bioabsorbable plug 5508*a* separated from the reservoir 5505 by a protectant layer 5508*b*. In this embodiment, the inner volume of the capsule 5500 is divided into two sections separated by a sliding piston 5504. The left section (e.g., reservoir 5505) is filled with dispensable substance and a spring 5503 is mounted in the right section. The piston 5504 can freely move to the right or left depending on the net force exerted on the piston 5504 (FIG. 55). An O-ring 5510 is used to provide the sealing required between the two sections, with alternative sealing means possible. Compressed spring 5503 applies a force on the piston 5504 and the piston 5504 transfers this force to the liquid dispensable substance in form of pressure. The same pressure will be transferred to the plug 5508*a* sealing the nozzle 5512. However, this pressure acts on a small area (area of the plug 5508*a*). Therefore, the large force exerted by the spring 5503 translates into a small force on the sealing plug 5508*a*. As the capsule 5500 is digested, it moves through GI tract and the bioabsorbable sealing plug 5508*a* will start dissolving. After certain amount of time, the plug will weaken or fully dissolve in GI fluid. As soon as the plug 5508*a* weakens to the design threshold, the pressure inside the reservoir 5503 drops, the spring 5503 will expand delivering dispensable substance (e.g., in the form of a high-pressure jet of fluid) through the opening.

Figure 56:
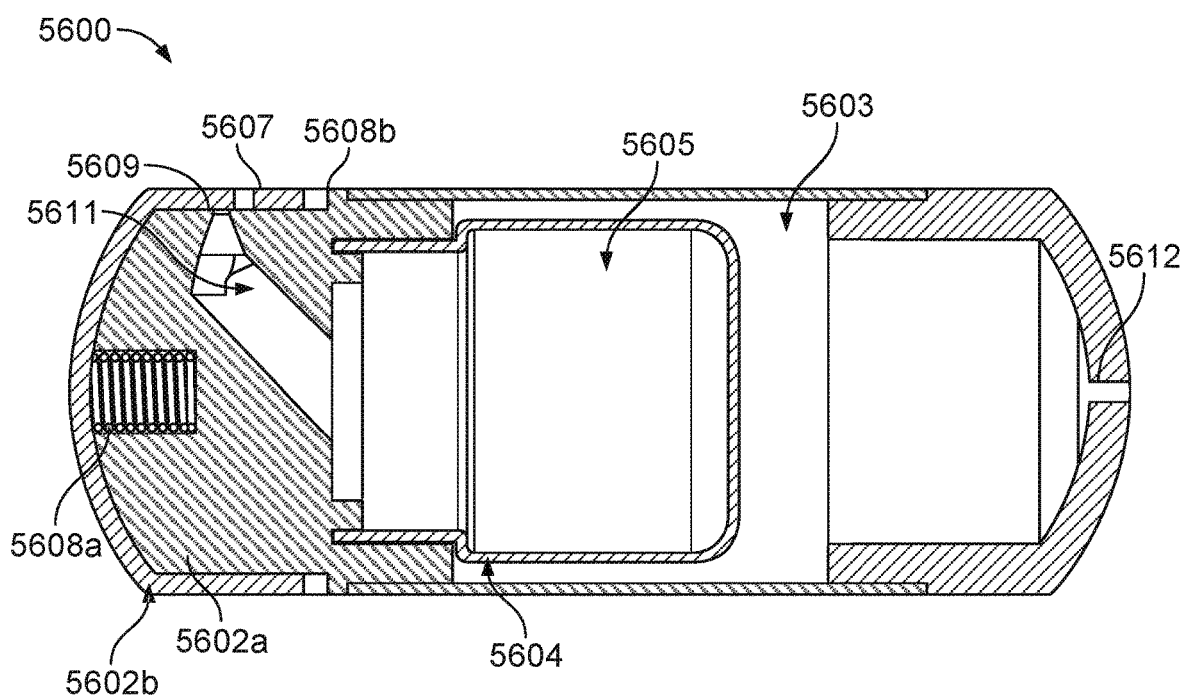
FIG. 56 illustrates an ingestible device including a spring actuated slidable housing portion, according to some embodiments described herein.

FIG. 56 illustrates an ingestible device 5600 including a spring actuated slidable housing portion 5602*b*, according to some embodiments described herein. Ingestible device 5600 consists of a pressurized actuator 5603 chamber, a reservoir 5605 separated from the pressure actuator chamber 5603 by a deformable body 5604 such as bellows and a spring/enteric coating release mechanism The spring 5608*a* is mounted on the polycarbonate cap 5602*a* from one end and to a sliding cap 5602*b* on the other end (FIG. 56). The stainless steel top slider 5602*b* can slide to the left and right opening and closing the nozzle 5611. An enteric ring 5608*b* is used to keep the top slider closed. An O-ring and a bioabsorbable plug 5609 are used to provide the required sealing. An adhesive seal 5612 is located on the housing, on the opposite end of the capsule 5600 from the spring 5608*a*. Compressed gas applies a force on the bellows 5604 and the bellows 5604 transfer this force to the liquid dispensable substance in form of pressure. The same pressure will be transferred to the slider 5602*b* in form of a radial force. However, this pressure acts on a small area (area of the exit orifice 5607). Therefore, the transverse load on the slider 5602*b* is relatively small.

TABLE 3

| OD (in) | Free length (in) | Solid length (in) | Rate (lbs/in) | Delivery pressure start-end (psi) | Item number-supplier |
| --- | --- | --- | --- | --- | --- |
| 0.301 | 1.15 | 0.663 | 45 | 150-110 | CDA-1115-0450-S, stocksprings.drtempleman.com |
| 0.42 | 1 | 0.504 | 72 | 250-100 | CEC-1000-0721-S stocksprings.drtempleman.com |
| 0.234 | 0.88 | 0.34 | 92 | 235-50 | PC040-234-7.500-MW-0.880-C-N-IN www.thespringstore.com |
| 0.36 | 0.8 | 0.46 | 94 | 190-10 | PC059-360-7.750-SST-0.810-CG-N-IN www.thespringstore.com |

FIG. 55 illustrates an ingestible 5500 device including a spring actuator 5503 and a sliding piston 5504, according to some embodiments described herein. Ingestible device 5500 uses the potential energy stored in a spring 5503 when compressed as the driving or actuating mechanism for jet delivery of the dispensable substance. The occlusion com- When the capsule 5600 is assembled, the spring 5608*a* is compressed (slider 5602*b* in closed mode), and the enteric coating 5608*b* keeps the slider 5602*b* in position. As the capsule 5600 is digested, it moves through GI tract. The enteric coating 5608*b* will dissolve when the capsule 5600 passes through the intestinal fluid. With the dissolution of the enteric coating 5608*b*, the spring 5608*a* will push the slider 5602*b* back away from the capsule 5600 (open mode). As a result, the exit orifice 5607 becomes concentric with the nozzle 5611 and the jet of fluid will be released.

Figure 57:
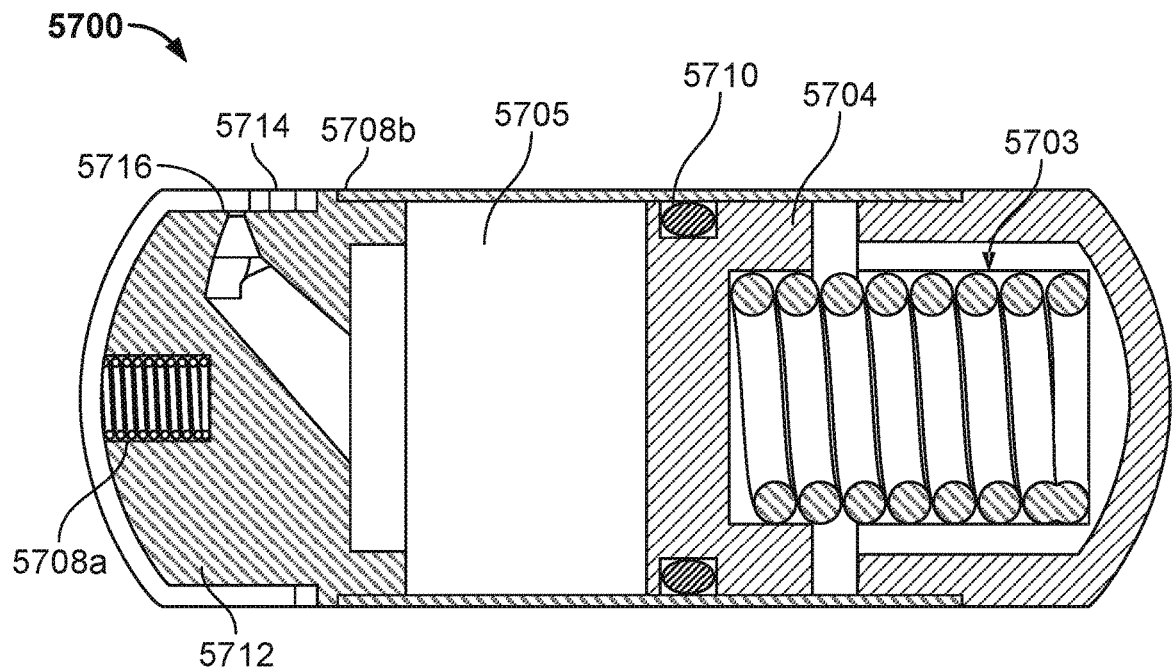
FIG. 57 illustrates an ingestible device with another spring actuated slidable housing portion, according to some embodiments described herein.

FIG. 57 illustrates an ingestible device 5700 with another spring actuated slidable housing portion 5712, according to some embodiments described herein. Ingestible device 5700 uses a compressed spring (spring 5703) as the drive mechanism and a compressed spring 5708*a* (spring with sliding top cap 5712 as the release mechanism. A piston 5704 separates the reservoir 5705 from the spring chamber and an enteric coating 5708*b* is used to initiate the release mechanism. An O-ring 5710 is used to provide sealing between the piston 5704 and cylinder. Compressed spring 5703 applies a force on the piston 5704 and the piston 5704 transfers this force to the liquid dispensable substance in the form of pressure. The same pressure will be transferred to the top cap slider 5712 in form of a radial force. However, this pressure acts on a small area (area of the exit orifice 5714) resulting in a small transverse force on the top slider 5712. When the capsule 5700 is assembled, spring 5703 is left in compressed mode (slider 5712 in closed position). As the capsule 5700 is digested, it moves through GI tract. The enteric coating 5708*b* will dissolve when the capsule 5700 passes through the intestinal fluid. With the dissolution of the enteric coating 5708*b*, the spring 5708*a* will push the slider 5712 back away from the capsule 5700 (open mode). As a result, the exit orifice 5714 becomes concentric with the nozzle 5716 and the jet of fluid will be released.

Figure 58:
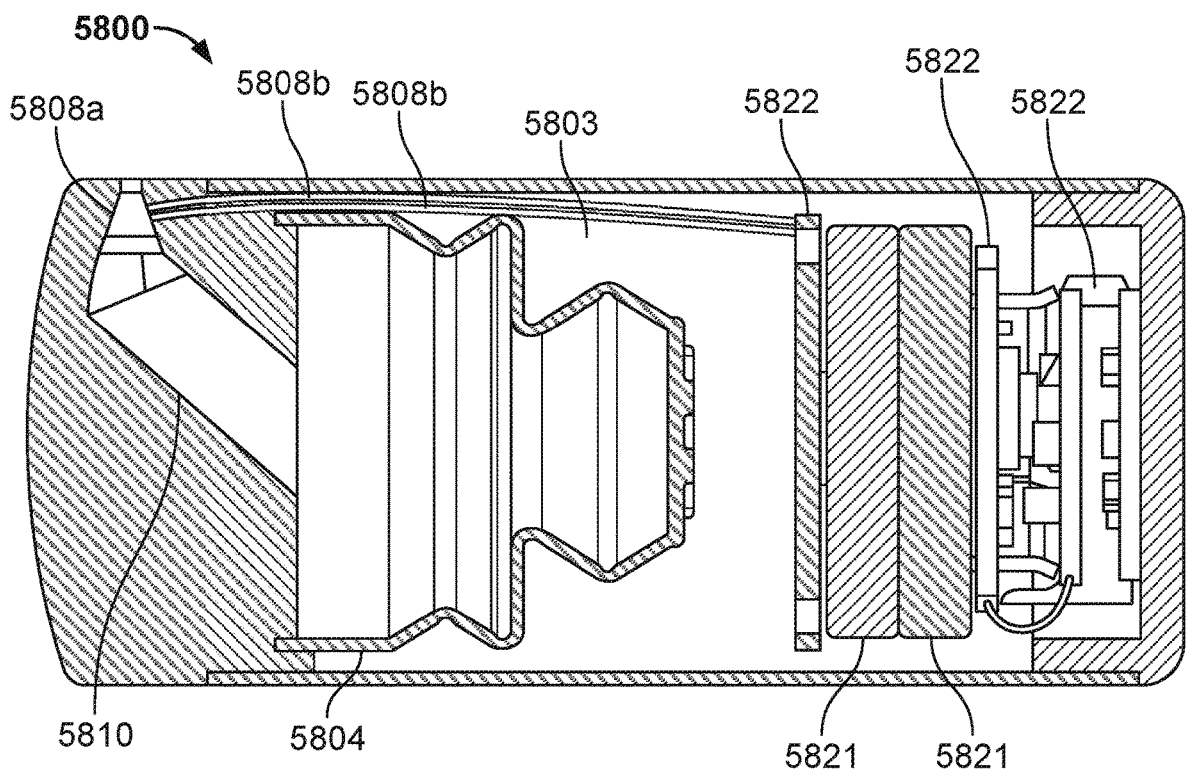
FIG. 58 illustrates an ingestible device including a melt away occlusion component and a pressurized chamber, according to some embodiments described herein.

FIG. 58 illustrates an ingestible device 5800 including a melt away occlusion component 5808*a* and a pressurized chamber 5803, according to some embodiments described herein. Ingestible device 5800 consists of two chambers, one chamber is filled with dispensable substance and the other chamber is filled with pressurized gas. A wax valve 5808*a* actuated by localization board 5822 is used as the occlusion component. A large section of the pressure chamber 5803 is occupied by the release mechanism and the required batteries 5821. Wax valve wires 5808*b* are connected to the wax valve 5808*a* and will melt the wax using an electric current. The timing of this operation is controlled by the localization board 5822. In this embodiment, a fully controlled release mechanism is used. As the capsule 5800 reaches target area, the localization kit will activate and direct a predetermined electric current toward the wax valve 5808*a*. A heating element will receive this current and will melt or weaken the wax valve 5808*a*. With weakening or removal of the wax from the nozzle 5810, gas pressure from the pressurized chamber 5803 will push the bellows 5804 resulting in a pressurized jet of liquid dispensable substance exiting the nozzle 5810, thus delivering the dispensable substance.

Figure 59:
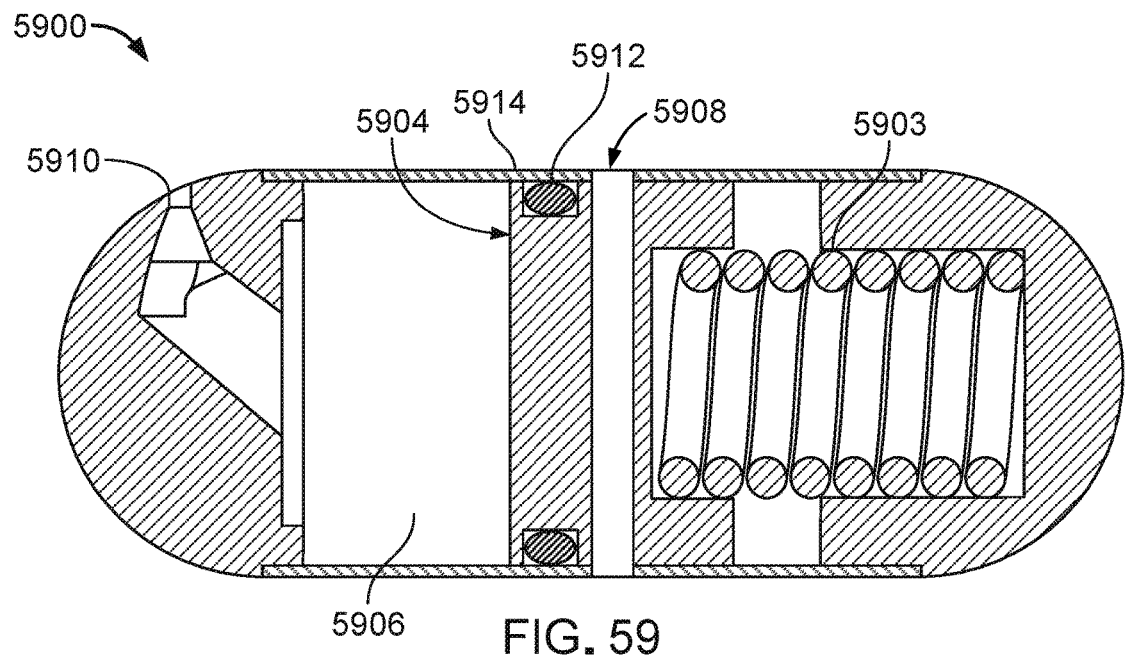
FIG. 59 illustrates an ingestible device including a dissolvable pin occlusion component and a spring actuated sliding piston, according to some embodiments described herein.

FIG. 59 illustrates an ingestible device 5900 including a dissolvable pin occlusion component 5908 and a spring actuated sliding piston 5914, according to some embodiments described herein. One of the main challenges of designing an effective capsule is the sealing between the two chambers inside the capsule since there is a significant pressure difference between the two chambers, the dispensable substance tends to move from the dispensable substance chamber into the pressure or spring chamber. Certain embodiments address this by reducing the pressure difference between the two chambers during the shelf life and before jet delivery. For example, ingestible device 5900 includes a compressed spring 5903 is retained using a dissolvable pin 5908. Additionally, an O-ring 5912 is used to provide sealing between the piston 5914 and housing. With this design, as long as the pin 5908 is in place, there is no force exerted on the piston 5904 and the liquid in chamber 5906. The force exerted by the spring 5903 will result in shear stress on the pin 5908. The pin 5908 will dissolve as the capsule 5900 is ingested and as a result, the spring force will translate into a pressurized jet of liquid. An enteric coating on the ends of the pin 5908 could further enhance the specificity of the triggering location. During the shelf life and before ingestion of the capsule 5900, there is not a significant amount of pressure acting on the dispensable substance and consequently, sealing challenges are easier to address. With a 200-psi design pressure, the pin would be expected to hold approximately 20 lbf, and would involve design consideration to the shear strength of the dissolvable pin. As the capsule 5900 passes through the GI tract, the pin 5908 will start dissolving. As the pin 5908 dissolves, there is no support for the piston 5904 to keep the piston 5904 in place. The force of the spring 5903 will result in a significant pressure in the fluid. At a certain point the pin 5908 will fail and the piston 5904 will move to the left releasing a high-pressure jet of fluid through the nozzle 5910.

Figure 60:
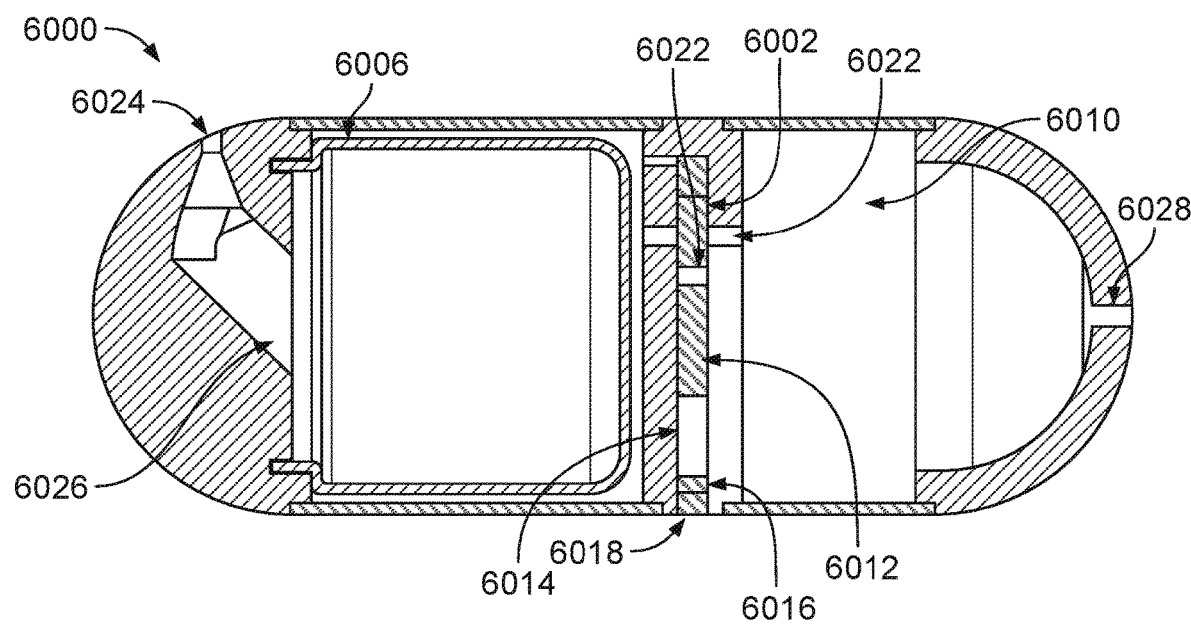
FIG. 60 illustrates an ingestible device including shuttle slider occlusion component and a pressurized chamber, according to some embodiments described herein.

FIG. 60 illustrates an ingestible device 6000 including shuttle slider occlusion component 6012 and a pressurized chamber 6010, according to some embodiments described herein. Ingestible device 6000 includes two chambers separated by a wall 6002 made of polycarbonate. The right chamber is an adhesive seal 6028 and a pressurized chamber 6010, pressurized with gas, and a bellows 6006 is installed in the left chamber. There are no openings connecting the two chambers 6006, 6010. An osmotic release mechanism is used to connect the two chambers 6006, 6010 through a sliding valve 6012. As shown in FIG. 60, osmogen 6014 is contained within a small container below the sliding valve 6012. Osmogen 6014 is separated from the GI fluid by a water permeable membrane 6016 covered with enteric coating 6018. On the top of the osmogen 6014, a shuttle slider 6012 is mounted. The slider 6012 has an opening 6020 in the middle. The slider shuttle 6012 is sandwiched between two slabs of polycarbonate with a pressure through port 6022. When the slider shuttle 6012 is in closed form, the holes on the polycarbonate slabs are not concentric with the hole on the slider shuttle 6012. When the slider shuttle 6012 is in open mode, the holes of the slider and polycarbonate slabs surrounding it all will be concentric letting gas and pressure exchange between the two chambers 6006, 6010.

As the ingestible device 6000 reaches the target location in the small intestine, the enteric coating 6018 separating the membrane 6016 from the GI fluid will dissolve. Water will start moving through the membrane 6016 into the osmogene 6014. With time, the volume of water within the osmogene 6014 will increase building up the pressure on the sliding shuttle 6012. As the pressure reaches certain value, the shuttle 6012 will slide up and its port will become concentric with the ports on the two-polycarbonate slab next to the slider. At this point, high-pressure gas will move to left chamber. This results in an increase in the pressure on the bellows 6006. As the pressure on the bellows 6006 reaches certain value, the bioabsorbable plug 6024 will be ejected from the nozzle 6026 and a jet of dispensable substance will be delivered to the target tissue.

Figure 61:
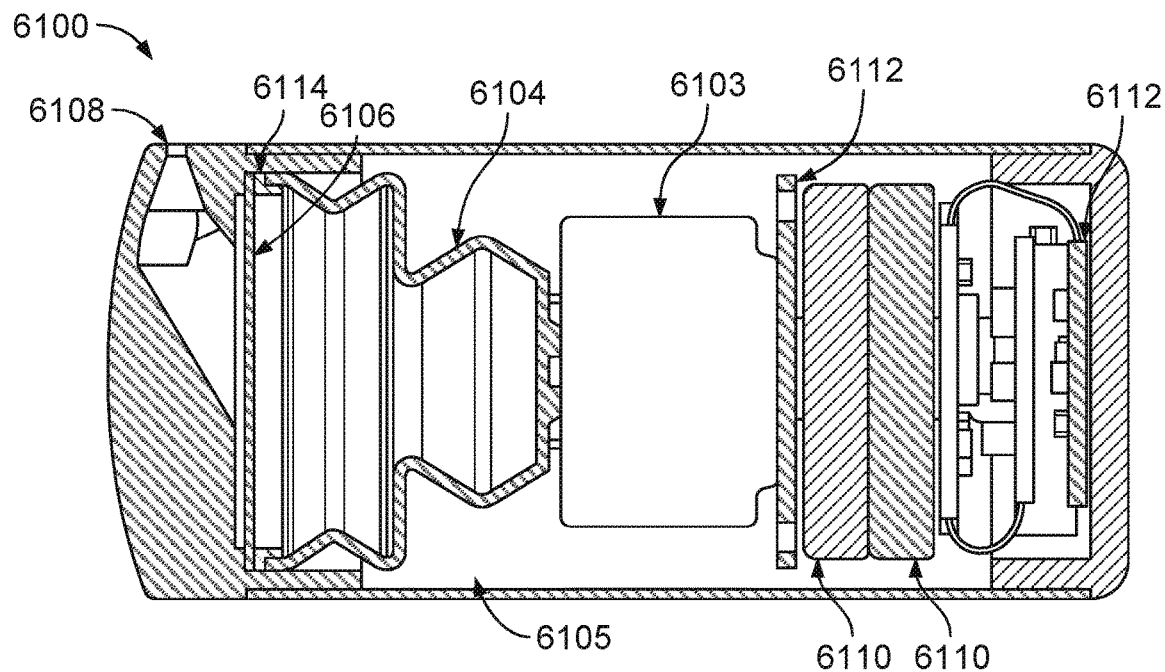
FIG. 61 illustrates an ingestible device including hydrogen cell actuator and burst disc occlusion component, according to some embodiments described herein.

FIG. 61 illustrates an ingestible device 6100 including a hydrogen cell actuator 6112 and a burst disc occlusion component 6106, according to some embodiments described herein. Ingestible device 6100 employs hydrogen cells 6103 as the dispensable substance actuator. The selection of the dispensing site is determined algorithmically. The localization algorithm is used to control the time of activation of hydrogen cell 6103. Bellows 6104 are used to separate the dispensable substance from the localization device and hydrogen cell 6103. A burst disc 6106 is used to ensure that the dispensable substance does not eject the nozzle 6108 before its pressure reaches the design pressure. The capsule 6100 may also include a retention disk 6114 proximate to the burst disk 6106. As the capsule 6100 reaches the target location in GI tract, localization kit will activate the hydrogen cell 6103. With activation, the cell will start releasing hydrogen into the small closed volume 6105 inside the capsule 6100 and the pressure will increase as more and more hydrogen releases. The hydrogen cell 6103 is powered using a battery 6110 and is controlled and/or actuated using a printed circuit board assembly 6112. As the hydrogen pressure increases in the capsule 6100, the pressure on the bellows 6104 will rise as well, pushing the dispensable substance on the burst disc 6106. When the pressure of the dispensable substance reaches the rupture pressure of the burst disc 6106, the disc 6106 will burst directing the high-pressure dispensable substance through the nozzle 6108 to the target tissue.

Figure 62:
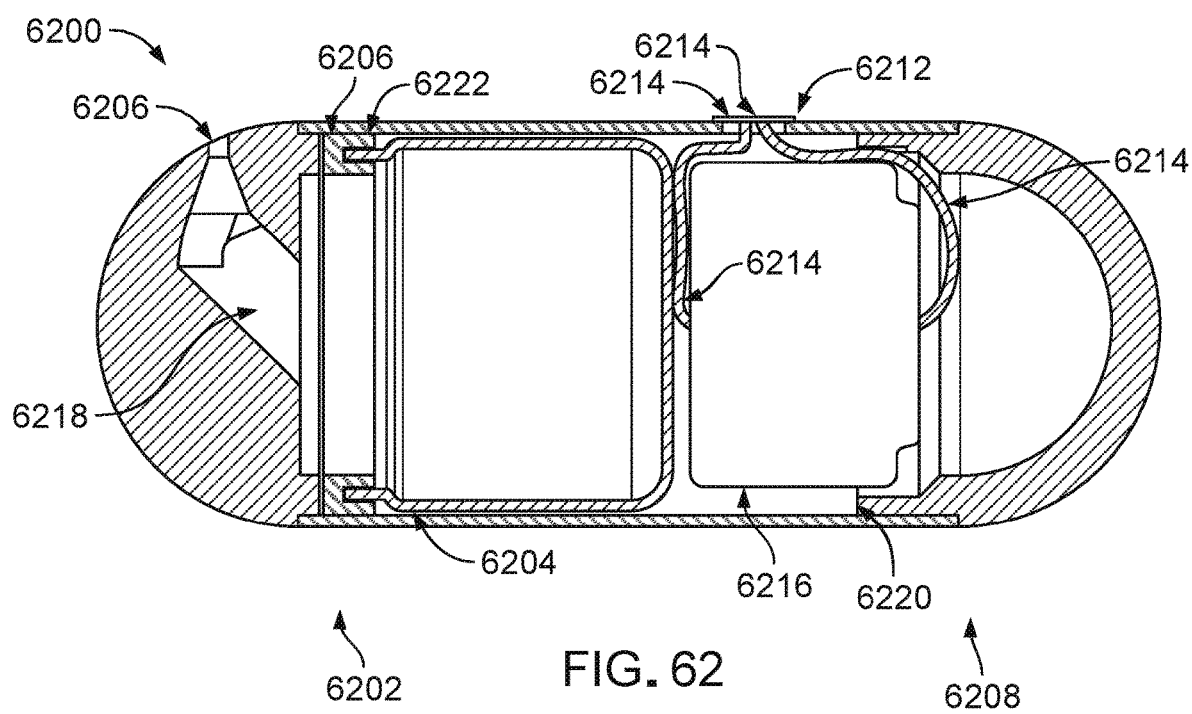
FIG. 62 illustrates another ingestible including hydrogen cell actuator and burst disc occlusion component, according to some embodiments described herein.

FIG. 62 illustrates another ingestible device 6200 including a hydrogen cell actuator 6014 and a burst disc occlusion component 6206, according to some embodiments described herein. In these embodiments, the internal chamber of the ingestible device 6200 is divided into two sections. The left section 6202, which is enclosed by bellows 6204, contains liquid dispensable substance. A burst disc 6206 is used to stop the flow of the dispensable substance though the nozzle 6218 until the dispensable substance pressure reaches the design criteria. The left section 6202 further includes a retention ring 6222. The drive mechanism is installed in the right chamber 6208. The drive mechanism is activated through a bioabsorbable coating mechanism, which is mounted on the outer surface 6210 of the capsule 6200. The main difference between FIGS. 61 and 62 is the replacement of localization kit with bioabsorbable coating mechanism. These results in reduced costs and increase in the volume available for the dispensable substance bellows.

As the capsule 6200 is ingested, it will pass through the digestion system. When the capsule 6200 enters small intestine, the bioabsorbable coating 6212 will dissolve in the intestinal fluid. The segmented conductors 6214 are exposed to the intestinal fluid, which acts as liquid conductor to close the hydrogen release circuit 6216. The capsule 6200 is activated and starts releasing hydrogen inside the right chamber 6208 of the capsule 6200, which includes a pressurizable chamber 6220. With the capsule 6200 fully sealed, release of hydrogen results in pressure rise inside the capsule 6200. As the gas pressure increases, the pressure on the bellows 6204 will rise and consequently, the dispensable substance pressure inside the bellows 6204 will increase. When the dispensable substance pressure reaches the design threshold of the burst disc 6206, the disc 6206 will rupture and high-pressure dispensable substance will flow through the nozzle 6218 toward the target area.

As an alternative to incorporating a pressurized air chamber, a vacuum may be substituted for the purposes of attachment to the intestinal wall. Similar to positive pressure concept, the suction concept incorporates an active release/localization mechanism which would activate as the capsule reaches the target location. As the release mechanism activates, the suction mechanism will provide the required drive to suck the tissue into the capsule (or attach the capsule to the tissue). Upon attachment, another drive mechanism (such as needle and osmotic pressure) may be used to inject the drug into the tissue. One potential advantage of this concept may be to deliver relatively large payloads of dispensable substance directly to the desired location, e.g., tissue of the GI tract of a subject.

Figure 63:
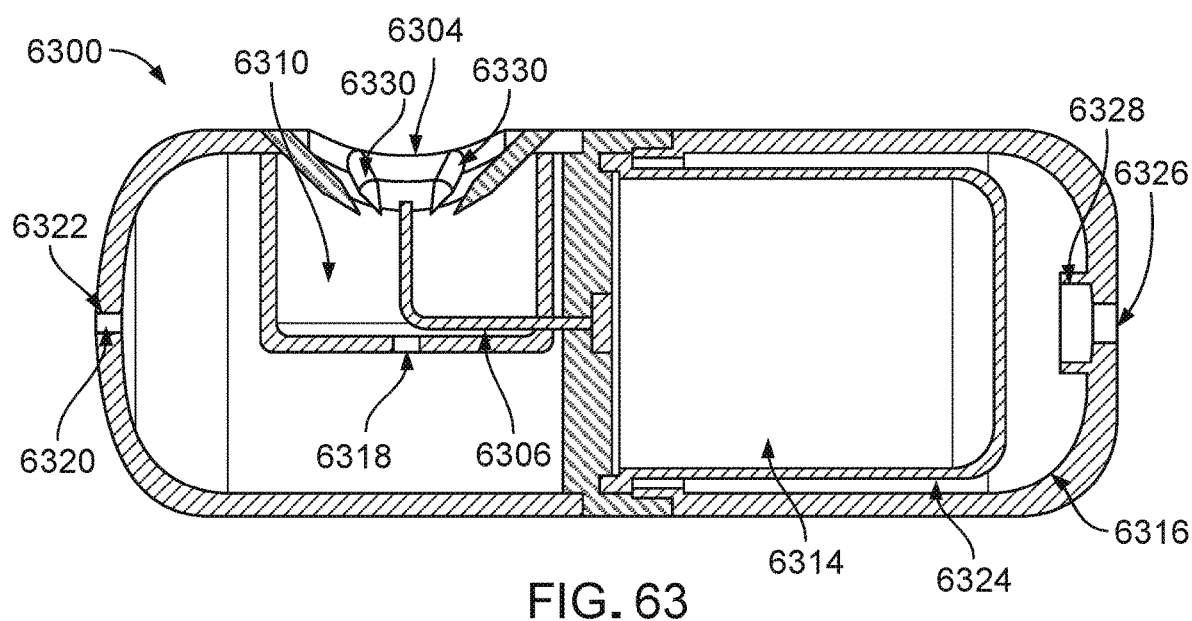
FIG. 63 illustrates an ingestible device including a vacuum actuator chamber and enteric coating occlusion components, according to some embodiments described herein.

FIG. 63 illustrates an ingestible device 6300 including a vacuum actuator chamber 6308 and enteric coating occlusion components, according to some embodiments described herein. Certain embodiments include a vacuum actuator. The vacuum actuator 6308 can be used to attach the ingestible device to the intestinal wall and/or draw the dispensable substance from the dispensable substance reservoir, for example during attachment to the intestinal wall. In certain embodiments, the ingestible device provides suction of approximately 7.5 psi vacuum (7.2 psi absolute pressure)

Similar to positive pressure embodiments, the suction actuator includes an active release/localization mechanism activated as the capsule reaches the target location in response to a detection signal, e.g., a coating configured to dissolve in response to chemical interactions with chemicals generally found in close proximity to the target location. As the release mechanism activates, the suction mechanism will provide the required drive to suck the tissue into the capsule 6300 (or attach the capsule to the tissue). Upon attachment, another drive mechanism (such as needle and osmotic pressure) can be used to inject the dispensable substance into the tissue.

Ingestible device 6300 describes a dispensable substance delivery mechanism based on such suction and direct needle injection. Unlike some of the previous concepts where a high-pressure jet of fluid is used to inject the dispensable substance into the tissue, in this concept, the direct penetration of needle 6306 into the tissue is the dispensable substance delivery mechanism. The capsule 6300 includes several chambers inside a steel body. These chambers are needle chamber 6310, pre-vacuumed chamber 6312 (on the left) and, dispensable substance bellows 6314, salt chamber 6316 (on the right). The needle chamber has an opening on the top with grip spears pointing toward the inner volume of the chamber. The sharp end of the needle 6306 is mounted in the middle of sucker opening 6304. The other end of the needle 3606 sits in the bellows 6314. The needle chamber 6310 has a port 6318 on the bottom connecting it to the pre-vacuumed chamber 6312. This port 6318 is sealed with short delay enteric coating. The pre-vacuumed chamber 6312 sits at the bottom of the needle chamber 6310 and has two ports 6320, 6318. One 6320 on the left of the chamber is used to create the vacuum pressure and the other connects it to the needle chamber. The vacuum port 6320 is sealed with adhesive seal 6322 after the chamber 6312 is vacuumed to the required pressure. The right hand section of the capsule consists of two chambers: dispensable substance chamber 6314 and salt chamber 6316. One chamber 6314 is enclosed by the bellows 6324 and will hold the liquid dispensable substance. One end of the needle 3606 sits inside the chamber 6314 providing a low resistance path for the dispensable substance to flow through the needle 6306 toward the target. The bellows 6324 is surrounded by the salt chamber 6316. This chamber 6316 has an opening 6326 to the surroundings through a semi-permeable membrane 6328. This membrane is covered with long delay enteric coating.

As the capsule 6300 is ingested, it will move through the GI tract. The GI tract fluid will enter the needle chamber 6310 and will dissolve the short delay enteric coating. With proper design of the capsule 6300, it can be ensured that the coating will fully dissolve as the capsule 6300 reaches the target area. With the dissolution of the short delay coating, the port 6322 is exposed and the pre-vacuumed chamber 6312 will suck the target tissue into the needle chamber

6310. The needle 6306 will penetrate the tissue and the spears 6330 will keep the capsule 6300 attached to the tissue. With time, the long delay enteric coating will also dissolve exposing the port 6326 and the semi-permeable membrane 6328 to the GI fluid. Due to the osmotic effect, fluid will transport into the salt chamber 6316 through the membrane 6328 increasing the pressure of the salt chamber 6316 and the bellows 6324. As the pressure of the salt chamber 6316 increases, the dispensable substance will be pushed out of the bellows 6324 through the needle 6306 into the target tissue. With time, due to natural defense mechanism of the body, the spears' 6330 grip to the tissue will weaken and the tissue will be released.

Figure 64:
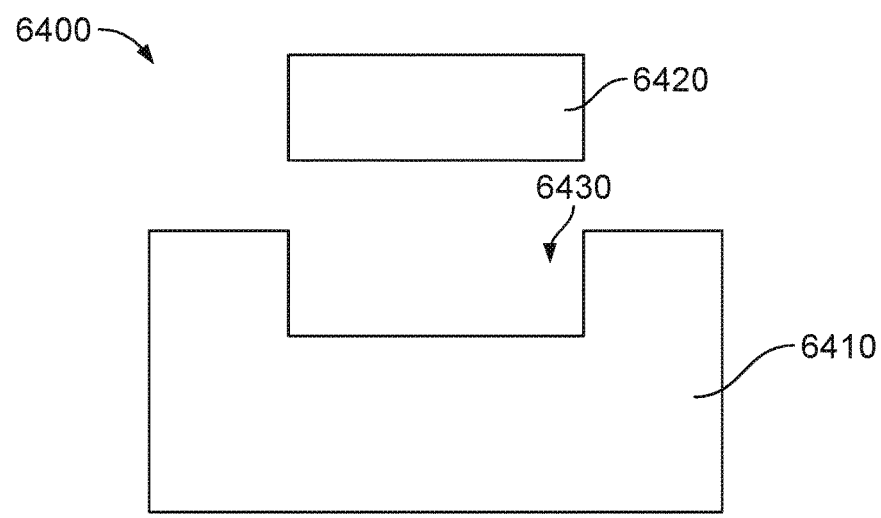
FIG. 64 illustrates an ingestible device including an attachable reservoir, according to some embodiments described herein.

FIG. 64 illustrates a system 6400 that includes an ingestible device 6410 and an attachable storage reservoir 6420. Ingestible device 6410 can be designed as described elsewhere herein, except that it does not include a storage reservoir as an integral component. Attachable reservoir 6420 can be designed as described elsewhere herein, except that it is not an integral component of ingestible device 6410.

In some embodiments, storage reservoir 6420 is loaded with a dispensable substance (e.g., therapeutic agent) prior to being positioned in and/or coupled to ingestible device 6410. As shown in FIG. 64, ingestible device housing 6410 includes one or more openings 6430 configured to house storage reservoir 6420. However, other embodiments can be implemented for attaching an attachable storage reservoir to an ingestible device, some of which are discussed below. Optionally ingestible device housing 6410 includes one or more openings configured as a vent.

Typically, a dispensable substance is disposed in storage reservoir 6410, and storage reservoir 6420 is subsequently attached to ingestible device 6410. For example, reservoir 6420 can be manufactured, packaged and/or shipped separately from device 6410. Optionally, reservoir 6420 and device 6410 are combined relatively soon before a subject is to ingest the device. Given that the safe life time for the ingestible device devoid of dispensable substance (e.g., therapeutic agent) is likely to be substantially longer than the safe life time of the dispensable substance (e.g., therapeutic agent), in some cases, using an attachable device can be desirable, particularly if it is considered undesirable or inconvenient to load dispensable substance into an ingestible device in which a storage reservoir is an integral component.

In general, an attachable storage reservoir and ingestible device can be designed in any appropriate fashion so that the storage reservoir can attach to the ingestible device when desired. Examples of designs include a storage reservoir that fits entirely within the ingestible device (e.g., in the ingestible device so that the storage reservoir is sealed within the device at the time the device is ingested by a subject), a storage reservoir that fits partially within the ingestible device, and a storage reservoir that is carried by the housing of the device. In some embodiments, the storage reservoir snap fits with the ingestible device. In certain embodiments, the storage reservoir is friction fit with the ingestible device. Optionally, the storage reservoir is connected with the ingestible device via a threaded connection. Such a threaded connection could include a seal, such as an O-ring seal. In some embodiments, the storage reservoir is held together with the ingestible device via a biasing mechanism, such as one or more springs, one or more latches, one or more hooks, one or more magnets, and/or electromagnetic radiation. In certain embodiments, the storage reservoir can be a pierceable member. In some embodiments, the ingestible device has a sleeve into which the storage reservoir securely fits. In some embodiments, the storage reservoir is disposed in/on a slidable track/groove so that it can move onto a piercing needle when delivery of the dispensable substance is desired. In certain embodiments a seal can be used in addition to the attachment mechanism to reduce or even prevent ingress of fluid and/or to capture internal pressure within the capsule (e.g., for gas-generating cell embodiments and/or pre-pressurized embodiments). In certain embodiments, the storage reservoir is made of a soft plastic coating, which is contacted with a needle at any orientation to deliver the dispensable substance when desired. Generally, the storage reservoir can be made of one or more appropriate materials, such as, for example, one or more plastics and/or one or more metals or alloys. Exemplary materials include silicone, polyvinyl chloride, polycarbonate and stainless steel. Optionally, the design may be such that the storage reservoir carries some or all of the electrical componentry to be used by the ingestible device. Although the foregoing discussion relates to one storage reservoir, it is to be understood that an ingestible device can be designed to carry any desired number (e.g., two, three, four, five) storage reservoirs. Different storage reservoirs can have the same or different designs. In some embodiments, the ingestible device (when fully assembled and packaged) satisfies the regulatory requirements for marketing a medical device in one or more jurisdictions selected from the United States of America, the European Union or any member state thereof, Japan, China, Brazil, Canada, Mexico, Colombia, Argentina, Chile, Peru, Russia, the UK, Switzerland, Norway, Turkey, Israel, any member state of the Gulf Cooperative Council, South Africa, India, Australia, New Zealand, South Korea, Singapore, Thailand, the Philippines, Malaysia, Viet Nam, and Indonesia.

Although the foregoing description is with respect to system 6400 including ingestible device 6410 and attachable reservoir 6420, the disclosure is not limited in this sense. For example, in some embodiments, an ingestible device can contain one or more storage reservoirs as an integral component and also be designed for use with one or more attachable reservoirs. Optionally, attachable reservoir 6420 can also include features to allow recognition of the reservoir for the purposes of adjusting the dispensing parameters of the capsule and/or prevent the re-use of the device. Typically, the ingestible devices disclosed herein include one or more processing devices, and one more machine readable hardware storage devices. In some embodiments, the one or more machine readable hardware storage devices store instructions that are executable by the one or more processing devices to determine the location of the ingestible device in a portion of a GI tract of the subject. In certain embodiments, the one or more machine readable hardware storage devices store instructions that are executable by the one or more processing devices to transmit data to an external device (e.g., a base station external to the subject, such as a base station carried on an article worn by the subject) capable of implementing the data to determine the location of the device within the GI tract of the subject.

In some embodiments, the location of the ingestible device within the GI tract of the subject can be determined to an accuracy of at least 85%, e.g., at least 90%, at least 95%, at least 97%, at least 98%, at least 99%, 100%. In such embodiments, the portion of the portion of the GI tract of the subject can include, for example, the esophagus, the stomach, duodenum, the jejunum, and/or the terminal ileum, cecum and colon.

In certain embodiments, the location of the ingestible device within the esophagus of the subject can be determined to an accuracy of at least 85%, e.g., at least 90%, at least 95%, at least 97%, at least 98%, at least 99%, 100%.

In some embodiments, the location of the ingestible device within the stomach of the subject can be determined to an accuracy of at least 85%, e.g., at least 90%, at least 95%, at least 97%, at least 98%, at least 99%, 100%.

In certain embodiments, the location of the ingestible device within the duodenum of the subject can be determined to an accuracy of at least 85%, e.g., at least 90%, at least 95%, at least 97%, at least 98%, at least 99%, 100%.

In some embodiments, the location of the ingestible device within the jejunum of the subject can be determined to an accuracy of at least 85%, e.g., at least 90%, at least 95%, at least 97%, at least 98%, at least 99%, 100%.

In certain embodiments, the location of the ingestible device within the terminal ileum, cecum and colon of the subject can be determined to an accuracy of at least 85%, e.g., at least 90%, at least 95%, at least 97%, at least 98%, at least 99%, 100%.

In some embodiments, the location of the ingestible device within the cecum of the subject can be determined to an accuracy of at least 85%, e.g., at least 90%, at least 95%, at least 97%, at least 98%, at least 99%, 100%.

As used herein, the term "reflectance" refers to a value derived from light emitted by the device, reflected back to the device, and received by a detector in or on the device. For example, in some embodiments this refers to light emitted by the device, wherein a portion of the light is reflected by a surface external to the device, and the light is received by a detector located in or on the device.

As used herein, the term "illumination" refers to any electromagnetic emission. In some embodiments, an illumination may be within the range of Infrared Light (IR), the visible spectrum and ultraviolet light (UV), and an illumination may have a majority of its power centered at a particular wavelength in the range of 100 nm to 1000 nm. In some embodiments, it may be advantageous to use an illumination with a majority of its power limited to one of the infrared (750 nm-1000 nm), red (600 nm-750 nm), green (495 nm-600 nm), blue (400 nm-495 nm), or ultraviolet (100 nm-400 nm) spectrums. In some embodiments a plurality of illuminations with different wavelengths may be used. For illustrative purposes, the embodiments described herein may refer to the use of green or blue spectrums of light. However, it is understood that these embodiments may use any suitable light having a wavelength that is substantially or approximately within the green or blue spectra defined above, and the localization systems and methods described herein may use any suitable spectra of light.

Figure 65:
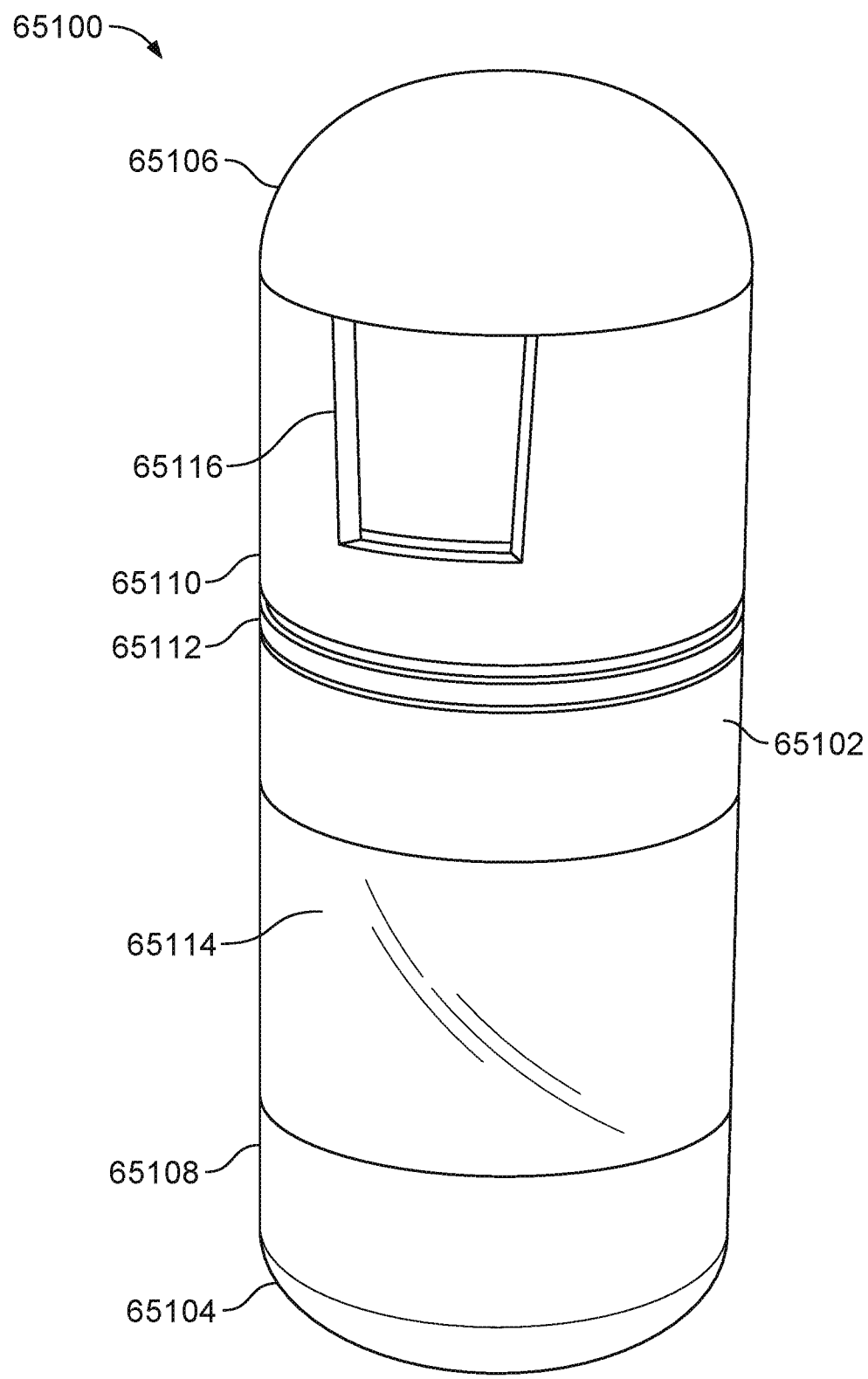
FIG. 65 is a view of an example embodiment of an ingestible device, in accordance with some embodiments of the disclosure.

Referring now to FIG. 65, shown therein is a view of an example embodiment of an ingestible device 65100, which may be used to identify a location within a gastrointestinal (GI) tract. It is to be understood that certain details regarding the design of ingestible device 65100 are not shown in FIG. 65 and the following figures, and that, in general, various aspect of ingestible devices described elsewhere herein can be implemented in ingestible device 65100 and the ingestible devices shown in the following figures.

In some embodiments, ingestible device 65100 may be configured to autonomously determine whether it is located in the stomach, a particular portion of the small intestine such as a duodenum, jejunum, or ileum, or the large intestine by utilizing sensors operating with different wavelengths of light. Additionally, ingestible device 65100 may be configured to autonomously determine whether it is located within certain portions of the small intestine or large intestine, such as the duodenum, the jejunum, the cecum, or the colon.

Ingestible device 65100 may have a housing 65102 shaped similar to a pill or capsule. The housing 65102 of ingestible device 65100 may have a first end portion 65104, and a second end portion 65106. The first end portion 65104 may include a first wall portion 65108, and second end portion 65106 may include a second wall portion 65110. In some embodiments, first end portion 65104 and second end portion 65106 of ingestible device 65100 may be manufactured separately, and may be affixed together by a connecting portion 65112.

In some embodiments, ingestible device 65100 may include an optically transparent window 65114. Optically transparent window 65114 may be transparent to various types of illumination in the visible spectrum, infrared spectrum, or ultraviolet light spectrum, and ingestible device 65100 may have various sensors and illuminators located within the housing 65102, and behind the transparent window 65114. This may allow ingestible device 65100 to be configured to transmit illumination at different wavelengths through transparent window 65114 to an environment external to housing 65102 of ingestible device 65100, and to detect a reflectance from a portion of the illumination that is reflected back through transparent window 65114 from the environment external to housing 65102. Ingestible device 65100 may then use the detected level of reflectance in order to determine a location of ingestible device 65100 within a GI tract. In some embodiments, optically transparent window 65114 may be of any shape and size, and may wrap around the circumference of ingestible device 65100. In this case, ingestible device 65100 may have multiple sets of sensors and illuminators positioned at different locations azimuthally behind window 65114.

In some embodiments, ingestible device 65100 may optionally include an opening 65116 in the second wall portion 65110. In some embodiments, the second wall portion 65110 may be configured to rotate around the longitudinal axis of ingestible device 65100 (e.g., via a suitable motor or other actuator housed within ingestible device 65100). This may allow ingestible device 65100 to obtain a fluid sample from the GI tract, or release a substance into the GI tract, through opening 65116.

Figure 66:
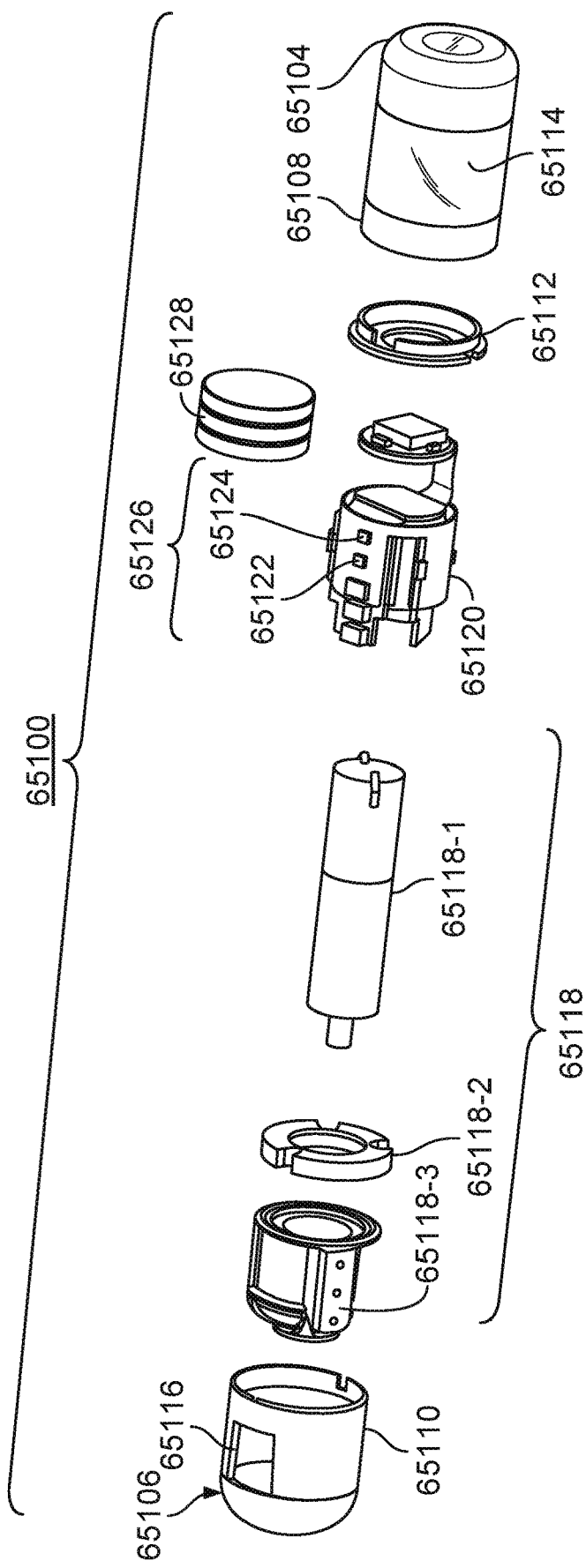
FIG. 66 is an exploded view of the ingestible device of FIG. 65, in accordance with some embodiments of the disclosure.

FIG. 66 shows an exploded view of ingestible device 65100. In some embodiments, ingestible device 65100 may optionally include a rotation assembly 65 118. Optional rotation assembly 65118 may include a motor 65118-1 driven by a microcontroller (e.g., a microcontroller coupled to printed circuit board 65120), a rotation position sensing ring 65118-2, and a storage sub-unit 65118-3 configured to fit snugly within the second end portion 65104. In some embodiments, rotation assembly 65118 may cause second end portion 65104, and opening 65116, to rotate relative to the storage sub-unit 65118-3. In some embodiments, there may be cavities on the side of storage sub-unit 65118-3 that function as storage chambers. When the opening 65116 is aligned with a cavity on the side of the storage sub-unit 65118-3, the cavity on the side of the storage sub-unit 65118-3 may be exposed to the environment external to the housing 65102 of ingestible device 65100. In some embodiments, the storage sub-unit 65118-3 may be loaded with a medicament or other substance prior to the ingestible device 65100 being administered to a subject. In this case, the medicament or other substance may be released from the ingestible device 65100 by aligning opening 65116 with the cavity within storage sub-unit 65118-3. In some embodiments, the storage sub-unit 65118-3 may be configured to hold a fluid sample obtained from the GI tract. For example, ingestible device 65100 may be configured to align opening 65116 with the cavity within storage sub-unit 65118-3, thus allowing a fluid sample from the GI tract to enter the cavity within storage sub-unit 65118-3. Afterwards, ingestible device 65100 may be configured to seal the fluid sample within storage sub-unit 65118-3 by further rotating the second end portion 65106 relative to storage sub-unit 65118-3. In some embodiments, storage sub-unit 118-3 may also contain a hydrophilic sponge, which may enable ingestible device 65100 to better draw certain types of fluid samples into ingestible device 65100. In some embodiments, ingestible device 65100 may be configured to either obtain a sample from within the GI tract, or to release a substance into the GI tract, in response to determining that ingestible device 65100 has reached a predetermined location within the GI tract. For example, ingestible device 65100 may be configured to obtain a fluid sample from the GI tract in response to determining that the ingestible device has entered the jejunum portion of the small intestine (e.g., as determined by process 65900 discussed in relation to FIG. 73). Other ingestible devices capable of obtaining samples or releasing substances are discussed in commonly-assigned PCT Application No. PCT/CA2013/000133 filed Feb. 15, 2013, commonly-assigned U.S. Provisional Application No. 62/385,553, and commonly-assigned U.S. Provisional Application No. 62/376,688, which each are hereby incorporated by reference herein in their entirety. It is understood that any suitable method of obtaining samples or releasing substances may be incorporated into some of the embodiments of the ingestible devices disclosed herein, and that the systems and methods for determining a location of an ingestible device may be incorporated into any suitable type of ingestible device.

Ingestible device 65100 may include a printed circuit board (PCB) 65120, and a battery 65128 configured to power PCB 65120. PCB 65120 may include a programmable microcontroller, and control and memory circuitry for holding and executing firmware or software for coordinating the operation of ingestible device 65100, and the various components of ingestible device 65100. For example, PCB 65120 may include memory circuitry for storing data, such as data sets of measurements collected by sensing sub-unit 65126, or instructions to be executed by control circuitry to implement a localization process, such as, for example, one or more of the processes, discussed herein, including those discussed below in connection with one or more of the associated flow charts. PCB 65120 may include a detector 65122 and an illuminator 65124, which together form sensing sub-unit 65126. In some embodiments, control circuitry within PCB 65120 may include processing units, communication circuitry, or any other suitable type of circuitry for operating ingestible device 65100. For illustrative purposes, only a single detector 65122 and a single illuminator 65124 forming a single sensing sub-unit 65 126 are shown. However, it is understood that in some embodiments there may be multiple sensing sub-units, each with a separate illuminator and detector, within ingestible device 65100. For example, there may be several sensing sub-units spaced azimuthally around the circumference of the PCB 65120, which may enable ingestible device 65100 to transmit illumination and detect reflectances or ambient light in all directions around the circumference of the device. In some embodiments, sensing sub-unit 65126 may be configured to generate an illumination using illuminator 65124, which is directed through the window 65114 in a radial direction away from ingestible device 65100. This illumination may reflect off of the environment external to ingestible device 65100, and the reflected light coming back into ingestible device 65100 through window 65114 may be detected as a reflectance by detector 65122.

In some embodiments, window 65114 may be of any suitable shape and size. For example, window 65114 may extend around a full circumference of ingestible device 65100. In some embodiments there may be a plurality of sensing sub-units (e.g., similar to sensing sub-unit 65126) located at different positions behind the window. For example, three sensing sub-units may be positioned behind the window at the same longitudinal location, but spaced 120 degrees apart azimuthally. This may enable ingestible device 65100 to transmit illuminations in all directions radially around ingestible device 65100, and to measure each of the corresponding reflectances.

In some embodiments, illuminator 65124 may be capable of producing illumination at a variety of different wavelengths in the ultraviolet, infrared, or visible spectrum. For example, illuminator 65124 may be implemented by using Red-Green-Blue Light-Emitting diode packages (RGB-LED). These types of RGB-LED packages are able to transmit red, blue, or green illumination, or combinations of red, blue, or green illumination. Similarly, detector 65122 may be configured to sense reflected light of the same wavelengths as the illumination produced by illuminator 65124. For example, if illuminator 65124 is configured to produce red, blue, or green illumination, detector 65122 may be configured to detect different reflectances produced by red, blue, or green illumination (e.g., through the use of an appropriately configured photodiode). These detected reflectances may be stored by ingestible device 65100 (e.g., within memory circuitry of PCB 65120), and may then be used by ingestible device 65100 in determining a location of ingestible device 65100 within the GI tract (e.g., through the use of process 65500 (FIG. 69), process 65600 (FIG. 70), or process 65900 (FIG. 73)).

It is understood that ingestible device 65100 is intended to be illustrative, and not limiting. It will be understood that modifications to the general shape and structure of the various devices and mechanisms described in relation to FIG. 65 and FIG. 66 may be made without significantly changing the functions and operations of the devices and mechanisms. For example, ingestible device 65100 may have a housing formed from a single piece of molded plastic, rather than being divided into a first end portion 65104 and a second end portion 65106. As an alternate example, the location of window 65114 within ingestible device 65100 may be moved to some other location, such as the center of ingestible device 65100, or to one of the ends of ingestible device 65100. Moreover, the systems and methods discussed in relation to FIGS. 65-74 may be implemented on any suitable type of ingestible device, provided that the ingestible device is capable of detecting reflectances or levels of illumination in some capacity. For example, in some embodiments ingestible device 65100 may be modified to replace detector 65122 with an image sensor, and the ingestible device may be configured to measure relative levels of red, blue, or green light by decomposing a recorded image into its individual spectral components. Other examples of ingestible devices with localization capabilities, which may be utilized in order to implement the systems and methods discussed in relation to FIG. 65-75, are discussed in co-owned PCT Application No. PCT/US2015/052500 filed on Sep. 25, 2015, which is hereby incorporated by reference herein in its entirety. Furthermore, it should be noted that the features and limitations described in any one embodiment may be applied to any other embodiment herein, and the descriptions and examples relating to one embodiment may be combined with any other embodiment in a suitable manner.

Figure 67:
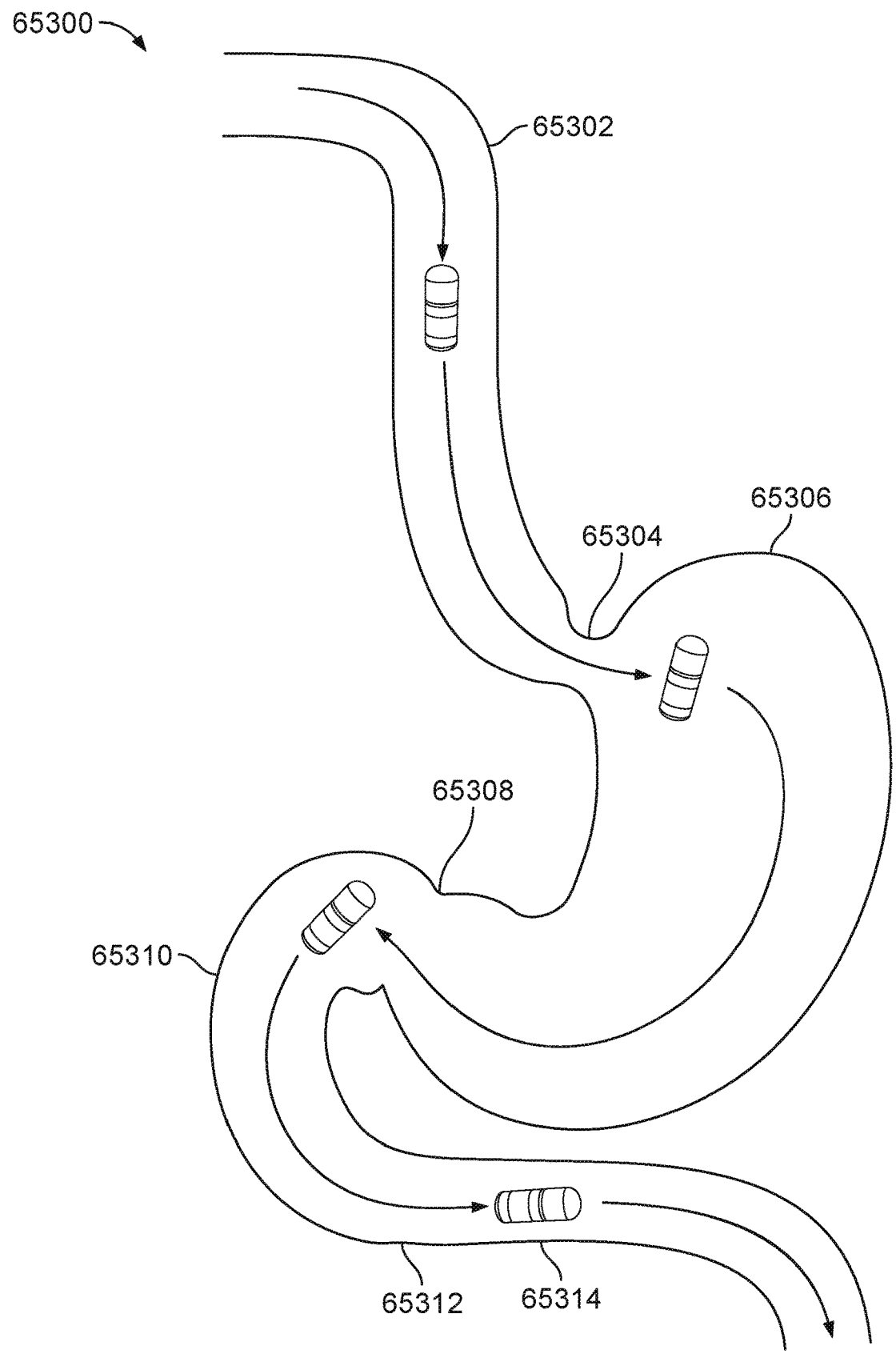
FIG. 67 is a diagram of an ingestible device during an example transit through a GI tract, in accordance with some embodiments of the disclosure.

FIG. 67 is a diagram of an ingestible device during an example transit through a gastrointestinal (GI) tract, in accordance with some embodiments of the disclosure. Ingestible device 65300 may include any portion of any other ingestible device discussed in this disclosure (e.g., ingestible device 65100 (FIG. 65)), and may be any suitable type of ingestible device with localization capabilities. For example, ingestible device 65300 may be one embodiment of ingestible device 65100 without the optional opening 65116 (FIG. 65) or optional rotation assembly 65118 (FIG. 66)). In some embodiments, ingestible device 65300 may be ingested by a subject, and as ingestible device 65300 traverses the GI tract, ingestible device 65300 may be configured to determine its location within the GI tract. For example, the movement of ingestible device 65300 and the amount of light detected by ingestible device 65300 (e.g., via detector 65122 (FIG. 66)) may vary substantially depending on the location of ingestible device 65300 within the GI tract, and ingestible device 65300 may be configured to use this information to determine a location of ingestible device 65300 within the GI tract. For instance, ingestible device 65300 may detect ambient light from the surrounding environment, or reflectances based on illumination generated by ingestible device 65300 (e.g., generated by illuminator 65124 (FIG. 65)), and use this information to determine a location of ingestible device 65300 through processes, such as described herein. The current location of ingestible device 65300, and the time that ingestible device 65300 detected each transition between the various portions of the GI tract, may then be stored by ingestible device 65300 (e.g., in memory circuitry of PCB 65120 (FIG. 66)), and may be used for any suitable purpose.

Shortly after ingestible device 65300 is ingested, ingestible device will traverse the esophagus 65302, which may connect the subject's mouth to a stomach 65306. In some embodiments, ingestible device 65300 may be configured to determine that it has entered the esophagus portion GI tract by measuring the amount and type of light (e.g., via detector 65122 (FIG. 66)) in the environment surrounding the ingestible device 65300. For instance, ingestible device 65300 may detect higher levels of light in the visible spectrum (e.g., via detector 65122 (FIG. 66)) while outside the subject's body, as compared to the levels of light detected while within the GI tract. In some embodiments, ingestible device 65300 may have previously stored data (e.g., on memory circuitry of PCB 65120 (FIG. 66)) indicating a typical level of light detected when outside of the body, and the ingestible device 65300 may be configured to determine that entry to the body has occurred when a detected level of light (e.g., detected via detector 65122 (FIG. 66)) has been reduced beyond a threshold level (e.g., at least a 20-30% reduction) for a sufficient period of time (e.g., 5.0 seconds).

In some embodiments, ingestible device 65300 may be configured to detect a transition from esophagus 65302 to stomach 65306 by passing through sphincter 65304. In some embodiments, ingestible device 65300 may be configured to determine whether it has entered stomach 65306 based at least in part on a plurality of parameters, such as but not limited to the use of light or temperature measurements (e.g., via detector 65122 (FIG. 66) or via a thermometer within ingestible device 65300), pH measurements (e.g., via a pH meter within ingestible device 65300), time measurements (e.g., as detected through the use of clock circuitry included within PCB 65120 (FIG. 66)), or any other suitable information. For instance, ingestible device 65300 may be configured to determine that ingestible device 65300 has entered stomach 65306 after detecting that a measured temperature of ingestible device 65300 exceeds 31 degrees Celsius. Additionally, or alternately, ingestible device 65300 may be configured to automatically determine it has entered stomach 65306 after one minute (or another pre-set time duration parameter, 80 seconds, 90 seconds, etc.) has elapsed from the time that ingestible device 65300 was ingested, or one minute (or another pre-set time duration parameter, 80 seconds, 90 seconds, etc.) from the time that ingestible device 65300 detected that it has entered the GI tract.

Stomach 65306 is a relatively large, open, and cavernous organ, and therefore ingestible device 65300 may have a relatively large range of motion. By comparison, the motion of ingestible device 65300 is relatively restricted within the tube-like structure of the duodenum 65310, the jejunum 65314, and the ileum (not shown), all of which collectively form the small intestine. Additionally, the interior of stomach 65306 has distinct optical properties from duodenum 65310 and jejunum 65314, which may enable ingestible device 65300 to detect a transition from stomach 65306 to duodenum 65310 through the appropriate use of measured reflectances (e.g., through the use of reflectances measured by detector 65122 (FIG. 66)), as used in conjunction with process 65600 (FIG. 70)).

In some embodiments, ingestible device 65300 may be configured to detect a pyloric transition from stomach 65306 to duodenum 65310 through the pylorus 65308. For instance, in some embodiments, ingestible device 65300 may be configured to periodically generate illumination in the green and blue wavelengths (e.g., via illuminator 65124 (FIG. 66)), and measure the resulting reflectances (e.g., via detector 65122 (FIG. 66)). Ingestible device 65300 may be configured to then use a ratio of the detected green reflectance to the detected blue reflectance to determine whether ingestible device 65300 is located within the stomach 65306, or duodenum 65310 (e.g., via process 65600 (FIG. 70)). In turn, this may enable ingestible device 65300 to detect a pyloric transition from stomach 65306 to duodenum 65310, an example of which is discussed in relation to FIG. 70.

Similarly, in some embodiments, ingestible device 65300 may be configured to detect a reverse pyloric transition from duodenum 65310 to stomach 65306. Ingestible device 65300 will typically transition naturally from stomach 65306 to duodenum 65310, and onward to jejunum 65314 and the remainder of the GI tract. However, similar to other ingested substances, ingestible device 65300 may occasionally transition from duodenum 65310 back to stomach 65306 as a result of motion of the subject, or due to the natural behavior of the organs with the GI tract. To accommodate this possibility, ingestible device 65300 may be configured to continue to periodically generate illumination in the green and blue wavelengths (e.g., via illuminator 65124 (FIG. 66)), and measure the resulting reflectances (e.g., via detector 65122 (FIG. 66)) to detect whether or not ingestible device 65300 has returned to stomach 65306. An exemplary detection process is described in additional detail in relation to FIG. 70.

After entering duodenum 65310, ingestible device 65300 may be configured to detect a transition to the jejunum 65314 through the duodenojejunal flexure 65312. For example, ingestible device 65300 may be configured to use reflectances to detect peristaltic waves within the jejunum 65314, caused by the contraction of the smooth muscle tissue lining the walls of the jejunum 65314. In particular, ingestible device 65300 may be configured to begin periodically transmitting illumination (and measuring the resulting reflectances (e.g., via detector 65122 and illuminator 65124 of sensing sub-unit 65126 (FIG. 66)) at a sufficiently high frequency in order to detect muscle contractions within the jejunum 65314. Ingestible device 65300 may then determine that it has entered the jejunum 65314 in response to having detected either a first muscle contraction, or a predetermined number of muscle contractions (e.g., after having detected three muscle contractions in sequence). The interaction of ingestible device 65300 with the walls of jejunum 65314 is also discussed in relation to FIG. 68, and an example of this detection process is described in additional detail in relation to FIG. 73.

Figure 68:
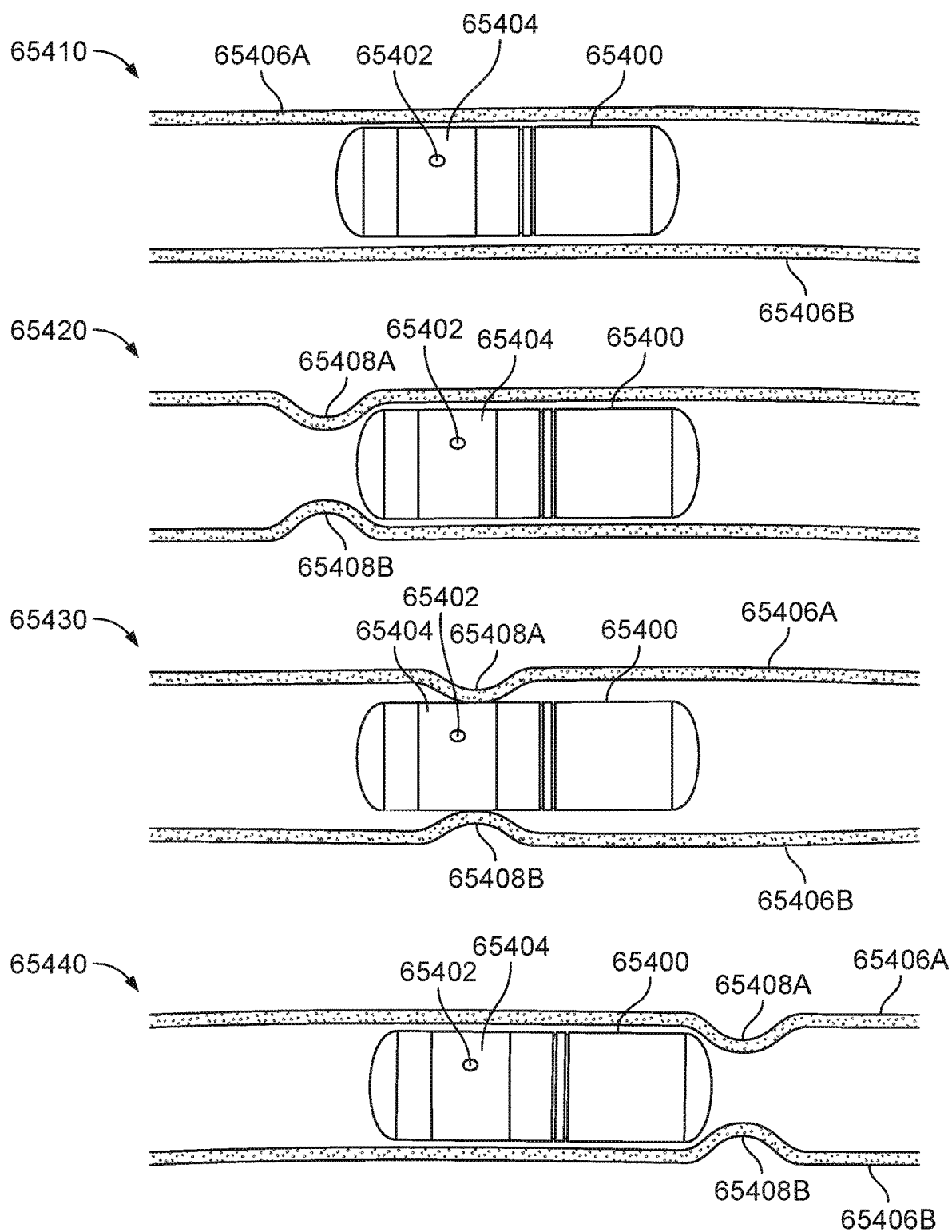
FIG. 68 is a diagram of an ingestible device during an example transit through a jejunum, in accordance with some embodiments of the disclosure.

FIG. 68 is a diagram of an ingestible device during an example transit through a jejunum, in accordance with some embodiments of the disclosure. Diagrams 65410, 65420, 65430, and 65440 depict ingestible device 65400 as it traverses through a jejunum (e.g., jejunum 65314), and how ingestible device 65400 interacts with peristaltic waves formed by walls 65406A and 65406B (collectively, walls 65406) of the jejunum. In some implementations, ingestible device 65400 may include any portion of any other ingestible device discussed in this disclosure (e.g., ingestible device 65100 (FIG. 65) or ingestible device 65300 (FIG. 67)), and may be any suitable type of ingestible device with localization capabilities. For example, ingestible device 65400 may be substantially similar to the ingestible device 65300 (FIG. 67) or ingestible device 65100 (FIG. 66), with window 65404 being the same as window 65114 (FIG. 65), and sensing sub-unit 65402 being the same as sensing sub-unit 65126 (FIG. 66).

Diagram 65410 depicts ingestible device 400 within the jejunum, when the walls 65406 of the jejunum are relaxed. In some embodiments, the confined tube-like structure of the jejunum naturally causes ingestible device 65400 to be oriented longitudinally along the length of the jejunum, with window 65404 facing walls 65406. In this orientation, ingestible device 65400 may use sensing sub-unit 65402 to generate illumination (e.g., via illuminator 65124 (FIG. 66)) oriented towards walls 65406, and to detect the resulting reflectances (e.g., via detector 65122 (FIG. 66)) from the portion of the illumination reflected off of walls 65406 and back through window 65404. In some embodiments, ingestible device 65400 may be configured to use sensing sub-unit 65402 to generate illumination and measure the resulting reflectance with sufficient frequency to detect peristaltic waves within the jejunum. For instance, in a healthy human subject, peristaltic waves may occur at a rate of approximately 0.05 Hz to 0.33 Hz. Therefore, the ingestible device 65400 may be configured to generate illumination and measure the resulting reflectance at least once every 2.5 seconds (i.e., potentially minimum rate to detect a 0.2 Hz signal), and preferably at a higher rate, such as once every 0.5 seconds, which may improve the overall reliability of the detection process due to more data points being available. It is understood that the ingestible device 65400 need not gather measurements at precise intervals, and in some embodiments the ingestible device 65400 may be adapted to analyze data gathered at more irregular intervals, provided that there are still a sufficient number of appropriately spaced data points to detect 0.05 Hz to 0.33 Hz signals.

Diagram 65420 depicts ingestible device 65400 within the jejunum, when the walls 65406 of the jejunum begin to contract and form a peristaltic wave. Diagram 65420 depicts contracting portion 65408A of wall 65406A and contracting portion 65408B of wall 65406B (collectively, contracting portion 65408 of wall 65406) that form a peristaltic wave within the jejunum. The peristaltic wave proceeds along the length of the jejunum as different portions of wall 65406 contract and relax, causing it to appear as if contracting portions 65408 of wall 65406 proceed along the length of the jejunum (i.e., as depicted by contracting portions 65408 proceeding from left to right in diagrams 65410-65430). While in this position, ingestible device 65400 may detect a similar level of reflectance (e.g., through the use of illuminator 65124 and detector 65122 of sensing sub-unit 65126 (FIG. 66)) as detected when there is no peristaltic wave occurring (e.g., as detected when ingestible device 65400 is in the position indicated in diagram 65410).

Diagram 65430 depicts ingestible device 65400 within the jejunum, when the walls 65406 of the jejunum continue to contract, squeezing around ingestible device 65400. As the peristaltic wave proceeds along the length of the jejunum, contracting portions 65408 of wall 65406 may squeeze tightly around ingestible device 65400, bringing the inner surface of wall 65406 into contact with window 65404. While in this position, ingestible device 65400 may detect a change in a reflectance detected as a result of illumination produced by sensing sub-unit 65402. The absolute value of the change in the measured reflectance may depend on several factors, such as the optical properties of the window 65404, the spectral components of the illumination, and the optical properties of the walls 65406. However, ingestible device 65400 may be configured to store a data set with the reflectance values over time, and search for periodic changes in the data set consistent with the frequency of the peristaltic waves (e.g., by analyzing the data set in the frequency domain, and searching for peaks between 0.05 Hz to 0.33 Hz). This may enable ingestible device 65400 to detect muscle contractions due to peristaltic waves without foreknowledge of the exact changes in reflectance signal amplitude that may occur as a result of detecting the muscle contractions of the peristaltic wave. An example procedure for detecting muscle contractions is discussed further in relation to FIG. 73, and an example of a reflectance data set gathered while ingestible device 65400 is located within the jejunum is discussed in relation to FIG. 74.

Diagram 440 depicts ingestible device 65400 within the jejunum, when the peristaltic wave has moved past ingestible device 65400. Diagram 65440 depicts contracting portions 65408 that form the peristaltic wave within the jejunum having moved past the end of ingestible device 65400. The peristaltic wave proceeds along the length of the jejunum as different portions of wall 65406 contract and relax, causing it to appear as if contracting portions 65408 of wall 65406 proceed along the length of the jejunum (i.e., as depicted by contracting portions 65408 proceeding from left to right in diagrams 65410-65430). While in this position, ingestible device 65400 may detect a similar level of reflectance (e.g., through the use of illuminator 65124 and detector 65122 of sensing sub-unit 65126 (FIG. 66)) as detected when there is no peristaltic wave occurring (e.g., as detected when ingestible device 65400 is in the position indicated in diagram 65410, or diagram 65420).

Depending on the species of the subject, peristaltic waves may occur with relatively predictable regularity. After the peristaltic wave has passed over ingestible device 65400 (e.g., as depicted in diagram 65440), the walls 65406 of the jejunum may relax again (e.g., as depicted in diagram 65410), until the next peristaltic wave begins to form. In some embodiments, ingestible device 65400 may be configured to continue to gather reflectance value data while it is within the GI tract, and may store a data set with the reflectance values over time. This may allow ingestible device 65400 to detect each of the muscle contractions as the peristaltic wave passes over ingestible device 65400 (e.g., as depicted in diagram 65430), and may enable ingestible device 65400 to both count the number of muscle contractions that occur, and to determine that a current location of the ingestible device 65400 is within the jejunum. For example, ingestible device 65400 may be configured to monitor for possible muscle contractions while is inside either the stomach or the duodenum, and may determine that ingestible device 65400 has moved to the jejunum in response to detecting a muscle contraction consistent with a peristaltic wave.

Figure 69:
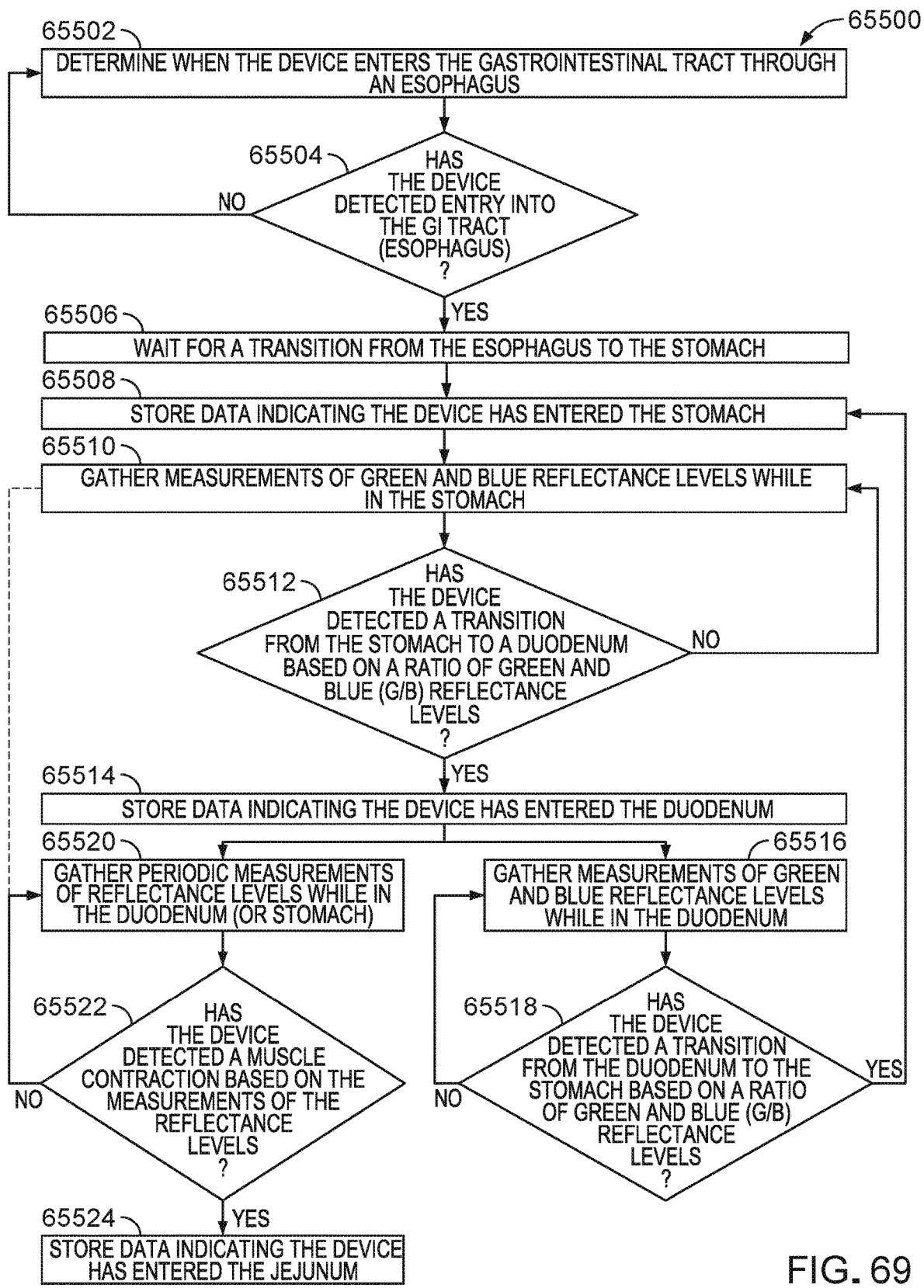
FIG. 69 is a flowchart of illustrative steps for determining a location of an ingestible device as it transits through a GI tract, in accordance with some embodiments of the disclosure.

FIG. 69 is a flowchart illustrating some aspects of a localization process used by the ingestible device. Although FIG. 69 may be described in connection with the ingestible device 65100 for illustrative purposes, this is not intended to be limiting, and either portions or the entirety of the localization procedure 65500 described in FIG. 69 may be applied to any device discussed in this application (e.g., the ingestible devices 65100, 65300, and 65400), and any of the ingestible devices may be used to perform one or more parts of the process described in FIG. 69. Furthermore, the features of FIG. 69 may be combined with any other systems, methods or processes described in this application. For example, portions of the process in FIG. 69 may be integrated into or combined with the pyloric transition detection procedure described by FIG. 70, or the jejunum detection process described by FIG. 73.

At 65502, the ingestible device (e.g., ingestible device 65100, 65300, or 65400) gathers measurements (e.g., through detector 65122 (FIG. 66)) of ambient light. For example, ingestible device 65100 may be configured to periodically measure (e.g., through detector 65122 (FIG. 66)) the level of ambient light in the environment surrounding ingestible device 65100. In some embodiments, the type of ambient light being measured may depend on the configuration of detector 65122 within ingestible device 65100. For example, if detector 65122 is configured to measure red, green, and blue wavelengths of light, ingestible device 65100 may be configured to measure the ambient amount of red, green, and blue light from the surrounding environment. In some embodiments, the amount of ambient light measured by ingestible device 65100 will be larger in the area external to the body (e.g., a well-lit room where ingestible device 65100 is being administered to a subject) and in the oral cavity of the subject, as compared to the ambient level of light measured by ingestible device 65100 when inside of an esophagus, stomach, or other portion of the GI tract (e.g., esophagus 65302, stomach 65306, duodenum 65310, or jejunum 65314 (FIG. 67)).

At 65504, the ingestible device (e.g., ingestible device 65100, 65300, or 65400) determines (e.g., via control circuitry within PCB 65120 (FIG. 66)) whether the ingestible device has detected entry into the GI tract. For example, ingestible device 65100 may be configured to determine when the most recent measurement of ambient light (e.g., the measurement gathered at 65502) indicates that the ingestible device has entered the GI tract. For instance, the first time that ingestible device 65100 gatherers a measurement of ambient light at 65502, ingestible device 65100 may store that measurement (e.g., via storage circuitry within PCB 65120 (FIG. 66)) as a typical level of ambient light external to the body. Ingestible device 65100 may be configured to then compare the most recent measurement of ambient light to the typical level of ambient light external to the body (e.g., via control circuitry within PCB 65120 (FIG. 66)), and determine that ingestible device 65100 has entered the GI tract when the most recent measurement of ambient light is substantially smaller than the typical level of ambient light external to the body. For example, ingestible device 65100 may be configured to detect that it has entered the GI tract in response to determining that the most recent measurement of ambient light is less than or equal to 20% of the typical level of ambient light external to the body. If ingestible device 65100 determines that it has detected entry into the GI tract (e.g., that ingestible device 65100 has entered at least the esophagus 65302 (FIG. 67)), process 65500 proceeds to 65506. Alternately, if ingestible device 65100 determines that it has not detected entry into the GI tract (e.g., as a result of the most recent measurement being similar to the typical level of ambient light external to the body), process 65500 proceeds back to 65502 where the ingestible device 65100 gathers further measurements. For instance, ingestible device 65100 may be configured to wait a predetermined amount of time (e.g., five seconds, ten seconds, etc.), and then gather another measurement of the level of ambient light from the environment surrounding ingestible device 65100.

At 65506, the ingestible device (e.g., ingestible device 65100, 65300, or 65400) waits for a transition from the esophagus to the stomach (e.g., from esophagus 65302 to stomach 65306 (FIG. 67)). For example, ingestible device 65100 may be configured to determine that it has entered the stomach (e.g., stomach 65306 (FIG. 67)) after waiting a predetermined period of time after having entered the GI tract. For instance, a typical esophageal transit time in a human patient may be on the order of 15-30 seconds. In this case, after having detected that ingestible device 65100 has entered the GI tract at 65504 (i.e., after detecting that ingestible device 65100 has reached at least esophagus 65302 (FIG. 67)), ingestible device 65100 may be configured to wait one minute, or a similar amount of time longer than the typical esophageal transmit time (e.g., ninety-seconds), before automatically determining that ingestible device 65100 has entered at least the stomach (e.g., stomach 65306 (FIG. 67)).

In some embodiments, the ingestible device (e.g., ingestible device 65100, 65300, or 65400) may also determine it has entered the stomach based on measurements of pH or temperature. For example, ingestible device 65100 may be configured to determine that it has entered the stomach if a temperature of ingestible device has increased to at least 31 degrees Celsius (i.e., consistent with the temperature inside the stomach), or if a measured pH of the environment surrounding ingestible device 65100 is sufficiently acidic (i.e., consistent with the acidic nature of gastric juices that may be found inside the stomach).

At 65508, the ingestible device (e.g., ingestible device 65100, 65300, or 65400) stores data indicating the ingestible device has entered the stomach (e.g., stomach 306 (FIG. 67)). For example, after having waited a sufficient amount of time at 65506, ingestible device 65100 may store data (e.g., within storage circuitry of PCB 65120 (FIG. 66)) indicative of ingestible device 65100 having entered at least the stomach. Once ingestible device 65100 reaches at least the stomach, process 65500 proceeds to 65510 where ingestible device 65100 may be configured to gather data to detect entry into the duodenum (e.g., duodenum 65310 (FIG. 67)).

In some embodiments, process 65500 may also simultaneously proceed from 65508 to 65520, where ingestible device 65100 may be configured to gather data in order to detect muscle contractions and detect entry into the jejunum (e.g., jejunum 65314 (FIG. 67)). In some embodiments, ingestible device 65100 may be configured to simultaneously monitor for entry into the duodenum at 65516-65518, as well as detect for entry into the jejunum at 65520-65524. This may allow ingestible device 65100 to determine when it has entered the jejunum (e.g., as a result of detecting muscle contractions), even when it fails to first detect entry into the duodenum (e.g., as a result of very quick transit times of the ingestible device through the duodenum).

At 65510, the ingestible device (e.g., ingestible device 65100, 65300, or 65400) gathers measurements of green and blue reflectance levels (e.g., through the use of illuminator 65124 and detector 65122 of sensing sub-unit 65126 (FIG. 66)) while in the stomach (e.g., stomach 65306 (FIG. 67)). For example, ingestible device 100 may be configured to periodically gather measurements of green and blue reflectance levels while in the stomach. For instance, ingestible device 65100 may be configured to transmit a green illumination and a blue illumination (e.g., via illuminator 65124 (FIG. 66)) every five to fifteen seconds, and measure the resulting reflectance (e.g., via detector 65122 (FIG. 66)). Every time that ingestible device 65100 gathers a new set of measurements, the measurements may be added to a stored data set (e.g., stored within memory circuitry of PCB 65120 (FIG. 66)). The ingestible device 65100 may then use this data set to determine whether or not ingestible device 65100 is still within a stomach (e.g., stomach 65306 (FIG. 67)), or a duodenum (e.g., duodenum 65310 (FIG. 67)).

In some embodiments, the ingestible device (e.g., ingestible device 65100, 65300, or 65400) may be configured to detect a first reflectance based on generating an illumination of a first wavelength in approximately the green spectrum of light (between 495-600 nm), and detecting a second reflectance based on generating an illumination of the second wavelength in approximately the blue spectrum of light (between 400-495 nm). In some embodiments, the ingestible device may ensure that the illumination in the green spectrum and the illumination in the blue spectrum have wavelengths separated by at least 50 nm. This may enable ingestible device 65100 to sufficiently distinguish between the two wavelengths when detecting the reflectances (e.g., via detector 65122 (FIG. 66)). It is understood that the separation of 50 nm is intended to be illustrative, and not limiting, and depending on the accuracy of the detectors within ingestible device 65100, smaller separations may be possible to be used.

At 65512, the ingestible device (e.g., ingestible device 65100, 65300, or 65400) determines (e.g., using control circuitry within PCB 65120 (FIG. 66)) whether the ingestible device has detected a transition from the stomach (e.g., stomach 65306 (FIG. 67)) to a duodenum (e.g., duodenum 65310 (FIG. 67)) based on a ratio of green and blue (G/B) reflectance levels. For example, ingestible device 65100 may obtain (e.g., from memory circuitry of PCB 65120 (FIG. 66)) a data set containing historical data for the respective ratio of the green reflectance to the blue reflectance as measured at a respective time. Generally speaking, a duodenum (e.g., duodenum 65310 (FIG. 67)) of a human subject reflects a higher ratio of green light to blue light, as compared to the ratio of green light to blue light that is reflected by a stomach (e.g., stomach 65306 (FIG. 67)). Based on this, ingestible device 65100 may be configured to take a first set of ratios from the data set, representing the result of recent measurements, and compare them to a second set of ratios from the data set, representing the results of past measurements. When the ingestible device 65100 determines that the mean value of the first set of ratios is substantially larger than the mean value of the second set of ratios (i.e., that the ratio of reflected green light to reflected blue light has increased), the ingestible device 65100 may determine that it has entered the duodenum (e.g., duodenum 65310 (FIG. 67)) from the stomach (e.g., stomach 65306 (FIG. 66)). If the ingestible device 65100 detects a transition from the stomach (e.g., stomach 65306 (FIG. 67)) to a duodenum (e.g., duodenum 65310 (FIG. 67)), process 65500 proceeds to 65514, where ingestible device 65100 stores data indicating that the ingestible device 65100 has entered the duodenum (e.g., duodenum 65310 (FIG. 67)). Alternatively, if the ingestible device determines that the ingestible device has not transitioned from the stomach (e.g., stomach 65306 (FIG. 67)) to the duodenum (e.g., duodenum 65310 (FIG. 67)), process 65500 proceeds back to 65510 to gather more measurements of green and blue reflectance levels while still in the stomach (e.g., stomach 65306 (FIG. 67)). An example procedure for using measurements of green and blue reflectances to monitor for transitions between the stomach and the duodenum is discussed in greater detail in relation to FIG. 70.

In some embodiments, the first time that ingestible device 65100 detects a transition from the stomach (e.g., stomach 65306 (FIG. 67)) to the duodenum (e.g., duodenum 65310 (FIG. 67)), ingestible device 65100 may be configured to take a mean of the second set of data, (e.g., the set of data previously recorded while in stomach 65306 (FIG. 67)) and store this as a typical ratio of green light to blue light detected within the stomach (e.g., stomach 65306 (FIG. 67)) (e.g., within memory circuitry of PCB 65120 (FIG. 67)). This stored information may later be used by ingestible device 65100 to determine when ingestible device 65100 re-enters the stomach (e.g., stomach 65306 (FIG. 67)) from the duodenum (e.g., duodenum 65310 (FIG. 67)) as a result of a reverse pyloric transition.

At 65514, the ingestible device (e.g., ingestible device 65100, 65300, or 65400) stores data indicating that the ingestible device has entered the duodenum (e.g., duodenum 65310 (FIG. 67)). For example, ingestible device 65100 may store a flag within local memory (e.g., memory circuitry of PCB 65120) indicating that the ingestible device 65100 is currently in the duodenum. In some embodiments, the ingestible device 65100 may also store a timestamp indicating the time when ingestible device 65100 entered the duodenum. Once ingestible device 65100 reaches the duodenum, process 65500 proceeds to 65520 where ingestible device 65100 may be configured to gather data in order to detect muscle contractions and detect entry into the jejunum (e.g., jejunum 65314 (FIG. 67)). Process 65500 also proceeds from 65514 to 65516, where ingestible device 65100 may be configured to gather data additional data in order to detect re-entry into the stomach (e.g., stomach 65306 (FIG. 67)) from the duodenum (e.g., duodenum 65310 (FIG. 67)).

At 65516, the ingestible device (e.g., ingestible device 65100, 65300, or 65400) gathers measurements (e.g., via sensing sub-unit 65126 (FIG. 66)) of green and blue reflectance levels while in the duodenum (e.g., duodenum 65310 (FIG. 67)). For example, ingestible device 65100 may be configured to periodically gather measurements (e.g., via sensing sub-unit 65126 (FIG. 66)) of green and blue reflectance levels while in the duodenum, similar to the measurements made at 65510 while in the stomach. For instance, ingestible device 65100 may be configured to transmit a green illumination and a blue illumination (e.g., via illuminator 65124 (FIG. 66)) every five to fifteen seconds, and measure the resulting reflectance (e.g., via detector 65122 (FIG. 66)). Every time that ingestible device 65100 gathers a new set of measurements, the measurements may be added to a stored data set (e.g., stored within memory circuitry of PCB 65120 (FIG. 66)). The ingestible device 65100 may then use this data set to determine whether or not ingestible device 65100 is still within the duodenum (e.g., duodenum 65310 (FIG. 67)), or if the ingestible device 65100 has transitioned back into the stomach (e.g., stomach 65306 (FIG. 67)).

At 65518, the ingestible device (e.g., ingestible device 65100, 65300, or 65400) determines a transition from the duodenum (e.g., duodenum 65310 (FIG. 67)) to the stomach (e.g., stomach 65306 (FIG. 67)) based on a ratio of the measured green reflectance levels to the measured blue reflectance levels. In some embodiments, ingestible device 65100 may compare the ratio of the measured green reflectance levels to the measured blue reflectance levels recently gathered by ingestible device 65100 (e.g., measurements gathered at 65516), and determine whether or not the ratio of the measured green reflectance levels to the measured blue reflectance levels is similar to the average ratio of the measured green reflectance levels to the measured blue reflectance levels seen in the stomach (e.g., stomach 65306 (FIG. 67)). For instance, ingestible device 65100 may retrieve data (e.g., from memory circuitry of PCB 65120 (FIG. 66)) indicative of the average ratio of the measured green reflectance levels to the measured blue reflectance levels seen in the stomach, and determine that ingestible device 65100 has transitioned back to the stomach if the recently measured ratio of the measured green reflectance levels to the measured blue reflectance levels is sufficiently similar to the average level in the stomach (e.g., within 20% of the average ratio of the measured green reflectance levels to the measured blue reflectance levels seen in the stomach, or within any other suitable threshold level). If the ingestible device detects a transition from the duodenum (e.g., duodenum 65310 (FIG. 67)) to the stomach (e.g., stomach 65 306 (FIG. 67)), process 65500 proceeds to 65508 to store data indicating the ingestible device has entered the stomach (e.g., stomach 65306 (FIG. 67)), and continues to monitor for further transitions. Alternatively, if the ingestible device does not detect a transition from the duodenum (e.g., duodenum 65310 (FIG. 67)) to the stomach (e.g., stomach 65306 (FIG. 67)), process 65500 proceeds to 65516 to gather additional measurements of green and blue reflectance levels while in the duodenum (e.g., duodenum 65310 (FIG. 67)), which may be used to continuously monitor for possible transitions back into the stomach. An example procedure for using measurements of green and blue reflectances to monitor for transitions between the stomach and the duodenum is discussed in greater detail in relation to FIG. 70.

At 65520, the ingestible device (e.g., ingestible device 65100, 65300, or 65400) gathers periodic measurements of the reflectance levels (e.g., via sensing sub-unit 65126 (FIG. 66)) while in the duodenum (e.g., duodenum 65310 (FIG. 67)). In some embodiments, the ingestible device (e.g., ingestible device 65100, 65300, or 65400) may gather similar periodic measurements while in the stomach as well. In some embodiments, these periodic measurements may enable ingestible device 65100 to detect muscle contractions (e.g., muscle contractions due to a peristaltic wave as discussed in relation to FIG. 68), which may be indicative of entry into a jejunum (e.g., jejunum 65314 (FIG. 67)). Ingestible device 65100 may be configured to gather periodic measurements using any suitable wavelength of illumination (e.g., by generating illumination using illuminator 65124, and detecting the resulting reflectance using detector 65122 (FIG. 66)), or combinations of wavelengths of illumination. For example, in some embodiments, ingestible device 65100 may be configured to generate red, green, and blue illumination, store separate data sets indicative of red, green, and blue illumination, and analyze each of the data sets separately to search for frequency components in the recorded data indicative of detected muscle contractions. In some embodiments, the measurements gathered by ingestible device 65100 at 65520 may be sufficiently fast as to detect peristaltic waves in a subject. For instance, in a healthy human subject, peristaltic waves may occur at a rate of approximately 0.05 Hz to 0.33 Hz. Therefore, the ingestible device 65400 may be configured to generate illumination and measure the resulting reflectance at least once every 2.5 seconds (i.e., potentially minimum rate to detect a 0.2 Hz signal), and preferably at a higher rate, such as once every 0.5 seconds or faster, and store values indicative of the resulting reflectances in a data set (e.g., within memory circuitry of PCB 65120 (FIG. 66)). After gathering additional data (e.g., after gathering one new data point, or a predetermined number of new data points), process 65500 proceeds to 65522, where ingestible device 65100 determines whether or not a muscle contraction has been detected.

At 65522, the ingestible device (e.g., ingestible device 65100, 65300, or 65400) determines (e.g., via control circuitry within PCB 65120 (FIG. 66)) whether the ingestible device detects a muscle contraction based on the measurements of reflectance levels (e.g., as gathered by sensing sub-unit 65126 (FIG. 66)). For example, ingestible device 65100 may obtain a fixed amount of data stored as a result of measurements made at 65520 (e.g., retrieve the past minute of data from memory circuitry within PCB 65120 (FIG. 66)). Ingestible device 65100 may then convert the obtained data into the frequency domain, and search for peaks in a frequency range that would be consistent with peristaltic waves. For example, in a healthy human subject, peristaltic waves may occur at a rate of approximately 0.05 Hz to 0.33 Hz, and an ingestible device 65100 may be configured to search for peaks in the frequency domain representation of the data between 0.05 Hz to 0.33 Hz above a threshold value. If the ingestible device 65100 detects a contraction based on the reflectance levels (e.g., based on detecting peaks in the frequency domain representation of the data between 0.05 Hz to 0.33 Hz), process 65500 proceeds to 65524 to store data indicating that the device has entered the jejunum. Alternatively, if the ingestible device 65100 does not detect a muscle contraction, process 65500 proceeds to 65520 to gather periodic measurements of the reflectance levels while in the duodenum (e.g., duodenum 65310 (FIG. 67)). In some embodiments, the ingestible device (e.g., ingestible device 65100, 65300, or 65400) may store data (e.g., within memory circuitry of PCB 65120 (FIG. 66)) indicating that a muscle contraction was detected, and process 65500 will not proceed from 65522 to 65524 until a sufficient number of muscle contractions have been detected.

At 65524, the ingestible device (e.g., ingestible device 65100, 65300, or 65400) stores data (e.g., within memory circuitry of PCB 65120 (FIG. 66)) indicating that the device has entered the jejunum (e.g., jejunum 65314 (FIG. 67)). For example, in response to detecting that muscle contraction has occurred at 65522, ingestible device 65100 may determine that it has entered the jejunum 65314, and is no longer inside of the duodenum (e.g., duodenum 65310 (FIG. 67)) or the stomach (e.g., stomach 65306 (FIG. 67)). In some embodiments, the ingestible device 65100 may continue to measure muscle contractions while in the jejunum, and may store data indicative of the frequency, number, or strength of the muscle contractions over time (e.g., within memory circuitry of PCB 65120 (FIG. 66)). In some embodiments, the ingestible device 65100 may also be configured to monitor for one or more transitions. Such transitions can include a transition from the jejunum to the ileum, an ileoceacal transition from the ileum to the cecum, a transition from the cecum to the colon, or detect exit from the body (e.g., by measuring reflectances, temperature, or levels of ambient light).

In some embodiments, the ingestible device (e.g., ingestible device 65100, 65300, or 65400) may also determine that it has entered the jejunum (e.g., jejunum 65314 (FIG. 67)) after a pre-determined amount of time has passed after having detected entry into the duodenum (e.g., duodenum 65310 (FIG. 67)). For example, barring a reverse pyloric transition from the duodenum (e.g., duodenum 65310 (FIG. 67)) back to the stomach (e.g., stomach 65306 (FIG. 67)), the typical transit time for an ingestible device to reach the jejunum from the duodenum in a healthy human subject is less than three minutes. In some embodiments, the ingestible device (e.g., ingestible device 65100, 65300, or 65400) may therefore be configured to automatically determine that it has entered the jejunum after spending at least three minutes within the duodenum. This determination may be made separately from the determination made based on measured muscle contractions (e.g., the determination made at 65522), and in some embodiments, ingestible device 65100 may determine that it has entered the jejunum in response to either detecting muscle contractions, or after three minutes has elapsed from having entered the duodenum (e.g., as determined by storing data at 65514 indicative of the time that ingestible device entered the duodenum).

For illustrative purposes, 65512-65518 of process 65500 describe the ingestible device (e.g., ingestible device 65100, 65300, or 65400) measuring green reflectances and blue reflectances, calculating a ratio of the two reflectances, and using this information to determine when the ingestible device has transitioned between the duodenum and stomach. However, in some embodiments, other wavelengths of light may be used other than green and blue, provided that the wavelengths of light chosen have different reflective properties within the stomach and the duodenum (e.g., as a result of different reflection coefficients of the stomach tissue and the tissue of the duodenum).

It will be understood that the steps and descriptions of the flowcharts of this disclosure, including FIG. 69, are merely illustrative. Any of the steps and descriptions of the flowcharts, including FIG. 69, may be modified, omitted, rearranged, and performed in alternate orders or in parallel, two or more of the steps may be combined, or any additional steps may be added, without departing from the scope of the present disclosure. For example, the ingestible device 65100 may calculate the mean and the standard deviation of multiple data sets in parallel in order to speed up the overall computation time. As another example, ingestible device 65100 may gather data periodic measurements and detect possible muscle contractions (e.g., at 65520-65522) while simultaneously gathering green and blue reflectance levels to determine transitions to and from the stomach and duodenum (e.g., at 65510-65518). Furthermore, it should be noted that the steps and descriptions of FIG. 69 may be combined with any other system, device, or method described in this application, including processes 65600 (FIG. 70) and 65900 (FIG. 73), and any of the ingestible devices or systems discussed in this application (e.g., ingestible devices 65100, 65300, or 65400) could be used to perform one or more of the steps in FIG. 69.

Figure 70:
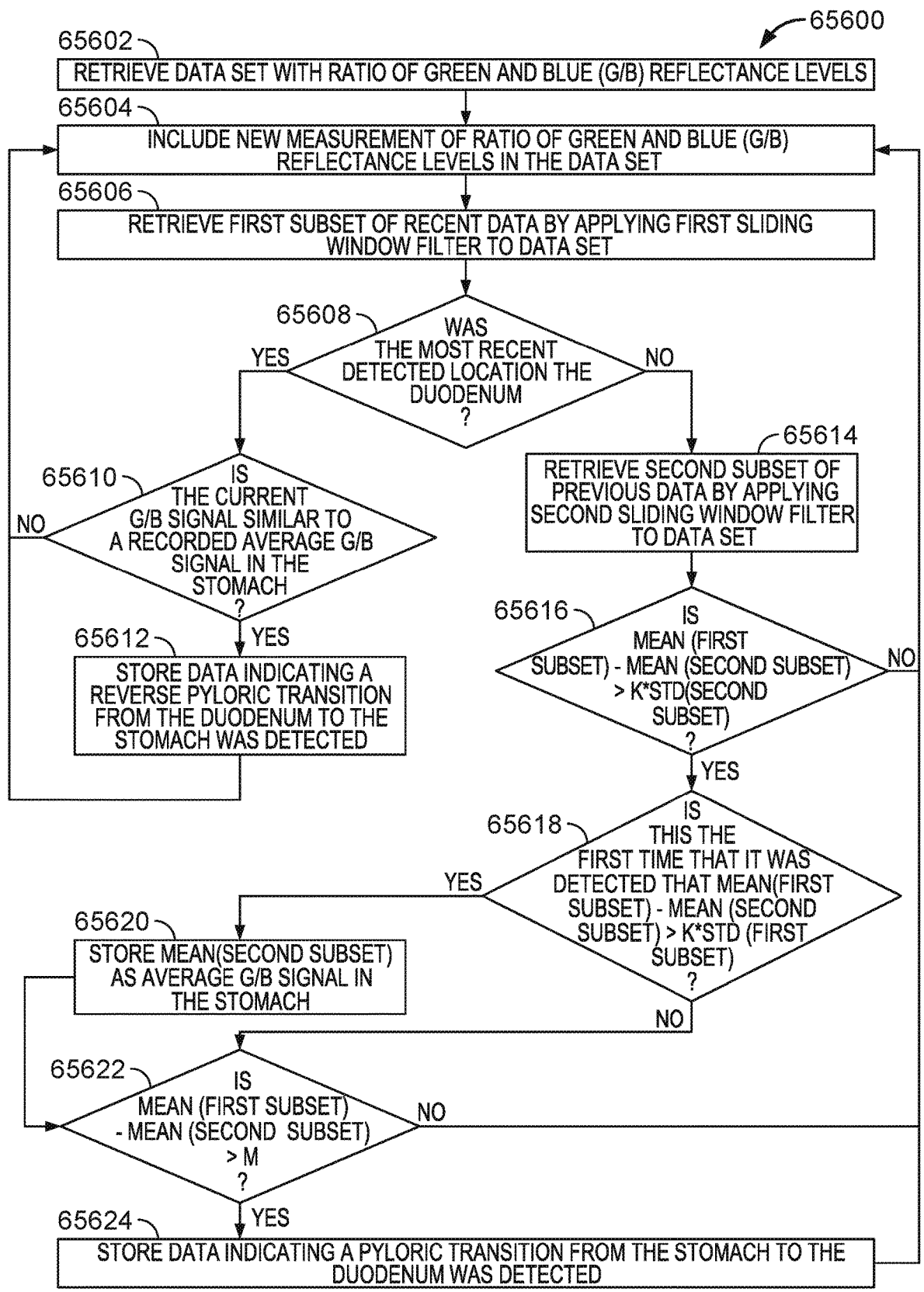
FIG. 70 is a flowchart of illustrative steps for detecting transitions from a stomach to a duodenum and from a duodenum back to a stomach, which may be used when determining a location of an ingestible device as it transits through a GI tract, in accordance with some embodiments of the disclosure.

FIG. 70 is a flowchart illustrating some aspects of a process for detecting transitions from a stomach to a duodenum and from a duodenum back to a stomach, which may be used when determining a location of an ingestible device as it transits through a gastrointestinal (GI) tract, in accordance with some embodiments of the disclosure. In some embodiments, process 65600 may begin when an ingestible device first detects that it has entered the stomach, and will continue as long as the ingestible device determines that it is within the stomach or the duodenum. In some embodiments, process 65600 may only be terminated when an ingestible device determines that it has entered the jejunum, or otherwise progressed past the duodenum and the stomach. Although FIG. 70 may be described in connection with the ingestible device 65100 for illustrative purposes, this is not intended to be limiting, and either portions or the entirety of the duodenum detection process 65600 described in FIG. 70 may be applied to any device discussed in this application (e.g., the ingestible devices 65100, 65300, or 65400), and any of the ingestible devices may be used to perform one or more parts of the process described in FIG. 70. Furthermore, the features of FIG. 70 may be combined with any other systems, methods or processes described in this application. For example, portions of the process described by the process in FIG. 70 may be integrated into process 65500 discussed in relation to FIG. 69.

At 65602, the ingestible device (e.g., ingestible device 65100, 65300, or 65400) retrieves a data set (e.g., from memory circuitry within PCB 65120 (FIG. 66)) with ratios of the measured green reflectance levels to the measured blue reflectance levels over time. For example, ingestible device 65100 may retrieve a data set from PCB 65120 containing recently recorded ratios of the measured green reflectance levels to the measured blue reflectance levels (e.g., as recorded at 65510 or 65516 of process 65500 (FIG. 69)). In some embodiments, the retrieved data set may include the ratios of the measured green reflectance levels to the measured blue reflectance levels over time. Example plots of data sets of ratios of the measured green reflectance levels to the measured blue reflectance levels are discussed further in relation to FIG. 71 and FIG. 72.

At 65604, the ingestible device (e.g., ingestible device 65100, 65300, or 65400) includes a new measurement (e.g., as made with sensing sub-unit 65126 (FIG. 66)) of a ratio of the measured green reflectance level to the measured blue reflectance level in the data set. For example, ingestible device 65100 may be configured to occasionally record new data by transmitting green and blue illumination (e.g., via illuminator 65124 (FIG. 66)), detecting the amount of reflectance received due to the green and blue illumination (e.g., via detector 65122 (FIG. 66)), and storing data indicative of the amount of the received reflectance (e.g., in memory circuitry of PCB 65120 (FIG. 66)). The ingestible device 65100 may be configured to record new data every five to fifteen seconds, or at any other convenient interval of time. For illustrative purposes, ingestible device 65100 is described as storing and retrieving the ratio of the measured green reflectance levels to the measured blue reflectance levels (e.g., if the amount of detected green reflectance was identical to the amount of detected blue reflectance at a given time, the ratio of the green and blue reflectances would be "1.0" at that given time); however, it is understood that the green reflectance data and the blue reflectance data may be stored separately within the memory of ingestible device

65100 (e.g., stored as two separate data sets within memory circuitry of PCB 65120 (FIG. 66)).

At 65606, the ingestible device (e.g., ingestible device 65100, 65300, or 65400) retrieves a first subset of recent data by applying a first sliding window filter to the data set. For example, ingestible device 65100 may use a sliding window filter to obtain a predetermined amount of the most recent data within the data set, which may include any new values of the ratio of the measured green reflectance level to the measured blue reflectance level obtained at 65604. For instance, the ingestible device may be configured to select between ten and forty data points from the data set, or ingestible device 65100 may be configured to select a predetermined range of data values between fifteen seconds of data and five minutes of data. In some embodiments, other ranges of data may be selected, depending on how frequently measurements are recorded, and the particular application at hand. For instance, any suitable amount of data may be selected in the sliding window, provided that it is sufficient to detect statistically significant differences between the data selected in a second sliding window (e.g., the second subset of data selected at 65614).

In some embodiments, the ingestible device (e.g., ingestible device 65100, 65300, or 65400) may also be configured to remove outliers from the data set, or to smooth out unwanted noise in the data set. For example, ingestible device 65100 may select the first subset of data, or any other subset of data, by first obtaining a raw set of values by applying a window filter to the data set (e.g., selecting a particular range of data to be included). Ingestible device 65100 may then be configured to identify outliers in the raw set of values; for instance, by identifying data points that are over three standard deviations away from the mean value of the raw set of values, or any other suitable threshold. Ingestible device 65100 may then determine the subset of data by removing outliers from the raw set of values. This may enable ingestible device 65100 to avoid spurious information when determining whether or not it is located within the stomach or the duodenum.

At 65608, the ingestible device (e.g., ingestible device 65100, 65300, or 65400) determines whether the most recently detected location was the duodenum (e.g., duodenum 65310 (FIG. 67)). In some embodiments, ingestible device 65100 may store a data flag (e.g., within memory circuitry of PCB 65120 (FIG. 66)) indicating the most recent portion of the GI tract that the ingestible device 65100 detected itself to be within. For instance, every time ingestible device 65100 detects entry to the stomach (e.g., detects entry into stomach 65306 (FIG. 67) as a result of the decision made at 65610), a flag is stored in memory indicating the ingestible device 65100 is in the stomach (e.g., as part of storing data at 65612). If ingestible device 65100 subsequently detects entry into the duodenum (e.g., detects entry into duodenum 65310 (FIG. 67) as a result of a decision made at 65624), another different flag is stored in memory indicating that the ingestible device 65100 is in the duodenum (e.g., as part of storing data at 65624). In this case, ingestible device 65100 may retrieve the most recently stored flag at 65608, and determine whether or not the flag indicates that the ingestible device 65100 was most recently within the duodenum. If ingestible device 65100 detects that it was most recently in the duodenum, process 65600 proceeds to 65610 where the ingestible device compares the recent measurements of the ratios of the measured green reflectance levels to the measured blue reflectance levels (e.g., measurements that include the recent measurement made at 65606) to the typical ratios measured within the stomach, and uses this information to determine whether a reverse pyloric transition from the duodenum back to the stomach has occurred. Alternately, if ingestible device 65100 detects that it was not most recently in the duodenum (e.g., because it was in the stomach instead), process 65600 proceeds to 65614 where the ingestible device compares the recent measurements of the ratios of the measured green reflectance levels to the measured blue reflectance levels (e.g., measurements that include the recent measurement made at 65606) to past measurements, and uses this information to determine whether a pyloric transition from the stomach to the duodenum has occurred.

Process 65 600 proceeds from 65608 to 65610 when the ingestible device determined that it was most recently in the duodenum. At 65610, the ingestible device (e.g., ingestible device 65100, 65300, or 65400) determines (e.g., via control circuitry within PCB 65120 (FIG. 66)) whether the current G/B signal is similar to a recorded average G/B signal in the stomach. For example, ingestible device 65100 may be configured to have previously stored data (e.g., within memory circuitry of PCB 65120 (FIG. 66)) indicative of the average ratio of the measured green reflectance levels to the measured blue reflectance levels measured in the stomach. Ingestible device 65100 may then retrieve this stored data indicative of the average ratio of the measured green reflectance levels to the measured blue reflectance levels in the stomach, and compare this against the recent measurements in order to determine whether or not ingestible device 65100 has returned back to the stomach from the duodenum. For instance, ingestible device 65100 may determine if the mean value of the first subset of recent data (i.e., the average value of the recently measured ratios of the measured green reflectance levels to the measured blue reflectance levels) is less than the average ratio of the measured green reflectance levels to the measured blue reflectance levels within the stomach, or less that the average ratio measured within the stomach plus a predetermined number times the standard deviation of the ratios measured within the stomach. For instance, if the average ratio of the measured green reflectance levels to the measured blue reflectance levels in the stomach was "1," with a standard deviation of "0.2," ingestible device 100 may determine whether or not the mean value of the first subset of data is less than "1.0+k*0.2," where "k" is a number between zero and five. It is understood that, in some embodiments, the ingestible device 65100 may be configured to use a different threshold level to determine whether or not the mean value of the first subset of recent data is sufficiently similar to the average ratio of the measured green reflectance levels to the measured blue reflectance levels within the stomach. In response to determining that the recent ratio of the measured green reflectance levels to the measured blue reflectance levels is similar to the average ratio of measured green and blue reflectance levels seen in the stomach, process 65600 proceeds to 65612 where ingestible device 65100 stores data indicating that it has re-entered the stomach from the duodenum. Alternately, in response to determining that the recent ratio of measured green and blue reflectance levels is sufficiently different from the average ratio of measured green and blue reflectance levels seen in the stomach, ingestible device 65100 proceeds directly to 65604, and continues to obtain new data on an ongoing basis.

At 65612, the ingestible device (e.g., ingestible device 65100, 65300, or 65400) stores data indicating a reverse pyloric transition from the duodenum to the stomach was detected. For example, ingestible device 65100 may store a data flag (e.g., within memory circuitry of PCB 65120 (FIG.

66)) indicating that the ingestible device 65100 most recently detected itself to be within the stomach portion of the GI tract (e.g., stomach 65306 (FIG. 67)). In some embodiments, ingestible device 65100 may also store data (e.g., within memory circuitry of PCB 65120 (FIG. 66)) indicating a time that ingestible device 65100 detected the reverse pyloric transition from the duodenum to the stomach. This information may be used by ingestible device 65100 at 65608, and as a result process 65600 may proceed from 65608 to 65614, rather than proceeding from 65618 to 65610. After ingestible device 65100 stores the data indicating a reverse pyloric transition from the duodenum to the stomach was detected, process 65600 proceeds to 65604 where ingestible device 65100 continues to gather additional measurements, and continues to monitor for further transitions between the stomach and the duodenum.

Process 65600 proceeds from 65608 to 65614 when the ingestible device determined that it was not most recently in the duodenum (e.g., as a result of having most recently been in the stomach instead). At 65614, the ingestible device (e.g., ingestible device 65100, 65300, or 65400) retrieves a second subset of previous data by applying a second sliding window filter to the data set. For example, ingestible device 65100 may use a sliding window filter to obtain a predetermined amount of older data from a past time range, which may be separated from recent time range used to select the first subset of data gathered at 65606 by a predetermined period of time. In some embodiments, any suitable amount of data may be selected by the first and second window filters, and the first and second window filters may be separated by any appropriate predetermined amount of time. For example, in some embodiments, the first window filter and the second window filter may each be configured to select a predetermined range of data values from the data set, the predetermined range being between fifteen seconds of data and five minutes of data. In some embodiments, the recent measurements and the past measurements may then be separated by a predetermined period of time that is between one to five times the predetermined range of data values. For instance, ingestible device 65100 may select the first subset of data and the second subset of data to each be one minute of data selected from the dataset (i.e., selected to have a predetermined range of one minute), and the first subset of data and the second subset of data are selected from recorded measurements that are at least two minutes apart (i.e., the predetermined period of time is two minutes, which is twice the range used to select the subsets of data using the window filters). As another example, ingestible device 100 may select the first subset of data and the second subset of data to each be five minutes of data selected from the dataset (i.e., selected to have a predetermined range of five minutes), and the first subset of data and the second subset of data are selected from recorded measurements that are at least 10 minutes apart (i.e., the predetermined period of time is two minutes, which is twice the range used to select the subsets of data using the window filters).

In some embodiments, if ingestible device 65100 recently transitioned to the stomach from the duodenum (e.g., as determined by checking for recent data stored within ingestible device 65100 at 65612), ingestible device 65100 may select the second subset of data at 65614 from a time frame when ingestible device 65100 is known to be within the stomach. In some embodiments, ingestible device 65100 may alternately select a previously recorded average and standard deviation for ratios of green reflectances and blue reflectances within the stomach (e.g., an average and standard deviation typical of data recorded within the stomach, as previously recorded within memory circuitry of PCB 65120 at 65620) in place of the second subset of data. In this case, ingestible device 65100 may simply use the previously recorded average and previously recorded standard deviation when making a determination at 65616, rather than expending resources to calculate the mean and standard deviation of the second subset.

At 65616, the ingestible device (e.g., ingestible device 65100, 65300, or 65400) determines whether the difference between the mean of the second subset and the mean of the first subset is greater than a predetermined multiple of the standard deviation of the first subset. For example, ingestible device 65100 may compute a difference between a mean of the first subset of recent data and a mean of a second subset of past data, and determine whether this difference is greater than three times the standard deviation of the second subset of past data. In some embodiments, it is understood that any convenient threshold level may be used other than three times the standard deviation, such as any value between one and five times the standard deviation. Also, in some embodiments, the ingestible device may instead set the threshold level based on the standard deviation of the second subset instead of the first subset. In response to determining that the difference between the mean of the first subset and the mean of the second subset is greater than a predetermined multiple of the standard deviation of the second subset, process 65600 proceeds to 65618. Otherwise, process 65600 proceeds back to 65604, where the ingestible device 65604 continues to gather new data to be used in monitoring for transitions between the stomach (e.g., stomach 65306 (FIG. 67)) and the duodenum (e.g., duodenum 65310 (FIG. 67)).

At 65618, the ingestible device (e.g., ingestible device 65100, 65300, or 65400) determines (e.g., via control circuitry within PCB 65120 (FIG. 66)) whether the determination made at 65616 is the first time that the difference between the mean of the first subset of recent data and the mean of the second subset of past data is calculated to be greater than the standard deviation of the second subset. If the ingestible device determines that this is the first time that the difference between the mean of the first subset and the mean of the second subset is calculated to be greater than the standard deviation of the second subset, process 65600 proceeds to 65620 to store the mean of the second subset of past data as an average G/B signal in the stomach. Alternatively, if the ingestible device determines that the immediately preceding determination made at 65616 is not the first time that the difference between the mean of the first subset of recent data and the mean of the second subset of past data is calculated to be greater than the standard deviation of the second subset, process 65600 proceeds directly to 65622.

At 65620, the ingestible device (e.g., ingestible device 65100, 65300, or 65400) stores the mean of the second subset as an average G/B signal in the stomach. For example, ingestible device 65100 may be configured to store the mean of the second subset of past data (e.g., store within memory circuitry of PCB 65120 (FIG. 66)) as the average ratio of the measured green reflectance levels to the measured blue reflectance levels measured in the stomach. In some embodiments, ingestible device 65100 may also store the standard deviation of the second subset of past data as a typical standard deviation of the ratios of the measured green reflectance levels to the measured blue reflectance levels detected within the stomach. This stored information may be used by the ingestible device later on (e.g., at 65610) to compare against future data, which may enable the ingestible device to detect reverse pyloric transitions from the duodenum (e.g., duodenum 65310 (FIG. 67)) back to the stomach (e.g., stomach 65306 (FIG. 67)), and may generally be used in place of other experimental data gathered from the stomach (e.g., in place of the second subset of data at 65616). After storing the mean of the second subset as an average G/B signal in the stomach, process 65600 proceeds to 65622.

At 65622, the ingestible device (e.g., ingestible device 65100, 65300, or 65400) determines whether a difference of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 65100 to ensure that it detected an actual transition to the duodenum. This may be particularly advantageous when the determination made at 65616 is potentially unreliable due to the standard deviation of the second subset of past data being abnormally small. For example, a typical value of the predetermined threshold "M," may be on the order of 0.1 to 0.5. If ingestible device 65100 determines that the difference of the mean of the first subset of recent data to the second subset of past data is greater than a predetermined threshold, process 65600 proceeds to 65624 to store data indicating that a pyloric transition from the stomach to the duodenum (e.g., from stomach 65306 to duodenum 65310 (FIG. 67)) was detected. Alternatively, if the ingestible device determines that the ratio of the mean of the first subset to the second subset is less than or equal to the predetermined threshold, "M" (i.e., determines that a transition to the duodenum has not occurred), process 65600 proceeds directly to 65604 where ingestible device 65100 continues to make new measurements and monitor for possible transitions between the stomach and the duodenum.

In some embodiments, instead of using a difference of the mean of the first subset of recent data to the mean of the second subset of past data, the ingestible device (e.g., ingestible device 65100, 65300, or 65400) determines whether the ratio of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 65100 to ensure that it detected an actual transition to the duodenum. This may be particularly advantageous when the determination made at 65616 is potentially unreliable due to the standard deviation of the second subset of past data being abnormally small. For example, a typical value of the predetermined threshold "M," may be on the order of 1.2 to 2.0. It is understood any convenient type of threshold or calculation may be used to determine whether or not the first subset of data and the second subset of data are both statistically distinct from one another, and also substantially different from one another in terms of overall average value.

At 65624, the ingestible device (e.g., ingestible device 65100, 65300, or 65400) stores data indicating a pyloric transition from the stomach to the duodenum was detected. For example, ingestible device 65100 may store a data flag (e.g., within memory circuitry of PCB 65120 (FIG. 66)) indicating that the ingestible device 65100 most recently detected itself to be within the duodenum portion of the GI tract (e.g., duodenum 65310 (FIG. 67)). In some embodiments, ingestible device 65100 may also store data (e.g., within memory circuitry of PCB 65120 (FIG. 66)) indicating a time that ingestible device 65100 detected the pyloric transition from the stomach to the duodenum. This information may be used by ingestible device 65100 at 65608, and as a result process 65600 may proceed from 65608 to 65610, rather than proceeding from 65618 to 65614. After ingestible device 65100 stores the data indicating a pyloric transition from the stomach to the duodenum was detected, process 65600 proceeds to 65604 where ingestible device 65100 continues to gather additional measurements, and continues to monitor for further transitions between the stomach and the duodenum.

It will be understood that the steps and descriptions of the flowcharts of this disclosure, including FIG. 70, are merely illustrative. Any of the steps and descriptions of the flowcharts, including FIG. 70, may be modified, omitted, rearranged, and performed in alternate orders or in parallel, two or more of the steps may be combined, or any additional steps may be added, without departing from the scope of the present disclosure. For example, the ingestible device 65100 may calculate the mean and the standard deviation of multiple data sets in parallel in order to speed up the overall computation time. Furthermore, it should be noted that the steps and descriptions of FIG. 70 may be combined with any other system, device, or method described in this application, and any of the ingestible devices or systems discussed in this application could be used to perform one or more of the steps in FIG. 70. For example, portions of process 65600 may be incorporated into 65508-65516 of process 65500 (FIG. 69), and may be part of a more general process for determining a location of the ingestible device. As another example, the ratio of detected blue and green light (e.g., as measured and added to the data set at 65604) may continue even outside of the stomach or duodenum, and similar information may be recorded by the ingestible device throughout its transit in the GI tract. Example plots of data sets of ratios of measured green and blue reflectance levels, which may be gathered throughout the GI tract, are discussed further in relation to FIG. 71 and FIG. 72 below.

Figure 71:
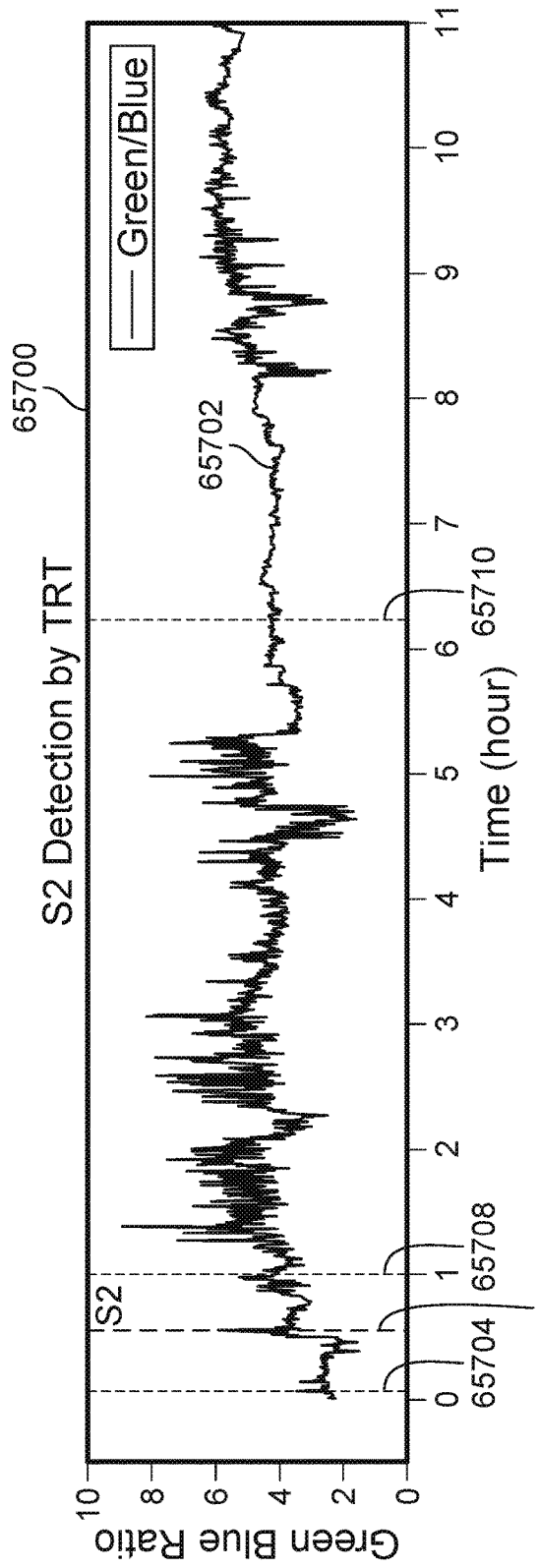
FIG. 71 is a plot illustrating data collected during an example operation of an ingestible device, which may be used when determining a location of an ingestible device as it transits through a GI tract, in accordance with some embodiments of the disclosure.

FIG. 71 is a plot illustrating data collected during an example operation of an ingestible device (e.g., ingestible device 65100, 65300, or 65400), which may be used when determining a location of an ingestible device as it transits through a gastrointestinal (GI) tract, in accordance with some embodiments of the disclosure.

Although FIG. 71 may be described in connection with ingestible device 65100 for illustrative purposes, this is not intended to be limiting, and plot 65700 and data set 65702 may be typical of data gathered by any device discussed in this application. Plot 65700 depicts the ratios of the measured green reflectance levels to the measured blue reflectance levels over time. For example, ingestible device 65100 may have computed the value for each point in the data set 65702 by transmitting green and blue illumination at a given time (e.g., via illuminator 65124 (FIG. 66)), measuring the resulting green and blue reflectances (e.g., via detector 65122 (FIG. 66)), calculating the ratio of the resulting reflectances, and storing the ratio in the data set along with a timestamp indicating the time that the reflectances were gathered.

At 65704, shortly after ingestible device 65100 begins operation, ingestible device 65100 determines that it has reached at least the stomach (e.g., as a result of making a determination similar to the determination discussed in relation to 65506 in process 65500 (FIG. 69)). Ingestible device 65100 continues to gather additional measurements of green and blue reflectance levels, and at 65706 ingestible device 65100 determines that a pyloric transition has occurred from the stomach to the duodenum (e.g., as a result of making a determination similar to the determinations discussed in relation to 65616-65624 of process 65600 (FIG. 70)). Notably, the values in data set 65702 around 65706 jump up precipitously, which is indicative of the higher ratios of measured green reflectance levels to measured blue reflectance levels typical of the duodenum.

The remainder of the data set 65702 depicts the ratios of the measured green reflectance levels to the measured blue reflectance levels throughout the remainder of the GI tract. At 65708, ingestible device 65100 has reached the jejunum (e.g., as determined through measurements of muscle contractions, as discussed in relation to FIG. 73), and by 65710, ingestible device 65100 has reached the cecum. It is understood that, in some embodiments, the overall character and appearance of data set 65702 changes within the small intestine (i.e., the duodenum, jejunum, and ileum) versus the cecum. Within the jejunum and ileum, there may typically be a wide variation in the ratios of the measured green reflectance levels to the measured blue reflectance levels, resulting in relatively noisy data with a high standard deviation. By comparison, within the cecum ingestible device 65100 may measure a relatively stable ratio of the measured green reflectance levels to the measured blue reflectance levels. In some embodiments, ingestible device 65100 may be configured to determine transitions from the small intestine to the cecum based on these differences. For example, ingestible device 65100 may compare recent windows of data to past windows of data, and detect a transition to the cecum in response to determining that the standard deviation of the ratios in the recent window of data is substantially less than the standard deviation of the ratios in the past window of data.

Figure 72:
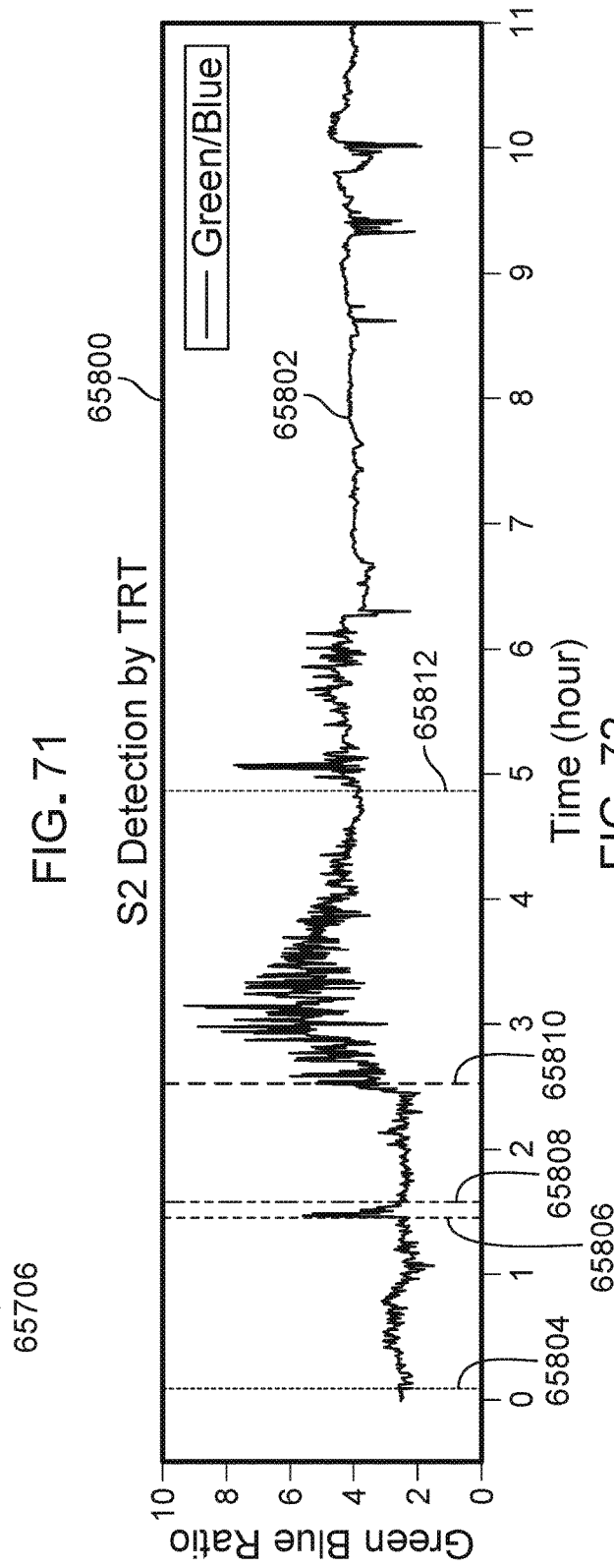
FIG. 72 is another plot illustrating data collected during an example operation of an ingestible device, which may be used when determining a location of an ingestible device as it transits through a GI tract, in accordance with some embodiments of the disclosure.

FIG. 72 is another plot illustrating data collected during an example operation of an ingestible device, which may be used when determining a location of an ingestible device as it transits through a gastrointestinal (GI) tract, in accordance with some embodiments of the disclosure. Similar to FIG. 71, FIG. 72 may be described in connection with the ingestible device 65100 for illustrative purposes. However, this is not intended to be limiting, and plot 65800 and data set 65802 may be typical of data gathered by any device discussed in this application.

At 65804, shortly after ingestible device 65100 begins operation, ingestible device 65100 determines that it has reached at least the stomach (e.g., as a result of making a determination similar to the determination discussed in relation to 65506 in process 500 (FIG. 69)). Ingestible device 65100 continues to gather additional measurements of green and blue reflectance levels (e.g., via sensing sub-unit 65126 (FIG. 66)), and at 65806 ingestible device 65100 determines that a pyloric transition has occurred from the stomach to the duodenum (e.g., as a result of making a determination similar to the determinations discussed in relation to 65616-65624 of process 65600 (FIG. 70)). Notably, the values in data set 65802 around 65806 jump up precipitously, which is indicative of the higher ratios of measured green reflectance levels to measured blue reflectance levels typical of the duodenum, before falling shortly thereafter. As a result of the reduced values in data set 65802, ingestible device 65100 determines that a reverse pyloric transition has occurred from the duodenum back to the stomach at 65808 (e.g., as a result of making a determination similar to the determinations discussed in relation to 65610-65612 of process 65600 (FIG. 70)). At 65810, as a result of the values in data set 65802 increasing again, ingestible device 65100 determines that another pyloric transition has occurred from the stomach to the duodenum, and shortly thereafter ingestible device 65100 proceeds onwards to the jejunum, ileum, and cecum.

The remainder of the data set 65802 depicts the ratios of the measured green reflectance levels to the measured blue reflectance levels throughout the remainder of the GI tract. Notably, at 65812, ingestible device reaches the transition point between the ileum and the cecum. As discussed above in relation to FIG. 71, the transition to the cecum is marked by a reduced standard deviation in the ratios of measured green reflectances and measured blue reflectances over time, and ingestible device 65100 may be configured to detect a transition to the cecum based on determining that the standard deviation of a recent set of measurements is substantially smaller than the standard deviation of past measurements taken from the jejunum or ileum.

Figure 73:
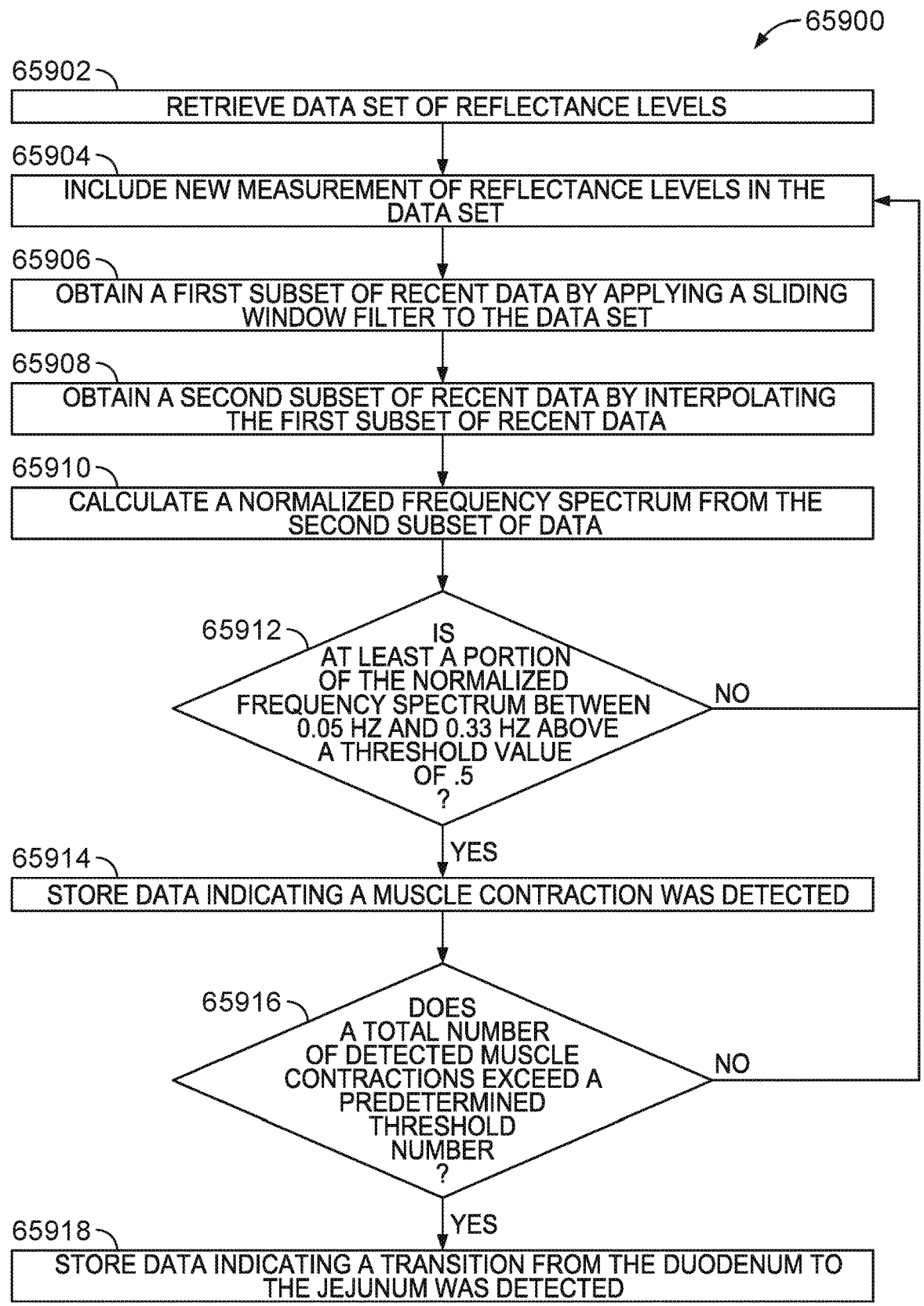
FIG. 73 is a flowchart of illustrative steps for detecting a transition from a duodenum to a jejunum, which may be used when determining a location of an ingestible device as it transits through a GI tract, in accordance with some embodiments of the disclosure.
Figure 74:
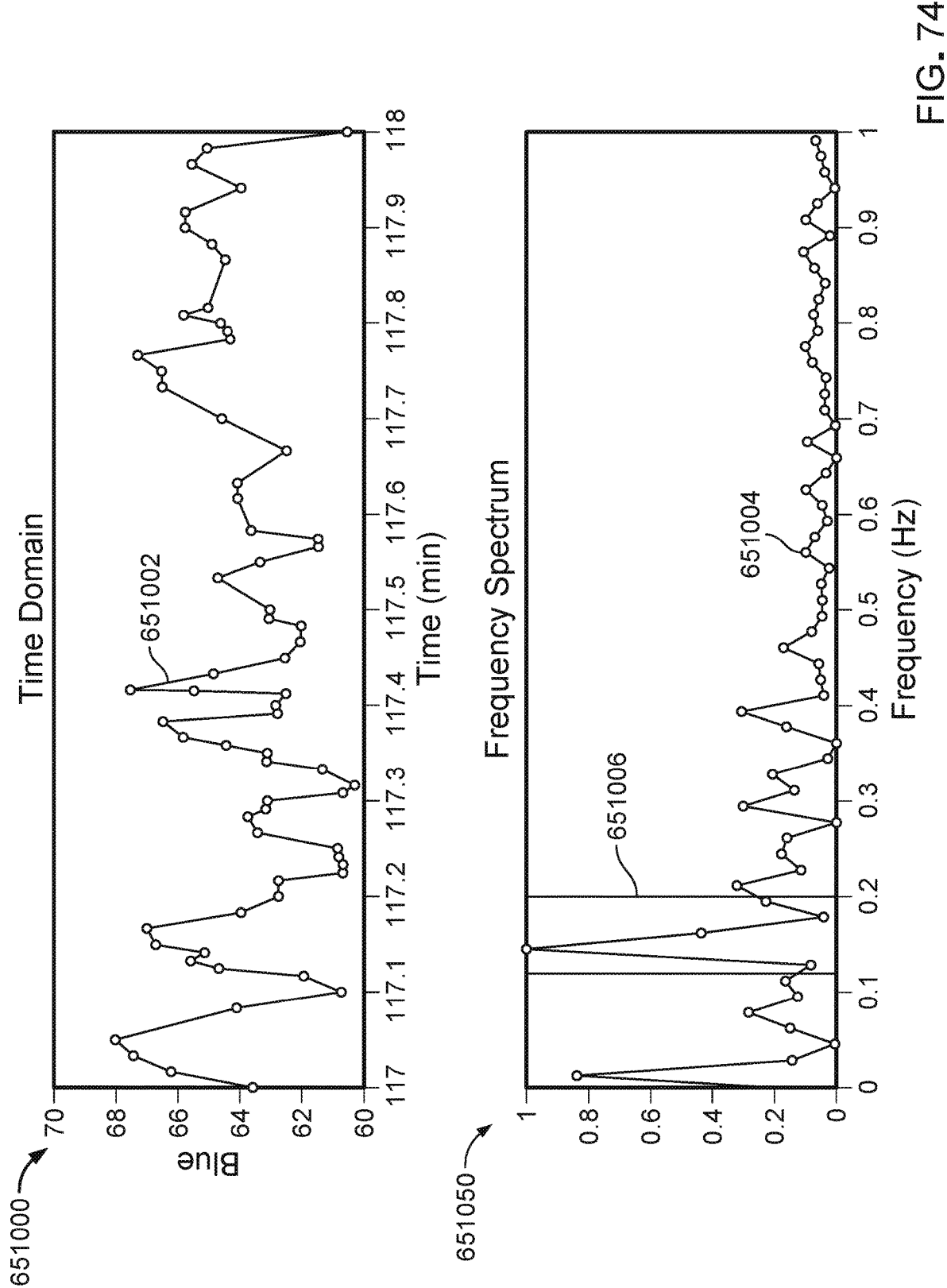
FIG. 74 is a plot illustrating data collected during an example operation of an ingestible device, which may be used when detecting a transition from a duodenum to a jejunum, in accordance with some embodiments of the disclosure.

FIG. 73 is a flowchart of illustrative steps for detecting a transition from a duodenum to a jejunum, which may be used when determining a location of an ingestible device as it transits through a gastrointestinal (GI) tract, in accordance with some embodiments of the disclosure. Although FIG. 73 may be described in connection with the ingestible device 65100 for illustrative purposes, this is not intended to be limiting, and either portions or the entirety of process 65900 described in FIG. 73 may be applied to any device discussed in this application (e.g., the ingestible devices 65100, 65300, and 65400), and any of these ingestible devices may be used to perform one or more parts of the process described in FIG. 73. Furthermore, the features of FIG. 73 may be combined with any other systems, methods or processes described in this application. For example, portions of the process described by the process in FIG. 73 may be integrated into the localization process described by FIG. 69 (e.g., as part of 65520-65524 of process 65500 (FIG. 69)). In some embodiments, an ingestible device 65100 may perform process 65900 while in the duodenum, or in response to detecting entry to the duodenum. In other embodiments, an ingestible device 65100 may perform process 65900 while in the stomach, or in response to detecting entry into the GI tract. It is also understood that process 65900 may be performed in parallel with any other process described in this disclosure (e.g., process 65600 (FIG. 70)), which may enable ingestible device 65100 to detect entry into various portions of the GI tract, without necessarily detecting entry into a preceding portion of the GI tract.

For illustrative purposes, FIG. 73 may be discussed in terms of ingestible device 65100 generating and making determinations based on a single set of reflectance levels generated at a single wavelength by a single sensing sub-unit (e.g., sensing sub-unit 65126 (FIG. 66)). However, it is understood that ingestible device 65100 may generate multiple wavelengths of illumination from multiple different sensing sub-units positioned around the circumference of ingestible device (e.g., multiple sensing sub-units positioned at different locations behind window 65114 of ingestible device 65100 (FIG. 65), and each of the resulting reflectances may be stored as a separate data set. Moreover, each of these sets of reflectance levels may be used to detect muscle contractions by running multiple versions of process 65900, each one of which processes data for a different set of reflectances corresponding to data sets obtained from measurements of different wavelengths or measurements made by different sensing sub-units.

At 65902, the ingestible device (e.g., ingestible device 65100, 65300, or 65400) retrieves a set of reflectance levels. For example, ingestible device 65100 may retrieve a data set of previously recorded reflectance levels from memory (e.g., from memory circuitry of PCB 65120 (FIG. 66)). Each of the reflectance levels may correspond to reflectances previously detected by ingestible device 65100 (e.g., via detector 65122 (FIG. 66)) from illumination generated by ingestible device 65100 (e.g., via illuminator 65124 (FIG. 66)), and may represent a value indicative of an amount of light detected in a given reflectance. However, it is understood that any suitable frequency of light may be used, such as light in the infrared, visible, or ultraviolet spectrums. In some embodiments, the reflectance levels may correspond to reflectances previously detected by ingestible device 65100 at periodic intervals.

At 904, the ingestible device (e.g., ingestible device 65100, 65300, or 65400) includes new measurements of reflectance levels in the data set. For example, ingestible device 65100 may be configured to detect a new reflectance (e.g., transmit illumination and detect the resulting reflectance using sensing sub-unit 65126 (FIG. 66)) at regular intervals, or with sufficient speed as to detect peristaltic waves. For example, ingestible device 65100 may be configured to generate illumination and measure the resulting reflectance once every three seconds (i.e., potentially minimum rate to detect a 0.17 Hz signal), and preferably at a higher rate, as fast at 0.1 second or even faster. It is understood that the periodic interval between measurements may be adapted as needed based on the species of the subject, and the expected frequency of the peristaltic waves to be measured. Every time ingestible device 65100 makes a new reflectance level measurement at 65904, the new data is included to the data set (e.g., a data set stored within memory circuitry of PCB 65120 (FIG. 66)).

At 65906, the ingestible device (e.g., ingestible device 65100, 65 300, or 65400) obtains a first subset of recent data by applying a sliding window filter to the data set. For example, ingestible device 65100 may retrieve a one-minute worth of data from the data set. If the data set includes values for reflectances measured every second, this would be approximately 60 data points worth of data. Any suitable type of window size may be used, provided that the size of the window is sufficiently large to detect peristaltic waves (e.g., fluctuations on the order of 0.05 Hz to 0.33 Hz for healthy human subjects). In some embodiments, ingestible device 65100 may also clean the data, for example, by removing outliers from the first subset of data obtained through the use of the sliding window filter.

At 65908, the ingestible device (e.g., ingestible device 65100, 65300, or 65400) obtains a second subset of recent data by interpolating the first subset of recent data. For example, ingestible device 65100 may interpolate the first subset of data in order to generate a second subset of data with a sufficient number of data points (e.g., data points spaced every 0.5 seconds or greater). In some embodiments, this may enable ingestible device 65100 to also replace any outlier data points that may have been removed as part of applying the window filter at 65906.

At 65910, the ingestible device (e.g., ingestible device 65100, 65300, or 65400) calculates a normalized frequency spectrum from the second subset of data. For example, ingestible device 65100 may be configured to perform a fast Fourier transform to convert the second subset of data from a time domain representation into a frequency domain representation. It is understood that depending on the application being used, and the nature of the subset of data, any number of suitable procedures (e.g., Fourier transform procedures) may be used to determine a frequency spectrum for the second subset of data. For example, the sampling frequency and size of the second subset of data may be known in advance, and ingestible device 65100 may be configured to have pre-stored values of a normalized discreet Fourier transform (DFT) matrix, or the rows of the DFT matrix corresponding to the 0.05 Hz to 0.33 Hz frequency components of interest, within memory (e.g., memory circuitry of PCB 65120 (FIG. 66)). In this case, the ingestible device may use matrix multiplication between the DFT matrix and the data set to generate an appropriate frequency spectrum. An example data set and corresponding frequency spectrum that may be obtained by the ingestible device is discussed in greater detail in relation to FIG. 74.

At 65912, the ingestible device (e.g., ingestible device 65100, 65300, or 65400) determines whether at least a portion of the normalized frequency spectrum is between 00.05 Hz to 0.33 Hz above a threshold value of 0.5 Hz. Peristaltic waves in a healthy human subject occur at a rate between 0.05 Hz to 0.33 Hz, and an ingestible device experiencing peristaltic waves (e.g., ingestible device 65400 detecting contractions in walls 65406 of the jejunum (FIG. 68)) may detect sinusoidal variations in the amplitude of detected reflectances levels that follow a similar 0.05 Hz to 0.33 Hz frequency. If the ingestible device determines that a portion of the normalized frequency spectrum between 0.05 Hz to 0.33 Hz is above a threshold value of 0.5 Hz, this measurement may be consistent with peristaltic waves in a healthy human subject, and process 65900 proceeds to 65914 where ingestible device 65100 stores data indicating a muscle contraction was detected. Alternatively, if the ingestible device determines that no portion of the normalized frequency spectrum between 0.05 Hz to 0.33 Hz above a threshold value of 0.5, process 65900 proceeds directly to 65904 to make new measurements and to continue to monitor for new muscle contractions. It is understood that a threshold value other than 0.5 may be used, and that the exact threshold may depend on the sampling frequency and type of frequency spectrum used by ingestible device 65100.

At 65914, the ingestible device (e.g., ingestible device 65100, 65300, or 65400) stores data indicating a muscle contraction was detected. For example, ingestible device 65100 may store data in memory (e.g., memory circuitry of PCB 65120 (FIG. 66)) indicating that a muscle contraction was detected, and indicating the time that the muscle contraction was detected. In some embodiments, ingestible device 65100 may also monitor the total number of muscle contractions detected, or the number of muscle contractions detected in a given time frame. In some embodiments, detecting a particular number of muscle contractions may be consistent with ingestible device 65100 being within the jejunum (e.g., jejunum 65314 (FIG. 67)) of a healthy human subject. After detecting a muscle contraction, process 65900 proceeds to 65916.

At 65916, the ingestible device (e.g., ingestible device 65100, 65300, or 65400) determines whether a total number of muscle contractions exceeds a predetermined threshold number. For example, ingestible device 65100 may retrieve the total number of muscle contractions detected from memory (e.g., from memory circuitry of PCB 65 120 (FIG. 66)), and compare the total number to a threshold value. In some embodiments, the threshold value may be one, or any number larger than one. The larger the threshold value, the more muscle contractions need to be detected before ingestible device 65100 stores data indicating that it has entered the jejunum. In practice, setting the threshold value as three or higher may prevent the ingestible device from detecting false positives (e.g., due to natural movement of the GI tract organs, or due to movement of the subject). If the total number of contractions exceeds the predetermined threshold number, process 65900 proceeds to 65918 to store data indicating detection of a transition from the duodenum to the jejunum. Alternatively, if the total number of contractions does not exceed a predetermined threshold number, process 65900 proceeds to 65904 to include new measurements of reflectance levels in the data set. An example plot of the muscle contractions detected over time is discussed in greater detail in relation to FIG. 75.

At 65918, the ingestible device (e.g., ingestible device 65100, 65300, or 65400) stores data indicating detection of a transition from the duodenum to the jejunum. For example, ingestible device 65100 may store data in memory (e.g., from memory circuitry of PCB 65120 (FIG. 66)) indicating that the jejunum has been reached. In some embodiments, if ingestible device 65100 is configured to perform all or part of process 65900 while in the stomach, ingestible device 65 100 may store data at 65918 indicating detection of a transition from the stomach directly to the jejunum (e.g., as a result of transitioning too quickly through the duodenum for the pyloric transition to be detected using process 65600 (FIG. 70)).

In some embodiments, the ingestible device (e.g., ingestible device 65100, 65300, or 65400) may be configured to obtain a fluid sample from the environment external to a housing of the ingestible device in response to identifying a change in the location of the ingestible device. For example, ingestible device 65100 may be configured to obtain a fluid sample from the environment external to the housing of ingestible device 65100 (e.g., through the use of optional opening 65116 and optional rotating assembly 65118 (FIG. 66)) in response to determining that the ingestible device is located within the jejunum (e.g., jejunum 65314 (FIG. 67)). In some embodiments, ingestible device 65100 may also be equipped with appropriate diagnostics to detect certain medical conditions based on the retrieved fluid sample, such as small intestinal bacterial overgrowth (SIBO).

In some embodiments, the ingestible device (e.g., ingestible device 65100, 65300, or 65400) may be configured to deliver a dispensable substance that is pre-stored within the ingestible device from the ingestible device into the gastrointestinal tract in response to identifying the change in the location of the ingestible device. For example, ingestible device 65100 may have a dispensable substance pre-stored within the ingestible device 65100 (e.g., within a storage chamber or cavity on optional storage sub-unit 65118-3 (FIG. 66)), and ingestible device 65100 may be configured to dispense the substance into the gastrointestinal tract (e.g., through the use of optional opening 65116 and optional rotating assembly 65118 (FIG. 66)) when the ingestible device 65100 detects that the ingestible device 65100 is located within the jejunum (e.g., jejunum 65314 (FIG. 67)). In some embodiments, this may enable ingestible device 65100 to deliver substances (e.g., therapeutics and medicaments) at targeted locations within the GI tract.

In some embodiments, the ingestible device (e.g., ingestible device 65100, 65300, or 65400) may be configured to perform an action based on the total number of detected muscle contractions. For example, ingestible device 65100 may be configured to retrieve data indicative of the total number of muscle contractions (e.g., from memory circuitry of PCB 65120 (FIG. 66)), and compare that to an expected number of muscle contractions in a healthy individual. In response, the ingestible device may either dispense a substance into the gastrointestinal tract (e.g., through the use of optional opening 65116 and optional rotating assembly 65118 (FIG. 66)), or may obtain a fluid sample from the environment external to the housing of ingestible device 65100 (e.g., through the use of optional opening 65116 and optional rotating assembly 65118 (FIG. 66)). For instance, ingestible device 65100 may be configured to obtain a sample in response to determining that a number of detected muscle contractions is abnormal, and differs greatly from the expected number. As another example, ingestible device 65100 may be configured to deliver a substance into the GI tract (such as a medicament), in response to determining that the detected muscle contractions are consistent with a functioning GI tract in a healthy individual.

It will be understood that the steps and descriptions of the flowcharts of this disclosure, including FIG. 73, are merely illustrative. Any of the steps and descriptions of the flowcharts, including FIG. 73, may be modified, omitted, rearranged, performed in alternate orders or in parallel, two or more of the steps may be combined, or any additional steps may be added, without departing from the scope of the present disclosure. For example, the ingestible device 65100 may calculate the mean and the standard deviation of multiple data sets in parallel (e.g., multiple data sets, each one corresponding to a different wavelength of reflectance or different sensing sub-unit used to detect the reflectance) in order to speed up the overall computation time. Furthermore, it should be noted that the steps and descriptions of FIG. 73 may be combined with any other system, device, or method described in this application, and any of the ingestible devices or systems discussed in this application could be used to perform one or more of the steps in FIG. 73.

FIG. 6510 is a plot illustrating data collected during an example operation of an ingestible device, which may be used when detecting a transition from a duodenum to a jejunum, in accordance with some embodiments of the disclosure. Diagram 651000 depicts a time domain plot 651002 of a data set of reflectance levels measured by an ingestible device (e.g., the second subset of data discussed in relation to 65908 of FIG. 73). In some embodiments, ingestible device 65100 may be configured to gather data points at semi-regular intervals approximately 0.5 seconds apart. By comparison, diagram 651050 depicts a frequency domain plot 651004 of the same data set of reflectance levels measured by an ingestible device (e.g., as a result of ingestible device 65100 calculating a frequency spectrum at 65910 of FIG. 73). In some embodiments, ingestible device 65100 may be configured to calculate the frequency spectrum through any convenient means.

In diagram 651050, the range of frequencies 651006 between 0.05 Hz to 0.33 Hz may be the range of frequencies that ingestible device 65100 searches in order to detect muscle contractions. As shown in diagram 651050, there is a strong peak in the frequency domain plot 651004 around 0.14 Hz, which is consistent with the frequency of peristaltic motion in a healthy human individual. In this case, an ingestible device 65100 analyzing frequency domain plot 651004 may be configured to determine that the data is consistent with a detected muscle contraction (e.g., using a process similar to 65912 of process 65900 (FIG. 73)), and may store data (e.g., in memory circuitry of PCB 65120 (FIG. 66)) indicating that a muscle contraction has been detected. Because the muscle contraction was detected from the one-minute window of data ending at 118 minutes, ingestible device 65100 may also store data indicating that the muscle contraction was detected at the 118-minute mark (i.e., which may indicate that the ingestible device 65100 was turned on and ingested by the subject 118 minutes ago).

Figure 75:
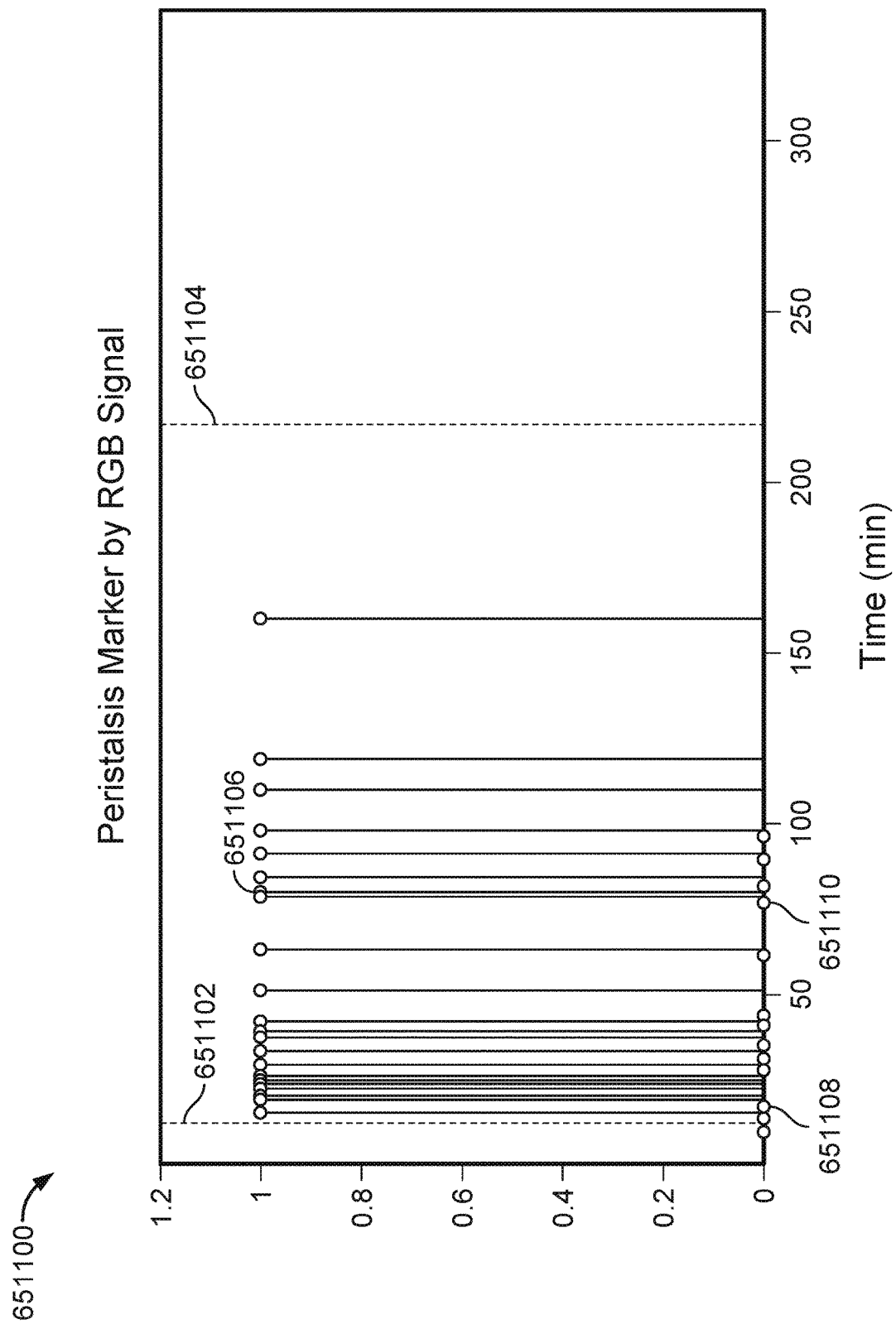
FIG. 75 is a plot illustrating muscle contractions detected by an ingestible device over time, which may be used when determining a location of an ingestible device as it transits through a GI tract, in accordance with some embodiments of the disclosure.

FIG. 75 is a plot illustrating muscle contractions detected by an ingestible device over time, which may be used when determining a location of an ingestible device as it transits through a gastrointestinal (GI) tract, in accordance with some embodiments of the disclosure. In some embodiments, ingestible device 65100 may be configured to detect muscle contractions, and store data indicative of when each muscle contraction is detected (e.g., as part of 65914 of process 65900 (FIG. 73)). Plot 651100 depicts the detected muscle contractions 651106 over time, with each muscle contraction being represented by a vertical line reaching from "0" to "1" on the y-axis.

At 651102, around the 10-minute mark, ingestible device 65100 first enters the duodenum (e.g., as determined by ingestible device 65100 performing process 65600 (FIG. 70)). Shortly thereafter, at 651108, ingestible device 65100 begins to detect several muscle contractions 1106 in quick succession, which may be indicative of the strong peristaltic waves that form in the jejunum (e.g., jejunum 65314 (FIG. 67)). Later, around 651110, ingestible device 65100 continues to detect intermittent muscle contractions, which may be consistent with an ingestible device 65100 within the ileum. Finally, at 651104, ingestible device 65100 transitions out of the small intestine, and into the cecum. Notably, ingestible device 65100 detects more frequent muscle contractions in the jejunum portion of the small intestine as compared to the ileum portion of the small intestine, and ingestible device 65100 does not measure any muscle contractions after having exited the small intestine. In some embodiments, ingestible device 65100 may incorporate this information into a localization process. For example, ingestible device 65100 may be configured to detect a transition from a jejunum to an ileum in response to determining that a frequency of detected muscle contractions (e.g., the number of muscle contractions measured in a given 10-minute window) has fallen below a threshold number. As another example, ingestible device 65100 may be configured to detect a transition from an ileum to a cecum in response to determining that no muscle contractions have been detected for a threshold period of time. It is understood that these examples are intended to be illustrative, and not limiting, and that measurements of muscle contractions may be combined with any of the other processes, systems, or methods discussed in this disclosure.

FIG. 75 is a flowchart 651200 for certain embodiments for determining a transition of the device from the jejunum to the ileum. It is to be noted that, in general, the jejunum is redder and more vascular than the ileum. Moreover, generally, in comparison to the ileum, the jejunum has a thicker intestine wall with more mesentery fat. These differences between the jejunum and the ileum are expected to result in differences in optical responses in the jejunum relative to the ileum. Optionally, one or more optical signals may be used to investigate the differences in optical responses. For example, the process can include monitoring a change in optical response in reflected red light, blue light, green light, ratio of red light to green light, ratio of red light to blue light, and/or ratio of green light to blue light. In some embodiments, reflected red light is detected in the process.

Flowchart 651200 represents a single sliding window process. In step 651210, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 651220, the detected signal (e.g., reflected red light) just after the period of time used in step 651210 is normalized to the reference signal determined in step 651210. In step 651230, the signal (e.g., reflected red light) is detected. In step 651240, the mean signal detected based on the single sliding window is compared to a signal threshold. The signal threshold in step 651240 is generally a fraction of the reference signal of the jejunum reference signal determined in step 651210. For example, the signal threshold can be from 60% to 90% (e.g., from 70% to 80%) of the jejunum reference signal. If the mean signal exceeds the signal threshold, then the process determines that the device has entered the ileum at step 651250. If the mean signal does not exceed the signal threshold, then the process returns to step 651230.

Figure 77:
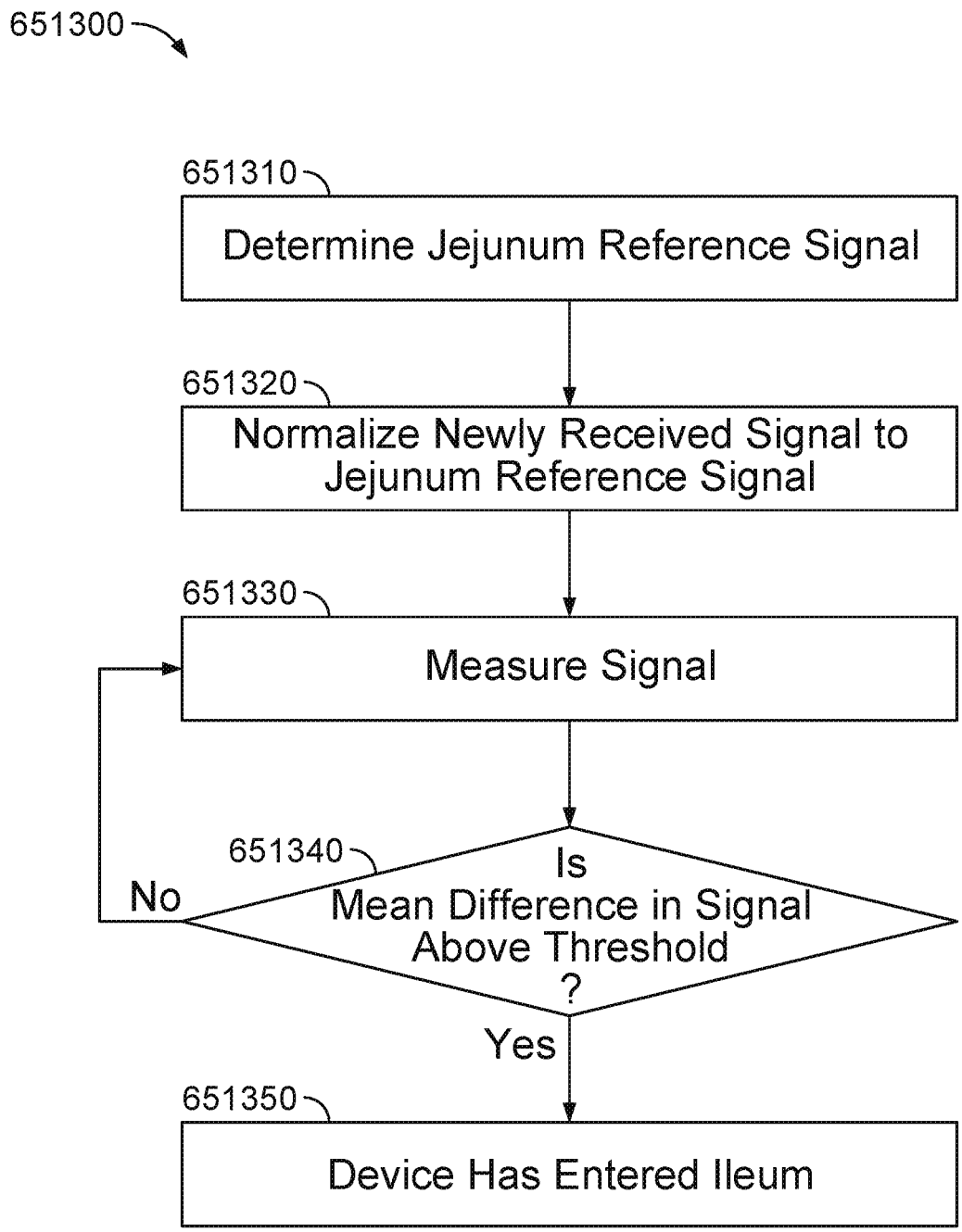
FIG. 77 is a flowchart of illustrative steps for detecting a transition from a jejunum to an ileum, which may be used when determining a location of an ingestible device as it transits through a GI tract, in accordance with some embodiments of the disclosure.

FIG. 77 is a flowchart 651200 for certain embodiments for determining a transition of the device from the jejunum to the ileum using a two sliding window process. In step 651310, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 651320, the detected signal (e.g., reflected red light) just after the period of time used in step 651310 is normalized to the reference signal determined in step 651310. In step 651330, the signal (e.g., reflected red light) is detected. In step 651340, the mean difference in the signal detected based on the two sliding windows is compared to a signal threshold. The signal threshold in step 651340 is based on whether the mean difference in the detected signal exceeds a multiple (e.g., from 1.5 times to five times, from two times to four times) of the detected signal of the first window. If signal threshold is exceeded, then the process determines that the device has entered the ileum at step 651350. If the signal threshold is not exceeded, then the process returns to step 651330.

Figure 78:
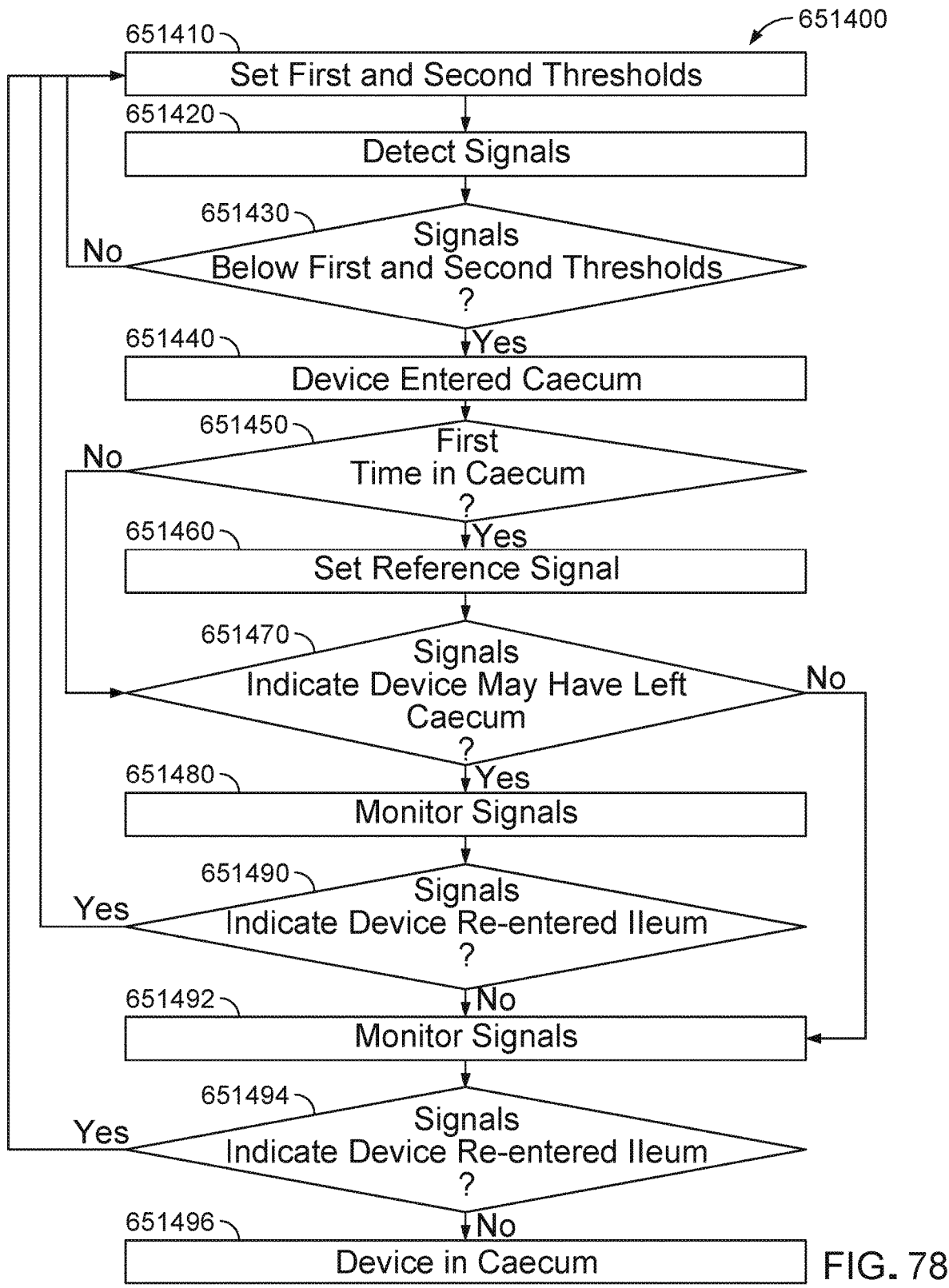
FIG. 78 is a flowchart of illustrative steps for detecting a transition from an ileum to a cecum, which may be used when determining a location of an ingestible device as it transits through a GI tract, in accordance with some embodiments of the disclosure.

FIG. 78 is a flowchart 651400 for a process for certain embodiments for determining a transition of the device from the ileum to the cecum. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected green light to reflected blue light. Generally, in the process 651400, the sliding window analysis (first and second windows) discussed with respect to process 65600 is continued.

Step 651410 includes setting a first threshold in a detected signal, e.g., ratio of detected red light to detected green light, and setting a second threshold for the coefficient of variation for a detected signal, e.g., the coefficient of variation for the ratio of detected green light to detected blue light. The first threshold can be set to a fraction (e.g., from 0.5 to 0.9, from 0.6 to 0.8) of the average signal (e.g., ratio of detected red light to detected green light) in the first window, or a fraction (e.g., from 0.4 to 0.8, from 0.5 to 0.7) of the mean difference between the detected signal (e.g., ratio of detected red light to detected green light) in the two windows. The second threshold can be set to 0.1 (e.g., 0.05, 0.02).

Step 651420 includes detecting the signals in the first and second windows that are to be used for comparing to the first and second thresholds.

Step 651430 includes comparing the detected signals to the first and second thresholds. If the corresponding value is not below the first threshold or the corresponding value is not below the second threshold, then it is determined that the device has not left the ileum and entered the cecum, and the process returns to step 651420. If the corresponding value is below the first threshold and the corresponding value is below the second threshold, then it is determined that the device has left the ileum and entered the cecum, and the proceeds to step 651440.

Step 651450 includes determining whether it is the first time that that the device was determined to leave the ileum and enter the cecum. If it is the first time that the device was determined to leave the ileum and enter the cecum, then the process proceeds to step 651460. If it is not the first time that the device has left the ileum and entered the cecum, then the process proceeds to step 651470.

Step 651460 includes setting a reference signal. In this step the optical signal (e.g., ratio of detected red light to detected green light) as a reference signal.

Step 651470 includes determining whether the device may have left the cecum and returned to the ileum. The device is determined to have left the cecum and returned to the ileum if the corresponding detected signal (e.g., ratio of detected red light to detected green light) is statistically comparable to the reference signal (determined in step 651460) and the coefficient of variation for the corresponding detected signal (e.g., ratio of detected green light to detected blue light) exceeds the second threshold. If it is determined that the device may have left the cecum and returned to the ileum, the process proceeds to step 651480.

Step 651480 includes continuing to detect the relevant optical signals for a period of time (e.g., at least one minute, from five minutes to 15 minutes).

Step 651490 includes determining whether the signals determined in step 651480 indicate (using the methodology discussed in step 651470) that the device re-entered the ileum. If the signals indicate that the device re-entered the ileum, the process proceeds to step 651420. If the signals indicate that the device is in the cecum, the process proceeds to step 651492.

Step 651492 includes continuing to monitor the relevant optical signals for a period of time (e.g., at least 30 minutes, at least one hour, at least two hours).

Step 651494 includes determining whether the signals determined in step 651492 indicate (using the methodology discussed in step 651470) that the device re-entered the ileum. If the signals indicate that the device re-entered the ileum, the process proceeds to step 651420. If the signals indicate that the device is in the cecum, the process proceeds to step 651496.

At step 651496, the process determines that the device is in the cecum.

Figure 79:
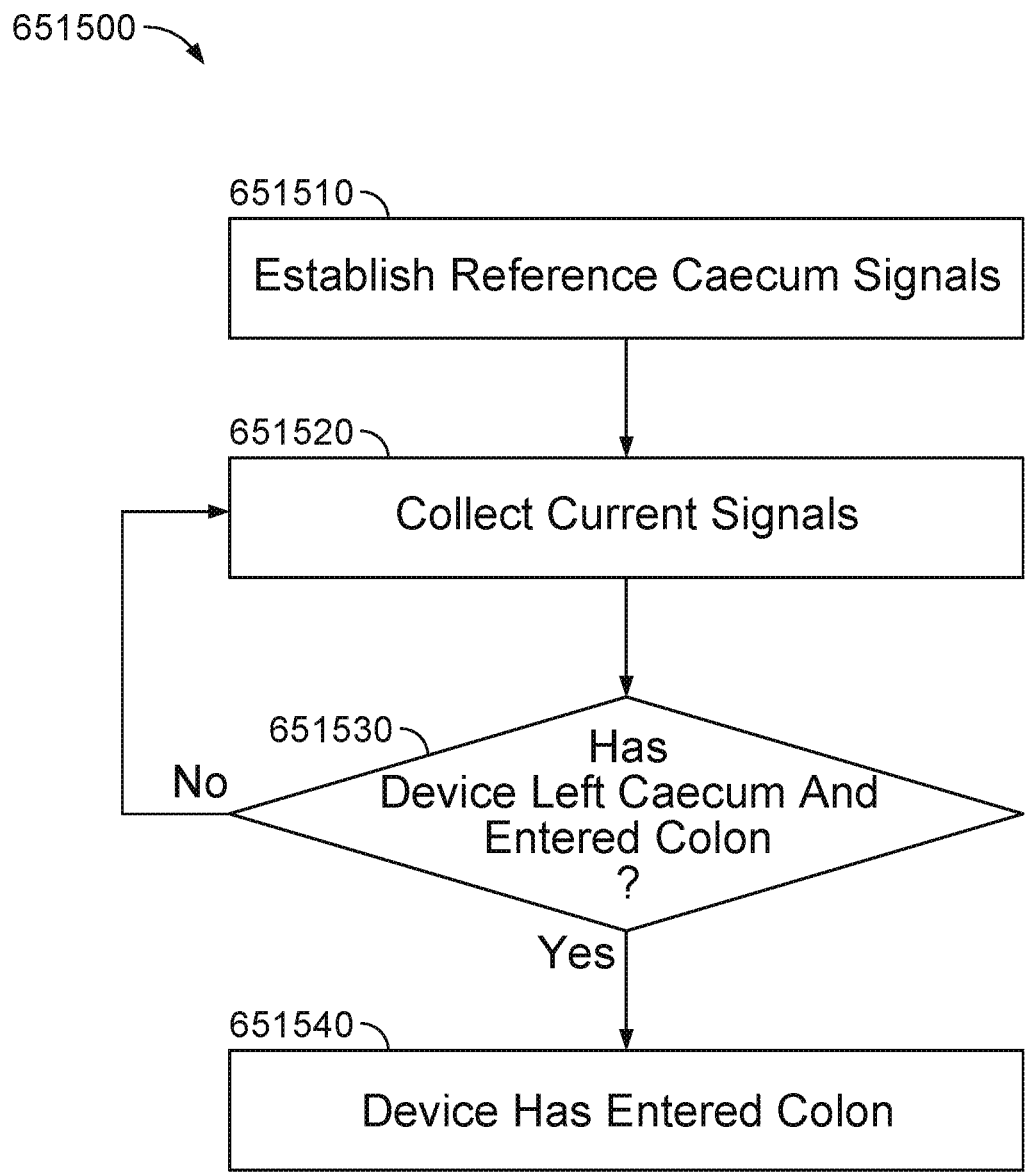
FIG. 79 is a flowchart of illustrative steps for detecting a transition from a cecum to a colon, which may be used when determining a location of an ingestible device as it transits through a GI tract, in accordance with some embodiments of the disclosure.

FIG. 79 is a flowchart 651500 for a process for certain embodiments for determining a transition of the device from the cecum to the colon. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected blue light. Generally, in the process 651500, the sliding window analysis (first and second windows) discussed with respect to process 651400 is continued.

In step 651510, optical signals (e.g., the ratio of reflected red signal to reflected green signal, and reflected blue signal) are collected for a period of time (e.g., at least one minute, at least five minutes, at least 10 minutes) while the device is in the cecum (e.g., during step 651480). The average values for the recorded optical signals (e.g., the ratio of reflected red signal to reflected green signal, and reflected blue signal) establish the cecum reference signals.

In step 651520, the optical signals are detected after it has been determined that the device entered the cecum (e.g., at step 651440). The optical signals are normalized to the cecum reference signals.

Step 651530 involves determining whether the device has entered the colon. This includes determining whether any of three different criteria are satisfied. The first criterion is satisfied if the mean difference in the ratio of a detected optical signal (e.g., ratio of detected red signal to the detected green) is a multiple greater than one (e.g., 2×, 3×, 4×) the standard deviation of the corresponding signal (e.g., ratio of detected red signal to the detected green) in the second window. The second criterion is satisfied if the mean of a detected optical signal (e.g., a ratio of detected red light to detected green light) exceeds a given value (e.g., exceeds one). The third criterion is satisfied if the coefficient of variation of an optical signal (e.g., detected blue light) in the first window exceeds a given value (e.g., exceeds 0.2). If any of the three criteria are satisfied, then the process proceeds to step 651540. Otherwise, none of the three criteria are satisfied, the process returns to step 651520.

Figure 76:
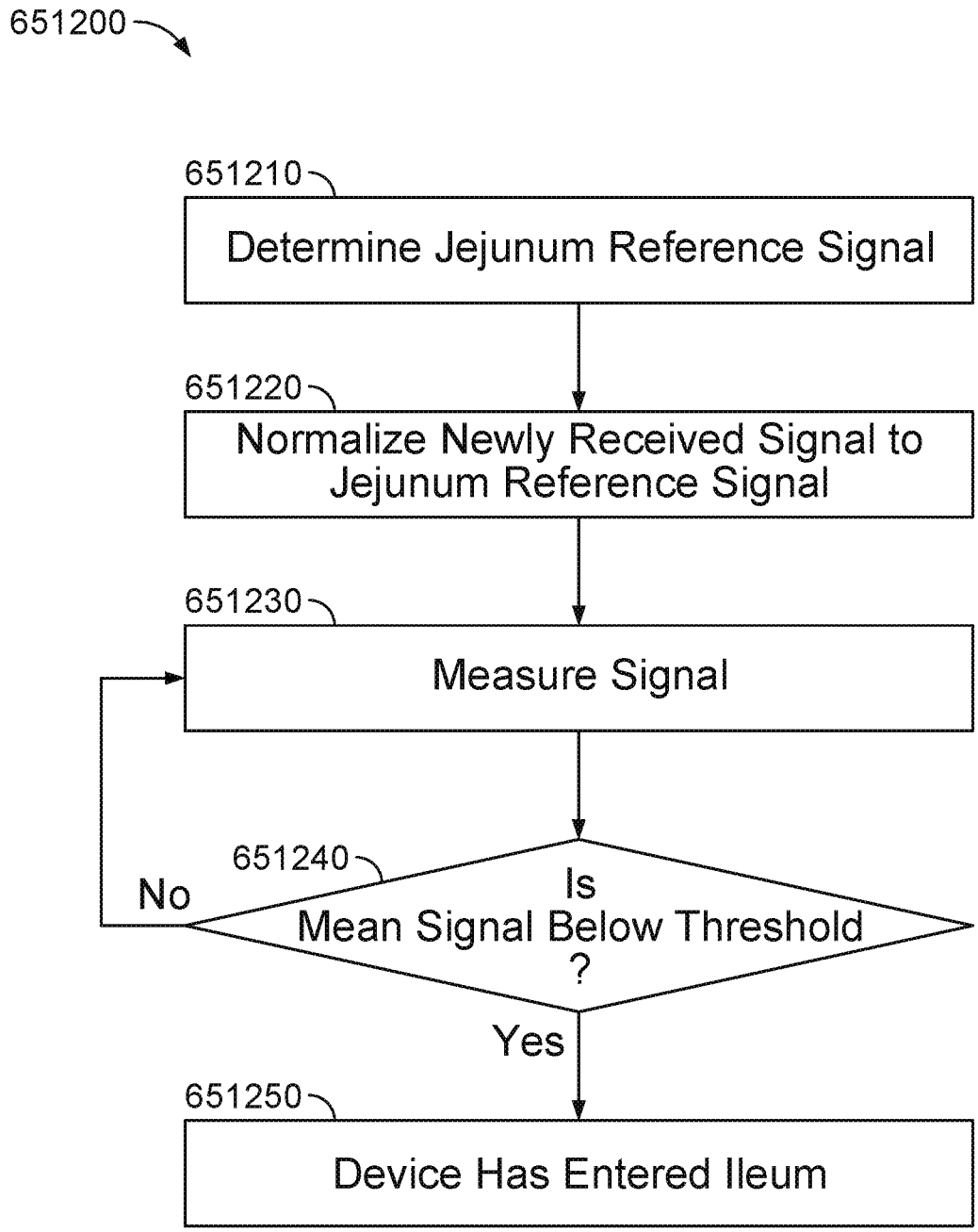
FIG. 76 is a flowchart of illustrative steps for detecting a transition from a jejunum to an ileum, which may be used when determining a location of an ingestible device as it transits through a GI tract, in accordance with some embodiments of the disclosure.

For illustrative purposes the disclosure focuses primarily on a number of different example embodiments of an ingestible device, and example embodiments of methods for determining a location of an ingestible device within a GI tract. However, the possible ingestible devices that may be constructed are not limited to these embodiments, and variations in the shape and design may be made without significantly changing the functions and operations of the device. Similarly, the possible procedures for determining a location of the ingestible device within the GI tract are not limited to the specific procedures and embodiments discussed (e.g., process 65500 (FIG. 69), process 65600 (FIG. 70), process 65900 (FIG. 73), process 651200 (FIG. 76), process 651300 (FIG. 77), process 651400 (FIG. 78) and process 651500 (FIG. 79)). Also, the applications of the ingestible devices described herein are not limited merely to gathering data, sampling and testing portions of the gastrointestinal tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain chemical compounds or impurities in the gastrointestinal tract, or the combination of localization, sampling, and appropriate diagnostic and assay techniques incorporated into a sampling chamber may be particularly well suited to determine the presence of small intestinal bacterial overgrowth (SIBO).

At least some of the elements of the various embodiments of the ingestible device described herein that are implemented via software (e.g., software executed by control circuitry within PCB 65120 (FIG. 66)) may be written in a high-level procedural language such as object oriented programming, a scripting language or both. Accordingly, the program code may be written in C, C$^{++}$ or any other suitable programming language and may comprise modules or classes, as is known to those skilled in object oriented programming. Alternatively, or in addition, at least some of the elements of the embodiments of the ingestible device described herein that are implemented via software may be written in assembly language, machine language or firmware as needed. In either case, the language may be a compiled or an interpreted language.

At least some of the program code used to implement the ingestible device can be stored on a storage media or on a computer readable medium that is readable by a general or special purpose programmable computing device having a processor, an operating system and the associated hardware and software to implement the functionality of at least one of the embodiments described herein. The program code, when read by the computing device, configures the computing device to operate in a new, specific and predefined manner in order to perform at least one of the methods described herein.

Furthermore, at least some of the programs associated with the systems, devices, and methods of the example embodiments described herein are capable of being distributed in a computer program product comprising a computer readable medium that bears computer usable instructions for one or more processors. The medium may be provided in various forms, including non-transitory forms such as, but not limited to, one or more discettes, compact discs, tapes, chips, and magnetic and electronic storage. In some embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The techniques described above can be implemented using software for execution on a computer. For instance, the software forms procedures in one or more computer programs that execute on one or more programmed or programmable computer systems (which may be of various architectures such as distributed, client/server, or grid) each including at least one processor, at least one data storage system (including volatile and non-volatile memory and/or storage elements), at least one input device or port, and at least one output device or port.

The software may be provided on a storage medium, such as a CD-ROM, readable by a general or special purpose programmable computer or delivered (encoded in a propagated signal) over a communication medium of a network to the computer where it is executed. All of the functions may be performed on a special purpose computer, or using special-purpose hardware, such as coprocessors. The software may be implemented in a distributed manner in which different parts of the computation specified by the software are performed by different computers. Each such computer program is preferably stored on or downloaded to a storage media or device (e.g., solid state memory or media, or magnetic or optical media) readable by a general or special purpose programmable computer, for configuring and operating the computer when the storage media or device is read by the computer system to perform the procedures described herein. The inventive system may also be considered to be implemented as a computer-readable storage medium, configured with a computer program, where the storage medium so configured causes a computer system to operate in a specific and predefined manner to perform the functions described herein.

For illustrative purposes the examples given herein focus primarily on a number of different example embodiments of an ingestible device. However, the possible ingestible devices that may be constructed are not limited to these embodiments, and variations in the general shape and design may be made without significantly changing the functions and operations of the device. For example, some embodiments of the ingestible device may feature a sampling chamber substantially towards the middle of the device, along with two sets of axial sensing sub-units, each located on substantially opposite ends of the device. In addition, the applications of the ingestible device are not limited merely to gathering data, sampling and testing portions of the gastrointestinal tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain analytes, chemical compounds or impurities in the gastrointestinal tract, or the combination of localization, sampling, and appropriate diagnostic and assay techniques incorporated into a sampling chamber may be particularly well suited to determine the presence of small intestinal bacterial overgrowth (SIBO). It is also noted that although embodiments described herein focus on an ingestible device in the GI tract, such ingestible device described in FIGS. 1-64 may be used for delivering substances including medicaments and therapeutics in other parts of the body, such as but not limited to the female reproductive tract, and/or the like.

The various embodiments of systems, processes and apparatuses have been described herein by way of example only. It is contemplated that the features and limitations described in any one embodiment may be applied to any other embodiment herein, and flowcharts or examples relating to one embodiment may be combined with any other embodiment in a suitable manner, done in different orders, or done in parallel. It should be noted, the systems and/or methods described above may be applied to, or used in accordance with, other systems and/or methods. Various modifications and variations may be made to these example embodiments without departing from the spirit and scope of the embodiments, which is limited only by the appended embodiments. The appended embodiments should be given the broadest interpretation consistent with the description as a whole.

Implementations of the subject matter and the operations described in this specification can be implemented by digital electronic circuitry, or via computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, discs, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical discs, or optical discs. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic discs, e.g., internal hard discs or removable discs; magneto optical discs; and CD ROM and DVD-ROM discs. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Implementations of the subject matter described in this specification can be implemented in a computing system that includes a back end component, e.g., as a data server, or that includes a middleware component, e.g., an application server, or that includes a front end component, e.g., a user computer having a graphical display or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some implementations, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary implementations, and that such variations are intended to be encompassed by the present disclosure. It is recognized that features of the disclosed implementations can be incorporated into other disclosed implementations.

EXAMPLES

Experiment 1

An ingestible medical device according to the disclosure ("TLC1") was tested on 20 subjects to investigate its localization ability. TLC1 was a biocompatible polycarbonate capsule that contained a power supply, electronics and software. An onboard software algorithm used time, temperature and reflected light spectral data to determine the location of the capsule as it traveled the GI tract. The capsule is 0.51×1.22 inches which is larger than a vitamin pill which is 0.4×0.85 inches. The subjects fasted overnight before participating in the study. Computerized tomography ("CT") were used as a basis for determining the accuracy of the localization data collected with TLC1. One of the 20 subjects did not follow the fasting rule. CT data was lacking for another one of the 20 subjects. Thus, these two subjects were excluded from further analysis. TLC1 sampled RGB data (radially transmitted) every 15 seconds for the first 14 hours after it entered the subject's stomach, and then samples every five minutes after that until battery dies. TLC1 did not start to record optical data until it reached the subject's stomach. Thus, there was no RGB-based data for the mouth-esophagus transition for any of the subjects.

In addition, a PillCam® SB (Given Imaging) device was tested on 57 subjects. The subjects fasted overnight before joining the study. PillCam videos were recorded within each subject. The sampling frequency of PillCam is velocity dependent. The faster PillCam travels, the faster it would sample data. Each video is about seven to eight hours long, starting from when the capsule was administrated into the subject's mouth. RGB optical data were recorded in a table. A physician provided notes on where stomach-duodenum transition and ileum-cecum transition occurred in each video. Computerized tomography ("CT") was used as a basis for determining the accuracy of the localization data collected with PillCam.

Esophagus-Stomach Transition

For TLC1, it was assumed that this transition occurred one minute after the patient ingested the device. For PillCam, the algorithm was as follows:
1. Start mouth-esophagus transition detection after capsule is activated/administrated
2. Check whether Green<102.3 and Blue<94.6
   a. If yes, mark as mouth-esophagus transition
   b. If no, continue to scan the data
3. After detecting mouth-esophagus transition, continue to monitor Green and Blue signals for another 30 seconds, in case of location reversal
   a. If either Green>110.1 or Blue>105.5, mark it as mouth-esophagus location reversal
   b. Reset the mouth-esophagus flag and loop through step 2 and 3 until the confirmed mouth-esophagus transition detected
4. Add one minute to the confirmed mouth-esophagus transition and mark it as esophagus-stomach transition For one of the PillCam subjects, there was not a clear cut difference between the esophagus and stomach, so this subject was excluded from future analysis of stomach localization. Among the 56 valid subjects, 54 of them have correct esophagus-stomach transition localization. The total agreement is 54/56=96%. Each of the two failed cases had prolonged esophageal of greater than one minute. Thus, adding one minute to mouth-esophagus transition was not enough to cover the transition in esophagus for these two subjects.

Stomach-Duodenum

For both TLC1 and PillCam, a sliding window analysis was used. The algorithm used a dumbbell shape two-sliding-window approach with a two-minute gap between the front (first) and back (second) windows. The two-minute gap was designed, at least in part, to skip the rapid transition from stomach to small intestine and capture the small intestine signal after capsule settles down in small intestine. The algorithm was as follows:
1. Start to check for stomach-duodenum transition after capsule enters stomach
2. Setup the two windows (front and back)
   a. Time length of each window: 3 minutes for TLC1; 30 seconds for PillCam
   b. Time gap between two windows: 2 minutes for both devices
   c. Window sliding step size: 0.5 minute for both devices
3. Compare signals in the two sliding windows
   a. If difference in mean is higher than 3 times the standard deviation of Green/Blue signal in the back window
      i. If this is the first time ever, record the mean and standard deviation of signals in the back window as stomach reference
      ii. If mean signal in the front window is higher than stomach reference signal by a certain threshold (0.3 for TLC1 and 0.18 for PillCam), mark this as a possible stomach-duodenum transition
   b. If a possible pyloric transition is detected, continue to scan for another 10 minutes in case of false positive flag
      i. If within this 10 minutes, location reversal is detected, the previous pyloric transition flag is a false positive flag. Clear the flag and continue to check
      ii. If no location reversal has been identified within 10 minutes following the possible pyloric transition flag, mark it as a confirmed pyloric transition
   c. Continue monitoring Green/Blue data for another 2 hours after the confirmed pyloric transition, in case of location reversal
      i. If a location reversal is identified, flag the timestamp when reversal happened and then repeat steps a-c to look for the next pyloric transition
      ii. If the capsule has not gone back to stomach 2 hours after previously confirmed pyloric transition, stops location reversal monitoring and assume the capsule would stay in intestinal area For TLC1, one of the 18 subjects had too few samples (<3 minutes) taken in the stomach due to the delayed esophagus-stomach transition identification by previously developed localization algorithm. Thus, this subject was excluded from the stomach-duodenum transition algorithm test. For the rest of the TLC1 subjects, CT images confirmed that the detected pyloric transitions for all the subjects were located somewhere between stomach and jejunum. Two out of the 17 subjects showed that the capsule went back to stomach after first the first stomach-duodenum transition. The total agreement between the TLC1 algorithm detection and CT scans was 17/17=100%.

For one of the PillCam subjects, the capsule stayed in the subject's stomach all the time before the video ended. For another two of the PillCam subjects, too few samples were taken in the stomach to run the localization algorithm. These three PillCam subjects were excluded from the stomach-duodenum transition localization algorithm performance test. The performance summary of pyloric transition localization algorithm for PillCam was as follows:
1. Good cases (48 subjects):
   a. For 25 subjects, our detection matches exactly with the physician's notes
   b. For 19 subjects, the difference between the two detections is less than five minutes
   c. For four subjects, the difference between the two detections is less than 10 minutes (The full transition could take up to 10 minutes before the G/B signal settled)
2. Failed cases (6 subjects):
   a. Four subjects had high standard deviation of Green/Blue signal in the stomach
   b. One subject had bile in the stomach, which greatly affected Green/Blue in stomach
   c. One subject had no Green/Blue change at pyloric transition The total agreement for the PillCam stomach-duodenum transition localization algorithm detection and physician's notes was 48/54=89%.

Duodenum-Jejenum Transition

For TLC1, it was assumed that the device left the duodenum and entered the jejunum three minutes after it was determined that the device entered the duodenum. Of the 17 subjects noted above with respect to the TLC1 investigation of the stomach-duodenum transition, 16 of the subjects mentioned had CT images that confirmed that the duodenum-jejenum transition was located somewhere between stomach and jejunum. One of the 17 subjects had a prolonged transit time in duodenum. The total agreement between algorithm detection and CT scans was 16/17=94%.

For PillCam, the duodenum-jejenum transition was not determined.

Jejenum-Ileum Transition

It is to be noted that the jejunum is redder and more vascular than ileum, and that the jejenum has a thicker intestine wall with more mesentery fat. These differences can cause various optical responses between jejunum and ileum, particularly for the reflected red light signal. For both TLC1 and PillCam, two different approaches were explored to track the change of red signal at the jejunum-ileum transition. The first approach was a single-sliding-window analysis, where the window is 10 minutes long, and the mean signal was compared with a threshold value while the window was moving along. The second approach was a two-sliding-window analysis, where each window was 10 minutes long with a 20 minute spacing between the two windows. The algorithm for the jejunum-ileum transition localization was as follows:
1. Obtain 20 minutes of Red signal after the duodenum-jejenum transition, average the data and record it as the jejunum reference signal
2. Start to check the jejunum-ileum transition 20 minutes after the device enters the jejunum
   a. Normalize the newly received data by the jejunum reference signal
   b. Two approaches:
      i. Single-sliding-window analysis
         Set the transition flag if the mean of reflected red signal is less than 0.8
      ii. Two-sliding-window analysis:
         Set the transition flag if the mean difference in reflected red is higher than 2× the standard deviation of the reflected red signal in the front window For TLC1, 16 of the 18 subjects had CT images that confirmed that the detected jejunum-ileum transition fell between jejunum and cecum. The total agreement between algorithm and CT scans was 16/18=89%. This was true for both the single-sliding-window and double-sliding-window approaches, and the same two subjects failed in both approaches.

The performance summary of the jejunum-ileum transition detection for PillCam is listed below:
1. Single-sliding-window analysis:
   a. 11 cases having jejunum-ileum transition detected somewhere between jejunum and cecum
   b. 24 cases having jejunum-ileum transition detected after cecum
   c. 19 cases having no jejunum-ileum transition detected
   d. Total agreement: 11/54=20%
2. Two-sliding-window analysis:
   a. 30 cases having jejunum-ileum transition detected somewhere between jejunum and cecum
   b. 24 cases having jejunum-ileum transition detected after cecum
   c. Total agreement: 30/54=56%

Ileum-Cecum Transition

Data demonstrated that, for TLC1, mean signal of reflected red/green provided the most statistical difference before and after the ileum-cecum transition. Data also demonstrated that, for TLC1, the coefficient of variation of reflected green/blue provided the most statistical contrast at ileum-cecum transition. The analysis based on PillCam videos showed very similar statistical trends to those results obtained with TLC1 device. Thus, the algorithm utilized changes in mean value of reflected red/green and the coefficient of variation of reflected green/blue. The algorithm was as follows:
1. Start to monitor ileum-cecum transition after the capsule enters the stomach
2. Setup the two windows (front (first) and back (second))
   a. Use a five-minute time length for each window
   b. Use a 10-minute gap between the two windows
   c. Use a one-minute window sliding step size
3. Compare signals in the two sliding windows
   a. Set ileum-cecum transition flag if
      i. Reflected red/green has a significant change or is lower than a threshold
      ii. Coefficient of variation of reflected green/blue is lower than a threshold b. If this is the first ileum-cecum transition detected, record average reflected red/green signal in small intestine as small intestine reference signal
c. Mark location reversal (i.e. capsule returns to terminal ileum) if
  i. Reflected red/green is statistically comparable with small intestine reference signal
  ii. Coefficient of variation of reflected green/blue is higher than a threshold
d. If a possible ileum-cecum transition is detected, continue to scan for another 10 minutes for TLC1 (15 minutes for PillCam) in case of false positive flag
  i. If within this time frame (10 minutes for TLC1, 15 minutes for PillCam), location reversal is detected, the previous ileum-cecum transition flag is a false positive flag. Clear the flag and continue to check
  ii. If no location reversal has been identified within this time frame (10 minutes for TLC1, 15 minutes for PillCam) following the possible ileum-cecum transition flag, mark it as a confirmed ileum-cecum transition
e. Continue monitoring data for another 2 hours after the confirmed ileum-cecum transition, in case of location reversal
  i. If a location reversal is identified, flag the timestamp when reversal happened and then repeat steps a-d to look for the next ileum-cecum transition
  ii. If the capsule has not gone back to small intestine 2 hours after previously confirmed ileum-cecum transition, stop location reversal monitoring and assume the capsule would stay in large intestinal area The flag setting and location reversal criteria particularly designed for TLC1 device were as follows:
1. Set ileum-cecum transition flag if
  a. The average reflected red/Green in the front window is less than 0.7 or mean difference between the two windows is higher than 0.6
  b. And the coefficient of variation of reflected green/blue is less than 0.02
2. Define as location reversal if
  a. The average reflected red/green in the front window is higher than small intestine reference signal
  b. And the coefficient of variation of reflected green/blue is higher than 0.086

For TLC1, 16 of the 18 subjects had CT images that confirmed that the detected ileum-cecum transition fell between terminal ileum and colon. The total agreement between algorithm and CT scans was 16/18=89%. Regarding those two subject where the ileum-cecum transition localization algorithm failed, for one subject the ileum-cecum transition was detected while TLC1 was still in the subject's terminal ileum, and for the other subject the ileum-cecum transition was detected when the device was in the colon.

Among the 57 available PillCam endoscopy videos, for three subjects the endoscopy video ended before PillCam reached cecum, and another two subjects had only very limited video data (less than five minutes) in the large intestine. These five subjects were excluded from ileum-cecum transition localization algorithm performance test. The performance summary of ileum-cecum transition detection for PillCam is listed below:

1. Good cases (39 subjects):
  a. For 31 subjects, the difference between the PillCam detection and the physician's notes was less than five minutes
  b. For 3 subjects, the difference between the PillCam detection and the physician's notes was less than 10 minutes
  c. For 5 subjects, the difference between the PillCam detection and the physician's notes was less than 20 minutes (the full transition can take up to 20 minutes before the signal settles)
2. Marginal/bad cases (13 subjects):
  a. Marginal cases (9 subjects)
    i. The PillCam ileum-cecum transition detection appeared in the terminal ileum or colon, but the difference between the two detections was within one hour
  b. Failed cases (4 subjects)
    i. Reasons of failure:
      1. The signal already stabilized in the terminal ileum
      2. The signal was highly variable from the entrance to exit
      3. There was no statistically significant change in reflected red/green at ileum-cecum transition The total agreement between ileocecal transition localization algorithm detection and the physician's notes is 39/52=75% if considering good cases only. Total agreement including possibly acceptable cases is 48/52=92.3%

Cecum-Colon Transition Data demonstrated that, for TLC1, mean signal of reflected red/green provided the most statistical difference before and after the cecum-colon transition. Data also demonstrated that, for TLC1, the coefficient of variation of reflected blue provided the most statistical contrast at cecum-colon transition. The same signals were used for PillCam. The cecum-colon transition localization algorithm was as follows:
1. Obtain 10 minutes of reflected red/green and reflected blue signals after ileum-cecum transition, average the data and record it as the cecum reference signals
2. Start to check cecum-colon transition after capsule enters cecum (The cecum-colon transition algorithm is dependent on the ileum-cecum transition flag)
  a. Normalize the newly received data by the cecum reference signals
  b. Two-sliding-window analysis:
    i. Use two adjacent 10 minute windows
    ii. Set the transition flag if any of the following criteria were met
      The mean difference in reflected red/green was more than 4× the standard deviation of reflected red/green in the back (second) window
      The mean of reflected red/green in the front (first) window was higher than 1.03
      The coefficient of variation of reflected blue signal in the front (first) window was greater than 0.23

The threshold values above were chosen based on a statistical analysis of data taken by TLC1.

For TLC1, 15 of the 18 subjects had the cecum-colon transition detected somewhere between cecum and colon. One of the subjects had the cecum-colon transition detected while TLC1 was still in cecum. The other two subjects had both wrong ileum-cecum transition detection and wrong cecum-colon transition detection. The total agreement between algorithm and CT scans was 15/18=83%.

For PillCam, for three subjects the endoscopy video ended before PillCam reached cecum, and for another two subjects there was very limited video data (less than five minutes) in the large intestine. These five subjects were excluded from cecum-colon transition localization algorithm performance test. The performance summary of cecum-colon transition detection for PillCam is listed below:
1. 27 cases had the cecum-colon transition detected somewhere between the cecum and the colon
2. one case had the cecum-colon transition detected in the ileum
3. 24 cases had no cecum-colon transition localized The total agreement: 27/52=52%.

The following table summarizes the localization accuracy results.

| Transition | TLC1 | PillCam |
|---|---|---|
| Stomach-Duodenum | 100% (17/17) | 89% (48/54) |
| Duodenum-Jejenum | 94% (16/17) | N/A |
| Ileum-Cecum | 89% (16/18) | 75% (39/52) |
| Ileum-terminal ileum/cecum/colon | 100% (18/18) | 92% (48/52) |

Experiment 2

Experiments were run to evaluate the effects that bellows material would have on the function of a drug used as the dispensable substance. The experiments also evaluated the effects on drug function due to shelf life in the bellows.

Figure 80:
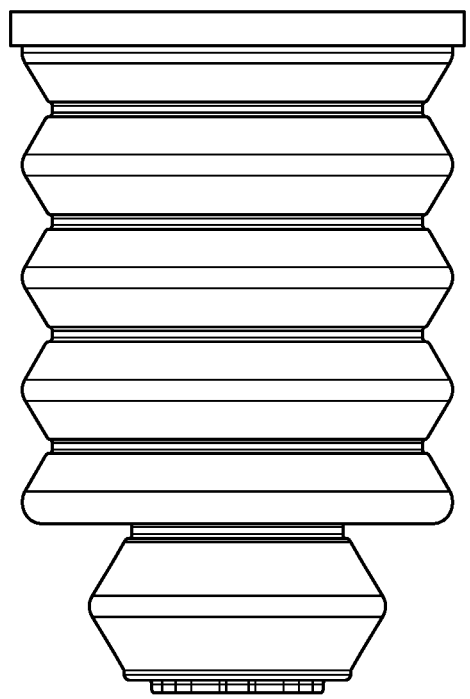
FIG. 80 illustrates a tapered silicon bellows.
Figure 81:
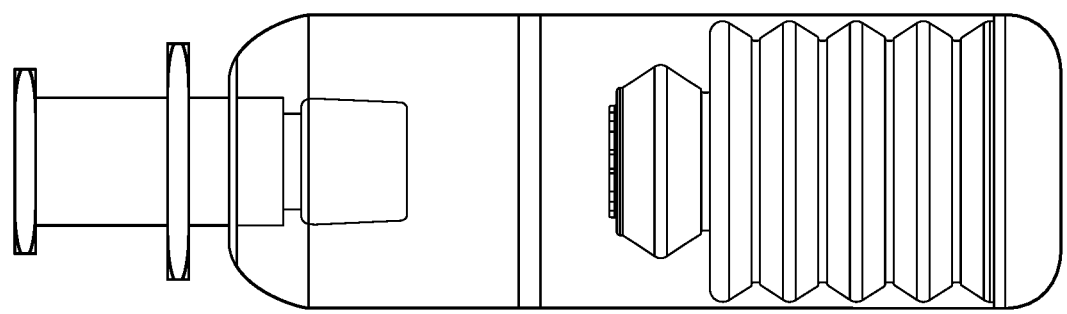
FIG. 81 illustrates a tapered silicone bellows in the simulated device jig.
Figure 82:
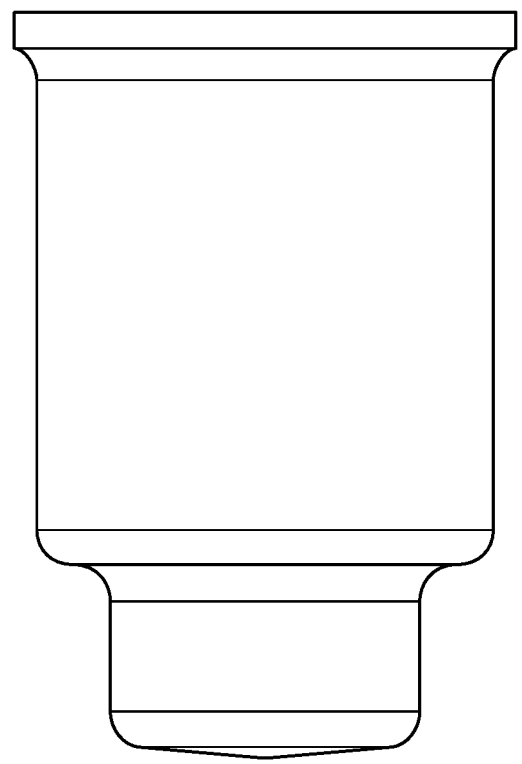
FIG. 82 illustrates a smooth PVC bellows.
Figure 83:
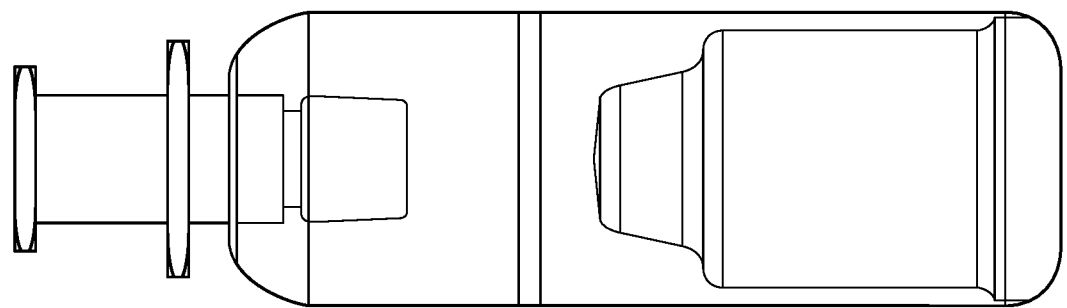
FIG. 83 illustrates a smooth PVC bellows in the simulated device jig.

The drug Exemptia (adalimumab) was loaded into simulated device jigs containing either tapered silicone bellows or smooth PVC bellows and allowed to incubate for 4, 24, or 336 hours at room temperature while protected from light. FIG. 80 illustrates the tapered silicone bellows, and FIG. 81 illustrates the tapered silicone bellows in the simulated device jig. FIG. 82 illustrates the smooth PVC bellows, and FIG. 83 illustrates the smooth PVC in the simulated device jig.

Figure 84:
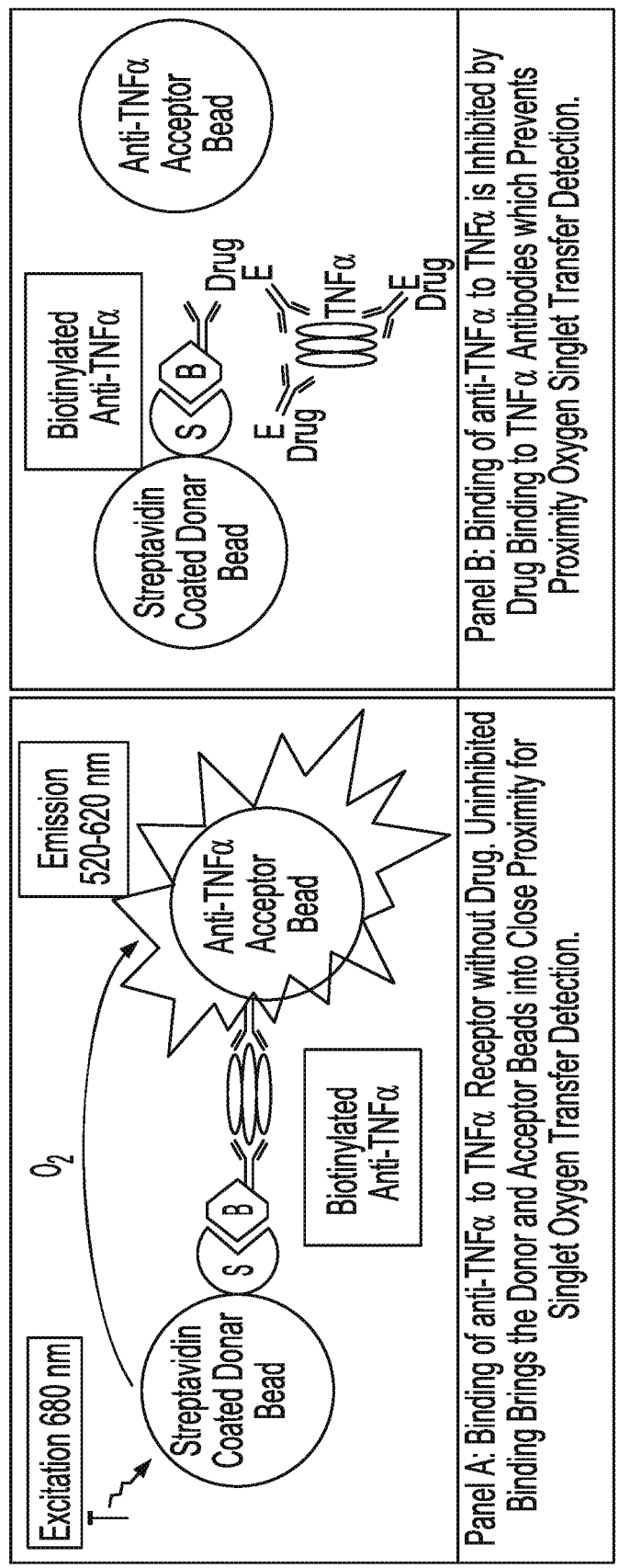
FIG. 84 demonstrates a principle of a competition assay performed in an experiment.

The drug was subsequently extracted using the respective dispensing systems and tested by a competitive inhibition assay. The test method has been developed from the literature (Velayudhan et al., "Demonstration of functional similarity of proposed biosimilar ABP501 to adalimumab" *BioDrugs* 30:339-351 (2016) and Barbeauet et al., "Application Note: Screening for inhibitors of TNFα/s TNFR1 Binding using AlphaScreen™ Technology". PerkinElmer Technical Note ASC-016. (2002)), as well as pre-testing development work using control drug and experiments using the provided AlphaLISA test kits. FIG. 84 demonstrates the principle of the competition assay performed in the experiment.

The bellows were loaded as follows: aseptically wiped the dispensing port of the simulated capsule jig with 70% ethanol; allowed to air dry for one minute; used an Exemptia delivery syringe to load each set of bellows with 200 µL of drug; took a photo of the loaded device; gently rotated the device such that the drug is allowed to come in contact with all bellows surfaces; protected the bellows from light; and incubate at room temperature for the predetermined time period to allow full contact of the drug with all bellows surfaces.

The drug was extracted as follows: after completion of the incubation period; the device jig was inverted such that the dispensing port was positioned over a sterile collection microfuge tube and petri dish below; five cubic centimeters of air was drawn into an appropriate syringe; the lure lock was attached to the device jig; the syringe was used to gently apply positive pressure to the bellow with air such that the drug was recovered in the collection microfuge tube; where possible, a video of drug dispensing was taken; samples were collected from each bellows type; a control drug sample was collected by directly dispensing 200 µL of drug from the commercial dispensing syringe into a sterile microfuge tube; the control drug-free sample was collected by directly dispensing 200 µL of PBS using a sterile pipette into a sterile microfuge tube; the collected drug was protected from light; and the drug was diluted over the following dilution range (250, 125, 25, 2.5, 0.25, 0.025, 0.0125, 0.0025 µg) in sterile PBS to determine the IC50 range of the drug.

To determine any effects storage conditions may have on drug efficacy in the device, the drug (stored either in the syringe, silicon bellows, PVC bellows) was stored at room temperature while protected from light for 24 hours and 72 hours. Samples were then extracted and the steps in the preceding paragraph were repeated.

The AlphaLISA (LOCI™) test method was used. Human TNFα standard dilution ranges were prepared as described in Table 4.

TABLE 4

| Tube | Vol. of human TNF α (µL) | Vol. of diluent (µL) * | [human TNFα] in standard curve (g/mL in 5 µL) | (pg/mL in 5 µL) |
|---|---|---|---|---|
| A | 10 µL of reconstituted human TNFα | 90 | 1E−07 | 100 000 |
| B | 60 µL of tube A | 140 | 3E−08 | 30 000 |
| C | 60 µL of tube B | 120 | 1E−08 | 10 000 |
| D | 60 µL of tube C | 140 | 3E−09 | 3 000 |
| E | 60 µL of tube D | 120 | 1E−09 | 1 000 |
| F | 60 µL of tube E | 140 | 3E−10 | 300 |
| G | 60 µL of tube F | 120 | 1E−10 | 100 |
| H | 60 µL of tube G | 140 | 3E−11 | 30 |
| I | 60 µL of tube H | 120 | 1E−11 | 10 |
| J | 60 µL of tube I | 140 | 3E−12 | 3 |
| K | 60 µL of tube J | 120 | 1E−12 | 1 |
| L | 60 µL of tube K | 140 | 3E−13 | 0.3 |
| M ** (background) | 0 | 100 | 0 | 0 |
| N ** (background) | 0 | 100 | 0 | 0 |
| O ** (background) | 0 | 100 | 0 | 0 |
| P ** (background) | 0 | 100 | 0 | 0 |

The test was performed as follows: the above standard dilution ranges were in a separate 96 well plate; to ensure consistent mixing, samples were mixed up and down gently with a pipette five times; a 384 well test plate was prepared according to the test layout diagram depicted Table 5; five microliters of 10,000 pg/mL TNFα standard from the previously made dilution plate was added to each corresponding concentration as shown in Table 5; five microliters of recovered drug (directly from the commercial syringe (A), from the silicone bellows (B Si), from the PVC bellows (B PVC), or from the PBS control (C)) was added into the corresponding wells described in Table 5; the test plate was incubated for one hour at room temperature while protected from light; 10 microliters of acceptor beads were added to each previously accessed well; the wells were incubated for 30 minutes at room temperature while protected from light; 10 μL of biotinylated antibody was added to each previously accessed well; the wells were incubated for 15 minutes at room temperature, while protected from light; the room lights were darkened and 25 microliters of SA donor beads were added to each previously accessed well; the wells were incubated for 30 minutes at room temperature while protected from light; the plate was read in Alpha Mode; and the results were recorded. Upon addition of reagent(s) in the various steps, each well was pipetted up and down three times to achieve good mixing.

TABLE 5

|   | 1 | 2 | 3 | 4 | 5 | 6 | 7 | 8 | 9 | 10 | 11 | 12 | 13 |
|---|---|---|---|---|---|---|---|---|---|----|----|----|----|
| A |   | STD2 1.00E+05 |   | STD10 10 | 250 A | 250 A | 250 A | 250 A | 250 AB | 250 Si | 250 B Si | 250 B Si | 250 B Si | 250 B Si |
| B |   |   |   |   |   |   |   |   |   |   |   |   |   |
| C |   | STD3 30000 |   | STD11 3 | 125 A | 125 A | 125 A | 125 A | 125 AB | 125 Si | 125 B Si | 125 B Si | 125 B Si | 125 B Si |
| D |   |   |   |   |   |   |   |   |   |   |   |   |   |
| E |   | STD4 10000 |   | STD12 1 | 25 A | 25 A | 25 A | 25 A | 25 AB | 25 Si | 25 B Si | 25 B Si | 25 B Si | 25 B Si |
| F |   |   |   |   |   |   |   |   |   |   |   |   |   |
| G |   | STD5 3000 |   | STD13 0.333 | 2.5 A | 2.5 A | 2.5 A | 2.5 A | 2.5 AB | 2.5 Si | 2.5 B Si | 2.5 B Si | 2.5 B Si | 2.5 B Si |
| H |   |   |   |   |   |   |   |   |   |   |   |   |   |
| I |   | STD6 1000 |   | Blank 0 | 0.25 A | 0.25 A | 0.25 A | 0.25 A | 0.25 AB | 0.25 Si | 0.25 B Si | 0.25 B Si | 0.25 B Si | 0.25 B Si |
| J |   |   |   |   |   |   |   |   |   |   |   |   |   |
| K |   | STD7 300 |   | Blank 0 | 0.025 A | 0.025 A | 0.025 A | 0.025 A | 0.025 AB | 0.025 Si | 0.025 B Si | 0.025 B Si | 0.025 B Si | 0.025 B Si |
| L |   |   |   |   |   |   |   |   |   |   |   |   |   |
| M |   | STD8 100 |   | Blank 0 | 0.013 A | 0.013 A | 0.013 A | 0.013 A | 0.013 AB | 0.013 Si | 0.013 B Si | 0.013 B Si | 0.013 B Si | 0.013 B Si |
| N |   |   |   |   |   |   |   |   |   |   |   |   |   |
| O |   | STD9 30 |   | Blank 0 | 0.003 A | 0.003 A | 0.003 A | 0.003 A | 0.003 AB | 0.003 Si | 0.003 B Si | 0.003 B Si | 0.003 B Si | 0.003 B Si |
| P |   |   |   |   |   |   |   |   |   |   |   |   |   |

|   | 14 | 15 | 16 | 17 | 18 | 19 | 20 | 21 | 22 | 23 |
|---|----|----|----|----|----|----|----|----|----|----|
| A | 250 B PVC | 250 B PVC | 250 B PVC | 250 B PVC | 250 B PVC | 250 C | 250 C | 250 C | 250 C | 250 C |
| B |   |   |   |   |   |   |   |   |   |   |
| C | 125 B PVC | 125 B PVC | 125 B PVC | 125 B PVC | 125 B PVC | 125 C | 125 C | 125 C | 125 C | 125 C |
| D |   |   |   |   |   |   |   |   |   |   |
| E | 25 B PVC | 25 PVC | 25 B PVC | 25 B PVC | 25 B PVC | 25 C | 25 C | 25 C | 25 C | 25 C |
| F |   |   |   |   |   |   |   |   |   |   |
| G | 2.5 B PVC | 2.5 B PVC | 2.5 B PVC | 2.5 B PVC | 2.5 B PVC | 2.5 C | 2.5 C | 2.5 C | 2.5 C | 2.5 C |
| H |   |   |   |   |   |   |   |   |   |   |
| I | 0.25 B PVC | 0.25 B PVC | 0.25 B PVC | 0.25 B PVC | 0.25 B PVC | 0.25 C | 0.25 C | 0.25 C | 0.25 C | 0.25 C |
| J |   |   |   |   |   |   |   |   |   |   |
| K | 0.025 B PVC | 0.025 B PVC | 0.025 B PVC | 0.025 B PVC | 0.025 B PVC | 0.025 C | 0.025 C | 0.025 C | 0.025 C | 0.025 C |
| L |   |   |   |   |   |   |   |   |   |   |
| M | 0.013 B PVC | 0.013 B PVC | 0.013 B PVC | 0.013 B PVC | 0.013 B PVC | 0.013 C | 0.013 C | 0.013 C | 0.013 C | 0.013 C |
| N |   |   |   |   |   |   |   |   |   |   |
| O | 0.003 B PVC | 0.003 B PVC | 0.003 B PVC | 0.003 B PVC | 0.003 B PVC | 0.003 C | 0.003 C | 0.003 C | 0.003 C | 0.003 C |
| P |   |   |   |   |   |   |   |   |   |   |

Figure 85:
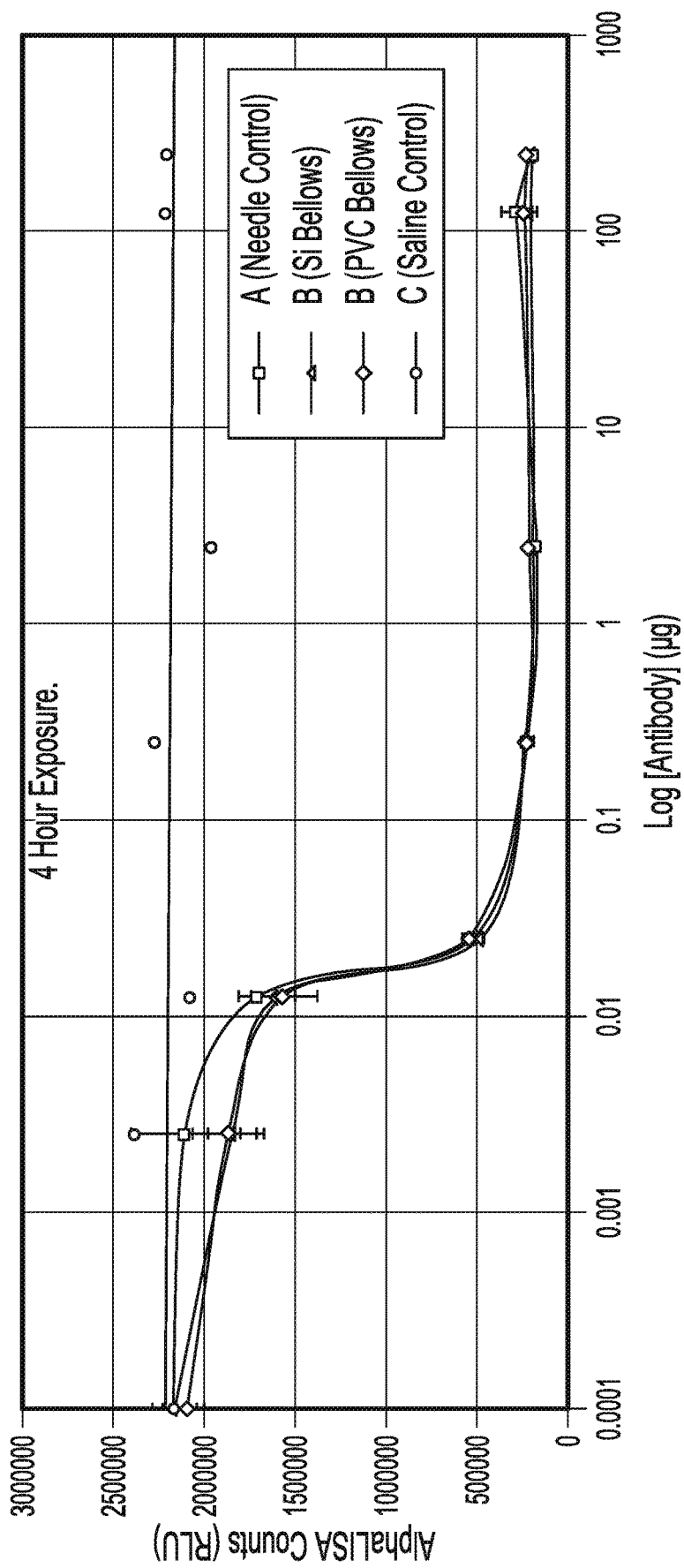
FIG. 85 shows AlphaLISA data.
Figure 86:
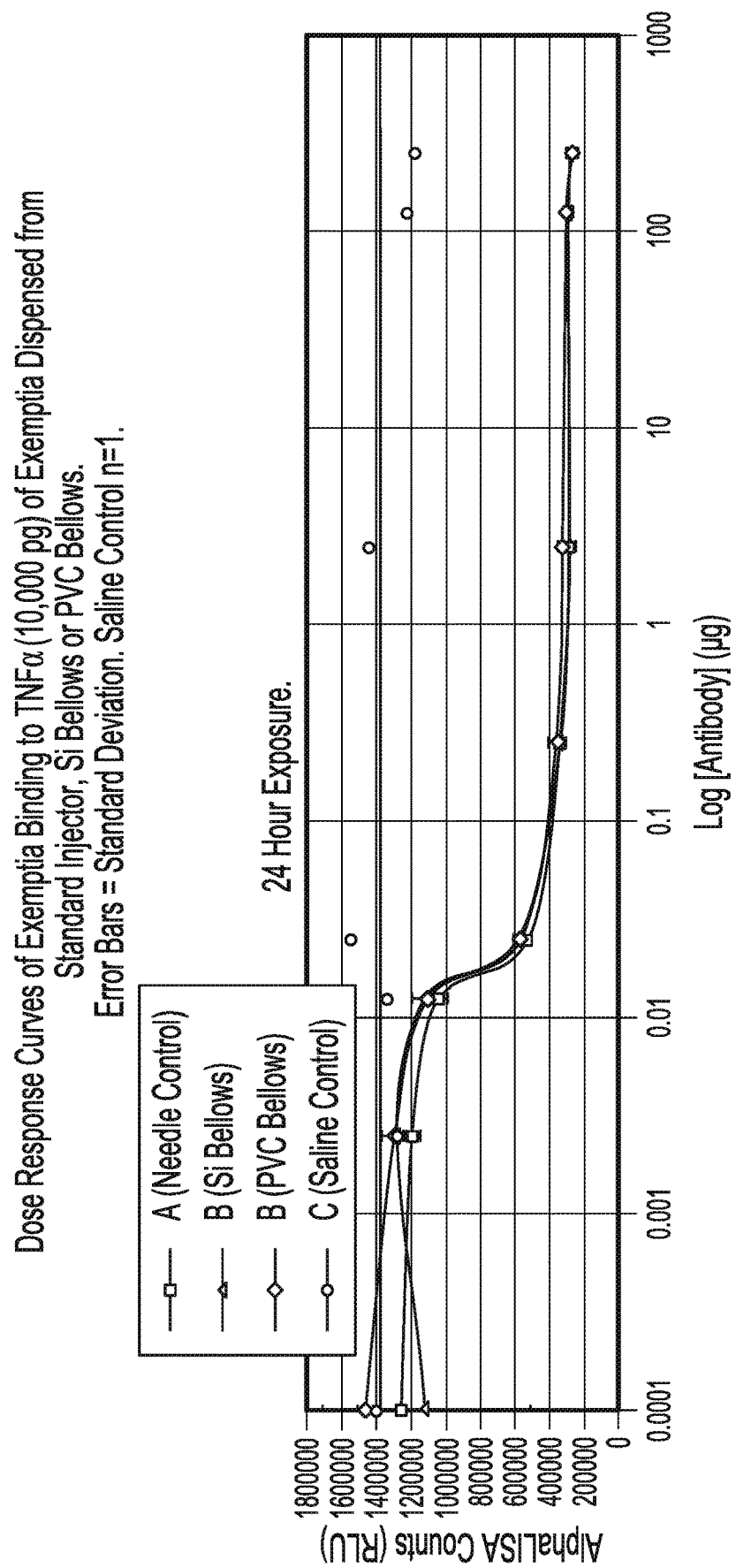
FIG. 86 shows AlphaLISA data.
Figure 87:
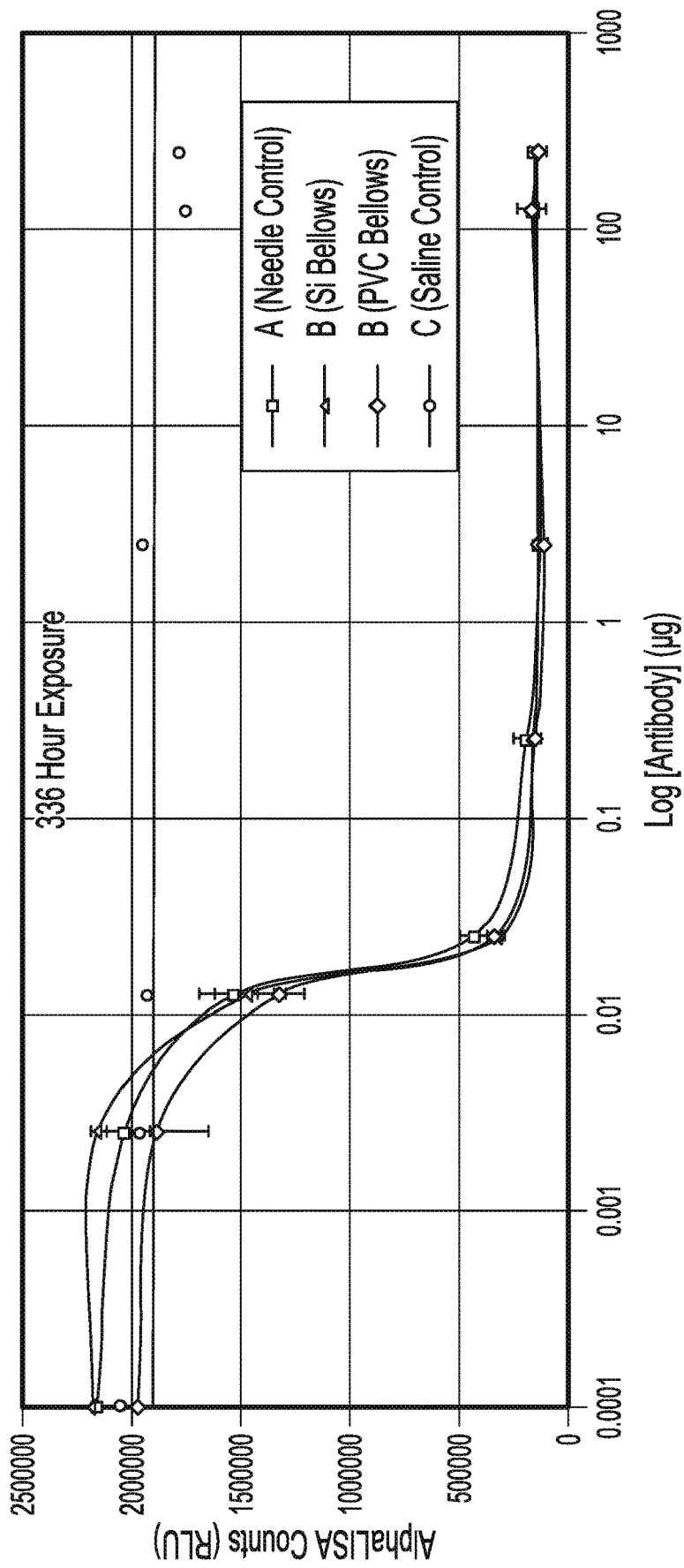
FIG. 87 shows AlphaLISA data.
Figure 88:
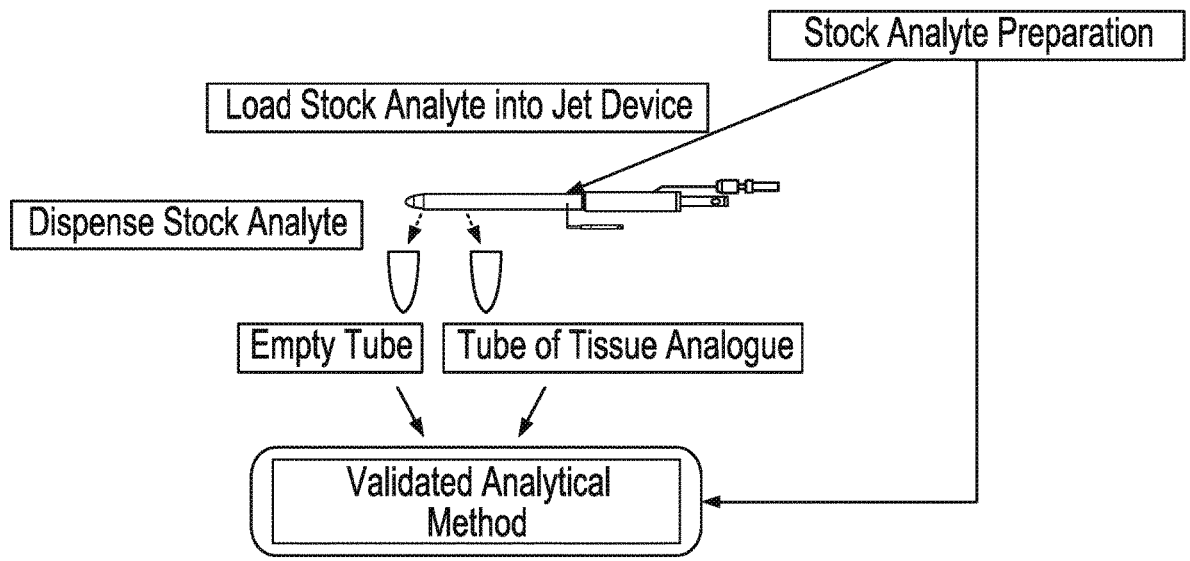
FIG. 88 illustrates a test method.
Figure 89:
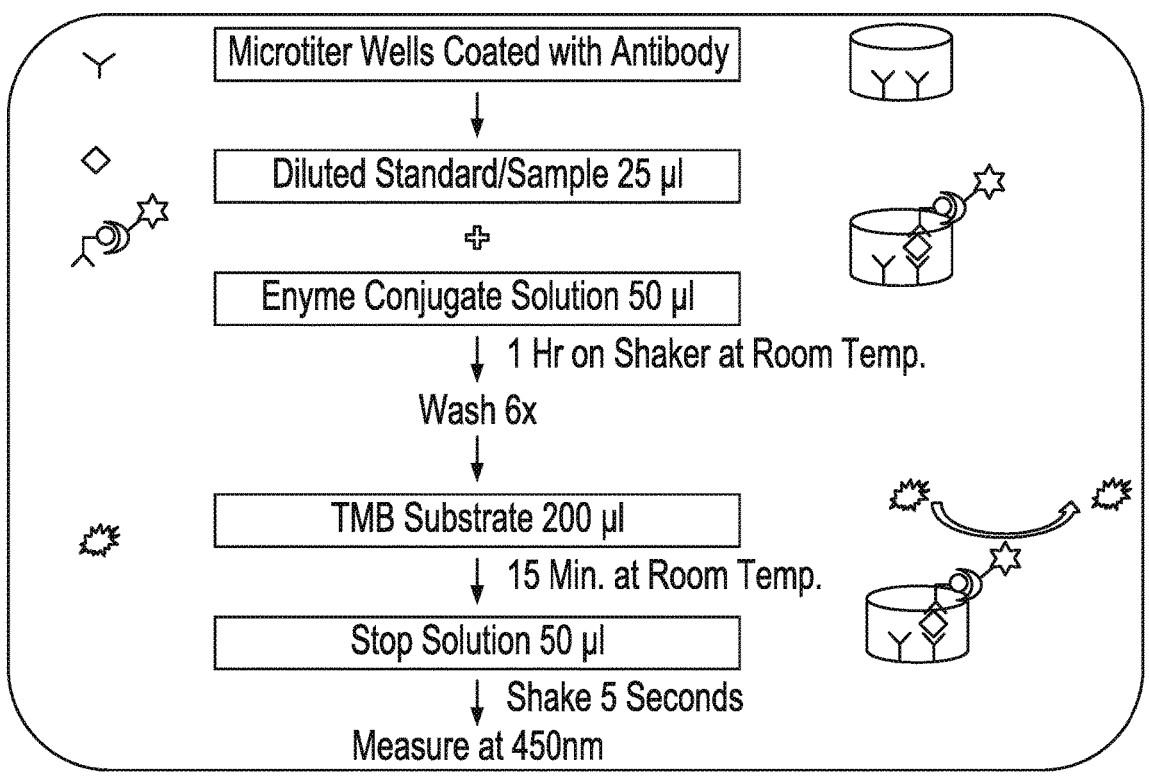
FIG. 89 illustrates an assay principle.
Figure 90:
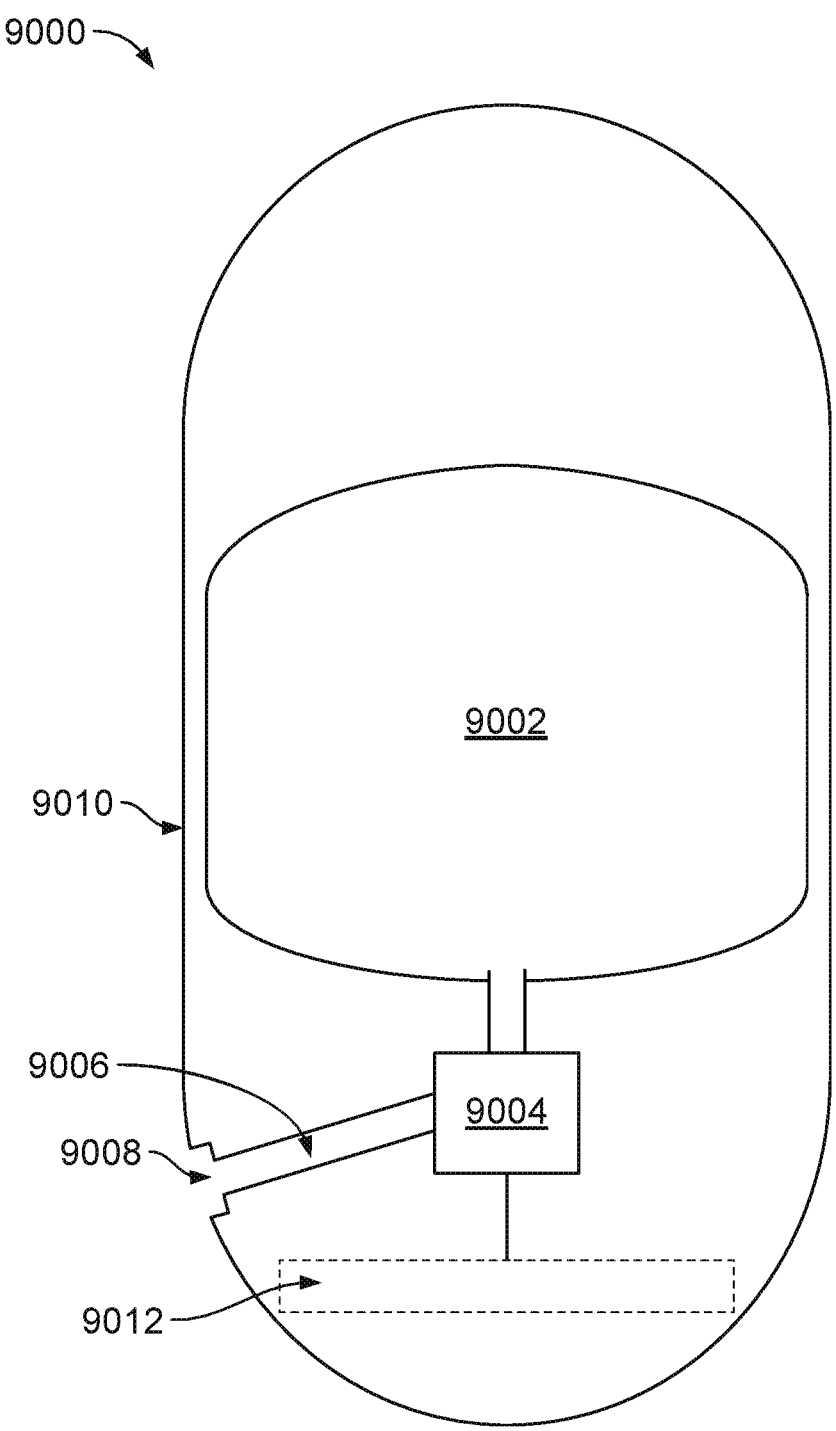
FIG. 90 illustrates an ingestible device.
Figure 91:
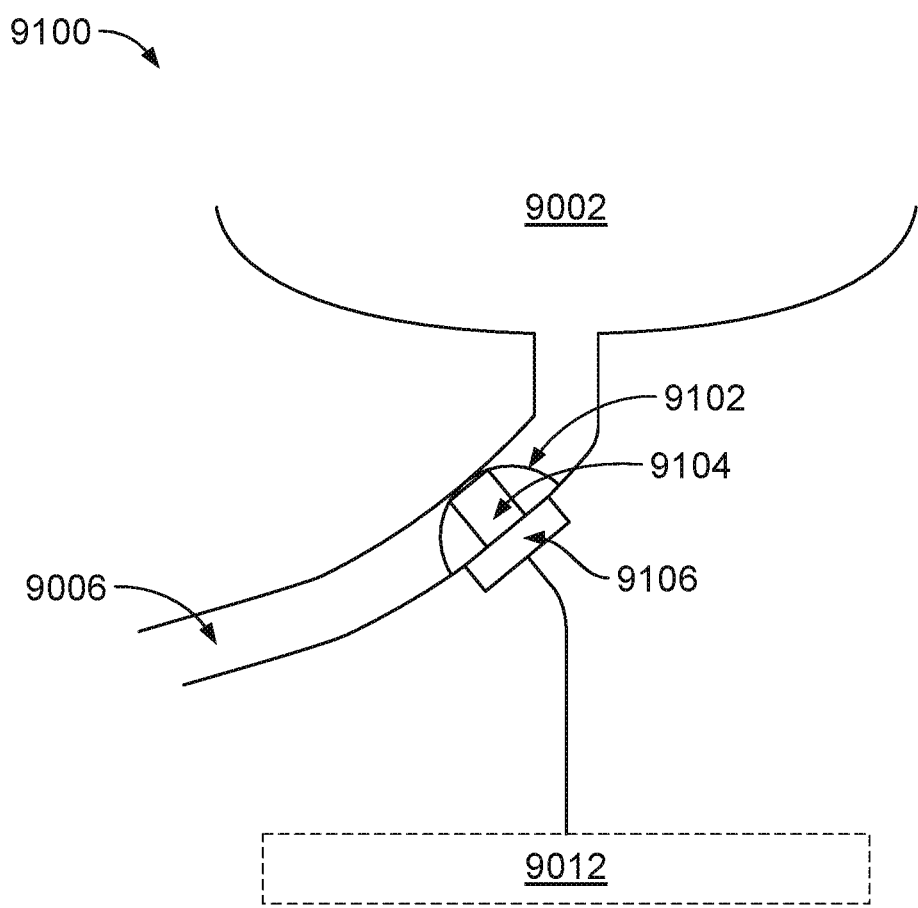
FIG. 91 illustrates a wax valve system.

The data are shown in FIGS. 85-87. The data demonstrate that the bellows do not negatively impact the drug function after shelf lives of 4, 24 hours, or 336 hours. IC50 values of the drug dispensed from the bellows were comparable to the IC50 values of the standard dispensation method (Table 6). A slight right shift was noted in the bellows curves after 24 hours (FIG. 86), but this shift was well within the error bars of the curves. Tables 7-9 represent data of FIGS. 85-87, respectively. Of note, when comparing mean (n=5) RFU data between test articles over the concentration ranges significant differences ($p<0.05$) were discerned. However, these significant differences did not favor either test article over time, suggesting that they were not related to the performance of the material in response to the drug (FIGS. 85-87).

TABLE 6

|  | Needle control (A) | Silicone Bellows (B) | PVC Bellows (C) |
| --- | --- | --- | --- |
| 4 Hours | 0.0174 | 0.0169 | 0.0172 |
| 24 Hours | 0.0180 | 0.0180 | 0.0180 |
| 336 Hours | 0.0144 | 0.0159 | 0.0163 |

TABLE 7

Statistics (Student's T-test, 2 tailed, non-pair-wise, for signficance $p < 0.05$)

| Drug (micrograms) | Needle control (A) vs. Silicone (B) | Needle control (A) vs. PVC | Silicone vs. PVC |
| --- | --- | --- | --- |
| 0.0001 | 0.911 | 0.008* | 0.268 |
| 0.0025 | 0.138 | 0.390 | 0.822 |
| 0.0125 | 0.122 | 0.118 | 0.771 |
| 0.025 | 0.143 | 0.465 | 0.020* |
| 0.25 | 0.591 | 0.984 | 0.350 |
| 2.5 | 0.243 | 0.124 | 0.169 |
| 125 | 0.867 | 0.688 | 0.182 |
| 250 | 0.681 | 0.184 | 0.108 |

*$p < 0.5$ data set

TABLE 8

Statistics (Student's T-test, 2 tailed, non-pair-wise, for signficance $p < 0.05$)

| Drug (micrograms) | Needle control (A) vs. Silicone (B) | Needle control (A) vs. PVC | Silicone vs. PVC |
| --- | --- | --- | --- |
| 0.0001 | 0.132 | 0.038* | 0.292 |
| 0.0025 | 0.003* | 0.076 | 0.575 |
| 0.0125 | 0.161 | 0.022* | 0.783 |
| 0.025 | 0.058 | 0.078 | 0.538 |
| 0.25 | 0.974 | 0.384 | 0.198 |
| 2.5 | 0.714 | 0.080 | 0.017* |
| 125 | 0.873 | 0.731 | 0.269 |
| 250 | 0.798 | 0.956 | 0.903 |

*$p < 0.5$ data set

TABLE 9

Statistics (Student's T-test, 2 tailed, non-pair-wise, for signficance $p < 0.05$)

| Drug (micrograms) | Needle control (A) vs. Silicone (B) | Needle control (A) vs. PVC | Silicone vs. PVC |
| --- | --- | --- | --- |
| 0.0001 | 0.858449 | 0.036847* | 0.026444* |
| 0.0025 | 0.087379 | 0.280302 | 0.046767* |
| 0.0125 | 0.469282 | 0.057232 | 0.117194 |
| 0.025 | 0.02758* | 0.078234 | 0.373419 |
| 0.25 | 0.411548 | 0.258928 | 0.400498 |
| 2.5 | 0.368959 | 0.156574 | 0.006719* |
| 125 | 0.948649 | 0.246702 | 0.463735 |
| 250 | 0.485046 | 0.128993 | 0.705543 |

*$p < 0.5$ data set

Experiment 3

Tests were conducted to determine whether certain pressures used to deliver a drug with an ingestible device disclosed herein would result in physical damage to the drug.

A target analyte (Novolog) was loaded into a jet device including a piston with a release mechanism. On the back side of the piston, pressure was provided by a hand pump, and the release mechanism was released to release Novolog. The end fastener was screwed on to secure the nozzle insert and seal the chamber. The jet device was operated at a target pressure to dispense target analyte into a polypropylene tube for collection and analysis. For the minimum pressure test, the jet was operated manually by slowly pushing the piston forward to dispense the target analyte. For the maximum pressure test, 150 pounds per square inch (psi) were applied to the jet device, and the target analyte was carefully dispensed into a collection tube. For a positive control, the analyte was dispensed using a standard syringe, and a negative control was prepared by running the analyte through a series of boiling and freeze thaw cycles to cause intentional physical damage. Drug efficacy was detected by running the collected samples in a commercial ELISA kit and comparing detected concentrations of drug against a standard curve. A reduction in drug recovery was correlated to an impact on physical drug conformation resulting in reduced detection by the ELISA kit. If the jet dispensing had no impact on drug conformation, the concentration of the drug recovered from the device would have been the same as the positive control. If damage occurred, the concentration detected would have been similar to the negative control. The test matrix is shown in Table 10.

TABLE 10

| Sample | Number of times replicated | Description |
|---|---|---|
| Negative control | 3 | Novolog (undiluted; inactivated with repeated boiling and freeze/thaw cycles) |
| Positive control | 3 | Novolog hand dispensed with standard syringe |
| Jet test (150 psi) | 5* | Maximum psi jet delivery of undiluted Novolog into collection tube |
| Jet test (hand dispense) | 3 | Minimum PSI jet delivery of undiluted Novolog into collection tube |

*one outlier data point removed

The test method is illustrated in FIG. 88. The assay principle is illustrated in FIG. 89. The results are shown in Table 11. The statistics are shown in Table 12.

TABLE 11

| Sample | Description | Mean Recovery (mU/mL) | ±Standard Deviation | % CV |
|---|---|---|---|---|
| Negative control | Novolog (undiluted; inactivated with repeated boiling and freeze/thaw cycles) | 7.99E+05 | 2.408E+05 | 30.14% |
| Positive control | Novolog hand dispensed with standard syringe | 1.47E+07 | 3.765E+06 | 25.58% |
| Jet test (150 psi) | Maximum psi jet delivery of undiluted Novolog into collection tube | 2.11E+07 | 1.490E+06 | 7.06% |
| Jet test (hand dispense) | Minimum PSI jet delivery of undiluted Novolog into collection tube | 2.13E+07 | 1.909E+06 | 8.98% |

TABLE 12

Statistics (Student's T-test, 2 tailed, non-pair-wise, for significance p < 0.05)

| Test | P | Significance |
|---|---|---|
| NC v. PC | 0.021296 | S |
| $JT_{max}$ v. $JT_{min}$ | 0.710398 | N/S |
| PC v. $JT_{max}$ | 0.184357 | N/S |
| PC v. $JT_{min}$ | 0.070188 | N/S |

The assay was able to demonstrate detection of a physically inactivated drug by this method and that this is significantly different than a positive control. Within the context of the test parameters of this experiment, there was no negative impact on drug conformation when dispensed through the jet delivery system at 150 psi. Within the context of the test parameters of this experiment, there was no negative impact on drug conformation when dispensed through the jet delivery system at <30 psi. There was no significant (p>0.7) difference between dispensing at 150 psi or <30 psi through the jet system. There was no significant difference compared to the positive control at either pressure.

Other Embodiments

While certain embodiments have been described, the disclosure is not limited to such embodiments.

As an example, in some embodiments, an elastomeric bladder can be used to contain a dispensable substance (e.g., a therapeutic agent) such that the dispensable substance is dispensed form the ingestible device via the compressive forces of the elastomeric bladder, when stretched, and a valve system.

FIG. 90 illustrates an ingestible device 9000 having a housing 9010. Ingestible device also has an elastomeric bladder 9002 and a valve system 9004. The ingestible device 9000 further includes a tube 9006, connecting a dispensing port 9008 to bladder 9002. In addition, ingestible device 9000 has a PCBA 9012. Initially, the elastomeric bladder 9002 contains a volume of a dispensable substance and stretches to accommodate the volume of dispensable substance. The stretched bladder 9002 exerts a compressive force on the dispensable substance, so that, ultimately, the dispensable substance exits the bladder 9002 through tube 9006, and finally through the dispensing port 9008 in the housing 9010. Valve system 9004 is disposed on or in the tube 9006 and has two positions, closed and open. When closed, valve system 9004 prevents fluid communication between bladder 9002 and dispensing port 9008. In the closed position, valve system 9004 fully obstructs the flow in tube 9006. In the open position, valve system 9004 facilitates fluid communication between bladder 9002 and dispensing port 9008. In the open position, valve system 9004 removes at least part of the obstruction from tube 9006. As a result, the compressive force of bladder 9002 presses the dispensable substance from bladder 9002, through tube 9006 and opens valve system 9004. The dispensable substance then dispenses onto a section of the GI tract from dispensing port 9008, as desired. Valve system 9004 is controlled by PCBA 9012. In general, PCBA 9012 is configured to receive a signal and actuate valve system 9004 based on the information contained in the received signal. PCBA 9012 may additionally power the valve system.

Elastomeric bladder 9002 may be made of any appropriate material. Generally, bladder 9002 is made of an elastomeric material. Exemplary materials include latex, silicone, PVC, rubber, low density polyethylene, polypropylene. Typically, bladder 9002 has a thickness that provides the desired flexibility. In some embodiments, bladder 9002 has a thickness of from 0.001 inch to 0.0020 inch (e.g., 0.002 inch to 0.0015 inch).

FIGS. 91 and 92A illustrate a wax valve system 9100 as an embodiment of valve system 9004. The wax valve system 9100 includes a diaphragm 9102, wax 9104, and a heating element 9106. Typically, heating element 9106 is in electronic communication with PCBA 9012, also shown in FIG. 90. Wax 9102 is solid and is completely covered by diaphragm 9102. The configuration of wax 9104 protrudes fully into tube 9006 so that no liquid or gas may pass through tube 9006. Diaphragm 9102 is stretched due to the configuration of wax 9104, however the natural state of diaphragm 9102 obstructs part or none of tube 9006. Wax valve system 9100 is considered closed when wax 9104 and stretched diaphragm 9102 fully obstructs tube 9006. Heating element 9106 is thermally coupled to wax 9104 so that when heating element 9106 produces heat, wax 9104 melts. As wax 9104 melts, the pressure from wax 9104 to stretch diaphragm 9102 decreases and diaphragm 9102 relaxes to a more natural state. Diaphragm 9102 and wax 9104 no longer fully obstruct tube 9006, and wax valve system 9100 is considered open.

FIGS. 92A and 92B show wax valve system 9100 in ingestible device 9000. In FIG. 92A wax valve system 9100 is closed, and in FIG. 92B wax valve system 9100 is open.

In FIG. 92A, bladder 9002 is stretched and contains dispensable substance. Bladder 9002 applies a compressive force on the dispensable substance so that is exits bladder 9002 through tube 9006. Wax valve system 9100 is in the closed position and bladder 9002 cannot compress. Wax 9104 supports diaphragm 9102 so that diaphragm 9102 stretches to obstruct tube 9006, preventing fluid communication between bladder 9002 and dispensing port 9008. Wax valve system 9100 is closed and the dispensable substance cannot be dispensed through dispensing port 9008.

PCBA 9012 then receives a signal to dispense the dispensable substance and sends an electrical current to heating element 9106. Heating element 9106 melts wax 9104. As a result, diaphragm 9102 is no longer supported by wax 9104, and relaxes from the obstructive, stretched position, to a neutral position, shown in FIG. 92B. In the neutral position, diaphragm 9102 may partially obstruct tube 9006 or it may obstruct none of tube 9006. The neutral position shown in FIG. 92B shows diaphragm 9102 partially obstructing tube 9006. When wax valve system 9100 opens, due to the relaxing of diaphragm 9102, bladder 9002 is in fluid communication with dispensing port 9008, also shown in FIG. 92B. The compressive force of bladder 9002 on the dispensable substance, presses the dispensable substance through tube 9006, open wax valve system 9100, and dispensing port 9008, into the GI tract, as desired. Bladder 9002 is fully compressed and may contain a residual volume of dispensable substance.

While certain embodiments have been described in which an ingestible device includes a single outlet, e.g. nozzle, the disclosure is not limited in this regard. In general, any of the embodiments of an ingestible device disclosed herein can be implemented with multiple outlets, e.g., nozzles. For example, an ingestible device may include two outlets, three outlets, four outlets, five outlets or more than five outlets. In such embodiments, the same type of delivery mechanism (e.g., gas generating cell) can be used for each outlet (e.g., nozzle), different types of delivery mechanisms can be used for different outlets, or a combination may be used. In some embodiments, the ingestible device may include a separate storage reservoir for each dispensable substance, the ingestible device may include a separate delivery system for each storage reservoir, or a combination of such approaches can be used. In certain embodiments, an ingestible device with multiple outlets is designed so that each outlet opens at the same time. Such an approach can enhance relatively high pressure delivery of the dispensable substance(s), which such relatively high pressure is desirable. In certain embodiments, using multiple outlets (e.g., two outlets) the amount of dispensable substance delivered to tissue of the GI tract (e.g., between the muscularis externa and the submucosal layer) can be increased. In some embodiments, using multiple outlets (e.g., two outlets) can allow for enhancement of force balancing (e.g., the jet of dispensable substance has a reduced tendency to case the ingestible device to move away from a desired location, such as the intestinal wall). In some embodiments, using multiple outlets (e.g., two outlets) can lead to an enhanced probability of delivering some dose of dispensable substance in the case where the ingestible device is located at a location relatively remote from the target location.

Figure 93:
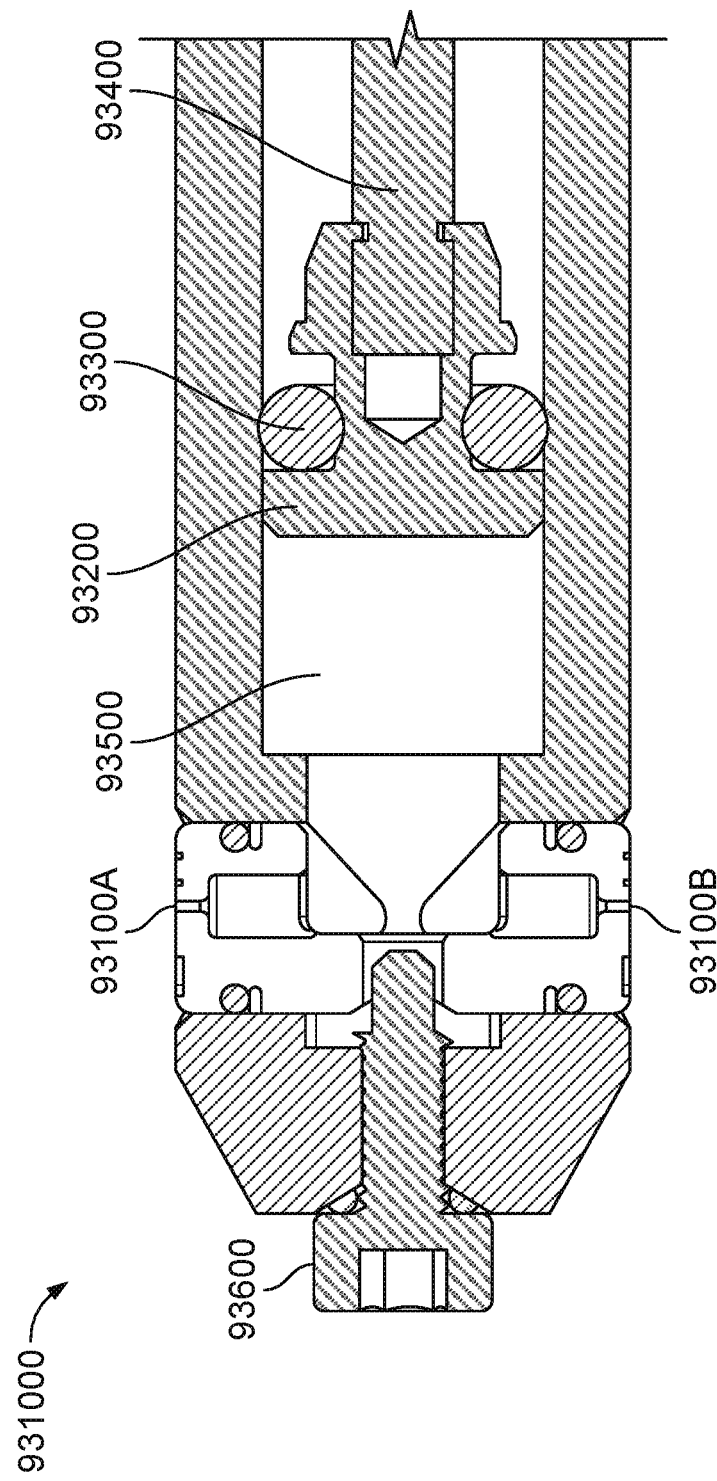
FIG. 93 illustrates an ingestible device with two outlets for dispensing.

FIG. 93 illustrates an exemplary embodiment of an ingestible device 93000 including a first outlet 93100A and a second outlet 93100B. Device 93000 also includes a piston 93200 sealed with an O-ring 93300 and an energy source (e.g., a gas generating cell) 93400 to move piston 93200. In addition, device 93000 includes a storage reservoir 93500 and a cap 93600. During use, energy source 93400 causes piston 93200 to move, forcing the dispensable substance in storage reservoir 93500 to exit device 93100 via outlets 93100A and 93100B.

A nozzle can be designed as appropriate. Examples of nozzle designs include nozzles that have straight sidewalls and nozzles that have tapered sidewalls. Examples of nozzles with tapered sidewalls are illustrated, for example, in FIGS. 31, 32, 45, 46A, 47, and 49-63.

While certain volumes for a storage reservoir have been disclosed, the disclosure is not limited to such volumes. Generally, a storage reservoir can have a volume as desired. For example, in any of the embodiments disclosed herein, a storage reservoir may have a volume of from 10 µL to 1500 µL (e.g., from 50 µL to 1000 µL, from 100 µL to 750 µL, from 200 µL to 600 µL, from 300 µL to 500 µL, from 350 µL to 450 µL, 400 µL).

In any embodiment, an ingestible device may include one or more storage reservoirs for containing a sample. For example, an ingestible device can be configured to obtain a sample while in the GI tract of a subject.

The various embodiments of systems, processes and apparatuses have been described herein by way of example only. It is contemplated that the features and limitations described in any one embodiment may be applied to any other embodiment herein, and flowcharts or examples relating to one embodiment may be combined with any other embodiment in a suitable manner, done in different orders, or done in parallel. It should be noted, the systems and/or methods described above may be applied to, or used in accordance with, other systems and/or methods. Various modifications and variations may be made to these example embodiments without departing from the spirit and scope of the embodiments, and the appended listing of embodiments should be given the broadest interpretation consistent with the description as a whole.

What is claimed is:

1. An ingestible device, comprising:
    a storage reservoir in a housing;
    a dispensable substance in the storage reservoir;
    a nozzle in the housing;
    a piston slidable within the housing;
    the storage reservoir formed between the piston and inner walls of the housing;
    and
    a pre-pressurized compressed gas chamber in the housing;
    an occluder having a first state configured to prevent the dispensable substance from exiting the ingestible device via the nozzle, and the occluder having a second state configured to allow compressed gas from the pre-pressurized compressed gas chamber to drive the piston to provide a jet of the dispensable substance out of the nozzle for systemic delivery of the dispensable substance.

2. The ingestible device of claim 1 wherein the compressed gas generates a pressure of 100-360 psi.

3. The ingestible device of claim 2 wherein the compressed gas generates a pressure of about 300 psi.

4. The ingestible device of claim 1 wherein the nozzle extends radially outward through a sidewall of the housing in a direction perpendicular to a longitudinal axis of the ingestible device.

5. The ingestible device of claim 1 comprising a plurality of nozzles.

6. The ingestible device of claim 5 comprising two, three, four, five or six nozzles equally spaced apart to balance reaction forces.

7. The ingestible device of claim 1 wherein the storage reservoir comprises a capillary structure.

8. The ingestible device of claim 1 wherein the occluder comprises a burst disc.

9. The ingestible device of claim 1 further comprising:
    a plurality of nozzles in the housing, each nozzle extending radially outward through the housing in a direction perpendicular to a longitudinal axis of the ingestible device.

10. The ingestible device of claim 9 wherein the occluder includes an occlusion component which weakens or dissolves after the ingestible device is ingested.

* * * * *